(12) United States Patent
Bell et al.

(10) Patent No.: US 6,441,017 B1
(45) Date of Patent: Aug. 27, 2002

(54) INHIBITORS OF PRENYL-PROTEIN TRANSFERASE

(75) Inventors: Ian M. Bell, Harleysville; Douglas C. Beshore, Lansdale; Steven N. Gallicchio, Ambler; C. Blair Zartman, Hatfield, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/656,653

(22) Filed: Sep. 7, 2000

Related U.S. Application Data

(60) Provisional application No. 60/153,017, filed on Sep. 9, 1999, now abandoned.

(51) Int. Cl.[7] .................. A61K 31/4015; C07D 291/00; C07D 512/00
(52) U.S. Cl. .................. 514/393; 540/456; 540/472
(58) Field of Search .................. 514/393; 540/456, 540/472

(56) References Cited

U.S. PATENT DOCUMENTS

| | | | |
|---|---|---|---|
| 5,756,528 A | 5/1998 | Anthony et al. | 514/399 |
| 5,780,488 A | 7/1998 | Bergman et al. | 514/357 |
| 5,856,326 A | 1/1999 | Anthony et al. | 514/252 |

FOREIGN PATENT DOCUMENTS

| | | | |
|---|---|---|---|
| WO | 9510515 | * | 4/1995 |

OTHER PUBLICATIONS

J. Med. Chem., vol. 42, pp. 3356–3368 (1999), by N. Anthony, et al.
J. Med. Chem., vol. 42, pp. 3779–3784 (1999), by T. Williams, et al.
Tetrahedron Ltrs., vol. 41, pp. 1141–1145 (2000), by I. Bell, et al.
J. Org. Chem., vol. 47, pp. 104–109 (1982), by R. Freidinger, et al.
Exp. Opin. Ther. Patents, vol. 6, No. 12, pp. 1295–1304 (1996), by S. Graham, et al.
Exp. Opin. Ther. Patents, vol. 5, No. 12, pp. 1269–1285 (1995), by S. L. Graham.
J. of Biol. Chem., vol. 268, No. 11, pp. 7617–7620 (1993), by J. B. Gibbs, et al.
J. of Biol. Chem., vol. 266, No. 24, pp. 15575–15578 (1991), by J. Goldstein, et al.
J. of Biol. Chem., vol. 269, No. 44, pp. 27705–27714 (1994), by G. James, et al.
J. of Biol. Chem., vol. 270, No. 11, pp. 6221–6226 (1995), by G. James, et al.
Nature Med, vol. 1, No. 8, pp. 792–797 (1995), by N. Kohl, et al.
Proc. Natl. Acad. Sci. USA, vol. 91, pp. 9141–9145 (1994), by N. Kohl, et al.
Science, vol. 260, pp. 1934–1937 (1993), by N. Kohl, et al.
Biochemistry, vol. 31, pp. 3800–3807 (1992), by D. Pompliano, et al.
Cancer Research, vol. 55, pp. 5302–5309 (1995), by L. Sepp–Lorenzino, et al.
Science, vol. 256, pp. 1331–1333 (1992), by J. Glenn, et al.
Cancer Research, vol. 55, pp. 4575–4580 (1995), by J. Rak, et al.
Am. J. of Pathology, vol. 142, No. 4, pp. 1051–1060 (1993), by D. Schaffner, et al.
FASEB Journal, vol. 2, A3160 (1988), by B. Cowley, et al.

* cited by examiner

Primary Examiner—Richard L. Raymond
Assistant Examiner—Sudhaker B. Patel
(74) Attorney, Agent, or Firm—Dianne Brown; Mark R. Deniel

(57) ABSTRACT

The present invention is directed to macrocyclic compounds which inhibit prenyl-protein transferase (FTase) and the prenylation of the oncogene protein Ras. The invention is further directed to chemothera-peutic compositions containing the compounds of this invention and methods for inhibiting prenyl-protein transferase and the prenylation of the oncogene protein Ras.

26 Claims, No Drawings

INHIBITORS OF PRENYL-PROTEIN TRANSFERASE

The priority of U.S. Provisional Application No. 60/153,017, filed on Sep. 9, 1999, now abandoned, is claimed.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. Such enzymes may be generally termed prenyl-protein transferases. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of poly-isoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1). It has also been disclosed that certain compounds which incorporate a pyrrolidine moiety are inhibitors of FPTase (WO 97/37900, and U.S. Pat. Nos. 5,627,202 and 5,661,161).

It is, therefore, an object of this invention to develop compounds that will inhibit prenyl-protein transferase and thus, the post-translational isoprenylation of proteins. It is a further object of this invention to develop chemotherapeutic compositions containing the compounds of this invention and methods for producing the compounds of this invention.

SUMMARY OF THE INVENTION

The present invention comprises macrocyclic compounds which inhibit prenyl-protein transferases. Further contained in this invention are chemotherapeutic compositions containing these prenyl-protein transferase inhibitors and methods for their production.

The compounds of this invention are illustrated by the formula A:

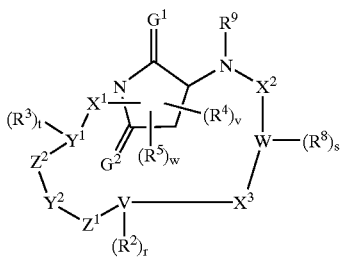

DETAILED DESCRIPTION OF THE INVENTION

The compounds of this invention are useful in the inhibition of prenyl-protein transferase and the prenylation of the oncogene protein Ras. In a first embodiment of this invention, the inhibitors of a prenyl-protein transferase are illustrated by the formula A:

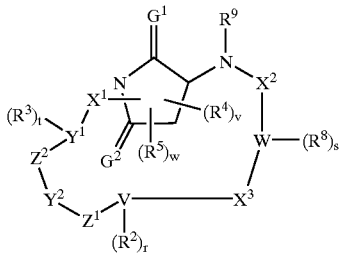

wherein $X^1$ is $(C(R^{1a})_2)_n A^1 (C(R^{1a})_2)_n A^2$;
$X^2$ is $(C(R^{1b})_2)_p A^3 (C(R^{1b})_2)_p$;
$X^3$ is $(C(R^{1c})_2)_q A^4 (C(R^{1c})_2)_q$;
$R^{1a}$, $R^{1b}$ and $R^{1c}$ are independently selected from:
  a) hydrogen;
  b) unsubstituted or substituted aryl, unsubstituted or substituted heterocycle, unsubstituted or substituted $C_3$–$C_{10}$ cycloalkyl, $R^{10}O$—, $R^{6a}S(O)_m$, unsubstituted or substituted $C_2$–$C_6$ alkenyl, unsubstituted or substituted $C_2$–$C_6$ alkynyl, —C(O)NR$^6$R$^7$, $R^{10}$C(O)NR$^{10}$—, $(R^{10})_2$NC(O) NR$^{10}$—, $R^{10}$C(O)—, —N(R$^{10}$)$_2$, $R^{10}$OC(O)—, or $R^{10}$OC(O)NR$^{10}$—; and
  c) unsubstituted or substituted $C_1$–$C_6$ alkyl, wherein one or more of the substituents on the substituted $C_1$–$C_6$ alkyl is selected from unsubstituted or substituted aryl, unsubstituted or substituted heterocycle, unsubstituted or substituted $C_3$–$C_{10}$cycloalkyl, unsubstituted or substituted $C_2$–$C_6$ alkenyl, unsubstituted or substituted $C_2$–$C_6$ alkynyl, $R^{10}O$—, $R^{6a}S(O)_m$, $R^{10}C(O)NR^{10}$—, $(R^{10})_2$NC(O) NR$^{10}$—, $R^{10}$C(O)—, —C(O)NR$^6$R$^7$, $R^{10}$OC(O)—, —N(R$^{10}$)$_2$, $R^{10}$OC(O)NR$^{10}$—, and halo;

$A^1$, $A^3$ and $A^4$ are independently selected from
  a) a bond,
  b) —C(=O)—,
  c) —HC=CH—,
  d) —C=C—,
  e) O,
  f) NR$^{10}$,
  g) NR$^{10}$C(O),
  h) C(O)NR$^{10}$,
  i) OC(O)NR$^{10}$,
  j) NR$^{10}$C(O)O,
  k) S(=O)$_m$,
  l) C(O)O, and
  m) OC(O);

$A^2$ is selected from
  a) a bond,
  b) —C(=O)—,
  c) NR$^{10}$C(O),
  d) S(=O)$_m$, and
  e) OC(O);

$R^2$ is independently selected from:
  a) hydrogen,
  b) CN,
  c) NO$_2$,
  d) halogen,
  e) aryl, unsubstituted or substituted,
  f) heterocycle, unsubstituted or substituted,
  g) $C_1$–$C_6$ alkyl, unsubstituted or substituted,
  h) OR,
  i) N$_3$,
  j) $R^{6a}$S(O)$_m$,
  k) $C_3$–$C_{10}$ cycloalkyl, unsubstituted or substituted,
  l) $C_2$–$C_6$ alkenyl, unsubstituted or substituted,
  m) $C_2$–$C_6$ alkynyl, unsubstituted or substituted,
  n) $(R^{10})_2$NC(O)NR$^{10}$—,
  o) $R^{10}$C(O)—,
  p) $R^{10}$C(O)NR$^{10}$—,
  q) $R^{10}$OC(O)—,
  r) —N(R$^{10}$)$_2$,
  s) $R^{10}$OC(O)NR$^{10}$—, and
  t) —(C$_1$–C$_6$ alkyl)NR$^{10}$C(O)R$^{13}$;

$R^3$ is independently selected from:
  H, CN, NO$_2$, halo, unsubstituted or substituted $C_1$–$C_6$ alkyl, N$_3$, oxido, unsubstituted or substituted aryl, unsubstituted or substituted heterocycle, unsubstituted or substituted $C_2$–$C_6$ alkenyl, unsubstituted or substituted $C_2$–$C_6$ alkynyl, unsubstituted or substituted aralkyl, unsubstituted or substituted heterocyclylalkyl, $C_1$–$C_6$ perfluoroalkyl, CF$_3$O—, CF$_3$CH$_2$—, unsubstituted or substituted $C_3$–$C_{10}$ cycloalkyl, OR$^{10}$, NR$^6$R$^7$, OR$^6$, —C(O)R$^{10}$, —O(C$_1$–C$_6$ alkyl)OR$^{10}$, S(O)$_m$R$^{6a}$, —C(O)NR$^6$R$^7$, —NHC(O)R$^{10}$, —(C$_1$–C$_6$ alkyl)OR$^{10}$, and —(C$_1$–C$_6$ alkyl)C(O)R$^{10}$;

$R^4$ and $R^5$ are independently selected from:
  H, OR$^{10}$, unsubstituted or substituted $C_1$–$C_6$ alkyl, unsubstituted or substituted $C_2$–$C_8$ alkenyl, unsubstituted or substituted $C_2$–$C_8$ alkynyl, unsubstituted or substituted aryl, unsubstituted or substituted heterocycle,

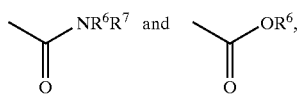

wherein the substituted group is substituted with one or more of:
  1) aryl or heterocycle, unsubstituted or substituted with:
    a) $C_1$–$C_6$ alkyl,
    b) (CH$_2$)$_n$OR$^6$,
    c) (CH$_2$)$_n$NR$^6$R$^7$,
    d) halogen,
    e) CN,
    f) aryl or heteroaryl, g) perfluoro-$C_1$–$C_4$ alkyl,
h) $S(O)_m R^{6a}$,
2) $C_3$–$C_6$ cycloalkyl,
3) $OR^6$,
4) $S(O)_m R^{6a}$,

5) —$NR^6R^7$,

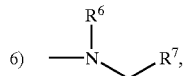

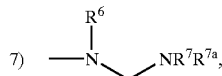

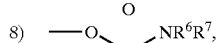

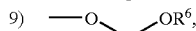

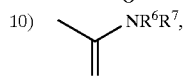

11) —$SO_2$—$NR^6R^7$,

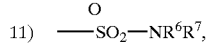

13) 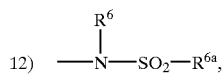

14) 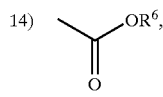

$R^4$ and $R^5$ are attached to the same C atom and are combined to form —$(CH_2)_u$— wherein one of the carbon atoms is optionally replaced by a moiety selected from: O, $S(O)_m$, —NC(O)—, and —$N(COR^{10})$—;

and any of $R^4$ and $R^5$ are optionally attached to the same carbon atom;

$R^6$, $R^7$ and $R^{7a}$ are independently selected from:

H, $C_1$–$C_6$ alkyl, $C_3$–$C_6$ cycloalkyl, heterocycle, aryl, aralkyl, aroyl, heteraroyl, arylsulfonyl, heteroarylsulfonyl, $C_1$–$C_4$ perfluoroalkyl, unsubstituted or substituted with one or two substituents selected from:
a) $C_1$–$C_6$ alkoxy,
b) substituted or unsubstituted aryl or substituted or unsubstituted heterocycle,
c) halogen,
d) HO, e) 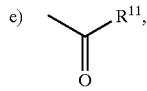

-continued f) 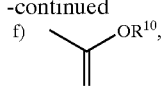

g) —$S(O)_m R^{6a}$, or g) —$S(O)_m R^{6a}$, or
h) $N(R^{10})_2$; or $R^6$ and $R^7$ may be joined in a ring;
$R^7$ and $R^{7a}$ may be joined in a ring;
$R^{6a}$ is selected from
a) $C_{3-6}$ cycloalkyl, heterocycle, aryl, unsubstituted or substituted with one or more of the following:
1) $C_{1-4}$ alkoxy,
2) aryl or heterocycle,
3) halogen,
4) HO, 5) 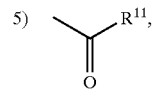

6) $SO_2 R^{6a}$,
7) $N(R^{10})_2$; and
b) $C_1$–$C_6$ alkyl, unsubstituted or substituted with one or more of the following:
1) —$C(R^{10})_2 C_{1-4}$ alkoxy,
2) aryl or heterocycle,
3) —$C(R^{10})_2$halogen,
4) —$C(R^{10})_2$OH, 5) 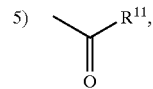

6) —$C(R^{10})_2 SO_2 R^{6a}$, and
7) —$C(R^{10})_2 N(R^{10})_2$;

$R^8$ is independently selected from
a) hydrogen,
b) unsubstituted or substituted $C_2$–$C_6$ alkenyl, unsubstituted or substituted $C_2$–$C_6$ alkynyl, unsubstituted or substituted $C_3$–$C_6$ cycloalkyl, unsubstituted or substituted $C_1$–$C_4$perfluoroalkyl, F, Cl, Br, $R^{10}O$—, CN, $R^{6a}S(O)_m$, —$C(O)NR^6R^7$, $R^{10}C(O)NR^{10}$—, $NO_2$, $(R^{10})_2 NC(O)NR^{10}$—, $R^{10}C(O)$—, $R^{10}OC(O)$—, $R^{10}OC(O)NR^{10}$—, $N_3$, or —$N(R^{10})_2$ and
c) $C_1$–$C_6$ alkyl, unsubstituted or substituted by $C_1$–$C_4$ perfluoroalkyl, F, Cl, Br, $R^{10}O$—, $R^{6a}S(O)_m$, $R^{10}C(O)NR^{10}$—, CN, —$C(O)NR^6R^7$, $(R^{10})_2 NC(O)NR^{10}$—, $R^{10}C(O)$—, $R^{10}OC(O)$—, $N_3$, —$N(R^{10})_2$, and $R^{10}OC(O)NR^{10}$—;

$R^9$ is independently selected from
1) H, unsubstituted or substituted $C_1$–$C_6$ alkyl, unsubstituted or substituted $C_2$–$C_8$ alkenyl, unsubstituted or substituted $C_2$–$C_8$ alkynyl, unsubstituted or substituted aryl, and unsubstituted or substituted heterocycle, wherein the substituted group is substituted with one or more of:
a) $C_1$–$C_6$ alkyl, unsubstituted or substituted,
b) $(CH_2)_n OR^6$,
c) $(CH_2)_n NR^6R^7$,
d) halogen,
e) CN,
f) aryl, unsubstituted or substituted,
g) heterocycle, unsubstituted or substituted,
h) perfluoro-$C_1$–$C_4$ alkyl,
i) $S(O)_m R^{6a}$, j) N(R$^{10}$)$_2$,
k) NR$^{10}$C(O)R$^{11}$,
l) NR$^{10}$C(O)R$^{11}$N(R$^{10}$)$_2$,
2) C$_3$–C$_6$ cycloalkyl,
3) S(O)$_{1-2}$R$^{6a}$, 4) 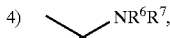

5) —SO$_2$—NR$^6$R$^7$,

6) 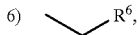

7) 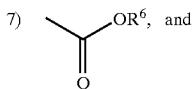

8) —(C$_1$–C$_6$ alkyl)NR$^{10}$C(O)R$^{13}$;

R$^{10}$ is independently selected from
  a) hydrogen,
  b) unsubstituted or substituted C$_1$–C$_6$ alkyl,
  c) unsubstituted or substituted C$_3$–C$_6$ cycloalkyl,
  d) 2,2,2-trifluoroethyl,
  e) unsubstituted or substituted heteroaryl,
  f) unsubstituted or substituted aralkyl,
  g) unsubstituted or substituted aryl, and
  h) unsubstituted or substituted heterocyclylalkyl;

R$^{11}$ is independently selected from
  a) unsubstituted or substituted C$_{1-6}$ alkyl,
  b) unsubstituted or substituted aralkyl,
  c) unsubstituted or substituted heterocycle,
  d) unsubstituted or substituted aryl, and
  e) unsubstituted or substituted heterocyclylalkyl;

R$^{13}$ is independently selected from
  a) H,
  b) unsubstituted or substituted C$_1$–C$_6$ alkyl,
  c) unsubstituted or substituted C$_2$–C$_6$ alkenyl,
  d) unsubstituted or substituted C$_2$–C$_6$ alkynyl,
  e) unsubstituted or substituted aryl,
  f) unsubstituted or substituted heterocycle,
  g) aralkyl, unsubstituted or substituted,
  h) heterocyclylalkyl, unsubstituted or substituted,
  i) CF$_3$,
  j) CF$_3$O—,
  k) CF$_3$CH$_2$—,
  l) C$_3$–C$_{10}$ cycloalkyl, unsubstituted or substituted,
  m) OR$^{10}$,
  n) —C(O)R$^{10}$,
  o) —O(C$_1$–C$_6$ alkyl)OR$^{10}$,
  p) —C(O)NR$^6$R$^7$,
  q) —(C$_1$–C$_6$ alkyl)OR$^{10}$, and
  r) —(C$_{1-6}$ alkyl)C(O)R$^{10}$;

G$^1$ and G$^2$ are independently selected from oxygen or H$_2$;

V is selected from
  a) a bond,
  b) heterocycle,
  c) aryl,
  d) C$_1$–C$_{20}$ alkyl wherein from 0 to 4 carbon atoms are replaced with a heteroatom selected from O, S(O)$_m$, and N, and
  e) C$_2$–C$_{20}$ alkenyl;

W is a heterocycle;

Y$^1$ and Y$^2$ are independently selected from
  a) a bond,
  b) C$_1$–C$_8$ alkyl,
  c) C$_2$–C$_3$ alkenyl,
  d) C$_2$–C$_8$ alkynyl,
  e) C$_3$–C$_{20}$ cycloalkyl,
  f) aryl, and
  g) heterocycle;

Z$^1$ and Z$^2$ are independently selected from
  a) a bond,
  b) O,
  c) C(O),
  d) S(O)$_m$,
  e) C(O)NR$^{10}$,
  f) (C(R$^{1a}$)$_2$)$_n$,
  g) (C(R$^{1a}$)$_2$)$_n$O,
  h) O(C(R$^{1a}$)$_2$)$_n$, and
  i) NR$^{10}$;

m is 0, 1 or 2;
n is 0, 1, 2, 3, 4, 5 or 6;
p is 0, 1, 2, 3, 4, 5 or 6;
q is 0, 1, 2, 3, 4, 5 or 6;
r is 0 to 5, provided that r is 0 when V is a bond;
s is 0, 1, 2, 3 or 4; provided that s is 0 when W is a bond;
t is 0, 1, 2, 3 or 4; provided that t is 0 when Y$^1$ is a bond;
u is 4 or 5;
v is 0, 1, 2, 3 or 4; and
w is 0, 1, 2, 3 or 4;

or a pharmaceutically acceptable salt, an optical isomer or stereoisomer thereof.

Another embodiment of the compounds of this invention is illustrated by formula A:

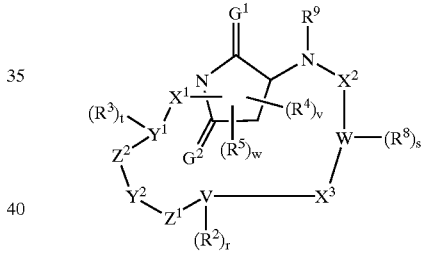

A wherein
X$^1$ is (C(R$^{1c}$)$_2$)$_n$A$^1$(C(R$^{1c}$)$_2$)$_n$A$^2$;
X$^2$ is (C(R$^{1b}$)$_2$)$_p$A$^3$(C(R$^{1b}$)$_2$)$_p$;
X$^3$ i (C(R$^{1c}$)$_2$)$_q$A$^4$;

R$^{1a}$ and R$^{1b}$ are independently selected from:
  a) hydrogen;
  b) unsubstituted or substituted aryl, unsubstituted or substituted heterocycle, unsubstituted or substituted C$_3$–C$_{10}$ cycloalkyl, R$^{10}$O—, R$^{6a}$S(O)$_m$, unsubstituted or substituted C$_2$–C$_6$ alkenyl, unsubstituted or substituted C$_2$–C$_6$ alkynyl, —C(O)NR$^6$R$^7$, C(O)NR$^{10}$—, (R$^{10}$)$_2$NC(O)NR$^{10}$—, R$^{10}$C(O)—, —N(R$^{10}$)$_2$, R$^{10}$OC(O)—, and R$^{10}$OC(O)NR$^{10}$—, and
  c) unsubstituted or substituted C$_1$–C$_6$ alkyl, wherein the substituent on the substituted C$_1$–C$_6$ alkyl is selected from unsubstituted or substituted aryl, unsubstituted or substituted heterocycle, unsubstituted or substituted C$_3$–C$_{10}$cycloalkyl, unsubstituted or substituted C$_2$–C$_6$ alkenyl, unsubstituted or substituted C$_2$–C$_6$ alkynyl, R$^{10}$O—, R$^{6a}$S(O)$_m$, R$^{10}$C(O)NR$^{10}$—, (R$^{10}$)$_2$NC(O)NR$^{10}$—, —C(O)NR$^6$R$^7$, R$^{10}$C(O)—, R$^{10}$OC(O)—, halo, —N(R$^{10}$)$_2$, and R$^{10}$OC(O)NR$^{10}$—;

$R^{1c}$ is selected from
a) hydrogen and
b) unsubstituted or substituted $C_1$–$C_6$ alkyl, wherein the substituent on the substituted $C_1$–$C_6$ alkyl is selected from unsubstituted or substituted aryl, unsubstituted or substituted heterocycle, unsubstituted or substituted $C_3$–$C_{10}$cycloalkyl, unsubstituted or substituted $C_2$–$C_6$ alkenyl, unsubstituted or substituted $C_2$–$C_6$ alkynyl, $R^{10}O$—, $R^{6a}S(O)_m$, —C(O)NR$^6$R$^7$, $R^{10}C(O)NR^{10}$—, $(R^{10})_2NC(O)NR^{10}$—, $R^{10}C(O)$—, $R^{10}OC(O)$—, halo, —N(R$^{10}$)$_2$, and $R^{10}OC(O)NR^{10}$—;

$A^1$ and $A^3$ are independently selected from
a) a bond,
b) —C(=O)—,
c) O,
d) NR$^{10}$,
e) NR$^{10}$C(O),
f) C(O)NR$^{10}$,
g) OC(O)NR$^{10}$,
h) NR$^{10}$C(O)O,
i) S(=O)$_m$,
j) OC(O), and
k) C(O)O;

$A^2$ is selected from
a) a bond,
b) —C(=O)—,
c) NR$^{10}$C(O), and
d) S(=O)$_m$;

$A^4$ is a bond;

$R^2$ is independently selected from:
a) hydrogen,
b) CN,
c) NO$_2$,
d) halogen,
e) aryl, unsubstituted or substituted,
f) heterocycle, unsubstituted or substituted,
g) $C_1$–$C_6$ alkyl, unsubstituted or substituted,
h) OR$^{10}$,
i) N$_3$,
j) R$^{6a}$S(O)$_m$,
k) $C_3$–$C_{10}$ cycloalkyl, unsubstituted or substituted,
l) $C_2$–$C_6$ alkenyl, unsubstituted or substituted,
m) $C_2$–$C_6$ alkynyl, unsubstituted or substituted,
n) $(R^{10})_2NC(O)NR^{10}$—,
o) $R^{10}C(O)$—,
p) R C(O)NR$^{10}$—,
q) $R^{10}OC(O)$—,
r) —N(R$^{10}$)$_2$;
s) $R^{10}OC(O)NR^{10}$—, and
t) —($C_1$–$C_6$ alkyl)NR$^{10}$C(O)R$^{13}$;

$R^3$ is independently selected from:
H, CN, NO$_2$, halo, unsubstituted or substituted $C_1$–$C_6$ alkyl, N$_3$, oxido, unsubstituted or substituted aryl, unsubstituted or substituted heterocycle, unsubstituted or substituted C2–C6 alkenyl, unsubstituted or substituted $C_2$–$C_6$ alkynyl, unsubstituted or substituted aralkyl, unsubstituted or substituted heterocyclylalkyl, $C_1$–$C_6$ perfluoroalkyl, CF$_3$O—, CF$_3$CH$_2$—, unsubstituted or substituted $C_3$–$C_{10}$ cycloalkyl, OR$^{10}$, NR$^6$R$^7$, OR$^6$, —C(O)R$^{10}$, —O($C_1$–$C_6$ alkyl)OR$^{10}$, —S(O)$_m$R$^{6a}$, —C(O)NR$^6$R$^7$, —NHC(O)R$^{10}$, —($C_1$–$C_6$ alkyl)OR$^{10}$, and —($C_1$–$C_6$ alkyl)C(O)R$^{10}$;

$R^4$ and $R^5$ are independently selected from:
H, OR$^{10}$, unsubstituted or substituted $C_1$–$C_6$ alkyl, unsubstituted or substituted $C_2$–$C_8$ alkenyl, unsubstituted or substituted $C_2$–$C_8$ alkynyl, unsubstituted or substituted aryl, unsubstituted or substituted heterocycle,

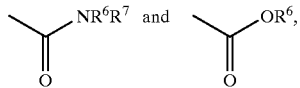

wherein the substituted group is substituted with one or more of:
1) aryl or heterocycle, unsubstituted or substituted with:
   a) $C_1$–$C_6$ alkyl,
   b) (CH$_2$)$_n$OR$^6$,
   c) (CH$_2$)$_n$NR$^6$R$^7$,
   d) halogen,
   e) CN,
   f) aryl or heteroaryl,
   g) perfluoro-$C_1$–$C_4$ alkyl,
   h) S(O)$_m$R$^{6a}$,
2) $C_3$–$C_6$ cycloalkyl,
3) OR,
4) S(O)$_m$R$^{6a}$,

5) —NR$^6$R$^7$,

6) 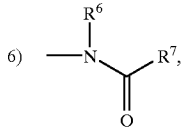

7) 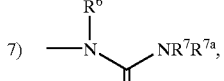

8) 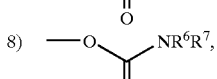

9) 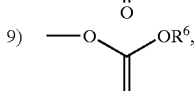

10) 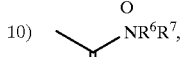

11) —SO$_2$—NR$^6$R$^7$,

12) 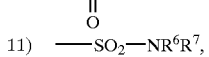

13) 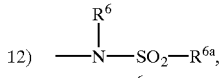

14) 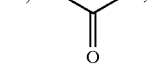

15) N$_3$,
16) halo, and
17) perfluoro-$C_{1-4}$-alkyl; or $R^4$ and $R^5$ are attached to the same C atom and are combined to form —(CH$_2$)$_u$— wherein one of the carbon atoms is optionally replaced by a moiety selected from: O, S(O)$_m$, NR$^{10}$, —NC(O)—, and —N(COR$^{10}$)—;

and any of $R^4$ and $R^5$ are optionally attached to the same carbon atom;

$R^6$, $R^7$ and $R^{7a}$ are independently selected from:
H, $C_1$–$C_6$ alkyl, $C_{3-C6}$ cycloalkyl, heterocycle, aryl, aralkyl, aroyl, heteraroyl, arylsulfonyl, heteroarylsulfonyl, $C_1$–$C_4$ perfluoroalkyl, unsubstituted or substituted with one or two substituents selected from:
a) $C_1$–$C_6$ alkoxy,
b) substituted or unsubstituted aryl or substituted or unsubstituted heterocycle,
c) halogen,
d) HO, e) 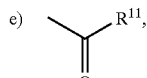

f) 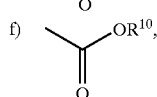

g) —$S(O)_m R^{6a}$, or
h) $N(R^{10})_2$; or
$R^6$ and $R^7$ may be joined in a ring;
$R^7$ and $R^{7a}$ may be joined in a ring;
$R^{6a}$ is selected from
a) $C_{3-6}$ cycloalkyl, heterocycle, aryl, unsubstituted or substituted with one or more of the following:
1) $C_{1-4}$ alkoxy,
2) aryl or heterocycle,
3) halogen,
4) HO, 5) 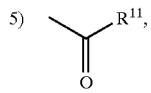

6) $SO_2 R^{6a}$,
7) $N(R^{10})_2$; and
b) $C_1$–$C_6$ alkyl, unsubstituted or substituted with one or more of the following:
b 1) —$C(R^{10})_2 C_{1-4}$ alkoxy,
2) aryl or heterocycle,
3) —$C(R^{10})_2$halogen,
4) —$C(R^{10})_2$OH, 5) 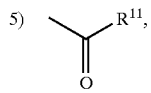

6) —$C(R^{10})_2 SO_2 R^{6a}$, and
7) —$C(R^{10})_2 N(R^{10})_2$;
$R^8$ is independently selected from
a) hydrogen,
b) unsubstituted or substituted $C_2$–$C_6$ alkenyl, unsubstituted or substituted $C_2$–$C_6$ alkynyl, unsubstituted or substituted $C_3$–$C_6$ cycloalkyl, unsubstituted or substituted $C_1$–$C_4$ perfluoroalkyl, F, Cl, Br, $R^{10}O$—, CN, $R^{6a}S(O)_m$—, —$C(O)NR^6R^7$, $R^{10}C(O)NR^{10}$—, $NO_2$, $(R^{10})_2 NC(O)NR^{10}$—, $R^{10}C(O)$—, $R^{10}OC(O)$—, $R^{10}OC(O)NR^{10}$—, $N_3$, or —$N(R^{10})_2$, and
c) $C_1$–$C_6$ alkyl, unsubstituted or substituted by $C_1$–$C_4$ perfluoroalkyl, F, Cl, Br, $R^{10}O$—, $R^{6a}S(O)_m$—, $R^{10}C(O)NR^{10}$—, —$C(O)NR^6R^7$, CN, $(R^{10})_2 NC(O)NR^{10}$, $R^{10}C(O)$—, $R^{10}OC(O)$—, $N_3$, —$N(R^{10})_2$, and $R^{10}OC(O)NR^{10}$—;

$R^9$ is independently selected from
1) H, unsubstituted or substituted $C_1$–$C_6$ alkyl, unsubstituted or substituted $C_2$–$C_8$ alkenyl, unsubstituted or substituted $C_2$–$C_8$ alkynyl, unsubstituted or substituted aryl, and unsubstituted or substituted heterocycle, wherein the substituted group is substituted with one or more of:
a) $C_1$–$C_6$ alkyl, unsubstituted or substituted,
b) $(CH_2)_n OR^6$,
c) $(CH_2)_n NR^6R^7$,
d) halogen,
e) CN,
f) aryl, unsubstituted or substituted,
g) heterocycle, unsubstituted or substituted,
h) perfluoro-$C_1$–$C_4$ alkyl,
i) $S(O)_m R^{6a}$,
j) $N(R^{10})_2$,
k) $NR^{10}C(O)R^{11}$,
l) $NR^{10}OC(O)R^{11} N(R^{10})_2$,
2) $C_3$–$C_6$ cycloalkyl,
3) $S(O)_{1-2} R^{6a}$, 4) 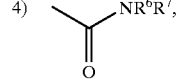

5) —$SO_2$—$NR^6R^7$,

6) 

7)  and

8) —($C_1$–$C_6$ alkyl)$NR^{10}C(O)R^{13}$;
$R^{10}$ is independently selected from
a) hydrogen,
b) unsubstituted or substituted $C_1$–$C_6$ alkyl,
c) $C_3$–$C_6$ cycloalkyl,
d) 2,2,2-trifluoroethyl,
e) unsubstituted or substituted heteroaryl,
f) unsubstituted or substituted aryl,
g) unsubstituted or substituted aralkyl, and
h) unsubstituted or substituted heterocyclylalkyl;
$R^{11}$ is independently selected from
a) unsubstituted or substituted $C_1$–$C_6$ alkyl,
b) unsubstituted or substituted aralkyl,
c) unsubstituted or substituted heterocycle,
d) unsubstituted or substituted aryl, and
e) unsubstituted or substituted heterocyclylalkyl;
$R^{13}$ is independently selected from
a) H,
b) unsubstituted or substituted $C_1$–$C_6$ alkyl,
c) unsubstituted or substituted $C_2$–$C_6$ alkenyl,
d) unsubstituted or substituted $C_2$–$C_6$ alkynyl,
e) unsubstituted or substituted aryl,
f) unsubstituted or substituted heterocycle,
g) aralkyl, unsubstituted or substituted,
h) heterocyclylalkyl, unsubstituted or substituted,
i) $CF_3$,
j) $CF_3O$—,
k) $CF_3CH_2$—,
l) $C_3$–$C_{10}$ cycloalkyl, unsubstituted or substituted,
m) $OR^{10}$,
n) —$C(O)R^{10}$,
o) —$O(C_1$–$C_6$ alkyl)$OR^{10}$, p) —C(O)NR⁶R⁷, q) —(C₁–C₆ alkyl)OR¹⁰, and r) —(C₁–C₆ alkyl)C(O)R¹⁰;

G¹ and G² are independently selected from oxygen or H₂;

V is selected from
  a) heterocycle,
  b) aryl, and
  c) C₁–C₂₀ alkyl wherein from 0 to 4 carbon atoms are replaced with a heteroatom selected from O, S(O)$_m$, and N, W is a heterocycle selected from pyrrolidinyl, imidazolyl, pyridinyl, thiazolyl, pyridonyl, 2-oxopiperidinyl, indolyl, quinolinyl, isoquinolinyl, and thienyl, Y¹ is selected from
  a) a bond,
  b) C₁–C₈ alkyl,
  c) C₃–C₂₀ cycloalkyl,
  d) aryl or
  e) heterocycle;

Y² is selected from
  a) a bond,
  b) aryl or
  c) heterocycle;

Z¹ is selected from
  a) a bond,
  b) O,
  c) C(O),
  d) S(O)$_m$,
  e) C(O)NR¹⁰,
  f) (C(R¹ᵃ)₂)$_n$,
  g) O(C(R¹ᵃ)₂)$_n$,
  h) (C(R¹ᵃ)₂)$_n$O, and
  i) NR¹⁰;

Z² is selected from:
  a) a bond,
  b) O,
  c) C(O),
  d) S(O)$_m$,
  e) (C(R¹ᵃ)₂)$_n$, and
  f) NR¹⁰;

m is 0, 1 or 2;

n is 0, 1, 2, 3, 4, 5 or 6;

p is 0, 1, 2, 3, 4, 5 or 6;

q is 0, 1, 2, or 3;

r is 0 to 5;

s is 0, 1, 2, 3 or 4;

t is 0, 1, 2, 3 or 4, provided t is 0 when Y¹ is a bond;

u is 4 or 5;

v is 0, 1, 2, 3 or 4; and w is 0, 1, 2, 3 or 4;

or a pharmaceutically acceptable salt, an optical isomer or stereoisomer thereof.

Another embodiment of the compounds of this invention is illustrated by the formula B:

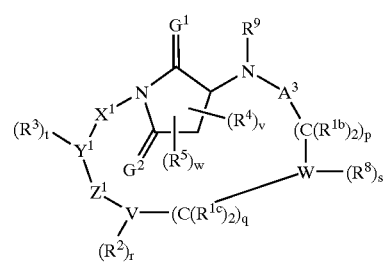

wherein

X¹ is (C(R¹ᵃ)₂)$_n$A¹(C(R¹ᵃ)₂)$_n$A²;

R¹ᵃ is selected from:
  a) hydrogen;
  b) unsubstituted or substituted aryl, unsubstituted or substituted heterocycle, unsubstituted or substituted C₃–C₁₀ cycloalkyl, R¹⁰O—, R⁶ᵃS(O)$_m$, unsubstituted or substituted C₂–C₆ alkenyl, unsubstituted or substituted C₂–C₆ alkynyl, —C(O)NR⁶R⁷, R¹⁰C(O)NR¹⁰—, (R¹⁰)₂NC(O)NR¹⁰—, R₁₀C(O)—, —N(R¹⁰)₂, R¹⁰OC(O)—, and R¹⁰OC(O)NR¹⁰—, and
  c) unsubstituted or substituted C₁–C₆ alkyl, wherein the substituent on the substituted C₁–C₆ alkyl is selected from unsubstituted or substituted aryl, unsubstituted or substituted heterocycle, unsubstituted or substituted C₃–C₁₀cycloalkyl, unsubstituted or substituted C₂–C₆ alkenyl, unsubstituted or substituted C₂–C₆ alkynyl, R¹⁰O—, R⁶ᵃS(O)$_m$, R¹⁰C(O)NR¹⁰—, —(C(O)NR⁶R⁷, (R¹⁰)₂NC(O)NR¹⁰—, R¹⁰C(O)—, R¹⁰OC(O)—, halo, —N(R¹⁰)₂, and R¹⁰OC(O)NR¹⁰—;

R¹ᵇ and R¹ᶜ are independently selected from
  a) hydrogen and
  b) unsubstituted or substituted C₁–C₆ alkyl, wherein the substituent on the substituted C₁–C₆ alkyl is selected from unsubstituted or substituted aryl, unsubstituted or substituted heterocycle, unsubstituted or substituted C₃–C₁₀cycloalkyl, unsubstituted or substituted C₂–C₆ alkenyl, unsubstituted or substituted C₂–C₆ alkynyl, R¹⁰O—, R⁶ᵃS(O)$_m$, —C(O)NR⁶R⁷, R¹⁰C(O)NR¹⁰, (R¹⁰)₂NC(O)NR¹⁰—, R¹⁰C(O)—, R¹⁰OC(O)—, halo, —N(R¹⁰)₂, and R¹⁰OC(O)NR¹⁰—;

A¹ is selected from
  a) a bond,
  b) —C(=O)—,
  c) O,
  d) NR¹⁰,
  e) NR¹⁰C(O),
  f) C(O)NR¹⁰,
  g) OC(O)NR¹⁰,
  h) NR¹⁰C(O)O,
  i) S(=O)$_m$,
  j) C(O)O, and
  k) OC(O);

A² is selected from
  a) a bond,
  b) —C(=O)—,
  c) NR¹⁰C(O), and
  d) S(=O)$_m$;

A³ is selected from a bond or C(=O);

R² is independently selected from:

a) hydrogen,
b) CN,
c) NO$_2$,
d) halogen,
e) aryl, unsubstituted or substituted,
f) heterocycle, unsubstituted or substituted,
g) C$_1$–C$_6$ alkyl, unsubstituted or substituted,
h) OR$^{10}$,
i) N$_3$,
j) R$^{6a}$S(O)$_m$,
k) C$_3$–C$_{10}$ cycloalkyl, unsubstituted or substituted,
l) C$_2$–C$_6$ alkenyl, unsubstituted or substituted,
m) C$_2$–C$_6$ alkynyl, unsubstituted or substituted,
n) (R$^{10}$)$_2$NC(O)NRO$^{10}$—,
o) R$^{10}$C(O)—,
p) R$^{10}$C(O)NR$^{10}$—,
q) R$^{10}$OC(O)—,
r) —N(R$^{10}$)$_2$,
s) R$^{10}$OC(O)NR$^{10}$—, and
t) —(C$_1$–C$_6$ alkyl)NR$^{10}$C(O)R$^{13}$;

R$^3$ is independently selected from:
H, CN, NO$_2$, halo, unsubstituted or substituted C$_1$–C$_6$ alkyl, N$_3$, oxido, unsubstituted or substituted aryl, unsubstituted or substituted heterocycle, unsubstituted or substituted C$_2$–C$_6$ alkenyl, unsubstituted or substituted C$_2$–C$_6$ alkynyl, unsubstituted or substituted aralkyl, unsubstituted or substituted heterocyclylalkyl, C$_1$–C$_6$ perfluoroalkyl, CF$_3$O—, CF$_3$CH$_2$—, unsubstituted or substituted C$_3$–C$_{10}$ cycloalkyl, OR$^{10}$O, NR$^6$R$^7$, OR$^6$, —C(O)R$^{10}$, —O(C$_1$–C$_6$ alkyl)OR$^{10}$, —S(O)$_m$R$^{6a}$, —C(O)NR$^6$R$^7$, —NHC(O)R$^{10}$, —(C$_1$–C$_6$ alkyl)OR$^{10}$, and —(C$_1$–C$_6$ alkyl)C(O)R$^{10}$;

R$^4$ and R$^5$ are independently selected from:
H, OR$^{10}$, unsubstituted or substituted C$_1$–C$_6$ alkyl, unsubstituted or substituted aryl, unsubstituted or substituted heterocycle, wherein the substituted group is substituted with one or two of:
1) aryl or heterocycle, unsubstituted or substituted with:
   a) C$_1$–C$_6$ alkyl,
   b) (CH$_2$)$_n$OR$^6$,
   c) (CH$_2$)$_n$NR$^6$R$^7$,
   d) halogen,
   e) CN,
   f) aryl or heteroaryl,
   g) perfluoro-C$_1$–C$_4$ alkyl,
   h) S(O)$_m$R$^{6a}$,
2) C$_3$–C$_6$ cycloalkyl,
3) OR$^6$,
4) S(O)$_m$R$^{6a}$,

5) —NR$_6$R$_7$,

6) 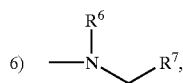

7) 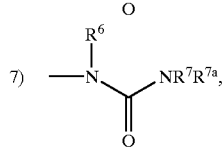

8) 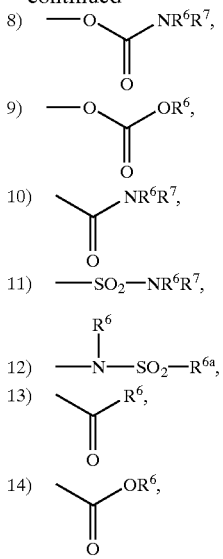

15) N$_3$,
16) halo, and
17) perfluoro-C$_{1-4}$-alkyl; or

R$^4$ and R$^5$ are attached to the same C atom and are combined to form —(CH$_2$)$_u$— wherein one of the carbon atoms is optionally replaced by a moiety selected from: O, S(O)$_m$, NR$^{10}$, —NC(O)—and —N(COR$^{10}$)—:

and any of R$^4$ and R$^5$ are optionally attached to the same carbon atom;

R$^6$, R$^7$ and R$^{7a}$ are independently selected from:
H, C$_1$–C$_6$ alkyl, C$_3$–C$_6$ cycloalkyl, heterocycle, aryl, aralkyl, aroyl, heteraroyl, arylsulfonyl, heteroarylsulfonyl, C$_1$–C$_4$ perfluoroalkyl, unsubstituted or substituted with one or two substituents selected from:
a) C$_1$–C$_6$ alkoxy,
b) substituted or unsubstituted aryl or substituted or unsubstituted heterocycle,
c) halogen,
d) HO, e) 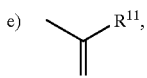

f) 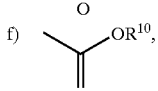

g) —S(O)$_m$R$^{6a}$, or
h) N(R$^{10}$)$_2$; or

R$^6$ and R$^7$ may be joined in a ring;
R$^7$ and R$^{7a}$ may be joined in a ring;
R$^{6a}$ is selected from
a) C$_{3-6}$ cycloalkyl, heterocycle, aryl, unsubstituted or substituted with one or more of the following:
   1) C$_{1-4}$ alkoxy,
   2) aryl or heterocycle, 3) halogen,
4) HO,
5) 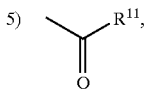
6) $SO_2R^{6a}$,
7) $N(R^{10})_2$; and
b) $C_1-C_6$ alkyl, unsubstituted or substituted with one or more of the following:
1) $-C(R^{10})_2C_{1-4}$ alkoxy,
2) aryl or heterocycle,
3) $-C(R^{10})_2$halogen,
4) $-C(R^{10})_2OH$,
5) 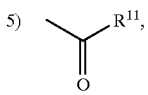
6) $-C(R^{10})_2SO_2R^{6a}$, and
7) $-C(R^{10})_2N(R^{10})_2$;

$R^8$ is independently selected from
a) hydrogen,
b) unsubstituted or substituted $C_2-C_6$ alkenyl, unsubstituted or substituted $C_2-C_6$ alkynyl, unsubstituted or substituted $C_3-C_6$ cycloalkyl, unsubstituted or substituted $C_1-C_4$perfluoroalkyl, F, Cl, Br, $R^{10}O-$, CN, $R^{6a}S(O)_m$, $-C(O)NR^6R^7$, $R^{10}C(O)NR^{10}-$, $NO_2$, $(R^{10})_2NC(O)NR^{10}-$, $R^{10}C(O)-$, $R^{10}OC(O)-$, $R^{10}OC(O)NR^{10}-$, $N_3$, or $-N(R^{10})_2$, and
c) $C_1-C_6$ alkyl, unsubstituted or substituted by $C_1-C_4$ perfluoroalkyl, F, Cl, Br, $R^{10}O-$, $R^{6a}S(O)_m-$, $R^{10}C(O)NR^{10}-$, $-C(O)NR^6R^7$, CN, $(R^{10})_2NC(O)NR^{10}-$, $R^{10}C(O)-$, $R^{10}OC(O)-$, $N_3$, $-N(R^{10})_2$, and $R^{10}OC(O)NR^{10}-$;

$R^9$ is independently selected from
1) H, unsubstituted or substituted $C_1-C_6$ alkyl, unsubstituted or substituted $C_2-C_8$ alkenyl, unsubstituted or substituted C2–C, alkynyl, unsubstituted or substituted aryl, and unsubstituted or substituted heterocycle, wherein the substituted group is substituted with one or more of:
a) $C_1-C_6$ alkyl, unsubstituted or substituted,
b) $(CH_2)_nOR^6$,
c) $(CH_2)_nNR^6R^7$,
d) halogen,
e) CN,
f) aryl, unsubstituted or substituted,
g) heterocycle, unsubstituted or substituted,
h) perfluoro-$C_1-C_4$ alkyl,
i) $S(O)_mR^{6a}$,
j) $N(R^{10})_2$,
k) $NR^{10}C(O)R^{11}$,
l) $NR^{10}C(O)R^{11}N(R^{10})_2$,
2) $C_3-C_6$ cycloalkyl,
3) $S(O)_{1-2}R^{6a}$,
4) 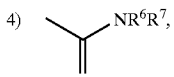
5) $-SO_2-NR^6R^7$, 6) 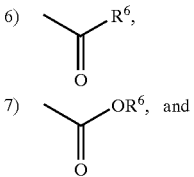
7) 
8) $-(C_1-C_6$ alkyl$)NR^{10}C(O)R^{13}$;

$R^{10}$ is independently selected from
a) hydrogen,
b) unsubstituted or substituted $C_1-C_6$ alkyl,
c) $C_3-C_6$ cycloalkyl,
d) 2,2,2-trifluoroethyl,
e) unsubstituted or substituted heteroaryl,
f) unsubstituted or substituted aryl,
g) unsubstituted or substituted aralkyl, and
h) unsubstituted or substituted heterocyclylalkyl;

$R^{11}$ is independently selected from
a) unsubstituted or substituted $C_1-C_6$ alkyl,
b) unsubstituted or substituted aralkyl,
c) unsubstituted or substituted heterocycle,
d) unsubstituted or substituted aryl, and
e) unsubstituted or substituted heterocyclylalkyl;

$R^{13}$ is independently selected from
a) H,
b) unsubstituted or substituted $C_1-C_6$ alkyl,
c) unsubstituted or substituted $C_2-C_6$ alkenyl,
d) unsubstituted or substituted $C_2-C_6$ alkynyl,
e) unsubstituted or substituted aryl,
f) unsubstituted or substituted heterocycle,
g) aralkyl, unsubstituted or substituted,
h) heterocyclylalkyl, unsubstituted or substituted,
i) $CF_3$,
j) $CF_3O-$,
k) $CF_3CH_2-$,
l) $C_3-C_{10}$ cycloalkyl, unsubstituted or substituted,
m) $OR^{10}$,
n) $-C(O)R^{10}$,
o) $-O(C_1-C_6$ alkyl$)OR^{10}$,
p) $-C(O)NR^6R^7$,
q) $-(C_1-C_6$ alkyl$)OR^{10}$, and
r) $-(C_1-C_6$ alkyl$)C(O)R^{10}$;

$G^1$ and $G^2$ are independently selected from oxygen or $H_2$;

V is aryl;

W is a heterocycle selected from pyrrolidinyl, imidazolyl, pyridinyl, thiazolyl, pyridonyl, 2-oxopiperidinyl, indolyl, quinolinyl, isoquinolinyl, and thienyl, $Y^1$ is selected from
a) a bond,
b) $C_1-C_8$ alkyl,
c) $C_3-C_{20}$ cycloalkyl,
d) aryl or
e) heterocycle, $Z^1$ is selected from
a) a bond,
b) O,
c) C(O),
d) $S(O)_m$,
e) $(C(R^{1a})_2)n$, and
f) $NR^{10}$;

m is 0, 1 or 2;
n is 0, 1, 2, 3, 4, 5 or 6;
p is 0, 1, 2, 3, or 4;

q is 0, 1, 2, or 3;
r is 0 to 5;
s is 0, 1, 2, 3 or 4;
t is 0, 1, 2, 3 or 4, provided t is 0 when $Y^1$ is a bond;
u is 4 or 5;
v is 0, 1, 2, 3 or 4; and
w is 0, 1, 2, 3 or 4;
or a pharmaceutically acceptable salt, an optical isomer or stereoisomer thereof.

Another embodiment of the compounds of this invention is illustrated by the formula C:

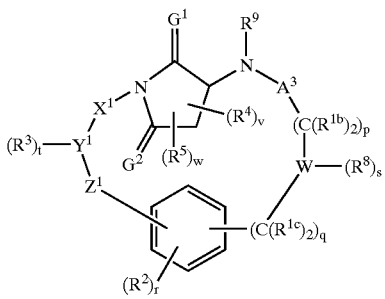

C wherein
$X^1$ is $(C(R^{1a})_2)_n A^1 (C(R^{1a})_2)_n A^2$;
$R^{1a}$ is selected from:
  a) hydrogen;
  b) unsubstituted or substituted aryl, unsubstituted or substituted heterocycle, unsubstituted or substituted $C_3$–$C_{10}$ cycloalkyl, $R^{10}O$—, $R^{6a}S(O)_m$, unsubstituted or substituted $C_2$–$C_6$ alkenyl, unsubstituted or substituted $C_2$–$C_6$ alkynyl, $R^{10}C(O)NR^{10}$—, —C(O)NR$^6$R$^7$, $(R^{10})_2NC(O)NR^{10}$, $R^{10}C(O)$—, —N(R$^{10}$)$_2$, $R^{10}OC(O)$—, and $R^{10}OC(O)NR^{10}$—, and
  c) unsubstituted or substituted $C_1$–$C_6$ alkyl, wherein the substituent on the substituted $C_1$–$C_6$ alkyl is selected from unsubstituted or substituted aryl, unsubstituted or substituted heterocycle, unsubstituted or substituted $C_3$–$C_{10}$cycloalkyl, unsubstituted or substituted $C_2$–$C_6$ alkenyl, unsubstituted or substituted $C_2$–$C_6$ alkynyl, $R^{10}O$—, $R^{6a}S(O)_m$, $R^{10}C(O)NR^{10}$—, —C(O)NR$^6$R$^7$, $(R^{10})_2NC(O)NR^{10}$—, $R^{10}OC(O)$—, $R^{10}OC(O)$—, halo, —N(R$^{10}$)$_2$, and $R^{10}OC(O)NR^{10}$—;
$R^{1b}$ and $R^{1c}$ are independently selected from
  a) hydrogen and
  b) unsubstituted or substituted $C_1$–$C_6$ alkyl, wherein the substituent on the substituted $C_1$–$C_6$ alkyl is selected from unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, unsubstituted or substituted $C_2$–$C_6$ alkynyl, $R^{10}O$—, $R^{6a}S(O)_m$, $R^{10}C(O)NR^{10}$—, —C(O)NR$^6$R$^7$, $(R^{10})_2NC(O)NR^{10}$—, $R^{10}OC(O)$—, $R^{10}OC(O)$—, halo, —N(R$^{10}$)$_2$, and $R^{10}OC(O)NR^{10}$—;
$A^1$ is selected from
  a) a bond,
  b) —C(=O)—,
  c) O,
  d) NR$^{10}$
  e) NR$^{10}$C(O),
  f) C(O)NR$^{10}$,
  g) OC(O)NR$^{10}$,
  h) NR$^{10}$C(O)O,
  i) S(=O)$_m$,
  j) C(O)O, and
  k) OC(O);
$A^2$ is selected from
  a) a bond,
  b) —C(=O)—,
  c) NR$^{10}$C(O), and
  d) S(=O)$_m$;
$A^3$ is selected from
  a) a bond, or
  b) C(=O);
$R^2$ is independently selected from:
  a) hydrogen,
  b) CN,
  c) NO$_2$,
  d) halogen,
  e) aryl, unsubstituted or substituted,
  f) heterocycle, unsubstituted or substituted,
  g) $C_1$–$C_6$ alkyl, unsubstituted or substituted,
  h) OR$^{10}$,
  i) N$_3$,
  j) $R^{6a}S(O)_m$,
  k) $C_3$–$C_{10}$ cycloalkyl, unsubstituted or substituted,
  l) $C_2$–$C_6$ alkenyl, unsubstituted or substituted,
  m) $C_2$–$C_6$ alkynyl, unsubstituted or substituted,
  n) $(R^{10})_2NC(O)NR^{10}$—,
  o) $R^{10}C(O)$—,
  p) $R^{10}C(O)NR^{10}$—,
  q) $R^{10}OC(O)$—,
  r) —N(R$^{10}$)$_2$,
  s) $R^{10}OC(O)NR^{10}$—, and
  t) —(C$_1$–C$_6$ alkyl)NR$^{10}$C(O)R$^{13}$;
$R^3$ is independently selected from:
  H, CN, NO$_2$, halo, unsubstituted or substituted $C_1$–$C_6$ alkyl, N$_3$, oxido, unsubstituted or substituted aryl, unsubstituted or substituted heterocycle, unsubstituted or substituted $C_2$–$C_6$ alkenyl, unsubstituted or substituted $C_2$–$C_6$ alkynyl, unsubstituted or substituted aralkyl, unsubstituted or substituted heterocyclylalkyl, $C_1$–$C_6$ perfluoroalkyl, CF$_3$O—CF$_3$CH$_2$—, unsubstituted or substituted $C_3$–$C_{10}$ cycloalkyl, OR$^{10}$, NR$^6$R$^7$, OR$^6$, —C(O)R$^{10}$, —O(C$_1$–C$_6$ alkyl)OR$^{10}$, —S(O)$_m$R$^{6a}$, —C(O)NR$^6$R$^7$, —NHC(O)R$^{10}$, —(C$_1$–C6 alkyl)OR$^{10}$, and —(C$_1$–C$_6$ alkyl)C(O)R$^{10}$;
$R^4$ and $R^5$ are independently selected from:
  H, OR$^{10}$, unsubstituted or substituted $C_1$–$C_6$ alkyl, unsubstituted or substituted aryl, unsubstituted or substituted heterocycle, wherein the substituted group is substituted with one or two of:
  1) aryl or heterocycle, unsubstituted or substituted with:
    a) $C_1$–$C_6$ alkyl,
    b) (CH$_2$)$_n$OR$^6$,
    c) (CH$_2$)$_n$NR$^6$R$^7$,
    d) halogen,
    e) CN,
    f) aryl or heteroaryl,
    g) perfluoro-$C_1$–$C_4$ alkyl,
    h) S(O)$_m$R$^{6a}$, 2) $C_3$–$C_6$ cycloalkyl,
3) $OR^6$,

4) —$NR^6R^7$,

5) 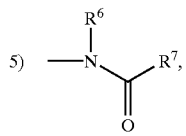

6) 

7) 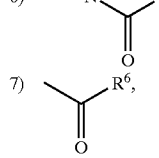

8) halo, and
9) perfluoro-$C_{1-4}$-alkyl; or $R^4$ and $R^5$ are attached to the same C atom and are combined to form —$(CH_2)_u$— wherein one of the carbon atoms is optionally replaced by a moiety selected from: O, $S(O)_m$, $NR^{10}$, —NC(O)—, and —$N(COR^{10})$—;

and any of $R^4$ and $R^5$ are optionally attached to the same carbon atom;

$R^6$, $R^7$ and $R^8$ are independently selected from:

H, $C_1$–$C_6$ alkyl, $C_3$–$C_6$ cycloalkyl, heterocycle, aryl, aralkyl, $C_1$–$C_4$ perfluoroalkyl, unsubstituted or substituted with one or two substituents selected from:
  a) $C_1$–$C_6$ alkoxy,
  b) substituted or unsubstituted aryl or substituted or unsubstituted heterocycle,
  c) halogen,
  d) HO, e) 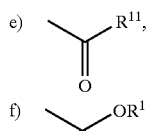

f) 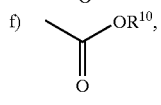

g) —$S(O)_mR^{6a}$, or
  h) $N(R^{10})_2$; or $R^6$ and $R^7$ may be joined in a ring;
$R^7$ and $R^{7a}$ may be joined in a ring;

$R^{6a}$ is selected from
  a) $C_{3-6}$ cycloalkyl, heterocycle, aryl, unsubstituted or substituted with one or more of the following:
    1) $C_{1-4}$ alkoxy,
    2) aryl or heterocycle,
    3) halogen,
    4) HO, 5) 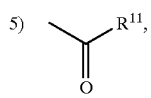

6) $SO_2R^{6a}$,
    7) $N(R^{10})_2$; and b) $C_1$–$C_6$ alkyl, unsubstituted or substituted with one or more of the following:
    1) —$C(R^{10})_2C_{1-4}$ alkoxy,
    2) aryl or heterocycle,
    3) —$C(R^{10})_2$halogen,
    4) —$C(R^{10})_2$OH, 5) 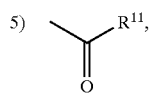

6) —$C(R^{10})_2SO_2R^{6a}$, and
    7) —$C(R^{10})_2N(R^{10})_2$;

$R^8$ is independently selected from
  a) hydrogen,
  b) F, Cl, Br, $R^{10}O$—, CN, $R^{6a}S(O)_m$—, $R^{10}C(O)NR^{10}$—, —$C(O)NR^6R^7$, $NO_2$, $(R^{10})_2NC(O)NR^{10}$—, $R^{10}C(O)$—, $R^{10}C(O)$—, $R^{10}OC(O)NR^{10}$—, $N_3$, or —$N(R^{10})_2$ and
  c) $C_1$–$C_6$ alkyl, unsubstituted or substituted by $C_1$–$C_4$ perfluoroalkyl, F, Cl, Br, $R^{10}O$—, $R^{6a}S(O)_m$—, $R^{10}C(O)NR^{10}$—, —$C(O)NR^6R^7$, CN, $(R^{10})_2NC(O)NR^{10}$—, $R^{10}C(O)$—, $R^{10}OC(O)$—, $N_3$, —$N(R^{10})_2$, and $R^{10}OC(O)NR^{10}$—;

$R^9$ is independently selected from
  1) H, unsubstituted or substituted $C_1$–$C_6$ alkyl, unsubstituted or substituted $C_2$–$C_8$ alkenyl, unsubstituted or substituted $C2$–$C_8$ alkynyl, unsubstituted or substituted aryl, and unsubstituted or substituted heterocycle, wherein the substituted group is substituted with one or more of:
    a) $C_1$–$C_6$ alkyl, unsubstituted or substituted,
    b) $(CH_2)_nOR^6$,
    c) $(CH_2)_nNR^6R^7$,
    d) halogen,
    e) CN,
    f) aryl, unsubstituted or substituted,
    g) heterocycle, unsubstituted or substituted,
    h) perfluoro-$C_1$–$C_4$ alkyl,
    i) $S(O)_mR^{6a}$,
    j) $N(R^{10})_2$,
    k) $NR^{10}C(O)R^{11}$,
    l) $NR^{10}C(O)R^{11}N(R^{10})_2$,
  2) $C_3$–$C_6$ cycloalkyl,
  3) $S(O)_{1-2}R^{6a}$, 4) 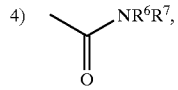

5) —$SO_2$—$NR^6R^7$,

6) 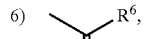

7) 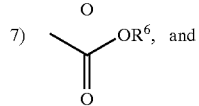

8) —$(C_1$–$C_6$ alkyl)$NR^{10}C(O)R^{13}$;

$R^{10}$ is independently selected from
  a) hydrogen,
  b) unsubstituted or substituted $C_1$–$C_6$ alkyl,
  c) $C_3$–$C_6$ cycloalkyl,
  d) 2,2,2-trifluoroethyl,
  e) unsubstituted or substituted heteroaryl, f) unsubstituted or substituted aryl,
g) unsubstituted or substituted aralkyl, and
h) unsubstituted or substituted heterocyclylalkyl;

$R^{11}$ is independently selected from
a) unsubstituted or substituted $C_1$–$C_6$ alkyl,
b) unsubstituted or substituted aralkyl,
c) unsubstituted or substituted heterocycle,
d) unsubstituted or substituted aryl, and
e) unsubstituted or substituted heterocyclylalkyl;

$R^{13}$ is independently selected from
a) H,
b) unsubstituted or substituted $C_1$–$C_6$ alkyl,
c) unsubstituted or substituted $C_2$–$C_6$ alkenyl,
d) unsubstituted or substituted $C_2$–$C_6$ alkynyl,
e) unsubstituted or substituted aryl,
f) unsubstituted or substituted heterocycle,
g) aralkyl, unsubstituted or substituted,
h) heterocyclylalkyl, unsubstituted or substituted,
i) $CF_3$,
j) $CF_3O$—,
k) $CF_3CH_2$—,
l) $C_3$–$C_{10}$ cycloalkyl, unsubstituted or substituted,
m) $OR^{10}$,
n) —$C(O)R^{10}$,
o) —$O(C_1$–$C_6$ alkyl)$OR^{10}$,
p) —$C(O)NR^6R^7$,
q) —$(C_1$–$C_6$ alkyl)$OR^{10}$, and
r) —$(C_1$–$C_6$ alkyl)$C(O)R^{10}$;

$G^1$ and $G^2$ are independently selected from oxygen or $H_2$;

W is a heterocycle selected from pyrrolidinyl, imidazolyl, pyridinyl, thiazolyl, pyridonyl, 2-oxopiperidinyl, indolyl, quinolinyl, isoquinolinyl, and thienyl, $Y^1$ is selected from
a) a bond,
b) $C_1$–C8 alkyl,
c) $C_3$–$C_{20}$ cycloalkyl,
d) aryl or
e) heterocycle, $Z^1$ is selected from
a) a bond,
b) O,
c) C(O),
d) $S(O)_m$,
e) $(C(R^{1a})_2)_n$, and
f) $NR^{10}$;

m is 0, 1 or 2;
n is 0, 1, 2, 3, 4, 5 or 6;
p is 0, 1, 2, 3, or 4;
q is 0, 1, 2, or 3;
r is 0 to 5;
s is 0, 1, 2, 3 or 4;
t is 0, 1, 2, 3 or 4, provided t is 0 when $Y^1$ is a bond;
u is 4 or 5;
v is 0, 1, 2, 3 or 4; and
w is 0, 1, 2, 3 or 4;

or a pharmaceutically acceptable salt, an optical isomer or stereoisomer thereof.

Another embodiment of the compounds of this invention is illustrated by formula D:

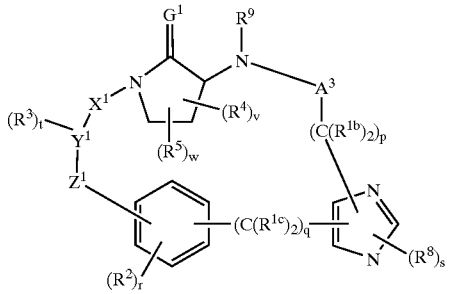

D wherein
$X^1$ is $(C(R^{1a})_2)_nA^1(C(R^{1a})_2)_nA^2$;

$R^{1a}$ is selected from:
a) hydrogen;
b) unsubstituted or substituted aryl, unsubstituted or substituted heterocycle, unsubstituted or substituted $C_3$–$C_{10}$ cycloalkyl, $R^{10}$)—, $R^{6a}S(O)_m$, unsubstituted or substituted $C_1$–$C_6$ alkenyl, unsubstituted or substituted $C_2$–$C_6$ alkynyl, —$C(O)NR^6R^7$, $R^{10}C(O)NR^{10}$—, $(R^{10})_2NC(O)(NR^{10})$—, $R^{10}C(O)$—, —$N(R^{10})_2$, $R^{10}OC(O)$—, and $R^{10}OC(O)NR^{10}$—, and
c) unsubstituted or substituted $C_1$–$C_6$ alkyl, wherein the substituent on the substituted $C_1$–$C_6$ alkyl is selected from unsubstituted or substituted aryl, unsubstituted or substituted heterocycle , unsubstituted or substituted $C_3$–$C_{10}$ cycloalkyl, unsubstituted or substituted $C_2$–$C_6$ alkenyl, unsubstituted or substituted $C_2$–$C_6$ alkynyl, $R^{10}O$—, $R^{6a}S(O)_m$, —$C(O)NR^6R^7$, $R^{10}C(O)NR^{10}$—, $(R^{10})_2NC(O)NR^{10}$—, $R^{10}C(O)$—, $R^{10}OC(O)$—, halo, —$N(R^{10})_2$, and $R^{10}OC(O)NR^{10}$—;

$R^{1b}$ and $R^{1c}$ are independently selected from
a) hydrogen and
b) unsubstituted or substituted $C_1$–$C_6$ alkyl, wherein the substituent on the substituted $C_1$–$C_6$ alkyl is selected from unsubstituted or substituted aryl, unsubstituted or substituted heterocycle, unsubstituted or substituted $C_3$–$C_{10}$cycloalkyl, unsubstituted or substituted $C_2$–$C_6$ alkenyl, unsubstituted or substituted $C_2$–$C_6$ alkynyl, $R^{10}O$—, $R^{6a}S(O)_m$, —$C(O)NR^6R^7$, $R^{10}C(O)NR^{10}$—, $(R^{10})_2NC(O)(NR^{10})$—, $R^{10}C(O)$—, $R^{10}OC(O)$—, halo, —$N(R^{10})_2$, and $R^{10}OC(O)NR^{10}$—;

$A^1$ is selected from
a) a bond,
b) —C(=O)—,
c) O,
d) $NR^{10}$,
e) $NR^{10}C(O)$,
f) $C(O)NR^{10}$,
g) $OC(O)NR^{10}$,
h) $NR^{10}C(O)O$,
i) $S(=O)_m$,
j) C(O)O, and
k) OC(O);

$A^2$ is selected from
a) a bond,
b) —C(=O)—,
c) $NR^{10}C(O)$, and
d) $S(=O)_m$;

A³ is selected from
a) a bond or
b) C(=O);

R² is independently selected from:
a) hydrogen,
b) CN,
c) NO₂,
d) halogen,
e) aryl, unsubstituted or substituted,
f) heterocycle, unsubstituted or substituted,
g) C₁–C₆ alkyl, unsubstituted or substituted,
h) OR¹⁰,
i) N₃,
j) R⁶ᵃS(O)ₘ,
k) C₃–C₁₀ cycloalkyl, unsubstituted or substituted,
l) C₂–C₆ alkenyl, unsubstituted or substituted,
m) C₂–C₆ alkynyl, unsubstituted or substituted,
n) (R₁₀)₂NC(O)NR¹⁰—,
o) R¹⁰C(O)—,
p) R¹⁰C(O)NR¹⁰—,
q) R¹⁰OC(O)—,
r) —N(R¹⁰)₂,
s) R¹⁰OC(O)NR¹⁰—, and
t) —(C₁–C₆ alkyl)NR¹⁰C(O)R¹³;

R³ is independently selected from:
H, CN, NO₂, halo, unsubstituted or substituted C₁–C₆ alkyl, N₃, oxido, unsubstituted or substituted aryl, unsubstituted or substituted heterocycle, unsubstituted or substituted C₂–C₆ alkenyl, unsubstituted or substituted C₂–C₆ alkynyl, unsubstituted or substituted aralkyl, unsubstituted or substituted heterocyclylalkyl, C₁–C₆ perfluoroalkyl, CF₃O—, CF₃CH₂—, unsubstituted or substituted C₃–C₁₀ cycloalkyl, OR¹⁰, NR⁶R⁷, OR⁶, —C(O)R¹⁰, —O(C₁–C₆ alkyl)OR¹⁰, —S(O)ₘR⁶ᵃ, —C(O)NR⁶R⁷, —NHC(O)R¹⁰, —(C₁–C₆ alkyl)OR¹⁰, and —(C₁–C₆ alkyl)C(O)R¹⁰;

R⁴ and R⁵ are independently selected from:
H, OR¹⁰, unsubstituted or substituted C₁–C₆ alkyl, wherein the substituted group is substituted with one or two of:
1) aryl or heterocycle, unsubstituted or substituted with:
a) C₁–C₆ alkyl,
b) (CH₂)ₙOR⁶,
c) (CH₂)ₙNR⁶R⁷,
d) halogen,
e) CN,
f) aryl or heteroaryl,
g) perfluoro-C₁–C₄ alkyl,
h) S(O)ₘR⁶ᵃ,
2) C₃–C₆ cycloalkyl,
3) OR⁶,
4) —NR⁶R⁷, 5) 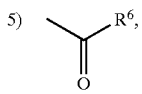

6) halo, and
7) perfluoro-C₁₋₄alkyl; or

R⁴ and R⁵ are attached to the same C atom and are combined to form —(CH₂)ᵤ— wherein one of the carbon atoms is optionally replaced by a moiety selected from: O, S(O)ₘ, NR¹⁰, —NC(O)—, and —N(COR¹⁰)—;

and any of R⁴ and R⁵ are optionally attached to the same carbon atom;

R⁶, R⁷ and R⁷ᵃ are independently selected from:
H, C₁–C₆ alkyl, C₃–C₆ cycloalkyl, heterocycle, aryl, aralkyl, C₁–C₄ perfluoroalkyl, unsubstituted or substituted with one or two substituents selected from:
a) C₁–C₆ alkoxy,
b) substituted or unsubstituted aryl or substituted or unsubstituted heterocycle,
c) halogen,
d) HO, e) 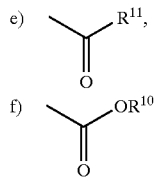

f)

g) —S(O)ₘR⁶ᵃ, or
h) N(R¹⁰)₂; or
R⁶ and R⁷ may be joined in a ring;
R⁷ and R⁷ᵃ may be joined in a ring;

R⁶ᵃ is selected from
a) C₃₋₆ cycloalkyl, heterocycle, aryl, unsubstituted or substituted with one or more of the following:
1) C₁₋₄ alkoxy,
2) aryl or heterocycle,
3) halogen,
4) HO, 5) 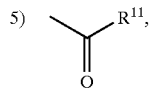

6) SO₂R⁶ᵃ,
7) N(R¹⁰)₂; and
b) C₁–C₆ alkyl, unsubstituted or substituted with one or more of the following:
1) —C(R¹⁰)₂C₁₋₄ alkoxy,
2) aryl or heterocycle,
3) —C(R¹⁰)₂halogen,
4) —C(R¹⁰)₂OH, 5) 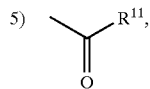

6) —C(R¹⁰)₂SO₂R⁶ᵃ, and
7) —C(R¹⁰)₂N(R¹⁰)₂;

R⁸ is independently selected from
a) hydrogen, and
b) C₁–C₆ alkyl, unsubstituted or substituted by C₁–C₄ perfluoroalkyl, F, Cl, Br, R¹⁰O—, R⁶ᵃS(O)ₘ, —C(O)NR⁶R⁷, R¹⁰C(O)NR¹⁰—, CN, (R¹⁰)₂NC(O)NR¹⁰—, R¹⁰C(O)—, R¹⁰OC(O)—, N₃, —N(R¹⁰)₂, and R¹⁰OC(O)NR¹⁰—;

R⁹ is independently selected from
1) H, unsubstituted or substituted C₁–C₆ alkyl, unsubstituted or substituted C₂–C₈ alkenyl, unsubstituted or substituted C₂–C₈ alkynyl, unsubstituted or substituted aryl, and unsubstituted or substituted heterocycle, wherein the substituted group is substituted with one or more of:

a) $C_1$–$C_6$ alkyl, unsubstituted or substituted,
b) $(CH_2)_n OR^6$,
c) $(CH_2)_n NR^6 R^7$,
d) halogen,
e) CN,
f) aryl, unsubstituted or substituted,
g) heterocycle, unsubstituted or substituted,
h) perfluoro-$C_1$–$C_4$ alkyl,
i) $S(O)_m R^{6a}$,
j) $N(R^{10})_2$,
k) $NR^{10}C(O)R^{11}$,
l) $NR^{10}C(O)R^{11}N(R^{10})_2$,
2) $C_3$–$C_6$ cycloalkyl,
3) $S(O)_{1-2} R^{6a}$, 4) 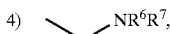

5) —$SO_2$—$NR^6 R^7$,

6) 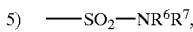

7)  and

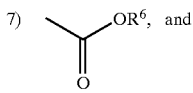

8) —$(C_1$–$C_6$ alkyl$)NR^{10}C(O)R^3$;

$R^{10}$ is independently selected from
  a) hydrogen,
  b) unsubstituted or substituted $C_1$–$C_6$ alkyl,
  c) $C_3$–$C_6$ cycloalkyl,
  d) 2,2,2-trifluoroethyl,
  e) unsubstituted or substituted heteroaryl,
  f) unsubstituted or substituted aryl,
  g) unsubstituted or substituted aralkyl, and
  h) unsubstituted or substituted heterocyclylalkyl;

$R^{11}$ is independently selected from
  a) unsubstituted or substituted $C_1$–$C_6$ alkyl,
  b) unsubstituted or substituted aralkyl,
  c) unsubstituted or substituted heterocycle,
  d) unsubstituted or substituted aryl,
  e) unsubstituted or substituted heterocyclylalkyl;

$R^{13}$ is independently selected from
  a) H,
  b) unsubstituted or substituted $C_1$–$C_6$ alkyl,
  c) unsubstituted or substituted $C_2$–$C_6$ alkenyl,
  d) unsubstituted or substituted $C_2$–$C_6$ alkynyl,
  e) unsubstituted or substituted aryl,
  f) unsubstituted or substituted heterocycle,
  g) aralkyl, unsubstituted or substituted,
  h) heterocyclylalkyl, unsubstituted or substituted,
  i) $CF_3$,
  j) $CF_3 O$—,
  k) $CF_3 CH_2$—,
  l) $C_3$–$C_{10}$ cycloalkyl, unsubstituted or substituted,
  m) $OR^{10}$,
  n) —$C(O)R^{10}$,
  o) —$O(C_1$–$C_6$ alkyl$)OR^{10}$,
  p) —$C(O)NR^6 R^7$,
  q) —$(C_1$–$C_6$ alkyl$)OR^{10}$, and
  r) —$(C_1$–$C_6$ alkyl$)C(O)R^{10}$;

$G^1$ is independently selected from oxygen or $H_2$;

$Y^1$ is selected from
  a) a bond,
  b) $C_1$–$C_8$ alkyl,
  c) $C_3$–$C_{20}$ cycloalkyl,
  d) aryl or
  e) heterocycle, $Z^1$ is selected from
  a) a bond,
  b) O, and
  c) C(O);

m is 0, 1 or 2;
n is 0, 1, 2, 3, 4, 5 or 6;
p is 0, 1, 2, 3, or 4;
q is 0, 1, 2, or 3;
r is 0 to 5;
s is 0, 1, 2, 3 or 4;
t is 0, 1, 2, 3 or 4, provided t is 0 when $Y^1$ is a bond;
u is 4 or 5;
v is 0, 1, 2, 3 or 4; and
w is 0, 1, 2, 3 or 4;

or a pharmaceutically acceptable salt, an optical isomer or stereoisomer thereof.

Specific compounds of the invention are:
(20R)-19,20,21,22-Tetrahydro-19-oxo-17H-18,20-ethano-6,10:12,16-dimetheno-16H-imidazo[3,4-h][1,8,11,14]oxatriazacycloeicosine-9-carbonitrile;
(20S)-19,20,21,22-Tetrahydro-19-oxo-17H-18,20-ethano-6,10:12,16-dimetheno-16H-imidazo[3,4-h][1,8,11,14]oxatriazacycloeicosine-9-carbonitrile;
(20R)-14-Chloro-19,20,21,22-tetrahydro-19-oxo-17H-18,20-ethano-6,10:12,16-dimetheno-16H-imidazo[3,4-h][1,8,11,14]oxatri-azacycloeicosine-9-carbonitrile;
(20S)-14-Chloro-19,20,21,22-tetrahydro-19-oxo-17H-18,20-ethano-6,10:12,16-dimetheno-16H-imidazo[3,4-h][1,8,11,14]oxatri-azacycloeicosine-9-carbonitrile;
(21R)-20,21,22,23-Tetrahydro-17-oxo-5H,17H,19H-18,21-methano-6,10:12,16-dimethenoimidazo[3,4-h][1,8,11,15]oxatriazacycloheneicosine-9-carbonitrile;
(21S)-20,21,22,23-Tetrahydro-17-oxo-5H,17H,19H-18,21-methano-6,10:12,16-dimethenoimidazo[3,4-h][1,8,11,15]oxatriazacycloheneicosine-9-carbonitrile;
(21R)-20,21,22,23-Tetrahydro-5H,19H-18,21-methano-6,10:12,16-dimetheno-16H-imidazo[4,3-n][1,8,12,15,7]oxatriazathia-cycloheneicosine-9-carbonitrile 17,17-dioxide;
(21S)-20,21,22,23-Tetrahydro-5H,19H-18,21-methano-6,10:12,16-dimetheno-16H-imidazo[4,3-n][1,8,12,15,7]oxatriazathia-cycloheneicosine-9-carbonitrile 17,17-dioxide;
(20S)-19,20,21,22-Tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;
(20R)-19,20,21,22-Tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;
(5R,20R)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;
(5S,20R)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;
(5R,20S)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;

(5S,20S)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;

(5R,20R)-19,20,21,22-Tetrahydro-5-methyl-19-oxo-5H-18,20-ethano-12,14-etheno-6,10-metheno-18H-benz[d]imidazo[4,3-k][1,6,9,12]oxatriaza-cyclooctadecosine-9-carbonitrile;

(5S,20R)-19,20,21,22-Tetrahydro-5-methyl-19-oxo-5H-18,20-ethano-12,14-etheno-6,10-metheno-18H-benz[d]imidazo[4,3-k][1,6,9,12]oxatriaza-cyclooctadecosine-9-carbonitrile;

(5R,20S)-19,20,21,22-Tetrahydro-5-methyl-19-oxo-5H-18,20-ethano-12,14-etheno-6,10-metheno-18H-benz[d]imidazo[4,3-k][1,6,9,12]oxatriaza-cyclooctadecosine-9-carbonitrile;

(5S,20S)-19,20,21,22-Tetrahydro-5-methyl-19-oxo-5H-18,20-ethano-12,14-etheno-6,10-metheno-18H-benz[d]imidazo[4,3-k][1,6,9,12]oxatriaza-cyclooctadecosine-9-carbonitrile;

(17R,20S)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile;

(17S,20S)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatniazacycloeicosine-9-carbonitrile;

(17R,20R)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile;

(17S,20R)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile;

(17R,20S)-19,20,21,22-Tetrahydro-19-oxo-17-phenyl-5H,18H-18,20-ethano-6,10:12,16-dimetheno-16H-imidazo[3,4-h][1,8,11,14]oxatriaza-cycloeicosine-9-carbonitrile;

(17S,20S)-19,20,21,22-Tetrahydro-19-oxo-17-phenyl-5H,18H-18,20-ethano-6,10:12,16-dimetheno-16H-imidazo[3,4-h][1,8,11,14]oxatriaza-cycloeicosine-9-carbonitrile;

(17R,20R)-19,20,21,22-Tetrahydro-19-oxo-17-phenyl-5H,18H-18,20-ethano-6,10:12,16-dimetheno-16H-imidazo[3,4-h][1,8,11,14]oxatriaza-cycloeicosine-9-carbonitrile;

(17S,20R)-19,20,21,22-Tetrahydro-19-oxo-17-phenyl-5H,18H-18,20-ethano-6,10:12,16-dimetheno-16H-imnidazo[3,4-h][1,8,11,14]oxatriaza-cycloeicosine-9-carbonitrile;

(20S)-19,20,21,22-Tetrahydro-21-methyl-19-oxo-5H,18,20-ethano-12,14-etheno-6,10-metheno-18H-benz[d]imidazo[4,3-k][1,6,9,12]oxatriaza-cyclooctadecosine-9-carbonitrile;

(20R)-19,20,21,22-Tetrahydro-21-methyl-19-oxo-5H,18,20-ethano-12,14-etheno-6,10-metheno-18H-benz[d]imidazo[4,3-k][1,6,9,12]oxatriaza-cyclooctadecosine-9-carbonitrile;

(20R)-19,20,22,23-Tetrahydro-19,22-dioxo-5H,21H-18,20-ethano-12,14-etheno-6,10-methenobenz[d]imidazo[4,3-l][1,6,9,13]oxatriaza-cyclononadecosine-9-carbonitrile;

(20S)-19,20,22,23-Tetrahydro-19,22-dioxo-5H,21H-18,20-ethano-12,14-etheno-6,10-methenobenz[d]imidazo[4,3-l][1,6,9,13]oxatriaza-cyclononadecosine-9-carbonitrile;

(20R)-15-Bromo-19,20,21,22-tetrahydro-19-oxo-5H,18,20-ethano-12,14-etheno-6,10-metheno-18H-benz[d]imidazo[4,3-k][1,6,9,12]oxatriaza-cyclooctadecosine-9-carbonitrile;

(20S)-15-Bromo-19,20,21,22-tetrahydro-19-oxo-5H,18,20-ethano-12,14-etheno-6,10-metheno-18H-benz[d]imidazo[4,3-k][1,6,9,12]oxatriaza-cyclooctadecosine-9-carbonitrile;

(20R)-15-Cyclopropylethynyl-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;

(20S)-15-Cyclopropylethynyl-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;

(20S)-15-(2-Cyclopropylethyl)-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;

(20R)-15-(2-Cyclopropylethyl)-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;

(20R)-19,20,21,22-Tetrahydro-5H-18,20-ethano-12,14-etheno-6,10-metheno-18H-benz[d]imidazo[4,3-k][1,6,9,12]oxatriazacyclooctadecosine-9-carbonitrile;

(20S)-19,20,21,22-Tetrahydro-5H-18,20-ethano-12,14-etheno-6,10-metheno-18H-benz[d]imidazo[4,3-k][1,6,9,12]oxatriazacyclooctadecosine-9-carbonitrile;

(20S)-19,20,22,23-Tetrahydro-19-oxo-5H,21H-18,20-ethano-12,14-etheno-6,10-methenobenz[d]imidazo[4,3-l][1,6,9,13]oxatriazacyclononadecosine-9-carbonitrile;

(20R)-19,20,22,23-Tetrahydro-19-oxo-5H,21H-18,20-ethano-12,14-etheno-6,10-methenobenz[d]imidazo[4,3-l][1,6,9,13]oxatriazacyclononadecosine-9-carbonitrile;

(5R,20R)-19,20,22,23-Tetrahydro-5-hydroxy-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile;

(5S,20R)-19,20,22,23-Tetrahydro-5-hydroxy-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile;

(5S,20S)-19,20,22,23-Tetrahydro-5-hydroxy-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile;

(5R,20S)-19,20,22,23-Tetrahydro-5-hydroxy-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile;

(20S)-19,20,21,22,23,24-hexahydro-19,22-dioxo-5H,18H-18,20-ethano-12,14-etheno-6,10-methenobenz[d]imidazo[4,3-m][1,6,9,14]oxatriazacycloeiscosine-9-carbonitrile;

(20R)-19,20,21,22,23,24-hexahydro-19,22-dioxo-5H,18H-18,20-ethano-12,14-etheno-6,10-methenobenz[d]imidazo[4,3-m][1,6,9,14]oxatriazacycloeiscosine-9-carbonitrile;

(20S)-19,20,21,22,23,24-hexahydro-19-oxo-5H,18H-18,20-ethano-12,14-etheno-6,10-methenobenz[d]imidazo[4,3-m][1,6,9,14]oxatriazacycloeiscosine-9-carbonitrile;

(20R)-19,20,21,22,23,24-hexahydro-19-oxo-5H,18H-18,20-ethano-12,14-etheno-6,10-methenobenz[d]imidazo[4,3-m][1,6,9,14]oxatriazacycloeiscosine-9-carbonitrile;

15-Bromo-19,20,21,22-tetrahydro-19-oxo-17H-18,20-ethano-6,10:12,16-dimetheno-16H-imidazo[3,4-h][1,8,11,14]oxatriazacycloeicosine-9-carbonitrile;

(17R,20R)-19,20,21,22-tetrahydro-19-oxo-17H-15,17:18,20-diethano-6,10:12,16-dimetheno-16H-imidazo[3,4-h][1,8,11,14]oxatriazacycloeicosine-9-carbonitrile;

(17S,20R)-19,20,21,22-tetrahydro-19-oxo-17H-15,17:18,20-diethano-6,10:12,16-dimetheno-16H-imidazo[3,4-h][1,8,11,14]oxatriazacycloeicosine-9-carbonitrile;

(17S,20S)-19,20,21,22-tetrahydro-19-oxo-17H-15,17:18,20-diethano-6,10:12,16-dimetheno-16H-imidazo[3,4-h][1,8,11,14]oxatriazacycloeicosine-9-carbonitrile;

(17R,20S)-19,20,21,22-tetrahydro-19-oxo-17H-15,17:18,20-diethano-6,10:12,16-dimetheno-16H-imidazo[3,4-h][1,8,11,14]oxatriazacycloeicosine-9-carbonitrile;

(20S)-19,20,22,23-Tetrahydro-21-methyl-19-oxo-5H,21H-18,20-ethano-12,14-etheno-6,10-methenobenz[d]imidazo[4,3-l][1,6,9,13]oxatriazacyclononadecosine-9-carbonitrile;

(20R)-19,20,22,23-Tetrahydro-21-methyl-19-oxo-5H,21H-18,20-ethano-12,14-etheno-6,10-methenobenz[d]imidazo[4,3-l][1,6,9,13]oxatriazacyclononadecosine-9-carbonitrile;

(17R,20R)-19,20,21,22-tetrahydro-21-methyl-19-oxo-17H-15,17:18,20-diethano-6,10:12,16-dimetheno-16H-imidazo[3,4-h][1,8,11,14]oxatriazacycloeicosine-9-carbonitrile;

(17S,20R)-19,20,21,22-tetrahydro-21-methyl-19-oxo-17H-15,17:18,20-diethano-6,10:12,16-dimetheno-16H-imidazo[3,4-h][1,8,11,14]oxatriazacycloeicosine-9-carbonitrile;

(17S,20S)-19,20,21,22-tetrahydro-21-methyl-19-oxo-17H-15,17:18,20-diethano-6,10:12,16-dimetheno-16H-imidazo[3,4-h][1,8,11,14]oxatriazacycloeicosine-9-carbonitrile;

(17R,20S)-19,20,21,22-tetrahydro-21-methyl-19-oxo-17H-15,17:18,20-diethano-6,10:12,16-dimetheno-16H-imidazo[3,4-h][1,8,11,14]oxatriazacycloeicosine-9-carbonitrile;

(20R)-16-bromo-19,20,22,23-tetrahydro-19,22-dioxo-5H,21H-18,20-ethano-12,14-etheno-6,10-methenobenz[d]imidazo[4,3-l][1,6,9,13]oxatriazacyclononadecosine-9-carbonitrile;

(20S)-16-bromo-19,20,22,23-tetrahydro-19,22-dioxo-5H,21H-18,20-ethano-12,14-etheno-6,10-methenobenz[d]imidazo[4,3-l][1,6,9,13]oxatriazacyclononadecosine-9-carbonitrile;

(23S)-22,23,24,25-tetrahydro-22-oxo-16H,21H-21H,23-ethano-6,10:12,16-dimethenobenz[g]imidazo[4,3-n][1,9,12,1]oxatriazacycloheneicosine-9-carbosntrile;

(23R)-22,23,24,25-tetrahydro-22-oxo-16H,21H-21,23-ethano-6,10:12,16-dimethenobenz[g]imidazo[4,3-n][1,9,12,15]oxatriazacycloheneicosine-9-carbonitrile;

(20S)-25-aza-19,20,21,22-tetrahydro-19-oxo-5H,18,20-ethano-12,14-etheno-6,10-metheno-18H-benz[d]imidazo[4,3-k][1,6,9,12]oxatriaza-cyclooctadecosine-9-carbonitrile;

(20R)-25-aza-19,20,21,22-tetrahydro-19-oxo-5H-18,20-ethano-12,14-etheno-6,10-metheno-18H-benz[d]imidazo[4,3-k][1,6,9,12]oxatriaza-cyclooctadecosine-9-carbonitrile;

(20S)-19,20,21,22-tetrahydro-19-oxo-5H-18,20-ethano-12,14-etheno-6,10-metheno-18H-benz[d]imidazo[4,3-k][1,3,6,9,12]oxatetraaza-cyclooctadecosine-9-carbonitrile;

(20R)-19,20,21,22-tetrahydro-19-oxo-5H-18,20-ethano-12,14-etheno-6,10-metheno-18H-benz[d]imidazo[4,3-k][1,3,6,9,12]oxatetraaza-cyclooctadecosine-9-carbonitrile;

(21S)-19,20,22,23-tetrahydro-18-oxo-5H,21H-19,21-ethano-12,14-etheno-6,10-methenobenz[d]imidazo[4,3-l][1,7,10,13]oxatriazacyclononadecosine-9-carbonitrile;

(21R)-19,20,22,23-tetrahydro-18-oxo-5H,21H-19,21-ethano-12,14-etheno-6,10-methenobenz[d]imidazo[4,3-l][1,7,10,13]oxatriazacyclononadecosine-9-carbonitrile;

(20S)-19,20,21,22-tetrahydro-3-methyl-19-oxo-5H-18,20-ethano-12, 14-etheno-6,10-metheno-18H-benz[d]imnidazo[4,3-k][1,6,9,12]oxatriazacyclooctadecosine-9-carbonitrile;

(20R)-19,20,21,22-tetrahydro-3-methyl-19-oxo-5H-18,20-ethano-12,14-etheno-6,10-metheno-18H-benz[d]imidazo[4,3-k][1,6,9,12]oxatriazacyclooctadecosine-9-carbonitrile;

(20S)-19,20,22,23-tetrahydro-5H,21H-18,20-ethano-12,14-etheno-6,10-methenobenz [d]imidazo[4,3-i][1,6,9,13]oxatriazacyclonon adecosine-9-carbonitrile;

(20R)-19,20,22,23-tetrahydro-5H,21H-18,20-ethano-12,14-etheno-6,10-methenobenz[d]imidazo[4,3-l][1,6,9,13]oxatriazacyclononadecosine-9-carbonitrile;

(21S)-19,20,22,23,24-pentahydro-18-oxo-5H,21H-19,21-ethano-12,14-etheno-6,10-methenobenz[d]imidazo[4,3-m][1,7,10,14]oxatriazacycloeicosine-9-carbonitrile;

(21R)-19,20,22,23,24-pentahydro-18-oxo-5H,21H-19,21-ethano-12,14-etheno-6,10-methenobenz[d]imidazo[4,3-m][1,7,10,14]oxatriazacycloeicosine-9-carbonitrile;

(20S)-17-bromo-19,20,22,23-tetrahydro-19,22-dioxo-5H,21H-18,20-ethano-12,14-etheno-6,10-methenobenz[d]imidazo[4,3-l][1,6,9,13]oxatriazacyclononadecosine-9-carbonitrile;

(20R)-17-bromo-19,20,22,23-tetrahydro-19,22-dioxo-5H,21H-18,20-ethano-12,14-etheno-6,10-methenobenz[d]imidazo[4,3-l][1,6,9,13]oxatriazacyclononadecosine-9-carbonitrile;

(5S,20S)-5-amino-19,20,22,23-tetrahydro-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile;

(5R,20S)-5-amino-19,20,22,23-tetrahydro-5-methyl-19,22-dioxo-5H,21H-18,20-ethano-12,14-etheno-6,10-methenobenz[d]imidazo[3,4-l][1,6,9,12]oxatliazacyclononadecosine-9-carbonitrile;

(5S,20R)-5-amino-19,20,22,23-tetrahydro-5-methyl-19,
22-dioxo-5H,21H-18,20-ethano-12,14-etheno-6,10-
methenobenz[d]imidazo[3,4-l][1,6,9,12]
oxattiazacyclononadecosine-9-carbonitrile;

(5R,20R)-5-amino-19,20,22,23-tetrahydro-5-methyl-19,
22-dioxo-5H,21H-18,20-ethano-12,14-etheno-6,10-
methenobenz[d]imidazo[3,4-i][1,6,9,12]
oxatriazacyclononadecosine-9-carbonitrile;

(20S)-15,16,17,17a,19,20,21,22-octahydro-15-oxa-19-
oxo-5H-18,20-ethano-12,14-etheno-6,10-metheno-
18H-benz[d]imidazo[4,3-k][1,6,9,12]
oxatriazacyclooctadecosine-9-carbonitrile;

(20R)-15,16,17,17a,19,20,21,22-octahydro-15-oxa-19-
oxo-5H-18,20-ethano-12,14-etheno-6,10-metheno-
18H-benz[d]imidazo[4,3-k][1,6,9,12]
oxatriazacyclooctadecosine-9-carbonitrile;

(20S)-15,16,17,17a,19,20,21,22-octahydro-19-oxo-5H-
18,20-ethano-12,14-etheno-6,10-metheno-18H-benz
[d]imidazo[4,3-k][1,6,9,12]oxatriaza-
cyclooctadecosine-9-carbonitrile;

(20R)-15,16,17,17a,19,20,21,22-octahydro-19-oxo-5H-
18,20-ethano-12,14-etheno-6,10-metheno-18H-benz
[d]imidazo[4,3-k][1,6,9,12]oxatriaza-
cyclooctadecosine-9-carbonitrile;

or a pharmaceutically acceptable salt, an optical isomer or stereoisomer thereof.

Specific examples of the compounds of the instant invention are:

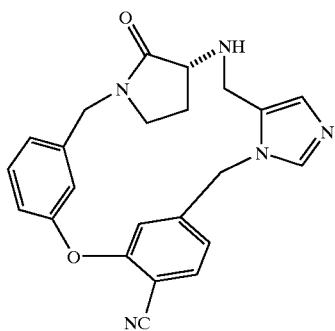

(20R)-19,20,21,22-Tetrahydro-19-oxo-17H-18,20-
ethano-6,10:12,16-dimetheno-16H-imidazo[3,4-h][1,
8,11,14]oxatriazacycloeicosine-9-carbonitrile;

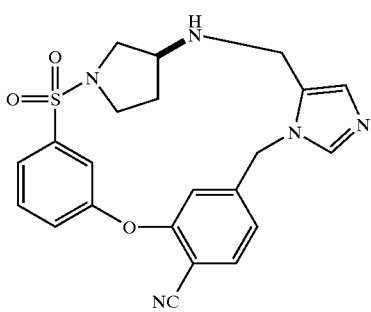

(21S)-20,21,22,23-Tetrahydro-5H,19H-18,21-methano-6,
10:12,16-dimetheno-16H-imidazo[4,3-n][1,8,12,15,7]
oxatriazathia-cycloheneicosine-9-carbonitrile 17,17-
dioxide;

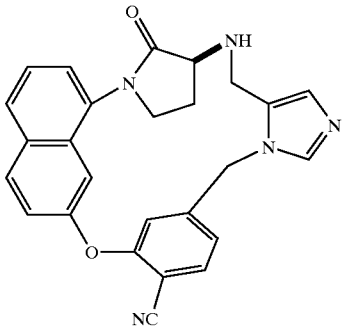

(20S)-19,20,21,22-Tetrahydro-19-oxo-5H-18,20-ethano-
12,14-etheno-6,10-metheno-18H-benz [d]imidazo[4,3-
k][1,6,9,12]oxatriazacyclooctadecosine-9-carbonitrile;

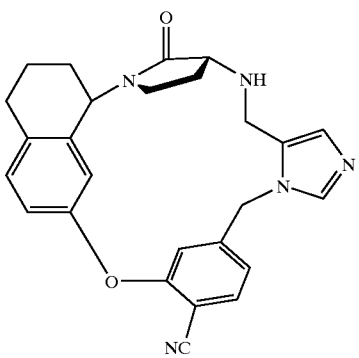

(20R)-15,16,17,17a,19,20,21,22-octahydro-19-oxo-5H-
18,20-ethano-12,14-etheno-6,10-metheno-18H-benz
[d]imidazo[4,3-k][1,6,9,12]
oxatriazacyclooctadecosine-9-carbonitrile;

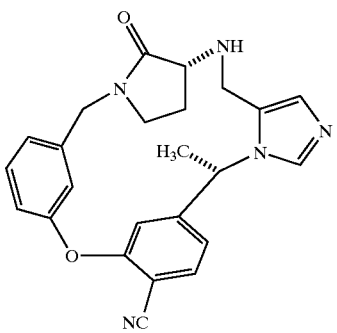

(5S,20R)-19,20,21,22-Tetrahydro-5-methyl-19-oxo-17H-
18,20-ethano-6,10:12,16-dimetheno-16H-imidazo[3,4-
h][1,8,11,14]oxatriaza-cycloeicosine-9-carbonitrile;

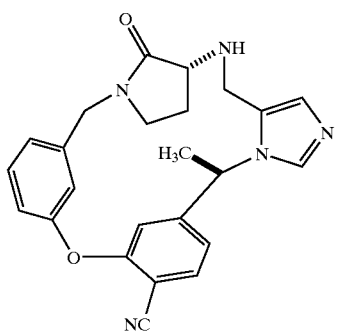

(5R,20R)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;

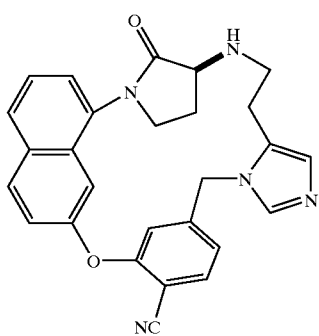

(20S)-19,20,22,23-Tetrahydro-19-oxo-5H,21H-18,20-ethano-12,14-etheno-6,10-methenobenz[d]imidazo[4,3-1][1,6,9,13]oxatriazacyclononadecosine-9-carbonitrile;

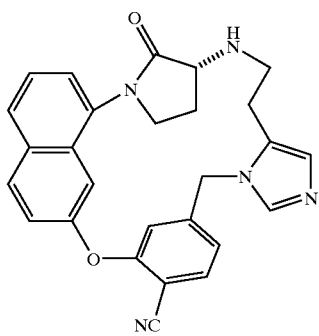

(20R)-19,20,22,23-Tetrahydro-19-oxo-5H,21H-18,20-ethano-12,14-etheno-6,10-methenobenz[d]imidazo[4,3-1][1,6,9,13]oxatriazacyclononadecosine-9-carbonitrile;

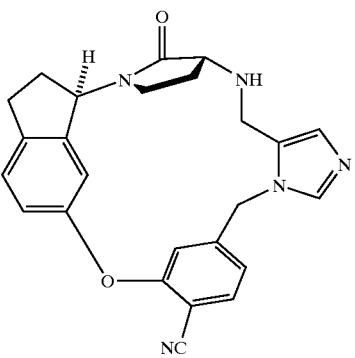

(17R,20R)-19,20,21,22-tetrahydro-19-oxo-17H-15,17:18,20-diethano-6,10:12,16-dimetheno-16H-imidazo[3,4-h][1,8,11,14]oxatriazacycloeicosine-9-carbonitrile;

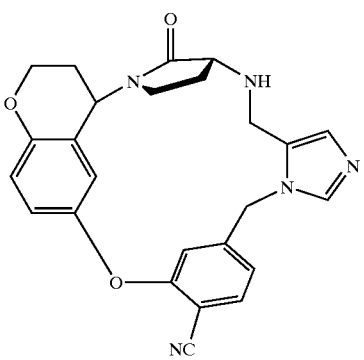

(20R)-15,16,17,17a,19,20,21,22-octahydro-15-oxa-19-oxo-5H-18,20-ethano-12,14-etheno-6,10-metheno-18H-benz[d]imidazo[4,3-k][1,6,9,12]oxatriazacyclooctadecosine-9-carbonitrile;

or a pharmaceutically acceptable salt, an optical isomer or stereoisomer thereof.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Sterochemistry of Carbon Compounds* (John Wiley and Sons, New York 1994), in particular pages 1119–1190). When any variable, term or substituent (e.g. aryl, heterocycle, n, $R^{1a}$, etc.) occurs more than one time in any formula or generic structure, its definition on each occurrence is independent from the definition at every other occurrence. Also, combinations of substituents and/or variables are permissible only if such combinations result in stable compounds.

As used herein, "alkyl" is intended to include both branched and straight-chain saturated aliphatic hydrocarbon groups having 1 to 6 carbon atoms, unless otherwise specified; "alkoxy" represents an alkyl group having 1 to 6 carbon atoms, unless otherwise indicated, attached through an oxygen bridge. "Halogen" or "halo" as used herein means fluoro, chloro, bromo and iodo. "Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, cycloheptyl, and the like.

If no number of carbon atoms is specified, the term "alkenyl" refers to a non-aromatic hydrocarbon, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$–$C_6$ alkenyl" means an alkenyl radical having from 2 to 6 carbon atoms. Examples of such alkenyl groups include, but are not limited to, ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refrs to a hydrocarbon radical straight, branched or cyclic, containing from 2 to 10 carbon atoms and at least one carbon to carbon triple bond. Up to three carbon-carbon triple bonds may be present. Thus, "$C_2$–$C_6$ alkynyl" means an alkynyl radical having from 2 to 6 carbon atoms. Examples of such alkynyl groups include, but are not limited to, ethynyl, propynyl and butynyl. As described above with respect to alkyl, the straight, branched or cyclic portion of the alkynyl group may contain triple bonds and may be substituted if a substituted alkynyl group is indicated.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, indanonyl, biphenyl, tetralinyl, tetralonyl, fluorenonyl, phenanthryl, anthryl or acenaphthyl.

As used herein, "aralkyl" is intended to mean an aryl moiety, as defined above, attached through a $C_1$–$C_6$ alkyl linker, where alkyl is defined above. Examples of aralkyls include, but are not limited to, benzyl, naphthylmethyl and phenylbutyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofuranyl, benzofurazanyl, benzopyranyl, benzothiopyranyl, benzofuryl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperdinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heteroaryl elements include, but are not limited to, azepinyl, benzimidazolyl, benzisoxazolyl, benzofuranyl, benzofurazanyl, benzopyranyl, benzopyrazolyl, benzothiopyranyl, benzofuryl, benzothiazolyl, benzothienyl, benzotriazolyl, benzoxazolyl, chromanyl, cinnolinyl, dihydrobenzofuryl, dihydrobenzothienyl, dihydrobenzothiopyranyl, dihydrobenzothiopyranyl sulfone, furanyl, furyl, imidazolyl, indolinyl, indolyl, isochromanyl, isoindolinyl, isoquinolinyl, isothiazolyl, naphthyridinyl, oxadiazolyl, pyrazinyl, pyrazolyl, pyridazinyl, pyridinyl, pyridyl, pyrimidinyl, pyrimidyl, pyrrolyl, quinazolinyl, quinolinyl, quinoxalinyl, tetrahydroimidazopyridinyl, tetrahydroisoquinolinyl, tetrahydroquinolinyl, thiazolyl, thienofuryl, thienothienyl, thienyl and triazolyl.

As used herein, "heterocyclylalkyl" is intended to mean a heterocyclic moiety, as defined above, attached through a $C_1$–$C_6$ alkyl linker, where alkyl is defined above. Examples of heterocyclylalkyls include, but are not limited to, 2-pyridylmethyl, 2-morpholinylethyl, 2-imidazolylethyl, 2-quinolinylmethyl, 2-imidazolylmethyl, 1-piperazineethyl, and the like.

As used herein, the terms "substituted alkyl", "substituted alkenyl", "substituted alkynyl" and "substituted alkoxy" are intended to include the branch or straight-chain alkyl group of the specified number of carbon atoms, wherein the carbon atoms may be substituted with one to three of the following substituents: F, Cl, Br, I, $CF_3$, $N_3$, $NO_2$, $NH_2$, oxo, OH, —O($C_1$–$C_6$ alkyl), $S(O)_{0-2}$, ($C_1$–$C_6$ alkyl)$S(O)_{0-2}$—, $C_2$–$C_6$ alkenyl, $C_2$–$C_6$ alkynyl, —($C_1$–$C_6$ alkyl)$S(O)_{0-2}$, ($C_1$–$C_6$ alkyl), $C_3$–$C_{20}$ cycloalkyl, $C_2$–$C_6$ alkenyl, $C_2$–$C_6$ alkynyl, —C(O)NH, ($C_1$–$C_6$ alkyl)C(O)NH—, $H_2$N—CH(NH)—, $H_2$NC(O)NH—, ($C_1$–$C_6$ alkyl)C(O)—, —O($C_1$–$C_6$ alkyl) $CF_3$, ($C_1$–$C_6$ alkyl)OC(O)—, ($C_1$–$C_6$ alkyl)O($C_1$–$C_6$ alkyl)—, ($C_1$–$C_6$ alkyl)C(O)$_2$($C_1$–$C_6$ alkyl)—, ($C_1$–$C_6$ alkyl)OC(O)NH—, aryl, benzyl, heterocycle, aralkyl, heterocyclylalkyl, halo-aryl, halo-benzyl, halo-heterocycle, cyano-aryl, cyano-benzyl and cyano-heterocycle.

As used herein, the terms "substituted aryl", "substituted heterocycle", "substituted heteroaryl", "substituted cycloalkyl", "substituted benzyl", "substituted aralkyl" and "substituted heterocyclylalkyl" are intended to include the cyclic group containing from 1 to 3 substitutents in addition to the point of attachment to the rest of the compound. Such substitutents are preferably selected from the group which includes but is not limited to F, Cl, Br, I, $CF_3$, $NH_2$, N($C_1$–$C_6$ alkyl)$_2$, $NO_2$, CN, $N_3$, $C_1$–$C_{20}$ alkyl, $C_1$–$C_6$ alkoxy, $C_3$–$C_{20}$ cycloalkyl, —OH, —O($C_1$–$C_6$ alkyl), $S(O)_{0-2}$, ($C_1$–$C_6$ alkyl)$S(O)_{0-2}$—, ($C_1$–$C_6$ alkyl)$S(O)_{0-2}$($C_1$–$C_6$ alkyl)—, ($C_1$–$C_6$ alkyl)C(O)NH—, $H_2$N—CH(NH)—, $H_2$N—C(O)NH—, ($C_1$–$C_6$ alkyl)C(O)—, ($C_1$–$C_6$ alkyl)OC(O)—, ($C_1$–$C_6$ alkyl)O($C_1$–$C_6$ alkyl)—, ($C_1$–$C_6$)C(O)$_2$($C_1$–$C_6$ alkyl)—, ($C_1$–$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

When $R^4$ and $R^5$ are combined to form $-(CH_2)_u-$, cyclic moieties are formed. Examples of such cyclic moieties include, but are not limited to:

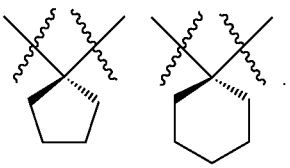

In addition, with respect to $R^4$ and $R^5$, such cyclic moieties may optionally include a heteroatom(s). Examples of such heteroatom-containing cyclic moieties include, but are not limited to:

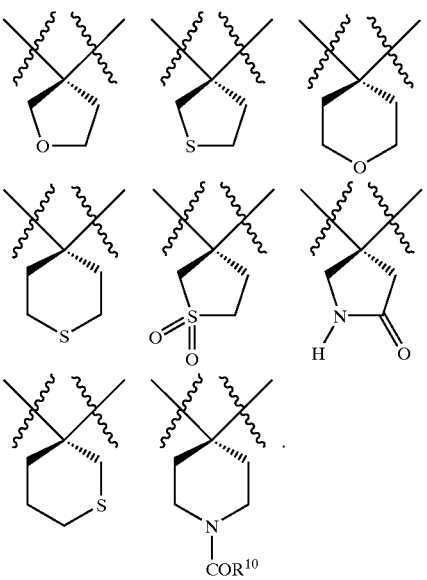

Examples of the ring structures which may be formed when $R^6$ and $R^7$, or $R^7$ and $R^{7a}$, are joined include, but are not limited to:

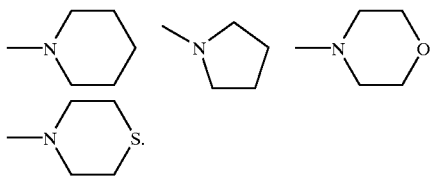

As used herein, examples of "$C_3-C_{20}$ cycloalkyl" may include, but are not limited to:

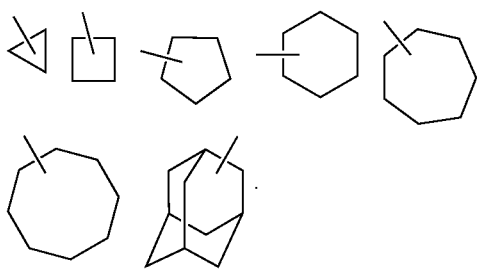

Lines drawn into the ring systems from substituents (such as from $R^4$, $R^5$, $X^1$, etc.) indicate that the indicated bond may be attached to any of the substitutable ring carbon atoms or heteroatoms.

Preferably, $R^2$ is independently selected from H, CN, $OR^{10}$, halo, unsubstituted or substituted $C_1-C_6$ alkyl, $-(C_1-C_6$ alkyl$)NR^{10}C(O)R^{13}$. Most preferably, r is 1 to 3 and at least one $R^2$ is CN.

Preferably, $R^3$ is independently selected from H, halo, unsubstituted or substituted $C_1-C_6$ alkyl, unsubstituted or substituted $C_1-C_6$ alkenyl, unsubstituted or substituted $C_1-C_6$ alkynyl, $-(C_1-C_6$ alkyl$)OR^{10}$, $-O(C_1-C_6$ alkyl$)OR^{10}$. Most preferably, $R^3$ is H, halo, unsubstituted or substituted $C_1-C_6$ alkyl, or unsubstituted or substituted $C_2-C_6$ alkynyl.

Preferably, $R^4$ and $R^5$ are independently selected from hydrogen, unsubstituted or substituted $C_1-C_6$ alkyl, and $OR^{10}$. Most preferably, $R^4$ and $R^5$ are independently selected from hydrogen or unsubstituted or substituted $C_1-C_6$ alkyl.

Preferably, $R^8$ is selected from hydrogen, or unsubstituted or substituted $C_1-C_6$ alkyl. Most preferably, $R^8$ is selected from hydrogen or methyl.

Preferably, $R^9$ is selected from hydrogen, unsubstituted or substituted $C_1-C_6$ alkyl, and unsubstituted or substituted aryl.

Preferably, $R^{10}$ is selected from hydrogen, unsubstituted or substituted $C_1-C_6$ alkyl, unsubstituted or substituted aryl, or unsubstituted or substituted heterocycle.

Preferably, $A^1$ is selected from a bond, $C(=O)$, $S(=O)_m$, $NR^{10}C(O)$, or $C(O)NR^{10}$.

Preferably, $A^2$ is selected from a bond, $C(=O)$, or $S(=O)_m$.

Preferably, $A^3$ is selected from a bond or $-C(=O)-$.

Preferably, $A^4$ is selected from a bond.

Preferably, $G^2$ is $H_2$.

Preferably, V is aryl or heterocycle. More preferably V is aryl. Most preferably, V is phenyl.

Preferably, W is imidazolyl or pyridyl. Most preferably, W is imidazolyl.

Preferably, $X^1$ represents $(C(R^{1a})_2)_n$, $C(O)$, $S(O)_m$, or a bond.

Preferably, $X^2$ represents $(C(R^{1b})_2)_p$, $(CH_2)_p$, $C(O)(CH_2)_p$, or a bond.

Preferably, $X^3$ represents $(C(R^{1c})_2)_q$.

Preferably, $Y^1$ is selected from aryl or heterocycle. More preferably, $Y^1$ is phenyl, biphenyl, naphthyl or pyridyl. Most preferably, $Y^1$ is phenyl or naphthyl.

Preferably, $Y^2$ is selected from a bond or heterocycle. Most preferably, $Y^2$ is a bond.

Preferably, $Z^1$ is selected from a bond, $(C(R^{1a})_2)_n$ or O. Most preferably, $Z^1$ is O.

Preferably, $Z^2$ is a bond, O, or $(C(R^{1a})_2)_n$. More preferably, $Z^2$ is a bond.

Preferably, variable n is independently selected from 0, 1, 2, 3, or 4. Preferably, variables p and q are independently selected from 0, 1, 2 or 3.

Preferably, the moiety

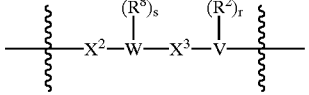

represents

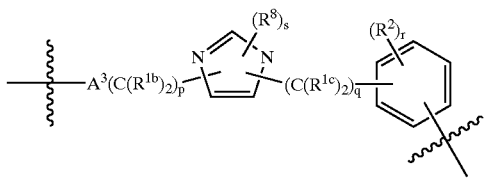

Preferably, the moiety

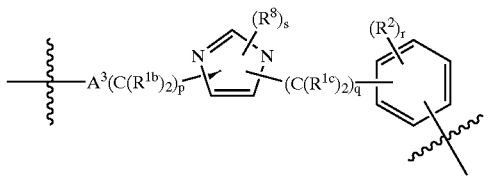

represents

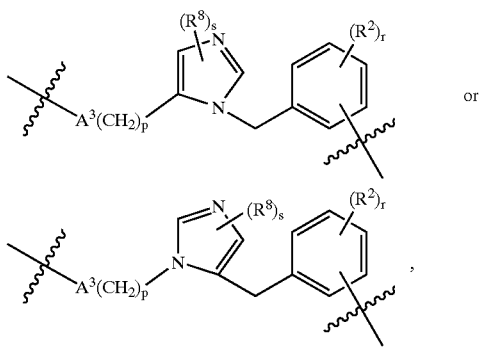

where p is 1 or 2.

It is intended that the definition of any substituent or variable (e.g., $R^{1a}$, $R^2$, m, p, etc.) at a particular location in a molecule is independent of its definitions elsewhere in that molecule. Thus, $-C(R^{1a})_2$ can represent $-CH_2$, $-CHCH_3$, $-CHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations which may be used in the description of the chemistry and in the Examples that follow include:

| | |
|---|---|
| $Ac_2O$ | Acetic anhydride; |
| AIBN | 2,2'-Azobisisobutylonitrile |
| BOC/Boc | t-Butoxycarbonyl or tert-butoxycarbonyl; |
| CBz | Carbobenzyloxy; |
| DBAD | Di-tert-butyl azodicarboxylate; |
| DBU | 1,8-Diazabicyclo[5.4.0]undec-7-ene; |
| DCE | 1,2-Dichloroethane; |
| DIEA | N,N-Diisopropylethylamine; |
| DMAP | 4-Dimethylaminopyridine; |
| DME | 1,2-Dimethoxyethane; |
| DMF | N,N-Dimethylformamide; |
| DMSO | Methyl sulfoxide; |
| DPPA | Diphenylphosphoryl azide; |
| DTT | Dithiothreitol; |
| EDC | 1-(3-Dimethylaminopropyl)-3-ethyl-carbodiimide hydrochloride; |
| EDTA | Ethylenediaminetetraacetic acid; |
| $Et_3N$ | Triethylamine; |
| EtOAc | Ethyl acetate; |
| EtOH | Ethanol; |
| FAB | Fast atom bombardment; |
| HEPES | 4-(2-Hydroxyethyl)-1-piperazineethanesulfonic acid; |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| LAH | Lithium aluminum hydride; |
| MCPBA | m-Chloroperoxybenzoic acid; |
| Me | Methyl; |
| MeOH | Methanol; |
| Ms | Methanesulfonyl; |
| MsCl | Methanesulfonyl chloride; |
| n-$Bu_3P$ | Tri-n-butylphosphine; |
| NaHMDS | Sodium bis(trimethylsilyl)amide; |
| NBS | N-Bromosuccinimide; |
| PMSF | a-Toluenesulfonyl chloride; |
| Py or pyr | Pyridine; |
| PYBOP | Benzotriazole-1-yl-oxy-trispyrrolidinophosphonium hexafluorophosphate; |
| t-Bu | tert-Butyl |
| TBAF | Tetrabutylammoniumfluoride |
| RPLC | Reverse Phase Liquid Chromatography |
| TBSCl | tert-Butyldimethylsilyl chloride |
| TFA | Trifluoroacetic acid; |
| THF | Tetrahydrofuran; |
| TMS | Tetramethylsilane; |
| Tr | Trityl. |

These reactions may be employed in a linear sequence to provide the compounds of the invention or they may be used to synthesize fragments which are subsequently joined by the alkylation reactions described in the Schemes. The procedures discussed and illustrated in the following schemes and synopsis may be used in the preparation of the compounds of the instant invention, for either (R) or (S) stereochemistry.

Synopsis of Schemes

Scheme 1 details the synthesis of a representative 3-aminopyrrolidinone. In this case, the benzyl alcohol 1 is converted into the benzyl azide 2 by treatment with DPPA and DBU in toluene. Reduction of this azide by LAH provides the benzylamine, which is coupled to BOC-methionine using PYBOP to provide amide 4. Treatment of compound 4 with excess iodomethane gives the corresponding dimethylsulfonium salt, which can be cyclized to the desired aminopyrrolidinone upon reaction with lithium bis (trimethylsilyl) amide in TBF. Deprotection of this pyrrolidinone 5, by hydrogenolysis followed by treatment with HCl in ethyl acetate, leads to the basic 3-aminopyrrolidinone 6.

Scheme 1A demonstrates the synthesis of an isomeric pyrrolidinone. The synthesis of the 3-aminopyrrolidinone 6a begins by treating the amine 3 and a BOC-protected aspartic acid ethyl ester with PYBOP and DIEA. The resulting amide is treated with Lawesson's reagent to give the thioamide, which is reduced using $NaBH_4$ and $NiCl_2$ and then cyclized to obtain the intermediate 5a. Using techniques described above, the intermediate 5a is converted to the compound 6a, which may be used as a substitute for the basic 3-aminopyrrolidinone 6 in any of the following schemes.

The synthesis of a key imidazole carboxaldehyde intermediate 10 is shown in Scheme 2. Starting from the bromotoluene derivative 7, a palladiumcatalyzed cyanation reaction, followed by benzylic bromination with NBS, leads to the benzyl bromide 8. This bromide is used to alkylate a trityl-protected imidazole derivative in acetonitrile, and the resulting imidazolium salt is detritylated by treatment with MeOH to provide the 1,5-disubstituted imidazole 9. Saponification of the acetyl ester of 9, followed by modified Swern conditions, leads to the desired aldehyde 10.

The amine 6 and the aldehyde 10 are then coupled via reductive amination, as shown in Scheme 3. The resulting secondary amine 11 is then treated with $Cs_2CO_3$ in DMF to give the cyclized product 12.

Scheme 3A illustrates the synthetic strategy that is employed when the $R^2$ substitutent is not an electronic withdrawing moiety either ortho or para to the fluorine atom. In the absence of the electronic withdrawing moiety, the intramolecular cyclization can be accomplished via an Ullmann reaction. Thus, the imidazolylmethylacetate is treated with a suitably substituted halobenzylbromide to provide the 1-benzylimidazolyl intermediate 9a. The acetate functionality of intermediate 9a was converted to an aldehyde which was then reductively coupled to intermediate 9a. Coupling under standard Ullmann conditions provided compound 12a of the instant invention.

Scheme 4 shows the synthesis of a chloro-substituted analog of structure 12. In this case, a 3,5-dichlorophenol is benzylated to give compound 14, which is converted to the corresponding Grignard Reagent followed by quenching with carbon dioxide to provide the benzoic acid 15. Reduction of this acid with LAH provides the corresponding benzyl alcohol 16, and this is subjected to the same sequence of reactions as alcohol 1 in Scheme 1 to ultimately provide the desired macrocycle 23.

In Scheme 5, the hydroxybenzoic acid 24 is coupled to (S)-3-(tert-butoxycarbonylamino)pyrrolidine (commercially available from TCI, U.S.A.) using EDC and HOBT in DMF. The resulting compound 25 is deprotected and then reductively alkylated with aldehyde 10 to provide structure 27. Cyclization of this phenol, with $Cs_2CO_3$ as a base, leads to the final product 28.

A sulfonamide analog of compound 28 is shown in Scheme 6. The synthetic sequence begins with bromobenzene 29, which is treated with Mg to provide the Grignard Reagent, which is reacted with sulfur dioxide to give the sulfinate derivative 30. Treatment of this with sulfuryl chloride yields the corresponding sulfonyl chloride, which is reacted with a suitable pyrrolidine derivative to provide sulfonamide 31. Deprotection of this sulfonamide by hydrogenolysis, followed by treatment with HCl in EtOAc, provides the amine hydrochloride 32, and subjection of this to the standard procedures used in the previous schemes gives the desired sulfonamide macrocycle 34.

The synthesis of another derivative of macrocycle 12, in which the benzylic site adjacent to the imidazole is substituted, is shown in Scheme 7. In this example, addition of methylmagnesium bromide to benzaldehyde 35 provides the secondary alcohol 36. A mixture of alcohol 36, a suitably protected imidazole, and DIEA, in dichloromethane is then treated with triflic anhydride to give the imidazolium salt 37 which, after methanolysis, affords compound 38. Cleavage of the silyl ether, then oxidation of the resulting alcohol yields the aldehyde 39, which may be treated analogously to aldehyde 10 to provide the macrocyclic analog 41.

A method for the synthesis of analogs that are substituted at the alternative benzylic position in macrocycle 12 is detailed in Schemes 8 and 9. The route starts with formation of the Grignard Reagent from bromide 29 and reaction of this organometallic derivative with 3-chlorobenzaldehyde. Application of a similar sequence of steps to that described in Scheme 1 converts the alcohol 42 to the pyrrolidinone derivative 46, obtained as a mixture of diastereomers. At this stage, the benzyl protecting group is removed and the diastereomers are separated by chromatography. As depicted in Scheme 8, for diastereomer B, modified cyclization conditions using KF on alumina in acetonitrile yield the final product 50. As shown in Scheme 9, for diastereomer A, application of the standard procedures of deprotection, reductive alkylation, and $Cs_2CO_3$-mediated cyclization provides the final product 54. In order to provide simple phenyl-substituted macrocycles, such as structure 54 in Scheme 9, the hydrogenolysis of benzyl ether 46 is conducted under 50 atm of hydrogen pressure in order to concomitantly remove the chloro substituent. The deschloro derivative 51 is subjected to an analogous sequence to that shown in Scheme 8 to provide the final macrocycle 54.

Scheme 10 illustrates the synthesis of the naphthyl intermediates 63. Following protection of the aminonaphthol 55 with BOC and mesylate groups to give structure 57, treatment with N-bromosuccinimide in acetic acid leads to the bromo derivative 58. The mesylate group is then removed by treatment with NaOH and the liberated phenol is converted to the ten-butyldimethylsilyl ether 59. Standard removal of the carbamate protecting group provides aniline 60 which is then coupled to (R)-BOC-methionine using PYBOP to yield 61. Treatment of compound 61 with excess iodomethane gives the corresponding dimethylsulfonium salt, which can be cyclized to the desired aminopyrrolidinone upon reaction with lithium bis(trimethylsilyl)amide in THF. Deprotection of this pyrrolidinone 62, using TBAF in THF, followed by treatment with HCl in ethyl acetate, leads to the basic 3-aminopyrrolidinone 63.

Synthesis of the macrocyclic pyrrolidinone 65 is depicted in Scheme 11. Intermediate 63 is reductively alkylated with aldehyde 10 to provide the phenol 64. Cyclization of this phenol 64 with cesium carbonate as a base leads to the final product 65.

Scheme 12 shows the synthesis of compound 70. The benzyl bromide 8 is used to alkylate a trityl-protected imidazole derivative in acetonitrile and the resulting imidazolium salt is detritylated by treatment with methanol to provide the 1,5-disubstituted imidazole 66. Treatment of the imidazole 66 with LiOH, in THF and water, yielded the lithium salt 67. The lithium salt 67 is coupled to intermediate 68, using EDC, HOBT, and DIEA in DMF. The resulting compound 69 is then cyclized, using cesium carbonate in DMSO, to provide the final product 70.

Scheme 13 illustrates the alkylation of compound 70 using $H_2CO$ and $NaCNBH_3$ in DIEA and methanol, to yield the final product 72.

The synthesis of compound 74 is depicted in Scheme 14. Compound 65 is treated with [2-(tri-n-butylstannyl-1-ethynyl]cyclopropane and tetrakis(triphenylphosphine) palladium in DMF to yield compound 73. Treatment of compound 73 with $H_2$, Pt-C and ethanol produced the final product 74.

Scheme 15 illustrates the synthesis of compound 82. Compound 57 is treated with HCl and EtOAc to provide the amine 75. The amine 75 is then coupled to BOC-methionine using PYBOP and DIEA in $CH_2Cl_2$, to yield the intermediate 76. Treatment of intermediate 76 with excess iodomethane gives the corresponding dimethylsulfonium salt, which can be cyclized to the desired aminopyrrolidinone upon reaction with lithium bis(trimethylsilyl)amide in THF. This pyrrolidinone 77 is then treated with Lawesson's Reagent in toluene to obtain the thioamide 78. Treatment with Raney Ni in ethanol gives the protected pyrrolidine 79. The pyrrolidine 79 is then treated with TBAF and THF, followed by HCl and EtOAc, to yield the deprotected aminopyrrolidine 80. Reductive alkylation of the amino pyrrolidine 80 yields compound 81, which is cyclized, using cesium carbonate and DMF, to the final product 82.

The syntheses of the useful intermediates imidazole 84 and alcohol 86 from previously described compounds are illustrated in Scheme 16A and Scheme 16B, respectively. These intermediates can be utilized in the synthesis of the macrocyclic structure 95, as shown in Scheme 17. Following deprotection, the aminopyrrolidinone 88 is coupled to 84 using standard EDC-mediated conditions. The TBS protecting group is then exchanged for the more robust TBDPS ether, and subsequent reaction with Lawesson's reagent affords thioamide 91. This thioamide is desulfurized using Raney nickel and the resulting amine is converted to the corresponding tert-butyl carbamate 92. A mixture of 92 and alcohol 86 in $CH_2Cl_2$ is then treated with trifluoromethanesulfonic anhydride in the presence of DIEA to provide, after methanolic work-up, compound 93. Standard removal of the silyl ether with TBAF provides the phenol 94, and this is subjected to the normal cyclization and deprotection conditions to afford the final compound 95.

Scheme 18 details the synthesis of compounds with an alternative substitution pattern on the imidazole ring. The iodoimidazole derivative 96 is converted to the corresponding Grignard reagent by treatment with EtMgBr and this organometallic adds to aldehyde 85 to provide the secondary alcohol 97. Oxidation of this to the corresponding ketone is achieved using manganese (IV) oxide, and this ketone is reacted with MeMgBr to provide the tertiary alcohol 99. Alkylation of imidazole 99 with the triflate derived from methyl glycolate, and subsequent methanolysis, affords ester 100, which is saponified using lithium hydroxide. The resulting carboxylate is coupled to aminopyrroldinone 68, and cyclization of the coupled product 102, utilizing cesium carbonate, gives the macrocycle 103.

Syntheses of carboxylic acid 109 and aldehyde 111, which are useful in the preparation of certain macrocyclic compounds, are detailed in Scheme 19. The urocanic acid 104 is esterified by treatment with acidic methanol, and then hydrogenated with a palladium on carbon catalyst to provide the propionate derivative 106. Standard regioselective protection with a trityl group affords compound 107, which is treated with a suitable benzyl bromide to give, after methanolic removal of the trityl group, the ester 108. Saponification of this ester with lithium hydroxide affords the desired acid salt 109. The lithium salt 109 may be converted to the corresponding Weinreb amide using standard EDC-coupling conditions, and reduction of this amide with DIBAL gives aldehyde 111.

Synthesis of compounds of the invention characterized by the incorporation of a third aromatic carbocyclic moiety into the macrocycle is illustrated in Scheme 20. A benzyloxyphenoxyaniline 115, prepared in three steps from a suitably substituted 2-benzyloxyphenol 113 and a suitably substituted 2-nitrobenzene chloride 112, is coupled to BOC-methionine using PYBOP to provide the amide 116. Treatment of the amide 116 with excess iodomethane gives the corresponding dimethylsulfonium salt, which can be cyclized to the desired aminopyrrolidinone 117 upon reaction with lithium bis(trimethylsilyl) amide in THF. Deprotection of this pyrrolidinone 117, by hydrogenolysis followed by treatment with HCl in ethyl acetate, leads to the 3-aminopyrrolidinone 118. The 3-aminopyrrolidinone 118 may then be converted to the final product 120 using techniques described in the above schemes, particularly Scheme 3.

Schemes 21–24 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

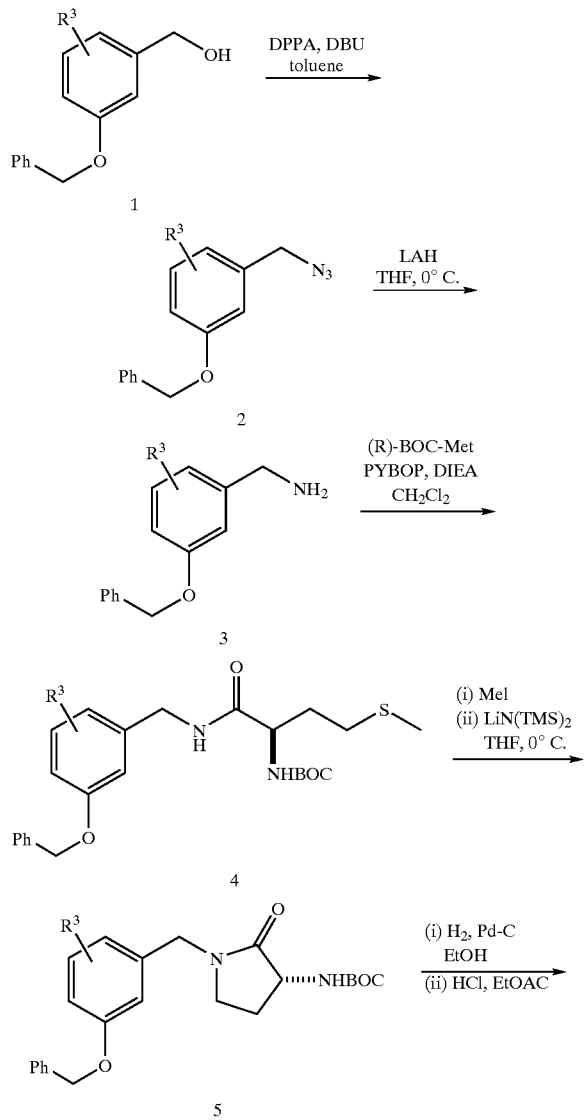

SCHEME 1

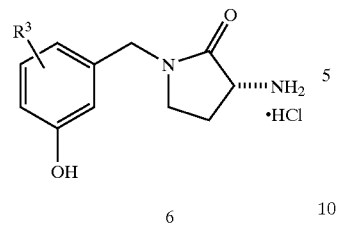
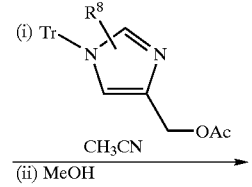
SCHEME 1A
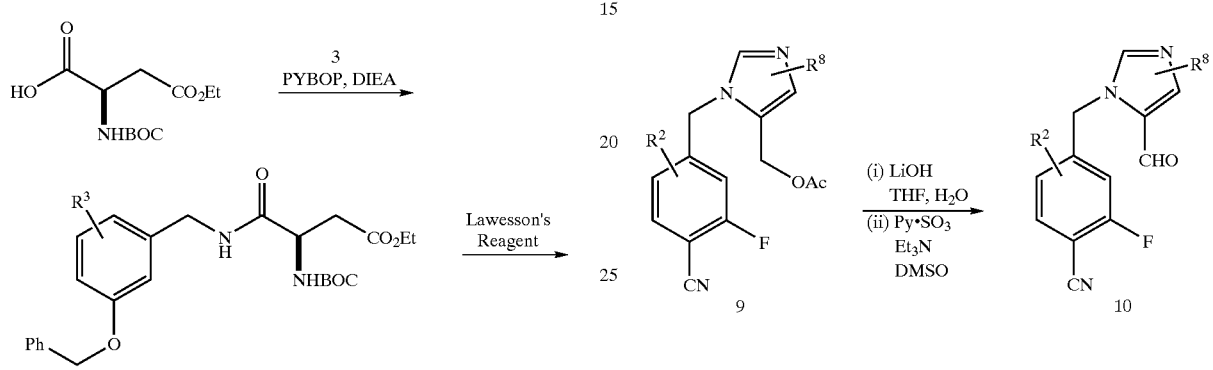
SCHEME 2
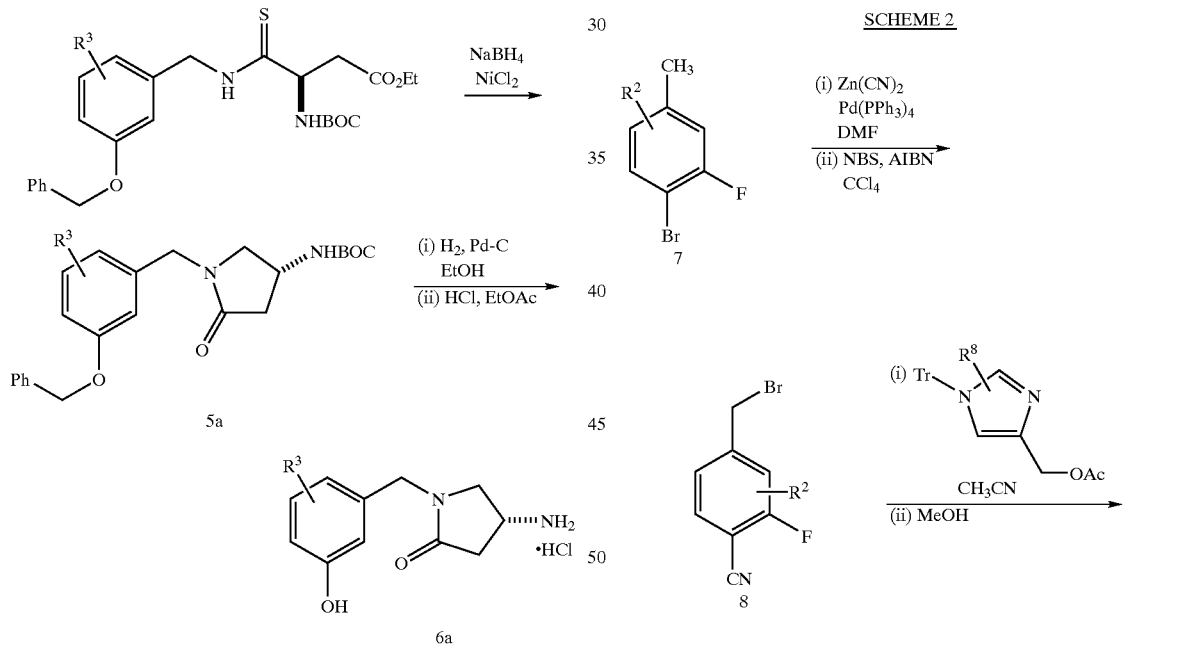
SCHEME 2
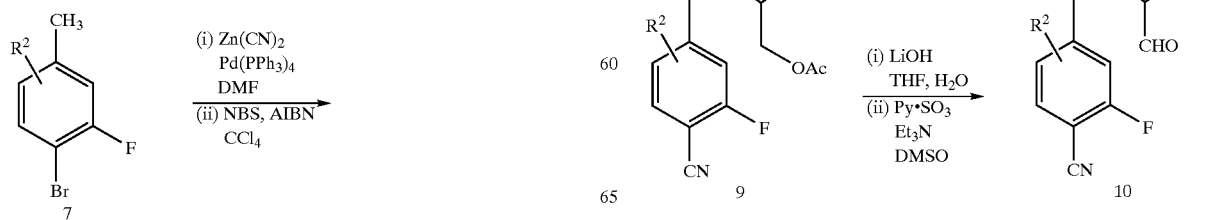

SCHEME 3
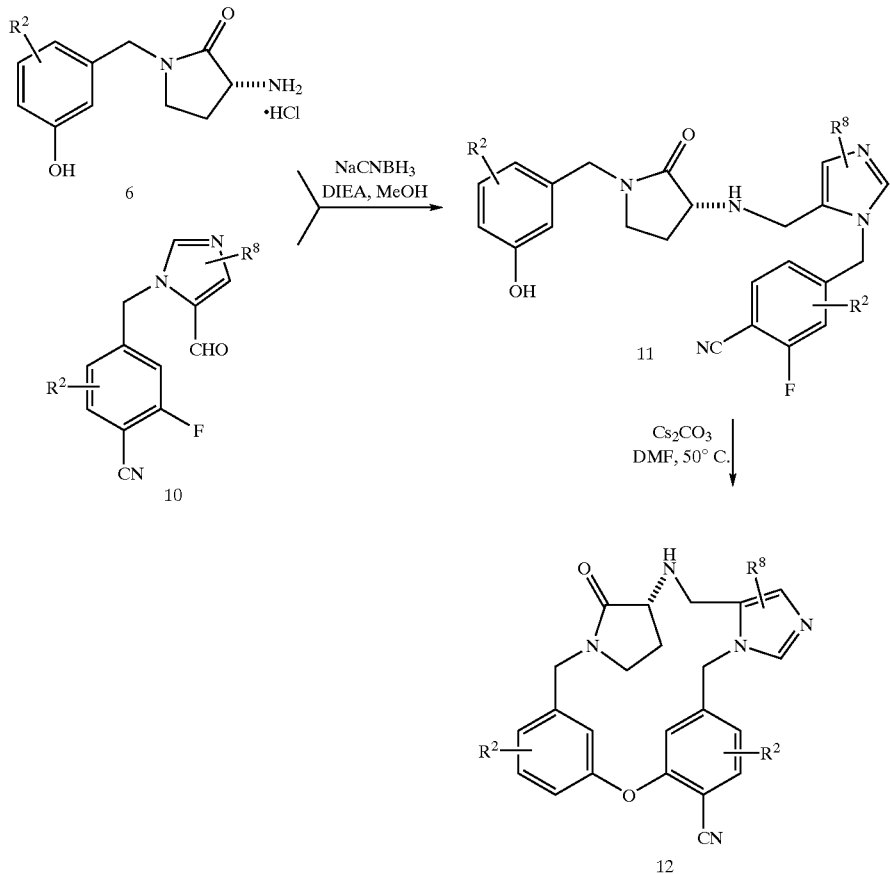
SCHEME 3A
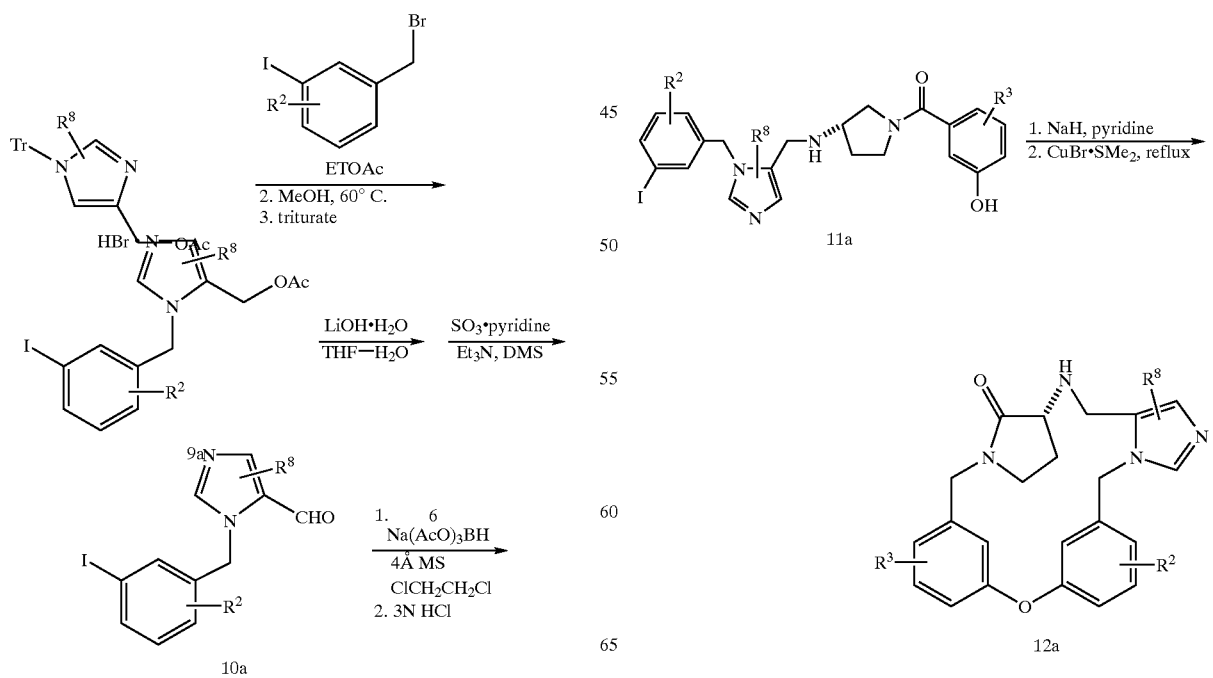

SCHEME 4
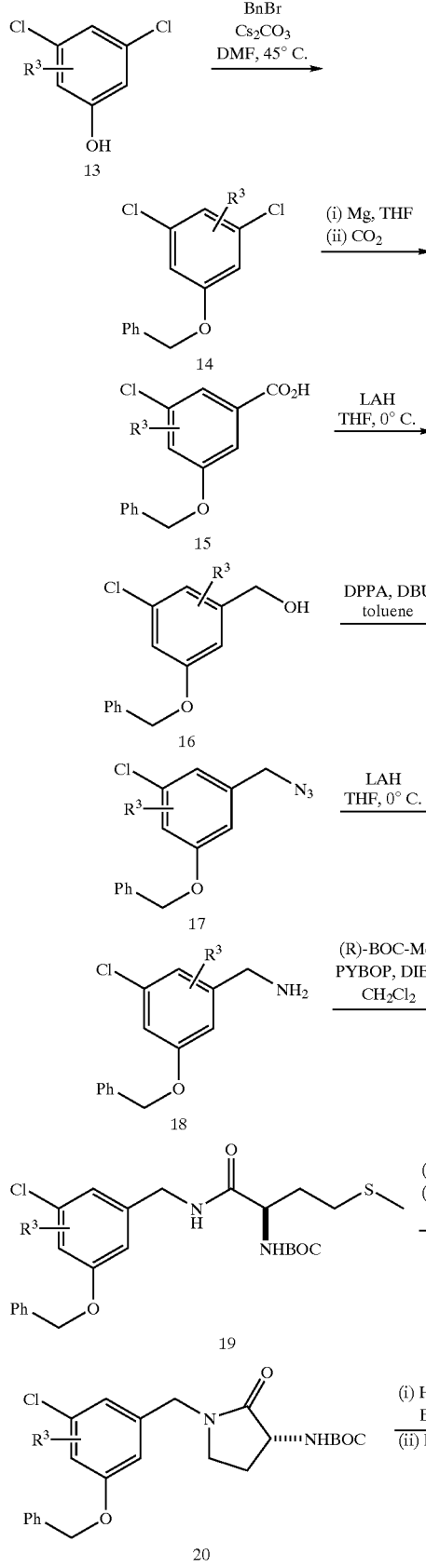
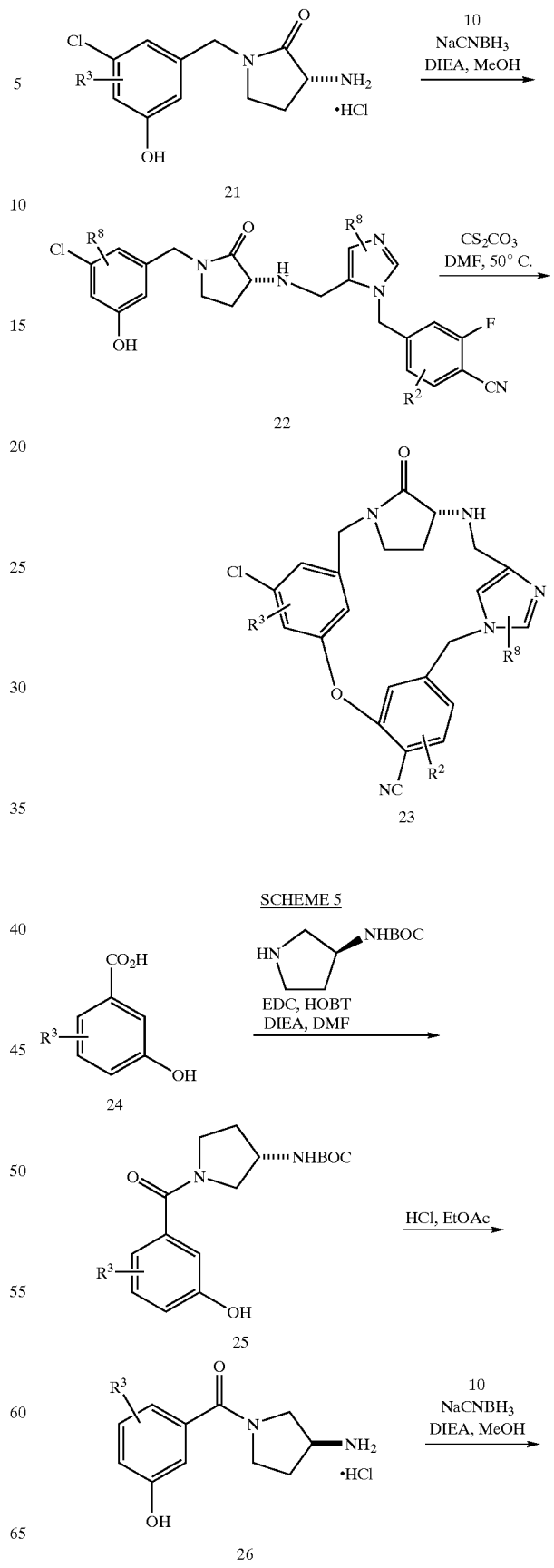
SCHEME 5

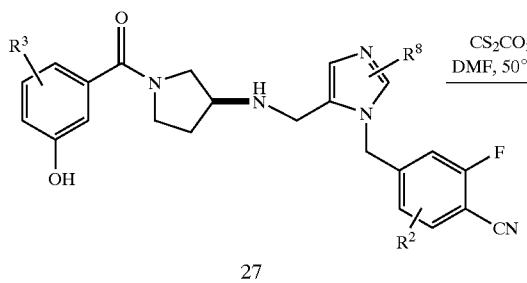
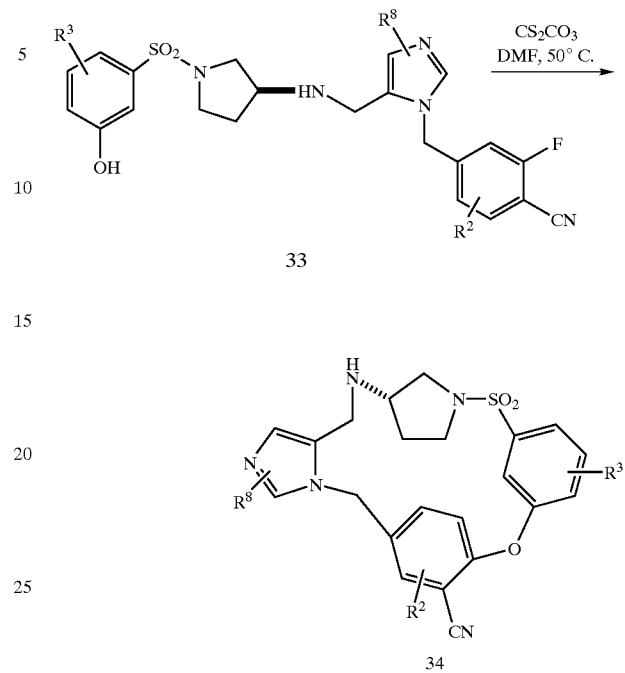
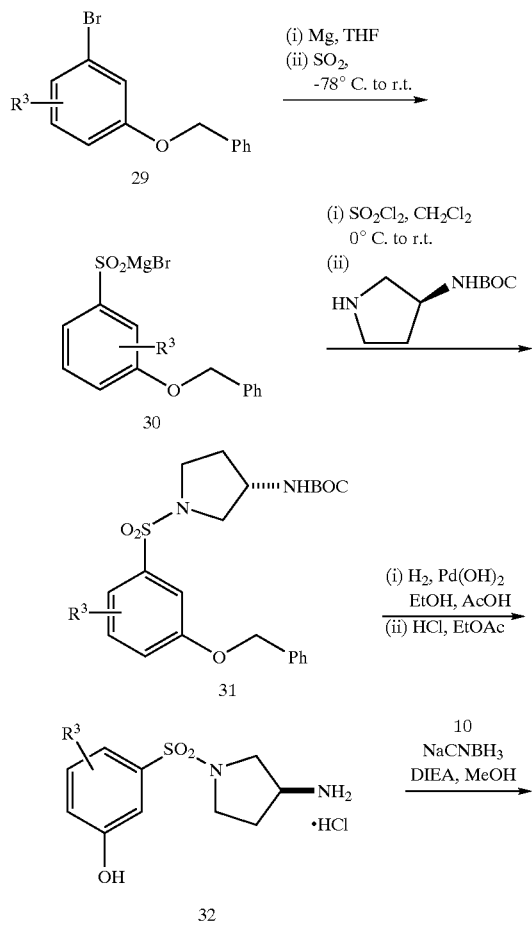
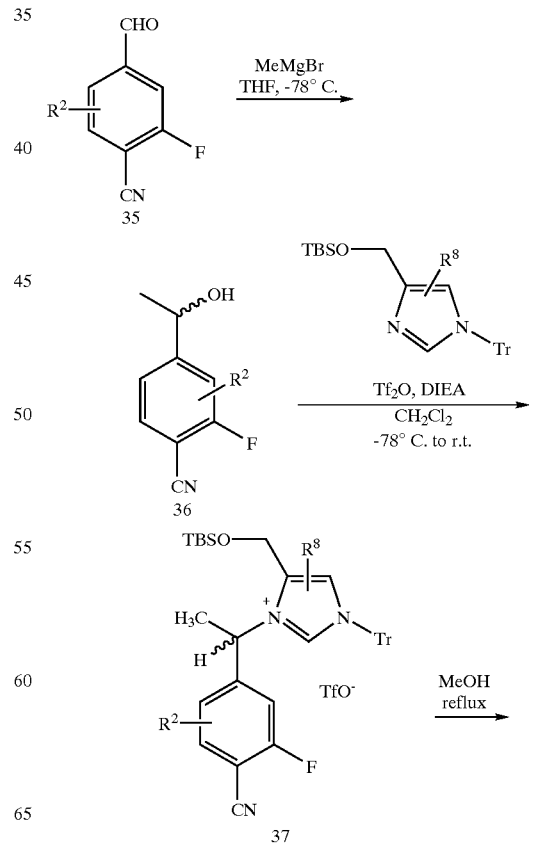

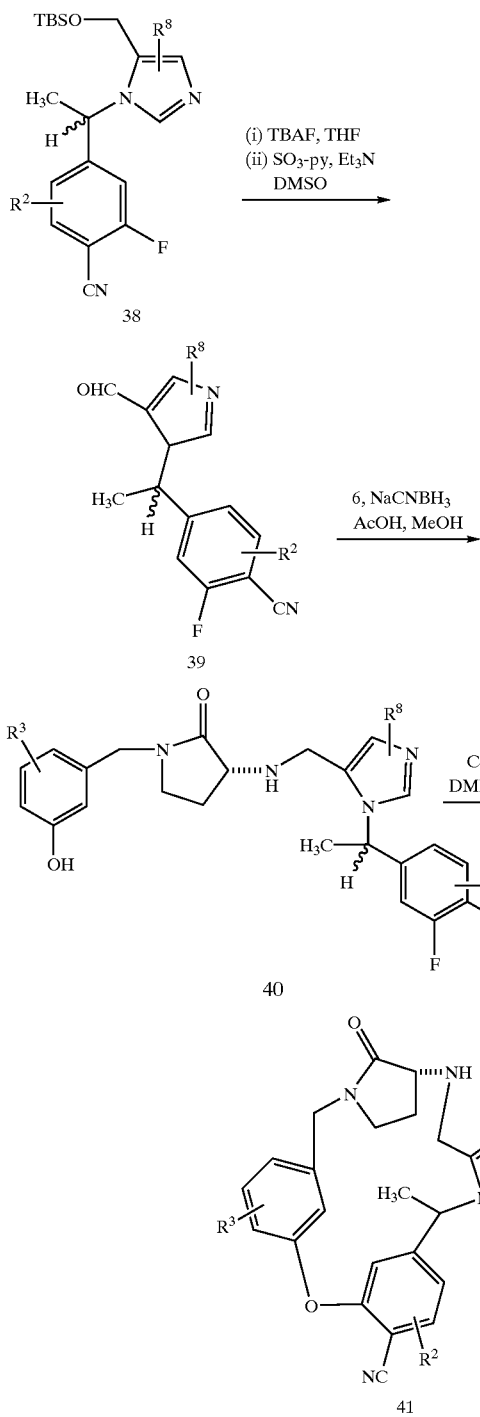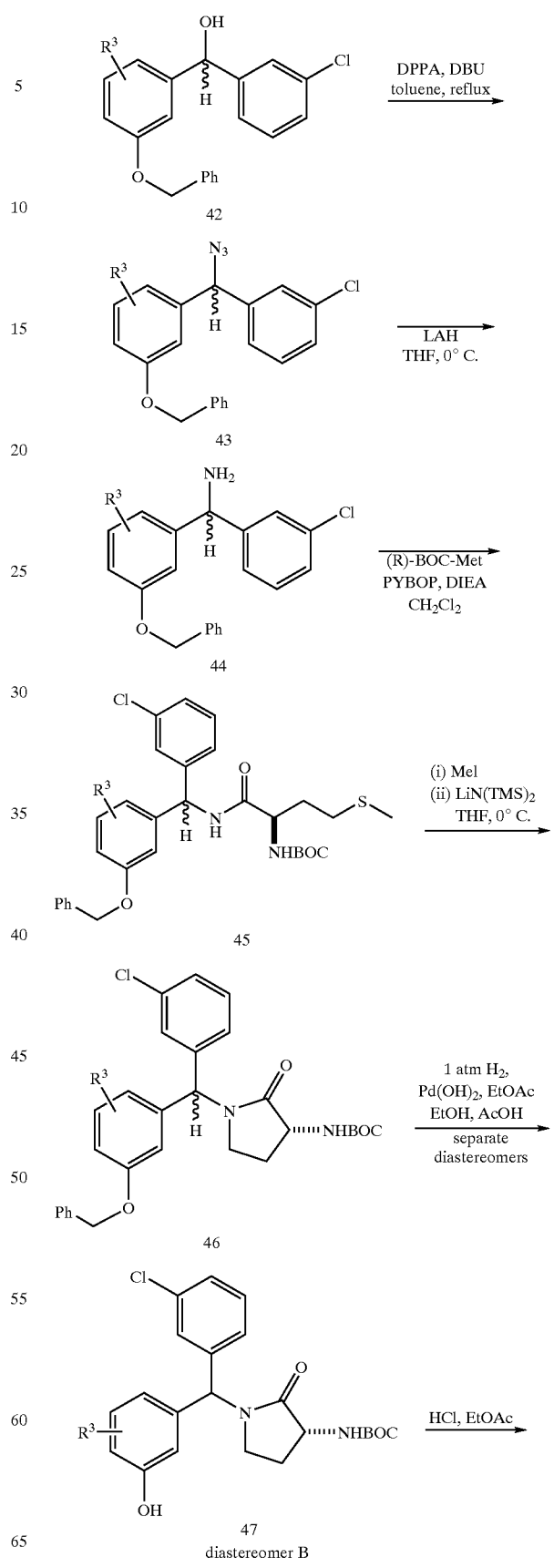
SCHEME 8
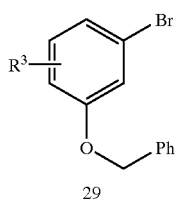

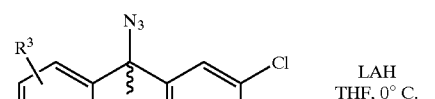
57
-continued
58
-continued
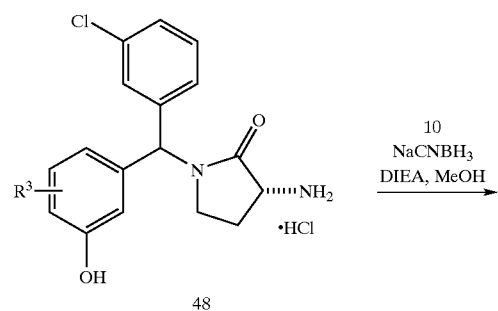
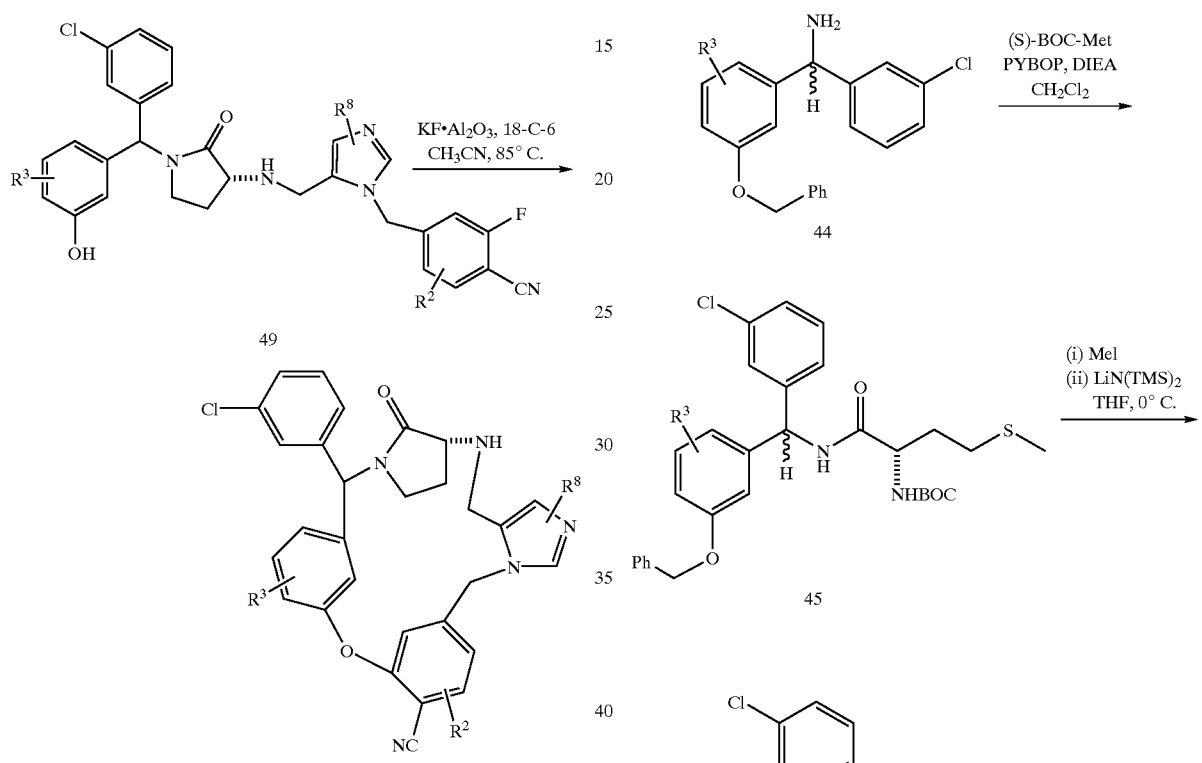
SCHEME 9
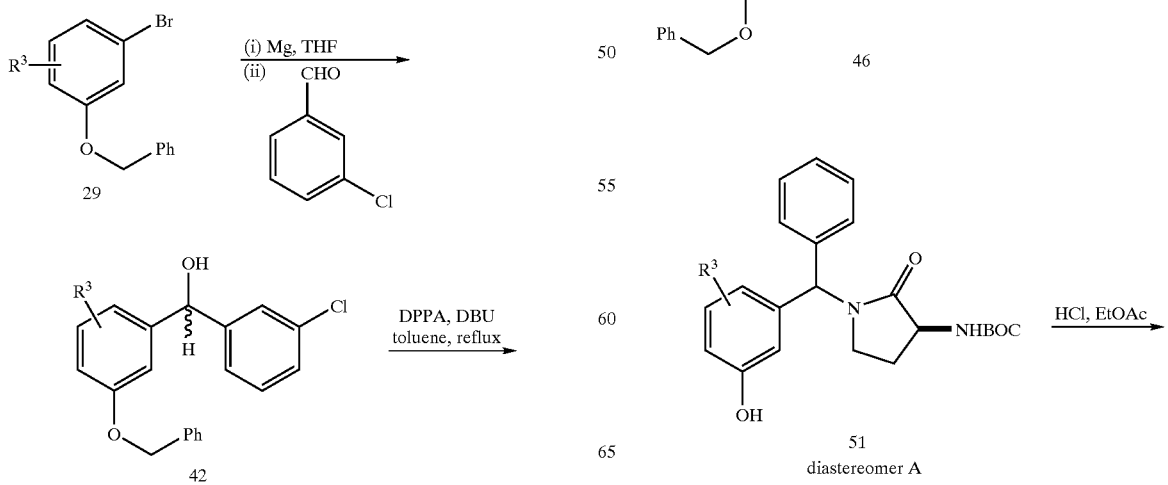

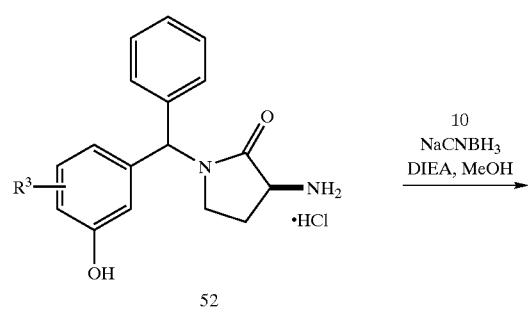
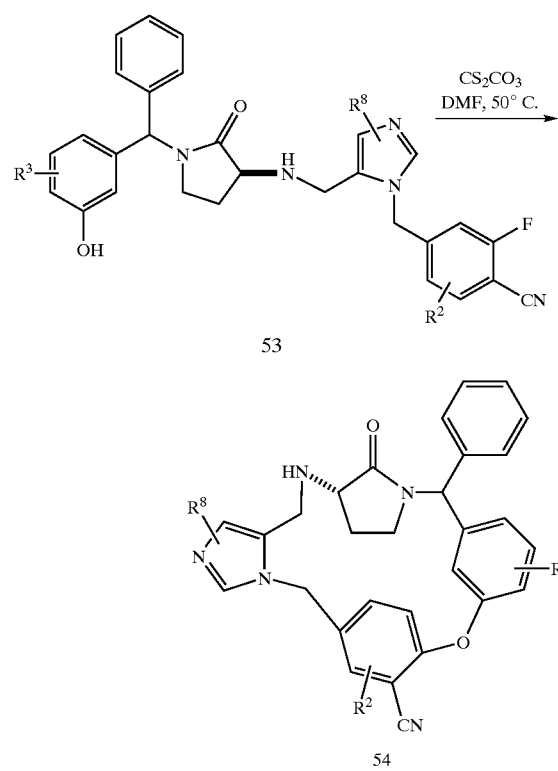
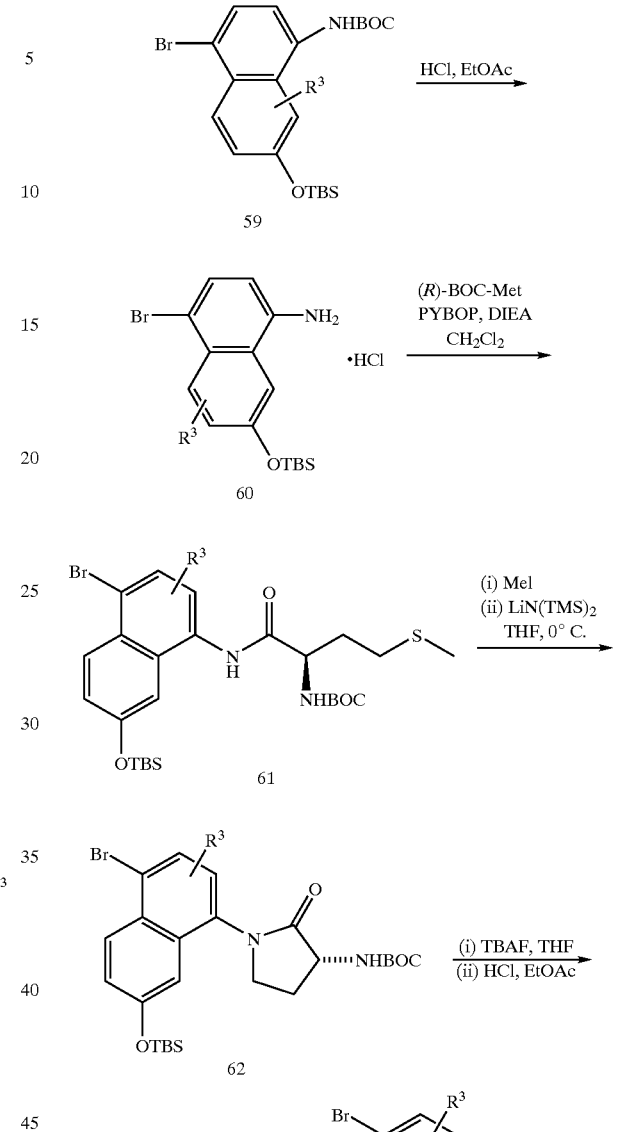
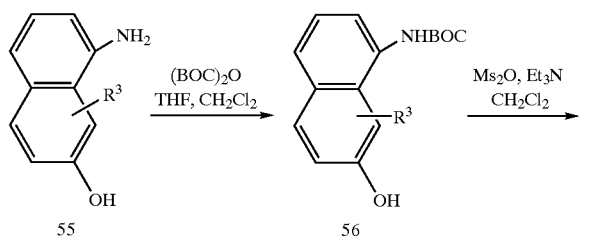
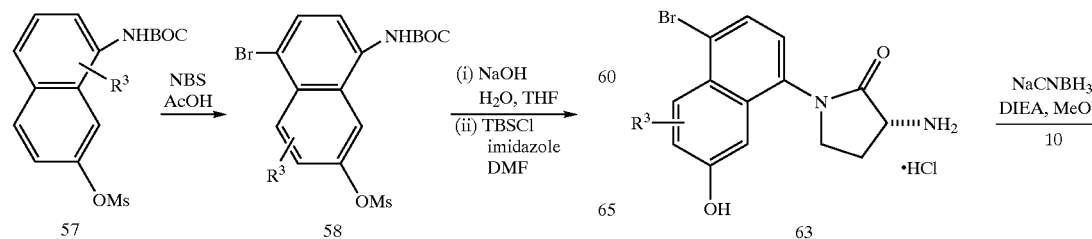

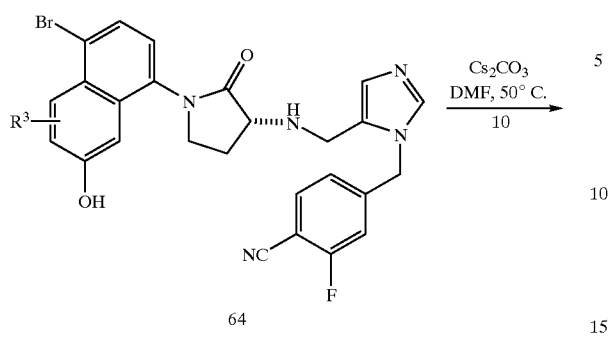
64
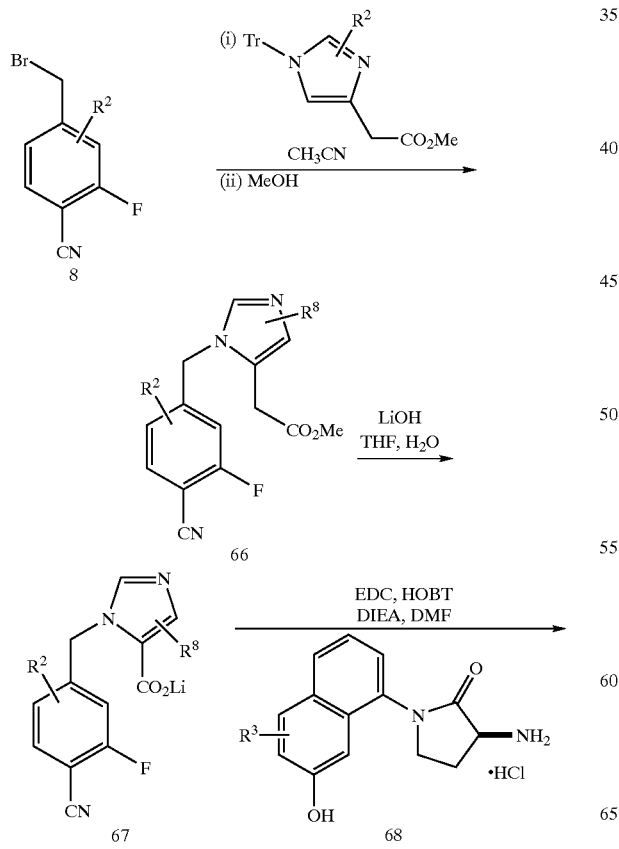
65
SCHEME 12
66
67  68
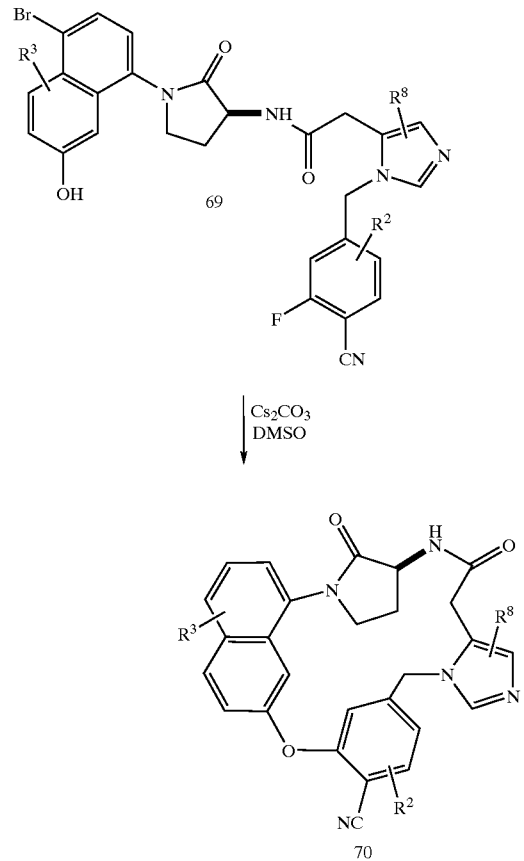
69
70
SCHEME 13
71
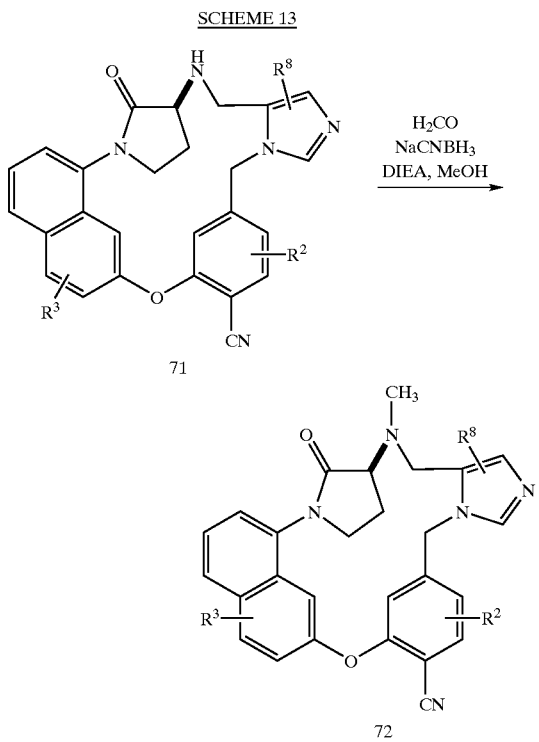
72

SCHEME 14
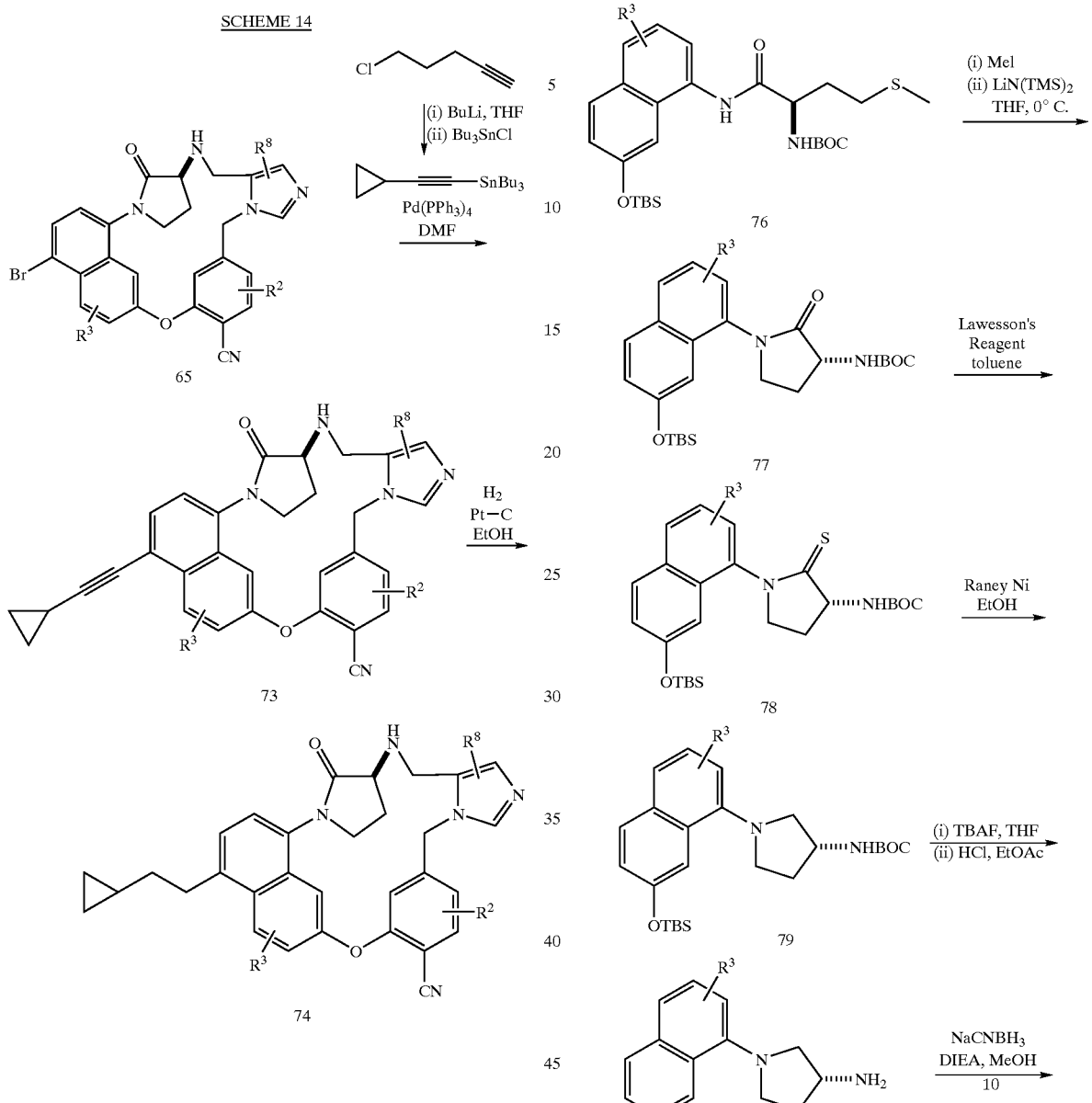
SCHEME 15
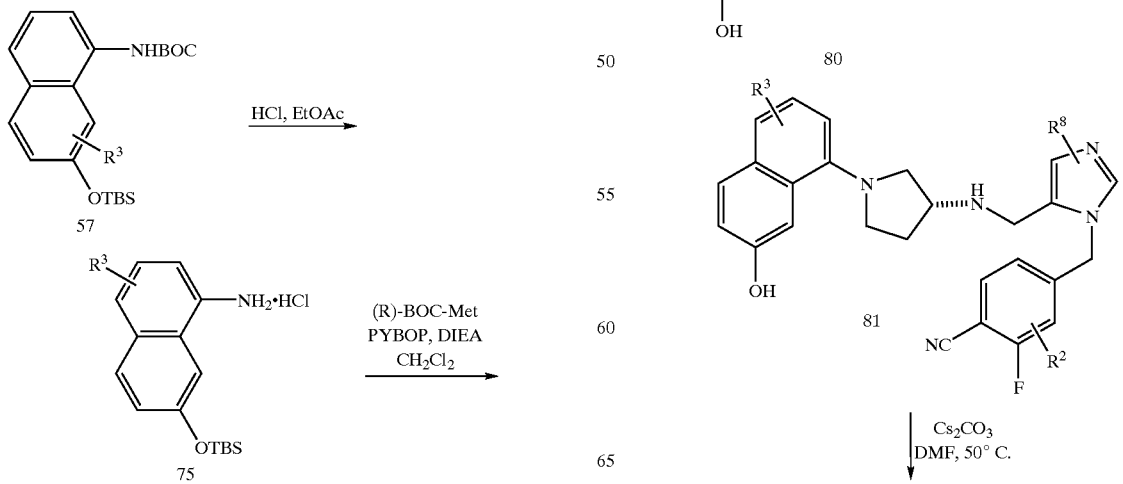

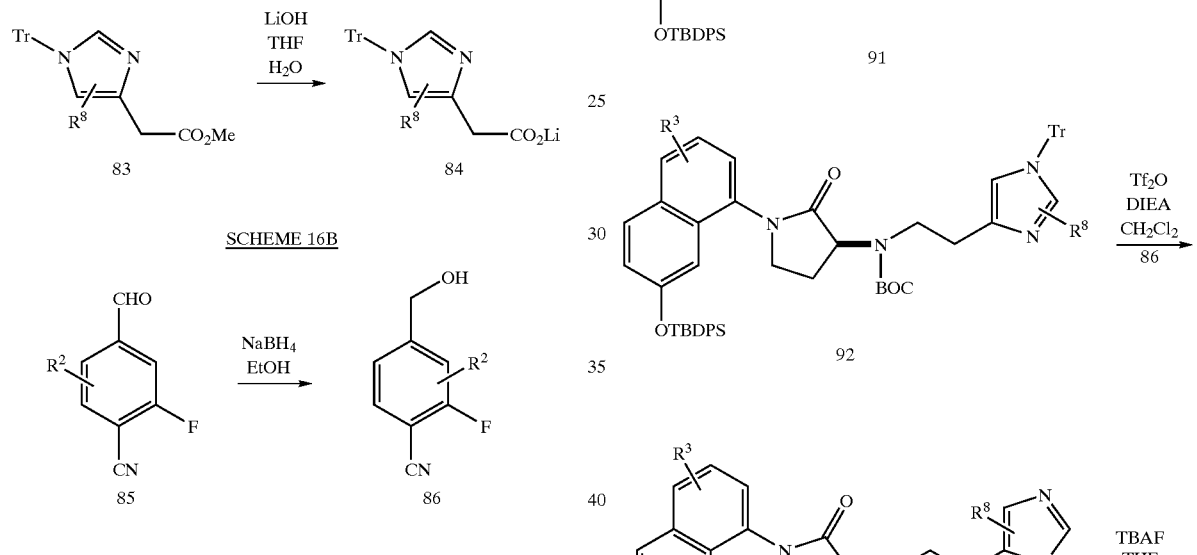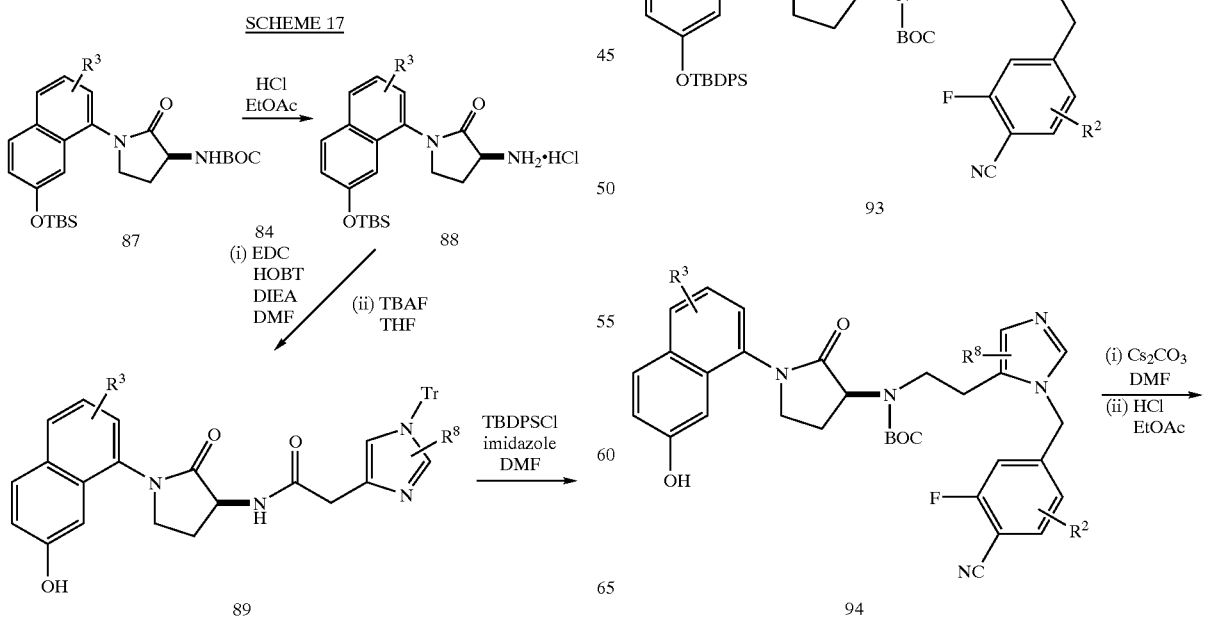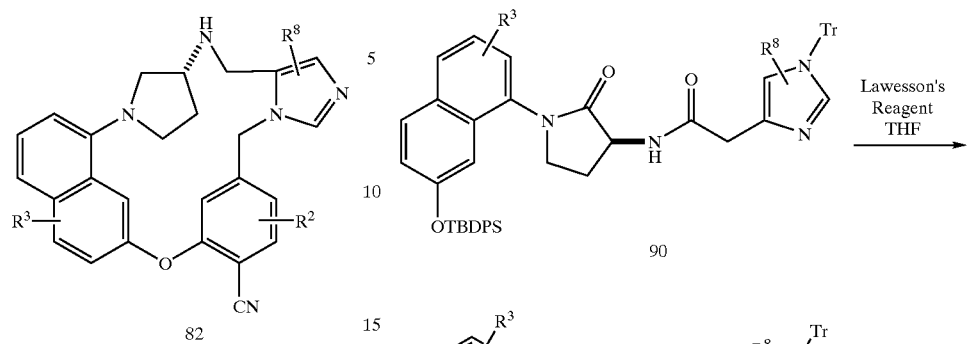

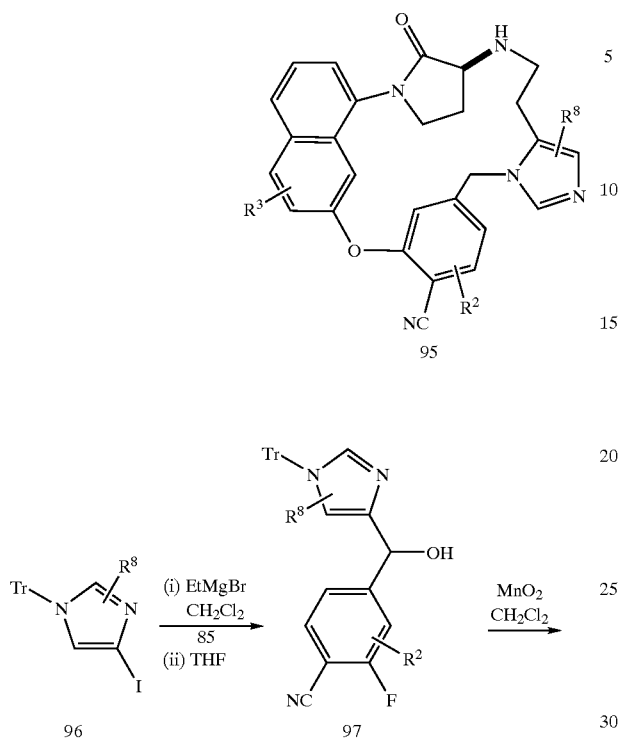
95
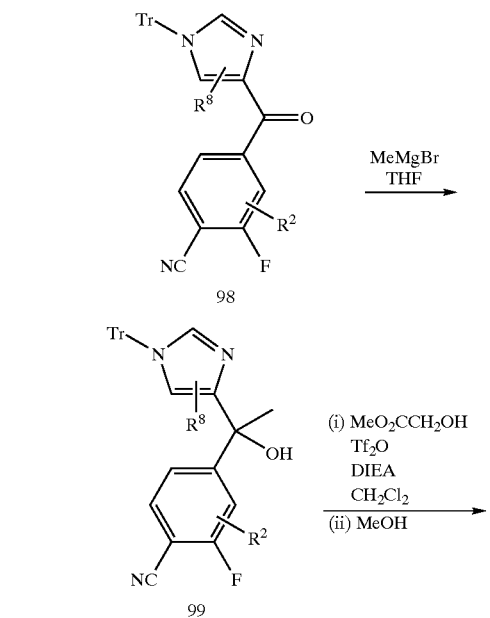
96 97
98
99
100
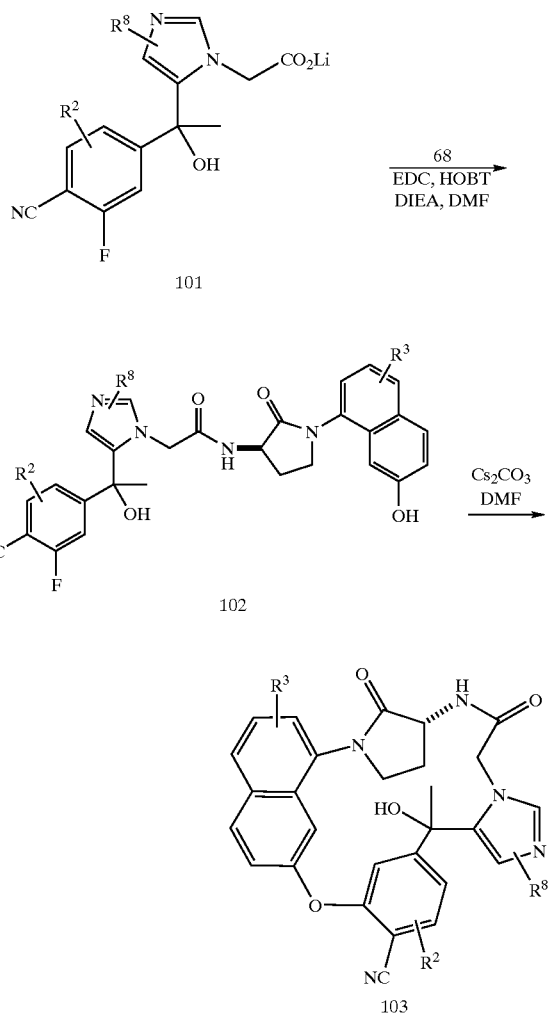
101
102
103
SCHEME 19
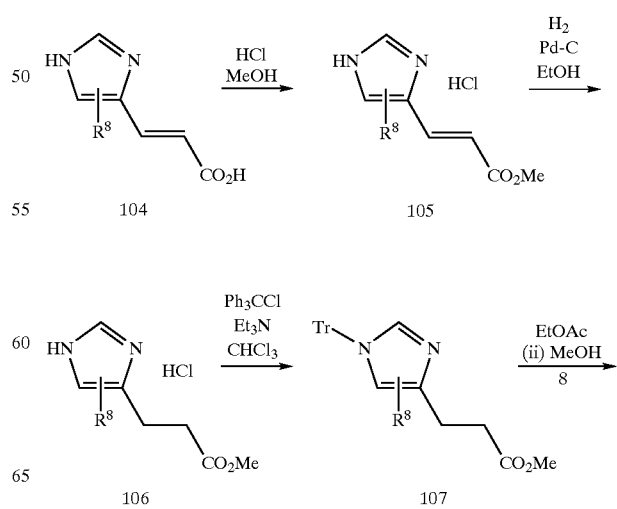
104 105
106 107

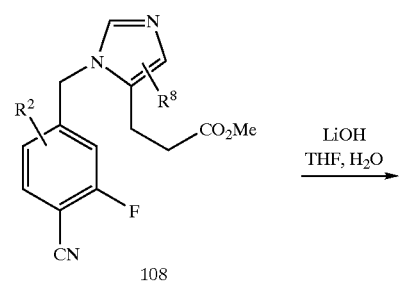
108
LiOH
THF, H₂O
→
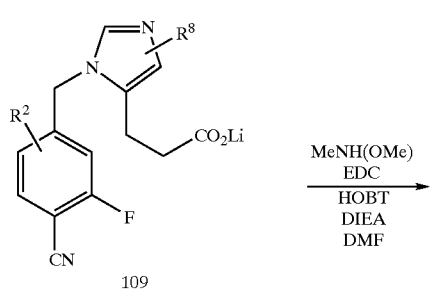
109
MeNH(OMe)
EDC
HOBT
DIEA
DMF
→
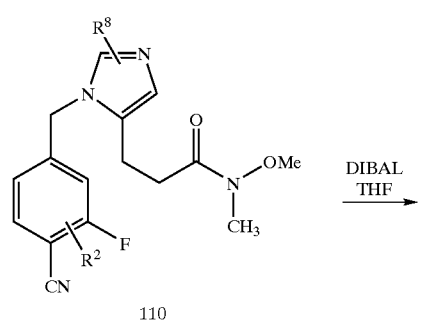
110
DIBAL
THF
→
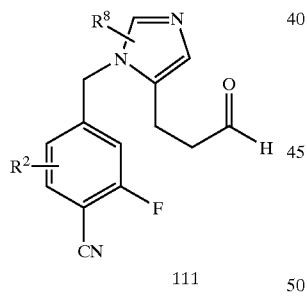
111
SCHEME 20
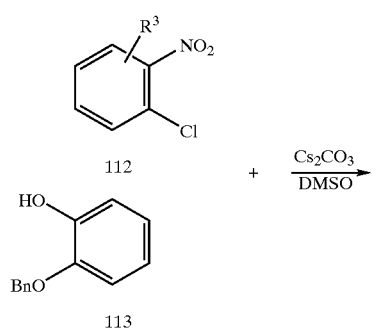
112
+
113
Cs₂CO₃
DMSO
→
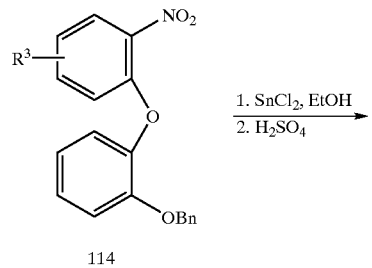
114
1. SnCl₂, EtOH
2. H₂SO₄
→
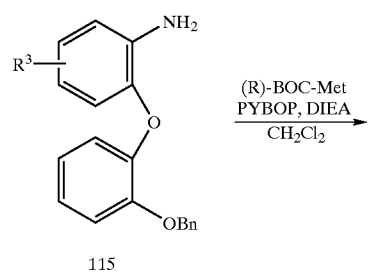
115
(R)-BOC-Met
PYBOP, DIEA
CH₂Cl₂
→
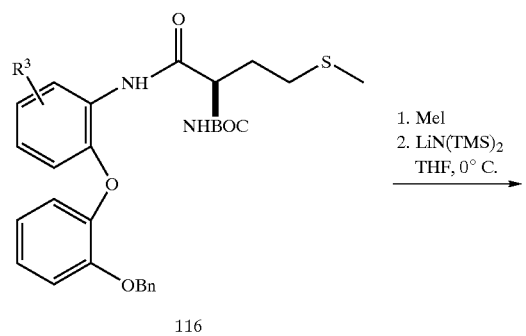
116
1. MeI
2. LiN(TMS)₂
THF, 0° C.
→
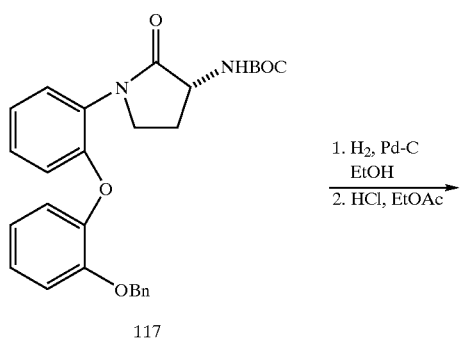
117
1. H₂, Pd-C
EtOH
2. HCl, EtOAc
→
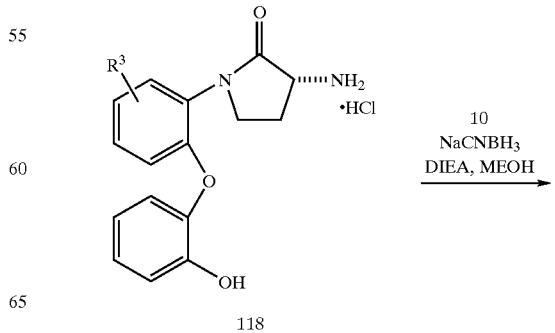
118
NaCNBH₃
DIEA, MEOH
→

-continued
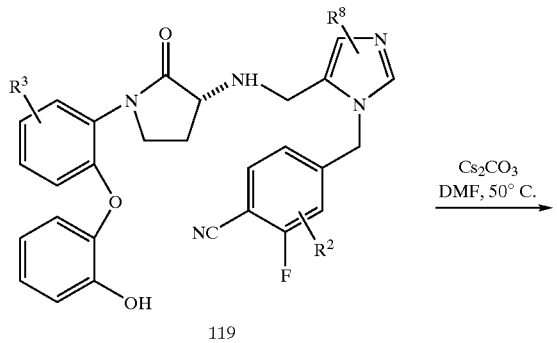
119
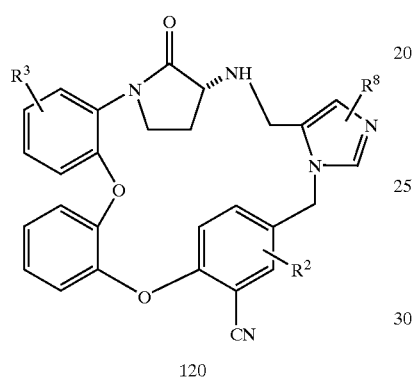
120
SCHEME 21
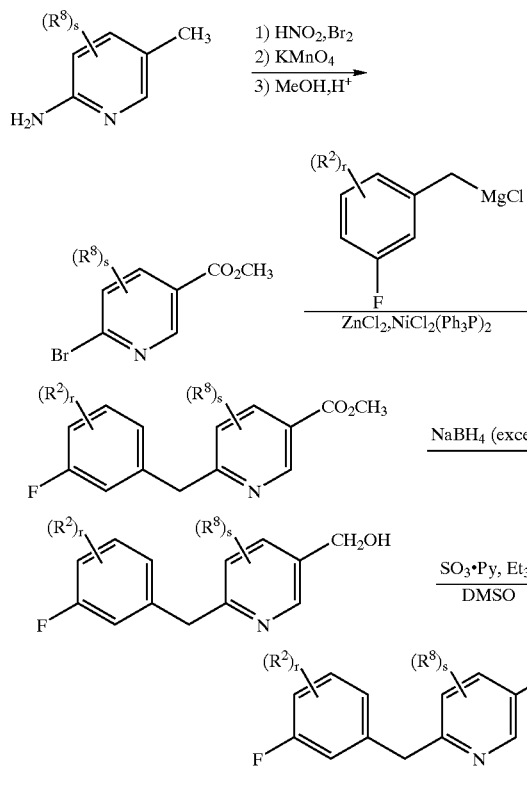
SCHEME 22
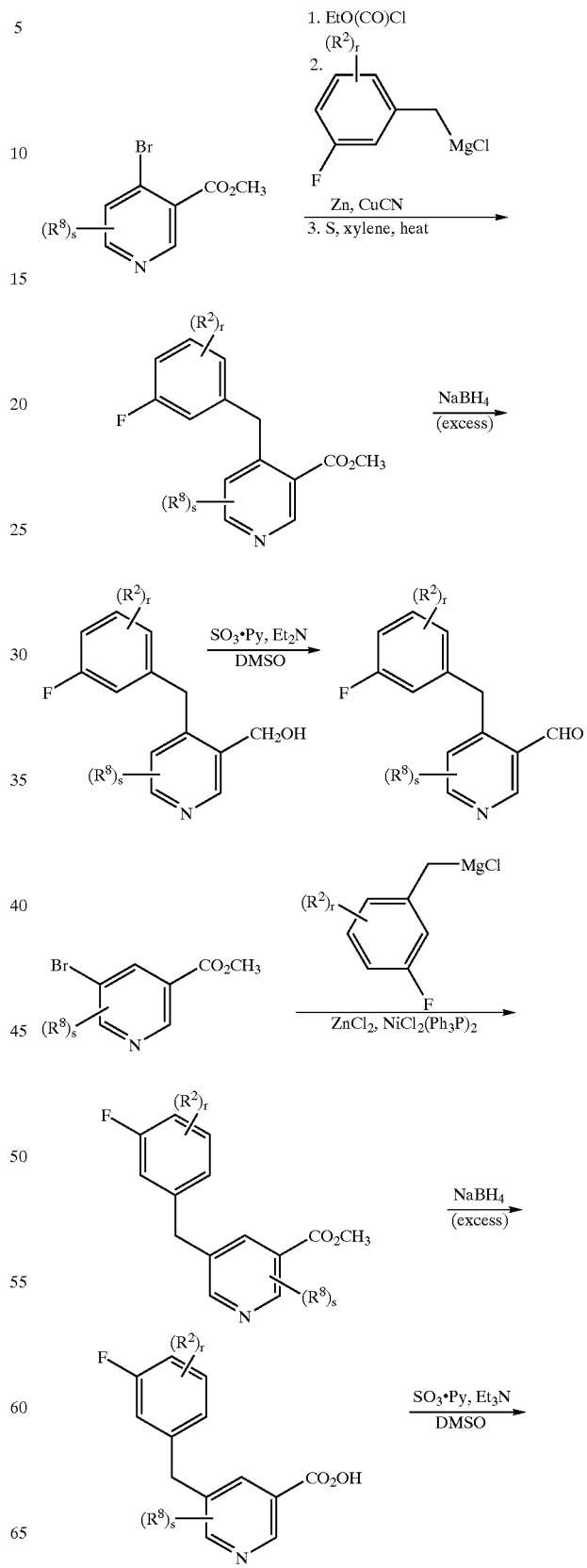

SCHEME 23

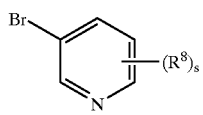

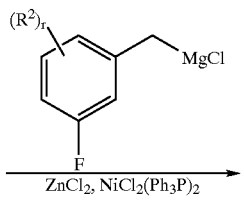

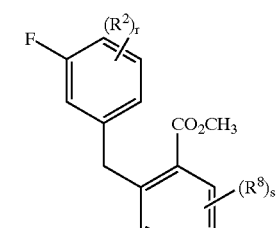

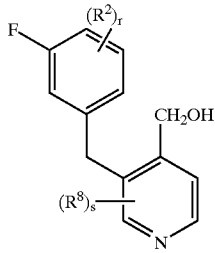

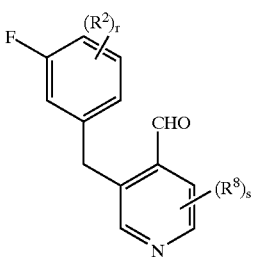

SCHEME 24

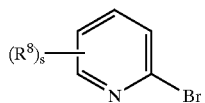

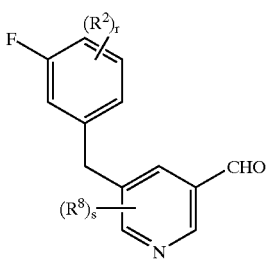

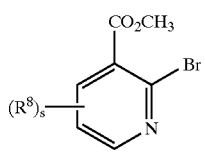

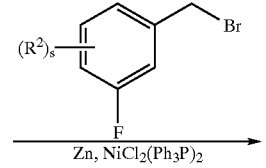

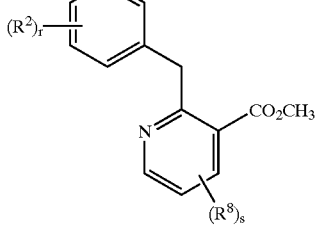

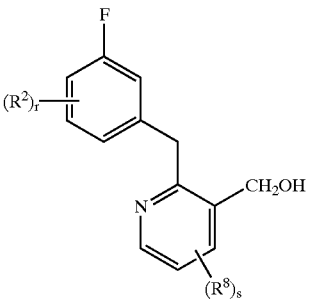

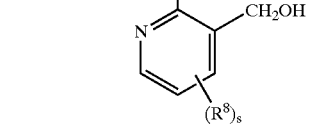

In order to simplify the structures described in the above schemes, mutiple designations of a substituent (i.e. $R^2$, $R^3$, $R^8$, etc.) have not always been included. However, it is understood that there may be several, independently selected substitutients around each of the rings described hereinabove, as seen in formulae A–D, hereinabove.

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 71, is at least 100 times greater than the in vitro activity of the same compound against geranylgeranyl-protein transferase-type I in the assay described in Example 72. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:

a) an $IC_{50}$ (a measure of in vitro inhibitory activity) for inhibition of the prenylation of newly synthesized K-Ras protein more than about 100-fold higher than the $EC_{50}$ for the inhibition of the farnesylation of hDJ protein. When measuring such $IC_{50}$s and $EC_{50}$s the assays described in Example 76 may be utilized.

It is also preferred that the selective inhibitor of farnesyl-protein transferase is further characterized by:

b) an $IC_{50}$ (a measurement of in vitro inhibitory activity) for inhibition of K4B-Ras dependent activation of MAP kinases in cells at least 100-fold greater than the $EC_{50}$ for inhibition of the farnesylation of the protein hDJ in cells.

It is also preferred that the selective inhibitor of farnesyl-protein transferase is further characterized by:

c) an $IC_{50}$ (a measurement of in vitro inhibitory activity) against H-Ras dependent activation of MAP kinases in cells at least 1000 fold lower than the inhibitory activity ($IC_{50}$) against H-ras-CVLL (SEQ.ID.NO.: 1) dependent activation of MAP kinases in cells.

When measuring Ras dependent activation of MAP kinases in cells the assays described in Example 75 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Example 75, it is preferred that the dual inhibitor compound has an in vitro inhibitory activity ($IC_{50}$) that is less than about 12 $\mu$M against K4B-Ras dependent activation of MAP kinases in cells.

The Class II prenyl-protein transferase inhibitor may also be characterized by:

a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 75.

In yet another embodiment, a compound of the instant invention may be a more potent inhibitor of geranylgeranyl-protein transferase-type I than it is an inhibitor of farnesyl-protein transferase.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, ab1, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the composition is useful in the treatment of neurofibromatosis, which is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of the instant invention may also be useful in the prevention and treatment of endometriosis, uterine fibroids, dysfunctional uterine bleeding and endometrial hyperplasia.

In such methods of prevention and treatment as described herein, the prenyl-protein transferase inhibitors of the instant invention may also be co-administered with other well known therapeutic agents that are selected for their particular usefulness against the condition that is being treated. For example, the prenyl-protein transferase inhibitor may be useful in further combination with drugs known to supress the activity of the ovaries and slow the growth of the endometrial tissue. Such drugs include but are not limited to oral contraceptives, progestins, danazol and GnRH (gonadotropin-releasing hormone) agonists.

Administration of the prenyl-protein transferase inhibitor may also be combined with surgical treatment of endometriosis (such as surgical removal of misplaced endometrial tissue) where appropriate.

The instant compounds may also be useful as inhibitors of corneal inflammation. These compounds may improve the treatment of corneal opacity which results from cauterization-induced corneal inflammation. The instant compounds may also be useful in reducing corneal edema and neovascularization. (K. Sonoda et al., *Invest. Ophthalmol. Vis. Sci.*, 1998, vol. 39, p 2245–2251).

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

Additionally, the compounds of the instant invention may be administered to a mammal in need thereof using a gel extrusion mechanism (GEM) device, such as that described in U.S. Ser. No. 60/144,643, filed on Jul. 20, 1999, which is hereby incorporated by reference.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant farnesyl-protein transferase inhibitors and an antineoplastic agent. It is also understood that such a combination of antineoplastic agent and inhibitor of farnesyl-protein transferase may be used in conjunction with other methods of treating cancer and/or tumors, including radiation therapy and surgery. It is further understood that any of the therapeutic agents described herein may also be used in combination with a compound of the instant invention and an antineoplastic agent.

Examples of an antineoplastic agent include, in general, microtubule-stabilizing agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, for example, nitrogen mustards, ethyleneimine compounds, alkyl sulfonates and other compounds with an alkylating action such as nitrosoureas, cisplatin, and dacarbazine; anti-metabolites, for example, folic acid, purine or pyrimidine antagonists; epidophyllotoxin; an antineoplastic enzyme; a topoisomerase inhibitor; procarbazine; mitoxantrone; platinum coordination complexes; biological response modifiers and growth inhibitors; mitotic inhibitors, for example, vinca alkaloids and derivatives of podophyllotoxin; cytotoxic antibiotics; hormonal/anti-hormonal therapeutic agents, haematopoietic growth factors and antibodies (such as trastuzumab (Herceptin™)).

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, canninomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, dactinomycin, mechlorethamine (nitrogen mustard), streptozocin, cyclophosphamide, carmustine (BCNU), lomustine (CCNU), procarbazine, mitomycin, cytarabine, etoposide, methotrexate, bleomycin, chlorambucil, camptothecin, CPT-11, topotecan, ara-C, bicalutamide, flutamide, leuprolide, pyridobenzoindole derivatives, interferons and interleukins. Particular examples of antineoplastic, or chemotherapeutic, agents are described, for example, by D. J. Stewart in "Nausea and Vomiting: Recent Research and Clinical Advances", Eds. J. Kucharczyk, et al., CRC Press Inc., Boca Raton, Fla., USA (1991), pages 177–203, especially page 188. See also, R. J. Gralla, et al., Cancer Treatment Reports, 68(1), 163–172 (1984).

The preferred class of antineoplastic agents is the taxanes and the preferred antineoplastic agent is paclitaxel.

A compound of the present invention may be employed in conjunction with antiemetic agents to treat nausea or emesis, including acute, delayed, late-phase, and anticipatory emesis, which may result from the use of a compound of the present invention, alone or with radiation therapy. For the prevention or treatment of emesis a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, or a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712. For the treatment or prevention of emesis, conjunctive therapy with a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95120575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

A particularly preferred neurokinin-1 receptor antagonist for use in conjunction with the compounds of the present invention is 2-(R)-(1-(R)-(3,5-bis(trifluoromethyl)phenyl) ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

For the treatment of cancer, it may be desirable to employ a compound of the present invention in conjunction with another pharmacologically active agent(s). A compound of the present invention and the other pharmacologically active agent(s) may be administered to a patient simultaneously, sequentially or in combination. For example, the present compound may employed directly in combination with the other active agent(s), or it may be administered prior, concurrent or subsequent to the administration of the other active agent(s). In general, the currently available dosage forms of the known therapeutic agents for use in such combinations will be suitable.

For example, a compound of the present invention may be presented together with another therapeutic agent in a combined preparation, such as with an antiemetic agent for simultaneous, separate, or sequential use in the relief of emesis associated with employing a compound of the present invention and radiation therapy. Such combined preparations may be, for example, in the form of a twin pack. A preferred combination comprises a compound of the present invention with antiemetic agents, as described above.

Radiation therapy, including x-rays or gamma rays which are delivered from either an externally applied beam or by implantation of tiny radioactive sources, may also be used in combination with the instant inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase.

In particular, if the compound of the instant invention is a selective inhibitor of farnesyl-protein transferase, co-administration with a compound(s) that is a selective inhibitor of geranylgeranyl protein transferase may provide an improved therapeutic effect.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, and WO 98/44797, published on Oct. 15, 1998, which are incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the αvβ3 integrin, which selectively antagonize, inhibit or counteract binding of a physiological ligand to the αvβ5 integrin, which antagonize, inhibit or counteract binding of a physiological ligand to both the αvβ3 integrin and the αvβ5 integrin, or which antagonize, inhibit or counteract the activity of the particular integrin(s) expressed on capillary endothelial cells. The term also refers to antagonists of the α1β1, α2β1, α5β1, α6β1 and α6β4 integrins. The term also refers to antagonists of any combination of αvβ3 integrin, αvβ5 integrin, α1β1, α2β1, α5β1, α6β1 and α6β4 integrins. The instant compounds may also be useful with other agents that inhibit angiogenisis and thereby inhibit the growth and invasiveness of tumor cells, including, but not limited to angiostatin and endostatin.

The instant compounds may also be useful in combination with an inhibitor of 3-hydroxy-3-methylglutaryl-CoA reductase (HMG-CoA reductase) for the treatment of cancer. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

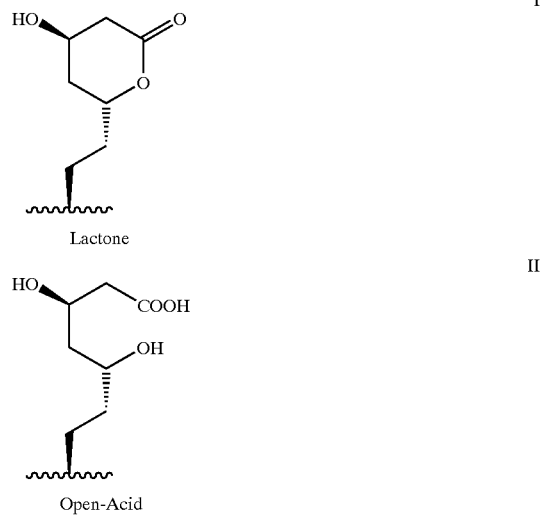

In HMG-CoA reductase inhibitor's where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methyl-benzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described above and the other pharmaceutically active agent(s) within its approved dosage range. Combinations of the instant invention may alternatively be used sequentially with known pharmaceutically acceptable agent(s) when a multiple combination formulation is inappropriate.

The instant compounds may also be useful in combination with prodrugs of antineoplastic agents. In particular, the instant compounds may be co-administered either concurrently or sequentially with a conjugate (termed a "PSA conjugate") which comprises an oligopeptide, that is selectively cleaved by enzymatically active prostate specific antigen (PSA), and an antineoplastic agent. Such co-administration will be particularly useful in the treatment of prostate cancer or other cancers which are characterized by the presence of enzymatically active PSA in the immediate surrounding cancer cells, which is secreted by the cancer cells.

Compounds which are PSA conjugates and are therefore useful in such a co-administration, and methods of synthesis thereof, can be found in the following patents, pending patent applications and publications which are herein incorporated by reference:
U.S. Pat. No. 5,599,686, granted on Feb. 4, 1997;
WO 96/00503 (Jan. 11, 1996); U.S. Ser. No. 08/404,833, filed on Mar. 15, 1995; U.S. Ser. No. 08/468,161, filed on Jun. 6, 1995;
U.S. Pat. No. 5,866,679, granted on Feb. 2, 1999;
WO 98/10651 (Mar. 19, 1998); U.S. Ser. No. 08/926,412, filed on Sep. 9, 1997;
WO 98/18493 (May 7, 1998); U.S. Ser. No. 08/950,805, filed on Oct. 14, 1997;
WO 99/02175 (Jan. 21, 1999); U.S. Ser. No. 09/112,656, filed on Jul. 9, 1998; and
WO 99/28345 (Jun. 10, 1999); U.S. Ser. No. 09/193,365, filed on Nov. 17, 1998.

Compounds which are described as prodrugs wherein the active therapeutic agent is released by the action of enzymatically active PSA and therefore may be useful in such a co-administration, and methods of synthesis thereof, can be found in the following patents, pending patent applications and publications, which are herein incorporated by reference: WO 98/52966 (Nov. 26, 1998).

All patents, publications and pending patent applications identified are herein incorporated by reference.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immuno-logical, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

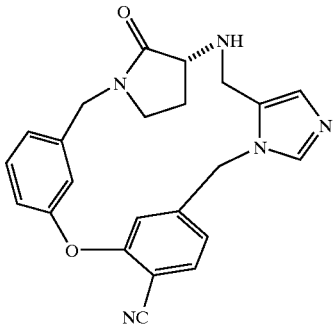

Preparation of (20R)-19,20,21,22-Tetrahydro-19-oxo-17H-18,20-ethano-6,10:12,16-dimetheno-16H-imidazo[3,4-h][1,8,11,14]oxatriazacycloeicosine-9-carbonitrile Hydrochloride Step A: 4-(Hydroxymethyl)-1-(triphenylmethyl)imidazole To a solution of 4-(hydroxymethyl)imidazole hydrochloride (35.0 g, 260 mmol) in dry DMF (250 mL) at room temperature was added triethylamine (90.6 mL, 650 mmol). A white solid precipitated from the solution. Chlorotriphenyl-methane (76.1 g, 273 mmol) in DMF (500 mL) was added dropwise. The reaction mixture was stirred for 20 hours, poured over ice, filtered, and washed with ice water. The resulting product was slurried with cold dioxane, filtered, and dried in vacuo to provide the titled product as a white solid.

Step B: 4-(Acetoxymethyl)-1-(triphenylmethyl)imidazole 4-(Hydroxymethyl)-1-(triphenylmethyl)imidazole, as described above in Step A, (88.5 g, 260 mmol) was suspended in pyridine (500 mL). Acetic anhydride (74 mL, 780 mmol) was added dropwise, and the reaction was stirred for 48 hours during which it became homogeneous. The solution was poured into EtOAc, and washed sequentially with water, 5% aqueous HCl solution, saturated aqueous NaHCO$_3$ solution, and brine. The organic extracts were dried (Na$_2$SO$_4$), and concentrated in vacuo to provide the ester as a white powder.

Step C: 4-Cyano-3-fluorotoluene

To a deoxygenated solution of 4-bromo-3-fluorotoluene (25.0 g, 132 mmol) in DMF (500 mL) was added $Zn(CN)_2$ (10.1 g, 86 mmol) and $Pd(PPh_3)_4$ (15 g, 13 mmol). The reaction was stirred at 100° C. for 18 hours, then cooled to room temperature. The solution was poured into toluene (1 L), washed with 30% aqueous $NH_4OH$ (2×1 L), then brine (800 mL), then dried ($Na_2SO_4$), filtered, and concentrated in vacuo to provide the crude product. Purification by silica gel chromatography, eluting with a gradient of hexane –0% to 7% EtOAc, yielded the titled product.

Step D: 4-Cyano-3-fluorobenzyl Bromide

To a solution of 4-cyano-3-fluorotoluene, as described above in Step C, (5.0 g, 37.0 mmol) in carbon tetrachloride (300 mL) was added N-bromosuccinimide (7.57 g, 42.6 mmol) and 2,2'-azobisisobutyronitrile (610 mg, 3.7 mmol). The reaction mixture was heated to reflux under argon for 24 hours, then cooled to room temperature, filtered, and concentrated under reduced pressure. The residue was purified by silica gel chromatography, eluting with a gradient of hexane—4% to 7% EtOAc, to yield the titled product as a yellow solid.

Step E: 5-(Acetoxymethyl)-1-(4-cyano-3-fluorobenzyl) imidazole Hydrobromide

A mixture of 4-(acetoxymethyl)-1-(triphenylmethyl) imidazole, as described above in Step B, (19.7 g, 51.4 mmol) and 4-cyano-3-fluorobenzyl bromide, as described above in Step D, (11.0 g, 51.4 mmol) in dry $CH_3CN$ (140 mL) was stirred at 50° C. for 3 hours, during which a white precipitate formed. The reaction was cooled to room temperature and filtered to provide the solid imidazolium bromide salt. The filtrate was concentrated in vacuo to a volume of 70 mL, reheated at 50° C. for 2 hours, cooled to room temperature, and filtered again. The solid material was combined and dissolved in MeOH (500 mL), and the solution was heated to reflux for 2 hours. The solution was concentrated in vacuo to a volume of 20 mL, then cold hexane—EtOAc (1:1, 500 mL) was added and the white precipitate was collected and dried in vacuo.

Step F: 1-(4-Cyano-3-fluorobenzyl)-5-(hydroxymethyl) imidazole

To a solution of 5-(acetoxymethyl)-1-(4-cyano-3-fluorobenzyl) imidazole, as described above in Step E, (19.8 g, 72.5 mmol) in 5:1 THF/water (430 mL) at ambient temperature was added lithium hydroxide monohydrate (3.33 g, 79.4 mmol). After 4 hours, the solution was adjusted to pH 7 with 1.0 N hydrochloric acid and concentrated in vacuo. The residue was concentrated from toluene in vacuo (3×100 mL) to give the titled product as a pale solid.

Step G: 1-(4-Cyano-3-fluorobenzyl)-5-imidazolecarboxaldehyde

To a solution of 1-(4-cyano-3-fluorobenzyl)-5-(hydroxymethyl) imidazole, as described above in Step F, (2.31 g, 10.0 mmol) in 20 mL of DMSO at 0° C. was added triethylamine (5.6 mL, 40 mmol), then $SO_3$-pyridine complex (3.89 g, 25 mmol). After 30 minutes, the reaction was poured into EtOAc, washed with water and brine, dried ($Na_2SO_4$), filtered, and concentrated in vacuo to provide the aldehyde as a pale yellow powder.

Step H: 3-Benzyloxybenzyl Azide

To a stirred solution of 3-benzyloxybenzyl alcohol (5.0 g, 23.3 mmol) and diphenylphosphoryl azide (7.7 g, 28.0 mmol) in dry toluene (40 mL) at 0° C., was added 1,8-diazabicyclo[5.4.0]undec-7-ene (3.9 g, 25.6 mmol). The resulting mixture was allowed to warm to ambient temperature, and stirred under argon for 18 hours, then washed with water (2×15 mL), then 5% hydrochloric acid (15 mL). The organic layer was dried over $MgSO_4$, filtered, and concentrated in vacuo. The crude product was purified by flash column chromatography on silica, eluting with hexane—4% EtOAc to yield the product as a colorless oil.

Step I: 3-Benzyloxybenzylamine

3-Benzyloxybenzyl azide, as described above in Step H, (5.0 g, 20.9 mmol) was dissolved in dry THF (100 mL) and the solution was cooled to –70° C. Lithium aluminum hydride (31.4 mL of a 1.0 M solution in THF, 31.4 mmol) was added dropwise, then the reaction mixture was warmed to 0° C. and stirred for 30 min. The reaction was quenched with EtOAc (1.2 mL), then water (1.2 mL), then 15% NaOH (1.2 mL), and finally water (3.6 mL). The resulting mixture was filtered, concentrated under reduced pressure and purified by flash column chromatography on silica, eluting with $CH_2Cl_2$—3% MeOH—0.3% $NH_4OH$, to yield the titled product as a colorless oil.

Step J: (R)-2-(tert-Butoxycarbonylamino)-4-(methylmercapto)-N-(3-benzyloxybenzyl)butyramide To (R)-N-(tert-butoxycarbonyl)methionine (1.20 g, 4.8 mmol) in dry $CH_2Cl_2$ (25 mL) under argon were added PYBOP (2.90 g, 5.6 mmol), 3-benzyloxybenzylamine, as described above in Step I, (1.0 g, 4.7 mmol), and N,N-diisopropylethylamine (0.89 mL, 5.1 mmol). The reaction mixture was stirred for 18 hours, then extracted with saturated aqueous $NaHCO_3$ (25 mL), dried over $MgSO_4$, filtered, and concentrated in vacuo. The crude product was purified by flash column chromatography on silica, eluting with hexane—25% EtOAc to yield the product as a white solid.

Step K: (R)-2-(tert-Butoxycarbonylamino)-4-(dimethylsulfonium)-N-(3-benzyloxybenzyl)butyramide Iodide (R)-2-(tert-Butoxycarbonylamino)-4-(methylmercapto)-N-(3-benzyloxybenzyl)butyramide, as described above in Step J, (2.00 g, 4.50 mmol) was dissolved in iodomethane (12 mL, 193 mmol) and the solution was stirred under argon for 18 hours. The iodomethane was removed by distillation under reduced pressure to give the sulfonium salt as a yellow solid.

Step L: (R)-1-(3-Benzyloxybenzyl)-3-(tert-butoxycarbonylamino)-2-oxopyrrolidine (R)-2-(tert-Butoxycarbonylamino)-4-(dimethylsulfonium)-N-(3-benzyloxybenzyl)butyramide iodide, as described above in Step K, (2.60 g, 4.43 mmol) was stirred in dry THF (75 mL), under argon, at 0° C. and lithium bis(trimethylsilyl)amide (1.0 M in THF, 4.2 mL, 4.2 mmol) was added dropwise. The reaction mixture was stirred at 0° C. for 2 h, then quenched with saturated aqueous $NH_4Cl$ (25 mL) and most of the THF was removed under reduced pressure. The residual solution was partitioned between saturated aqueous $NaHCO_3$ (25 mL) and $CH_2Cl_2$ (75 mL). The aqueous layer was extracted further with $CH_2Cl_2$ (2×25 mL). The combined organic extracts were dried over $MgSO_4$, filtered, and concentrated in vacuo. The crude product was purified by flash column chromatography on silica, eluting with hexane—40% EtOAc to yield the pyrrolidinone as a white semi-solid.

Step M: (R)-3-(tert-Butoxycarbonylamino)-1-(3-hydroxybenzyl)-2-oxopyrrolidine

To a solution of (R)-1-(3-benzyloxybenzyl)-3-(tert-butoxycarbonylamino)-2-oxopyrrolidine, as described above in Step L, (500 mg, 1.26 mmol) in EtOH (75 mL) was added 20% $Pd(OH)_2$ on carbon (75 mg) and the reaction mixture was stirred under an atmosphere of hydrogen (ca. 1 atm) at ambient temperature for 18 hours. The mixture was filtered through a pad of celite, washing with EtOH, and the filtrate was concentrated in vacuo to give a crude product. This was purified by flash column chromatography on silica, eluting with CHCl$_3$—3% MeOH—0.3% NH$_4$OH, to yield the titled product as a colorless oil.

Step N: (R)-3-Amino-1-(3-hydroxybenzyl)-2-oxopyrrolidine Hydrochloride

A solution of (R)-3-(tert-butoxycarbonylamino)-1-(3-hydroxybenzyl)-2-oxopyrrolidine, as described above in Step M, (350 mg, 1.14 mmol) in EtOAc (20 mL) at 0° C. was saturated with HCl (g). After 15 min, the mixture was concentrated in vacuo to yield the amine hydrochloride as a white solid.

Step O: (R)-2-Fluoro-4-(5-{[1-(3-hydroxybenzyl)-2-oxopyrrolidin-3-ylamino]methyl}imidazol-1-ylmethyl)benzonitrile (R)-3-Amino-1-(3-hydroxybenzyl)-2-oxopyrrolidine hydrochloride, as described above in Step N, (200 mg, 0.82 mmol) and 1-(4-cyano-3-fluorobenzyl)-5-imidazolecarboxaldehyde, as described above in Step G, (197 mg, 0.86 mmol), were stirred in MeOH (7 mL) and N,N-diisopropylethylamine was added dropwise to adjust the mixture to ca. pH 5, as judged by wetted pH paper. The mixture was stirred for 1 hour at ambient temperature, then NaCNBH$_3$ (54 mg, 0.86 mmol) was added and stirring was continued for 18 hours. The reaction was quenched with saturated aqueous NaHCO$_3$ (2 mL) and most of the MeOH was removed under reduced pressure. The residual solution was partitioned between saturated aqueous NaHCO$_3$ (3 mL) and CH$_2$Cl$_2$ (10 mL). The aqueous layer was extracted further with CH$_2$Cl$_2$ (3×10 mL). The combined organic extracts were dried over MgSO$_4$, filtered, and concentrated in vacuo. The crude product was purified by flash column chromatography on silica, eluting with two column volumes of EtOAc—10% MeOH, then two column volumes of CHCl$_3$—4% MeOH, then CHCl$_3$—4% MeOH—0.4% NH$_4$OH to yield the titled product as a colorless oil.

Step P: (20R)-19,20,21,22-Tetrahydro-19-oxo-17H-18,20-ethano-6,10:12,16-dimetheno-16H-imidazo[3,4-h][1,8,11,14]oxatriazacycloeicosine-9-carbonitrile Hydrochloride A mixture of (R)-2-fluoro-4-(5-{[1-(3-hydroxybenzyl)-2-oxopyrrolidin-3-ylamino]methyl}imidazol-1-ylmethyl)benzonitrile, as described above in Step O, (200 mg, 0.48 mmol) and Cs$_2$CO$_3$ (233 mg, 0.72 mmol) in dry, degassed DMF (4 mL) was stirred at 50° C. under argon for 18 hours. Acetic acid (60 mL, 1.0 mmol) was added and the solvent was removed under reduced pressure. The residue was partitioned between saturated aqueous NaHCO$_3$ (5 mL) and CHCl$_3$ (10 mL). The aqueous layer was extracted further with CHCl$_3$ (3×10 mL). The combined organic extracts were dried over MgSO$_4$, filtered, and concentrated in vacuo. The crude product was purified by flash column chromatography on silica, eluting with CHCl$_3$—4% MeOH—0.4% NH$_4$OH to yield the desired product which was converted to the hydrochloride salt by treatment with HCl in EtOAc.

Elemental analysis calculated for C$_{23}$H$_{21}$N$_5$O$_2$.1.7 HCl.1.9 H$_2$O: C: 55.83; H: 5.38; N: 14.16; Found: C: 55.88; H: 5.39; N: 13.91; FAB MS: 400 (MH$^+$).

Example 2

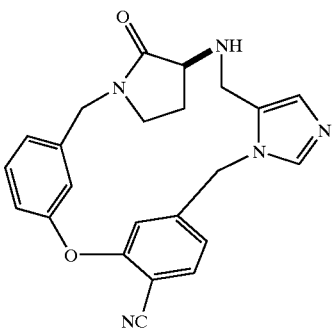

Preparation of (20S)-19,20,21,22-Tetrahydro-19-oxo-17H-18,20-ethano-6,10:12,16-dimetheno-16H-imidazo[3,4-h][1,8,11,14]oxatriaza-cycloeicosine-9-carbonitrile Hydrochloride The above-titled compound was prepared following the procedure described in Example 1, but using (S)-N-(tert-butoxycarbonyl)methionine in place of (R)-N-(tert-butoxycarbonyl)methionine in Step J.

Elemental analysis calculated for C$_{23}$H$_{21}$N$_5$O$_2$.2 HCl.1.2 H$_2$O: C: 55.92; H: 5.18; N: 14.18;

Found: C: 55.91; H: 5.19; N: 14.07; FAB MS: 400 (MH$^+$).

Example 3

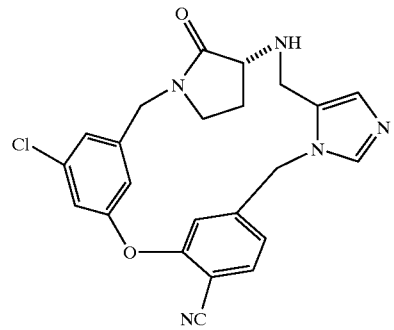

Preparation of (20R)-14-Chloro-19,20,21,22-tetrahydro-19-oxo-17H-18,20-ethano-6,10:12,16-dimetheno-16H-imidazo[3,4-h][1,8,11,14]oxatriaza-cycloeicosine-9-carbonitrile Hydrochloride Step A: Benzyl 3,5-dichlorophenyl Ether To a stirred mixture of 3,5-dichlorophenol (3.00 g, 18.4 mmol) and Cs$_2$CO$_3$ (12.0 g, 36.8 mmol) in dry, degassed DMF (150 mL) was added benzyl bromide (3.46 g, 20.2 mmol) dropwise. The reaction mixture was heated to 45° C. for 18 hours, then the solvent was removed under reduced pressure. The residue was partitioned between saturated aqueous NaHCO$_3$ (75 mL) and CH$_2$Cl$_2$ (100 mL). The aqueous layer was extracted further with CH$_2$Cl$_2$ (25 mL). The combined organic extracts were dried over MgSO$_4$, filtered, and concentrated in vacuo. The crude product was purified by flash column chromatography on silica, eluting with hexane—2% EtOAc to yield the desired product as a colorless oil.

Step B: 3-Benzyloxy-5-chlorobenzoic Acid

To a stirred suspension of Rieke Mg (1.0 g, 41 mmol) in refluxing dry THF (45 mL) and iodomethane (0.1 mL, 1.6 mmol) under argon was added benzyl 3,5-dichlorophenyl ether, as described above in Step A, (10.0 g, 39.5 mmol) in dry THF (100 mL) dropwise, over 10 min, with the heat source removed. The resulting mixture was heated to reflux for 1 hour, then cooled to −12° C. and $CO_2$ was bubbled into the solution slowly for 1 hour. The reaction mixture was stirred for an additional 1 hour at 0° C., then quenched with 10% hydrochloric acid (25 mL) and most of the THF was removed in vacuo. The residual mixture was partitioned between hexane (300 mL) and 10% aqueous NaOH (500 mL) containing MeOH (100 mL). The hexane layer was extracted twice more with 10% aqueous NaOH (100 mL) containing MeOH (20 mL), and the combined aqueous extracts were acidified to pH 2 with 25% hydrochloric acid, then extracted with $CHCl_3$ (2×250 mL). The combined organic extracts were dried over $MgSO_4$, filtered, and concentrated in vacuo to give the desired product as a white solid.

Step C: 3-Benzyloxy-5-chlorobenzyl Alcohol

To a stirred solution of 3-benzyloxy-5-chlorobenzoic acid, as described above in Step B, (5.0 g, 19 mmol) in dry THF (150 mL) at 0° C., under argon, was added $LiAlH_4$ (29 mL of a 1.0 M solution in THF, 29 mmol) dropwise. The reaction mixture was stirred at ambient temperature for 3 hours, then EtOAc (1 mL) was added, followed by water (1 mL), then 15% aqueous NaOH (1 mL), then water (3 mL). The resulting mixture was filtered and concentrated in vacuo. The crude residue was purified by flash column chromatography on silica, eluting with hexane—20% EtOAc to yield the desired product as a colorless oil.

Step D: (20R)-14-Chloro-19,20,21,22-tetrahydro-19-oxo-17H-18,20-ethano-6,10:12,16-dimetheno-16H-imidazo[3,4-h][1,8,11,14]oxatriazacycloeicosine-9-carbonitrile Hydrochloride Following the procedure described in Example 1, but using 3-benzyloxy-5-chlorobenzyl alcohol (as described in Example 3, Step C) in place of 3-benzyloxybenzyl alcohol in Step H, the above compound was prepared.

Elemental analysis calculated for $C_{23}H_{20}ClN_5O_2 \cdot 2.3$ $HCl \cdot 0.55 H_2O$: C: 52.53; H: 4.48; N: 13.32; Found: C: 52.53; H: 4.49; N: 13.14; FAB MS: 434 (MH⁺).

Example 4

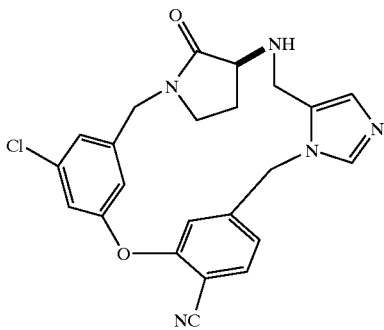

Preparation of (20S)-14-Chloro-19,20,21,22-tetrahydro-19-oxo-17H-18,20-ethano-6,10:12,16-dimetheno-16H-imidazo[3,4-h][1,8,11,14]oxatriazacycloeicosine-9-carbonitrile Hydrochloride Following the procedure described in Example 1, but using 3-benzyloxy-5-chlorobenzyl alcohol (from Example 3, Step C) in place of 3-benzyloxybenzyl alcohol in Step H, and (S)-N-(tert-butoxycarbonyl)methionine in place of (R)-N-(tert-butoxycarbonyl)methionine in Step J, the above-titled compound was prepared.

Elemental analysis calculated for $C_{23}H_{20}ClN_5O_2 \cdot 2$ $HCl \cdot H_2O$: C: 52.63; H: 4.61; N: 13.34; Found: C: 52.59; H: 4.60; N: 13.34; FAB MS: 434 (MH⁺).

Example 5

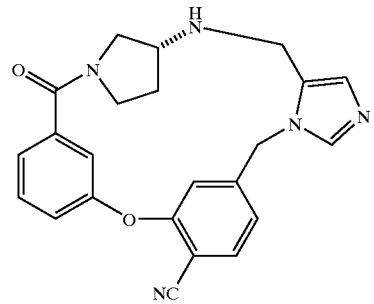

Preparation of (21R)-20,21,22,23-Tetrahydro-17-oxo-5H,17H,19H-18,21-methano-6,10:12,16-dimethenoimidazo[3,4-h][1,8,11,15]oxatriazacyclohenicosine-9-carbonitrile Hydrochloride Step A: (R)-3-(tert-Butoxycarbonylamino)-1-(3-hydroxybenzoyl)pyrrolidine 3-Hydroxybenzoic acid (500 mg, 3.62 mmol), (R)-3-(tert-butoxycarbonylamino)pyrrolidine (708 mg, 3.80 mmol), EDC (729 mg, 3.80 mmol), 1-hydroxybenzotriazole hydrate (514 mg, 3.80 mmol), and N,N-diisopropylethylamine (631 mL, 3.62 mmol) were combined in DMF (20 mL) and the mixture was stirred at ambient temperature for 18 hours. The solvent was removed under reduced pressure and the residue was partitioned between saturated aqueous $NaHCO_3$ (25 mL) and $CH_2Cl_2$ (50 mL). The aqueous layer was extracted further with $CH_2Cl_2$ (2×25 mL). The combined organic extracts were dried over $MgSO_4$, filtered, and concentrated in vacuo. The crude product was purified by flash column chromatography on silica, eluting with $CH_2Cl_2$—3% MeOH—0.3% $NH_4OH$ to yield the titled product as a white foam.

Step B: (R)-3-Amino-1-(3-hydroxybenzoyl)pyirolidine Hydrochloride

A solution of (R)-3-(tert-butoxycarbonylamino)-1-(3-hydroxybenzoyl) pyrrolidine, as described above in Step A, (1.19 g, 3.88 mmol) in EtOAc (100 mL) at 0° C. was saturated with HCl (g). After 15 min, the mixture was concentrated in vacuo to yield the amine hydrochloride as a white solid.

Step C: (R)-2-Fluoro-4-(5-{[1-(3-hydroxybenzoyl)pyrrolidin-3-ylamino]methyl}imidazol-1-ylmethyl) benzonitrile (R)-3-Amino-1-(3-hydroxybenzoyl)pyrrolidine hydrochloride, as described above in Step B, (350 mg, 1.44 mmol) and 1-(4-cyano-3-fluorobenzyl)-5-imidazolecarboxaldehyde as described in Example 1, Step G (363 mg, 1.58 mmol), were stirred in MeOH (8 mL) and N,N-diisopropylethylamine was added dropwise to adjust the mixture to ca. pH 5, as judged by wetted pH paper. The mixture was stirred for 1 hour at ambient temperature then $NaCNBH_3$ (109 mg, 1.73 mmol) was added and stirring was continued for 18 hours. The reaction was quenched with saturated aqueous $NaHCO_3$ (2 mL) and most of the MeOH was removed under reduced pressure. The residual solution was partitioned between saturated aqueous $NaHCO_3$ (10 mL) and $CHCl_3$ (20 mL). The aqueous layer was extracted further with CHCl₃ (3×15 mL). The combined organic extracts were dried over MgSO₄, filtered, and concentrated in vacuo. The crude product was purified by flash column chromatography on silica, eluting with a gradient of CHCl₃—3% MeOH—0.4% NH₄OH to CHCl₃—6% MeOH—0.6% NH₄OH to yield the titled product as a white foam.

Step D: (21R)-20,21,22,23-Tetrahydro-17-oxo-5H,17H, 19H-18,21 -methano-6,10:12,16-dimethenoimidazo[3,4-h] [1,8,11,15]oxatriazacycloheneicosine-9-carbonitrile Hydrochloride A mixture of (R)-2-fluoro-4-(5-{[1-(3-hydroxybenzoyl) pyrrolidin-3-ylamino]methyl}imidazol-1-ylmethyl) benzonitrile, as described above in Step C, (420 mg, 1.00 mmol) and Cs₂CO₃ (489 mg, 1.50 mmol) in dry, degassed DMF (10 mL) was stirred at 50° C. under argon for 18 hours. The solvent was removed under reduced pressure, and the residue was purified by flash column chromatography on silica, eluting with CHCl₃—5% MeOH—0.5% NH₄OH to yield the desired product which was converted to the hydrochloride salt by treatment with HCl in EtOAc.

Elemental analysis calculated for C₂₃H₂₁N₅O₂.2.5 HCl.0.45 H₂O.0.25 EtOAc: C: 55.35; H: 5.11; N: 13.45; Found: C: 55.32; H: 4.95; N: 13.39; FAB MS: 400 (MH⁺).

Example 6

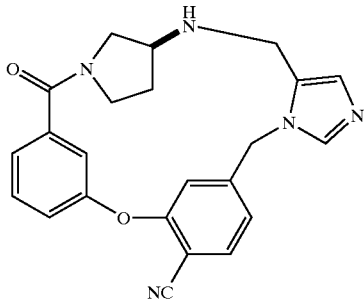

Preparation of (21S)-20,21,22,23-Tetrahydro-17-oxo-5H, 17H, 19H-18,21 -methano-6,10:12,16-dimethenoimidazo[3,4-h][1,8,11,1 5]oxatriaza-cycloheneicosine-9-carbonitrile Hydrochloride Following the procedure described in Example 5, but using (S)-3-(tert-butoxycarbonylamino)pyrrolidine in place of (R)-3-(tert-butoxycarbonylamino) pyrrolidine in Step A, the above-titled compound was prepared.

Elemental analysis calculated for C₂₃H₂₁N₅O₂.2 HCl.1.4 H₂O: C: 55.51; H: 5.23; N: 14.08; Found: C: 55.46; H: 4.93; N: 14.26; FAB MS: 400 (MH⁺).

Example 7

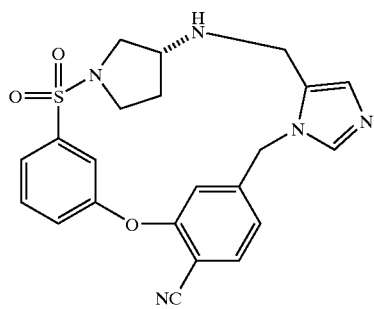

Preparation of (21R)-20,21,22,23-Tetrahydro-5H, 19H-18,21-methano-6,10:12,16-dimetheno-16H-imidazo[4,3-n][1,8,12,15,7]oxatriazathia-cycloheneicosine-9-carbonitrile 17,17-dioxide Hydrochloride Step A: Benzyl 3-bromophenyl Ether To a stirred solution of 3-bromophenol (9.50 g, 54.9 mmol) in degassed DMF (150 mL) at 0° C., under argon, was added Cs₂CO₃ (35.8 g, 109 mmol). The resulting mixture was stirred for 1 hour, then benzyl bromide (10.3 g, 60.2 mmol) was added and stirring was continued for 2 hours at 0° C. The solvent was removed under reduced pressure, and the residue was partitioned between 20% aqueous NaOH (250 mL) and CHCl₃ (500 mL). The organic layer was dried over MgSO₄, filtered, and concentrated in vacuo. The crude product was purified by flash column chromatography on silica, eluting first with two column volumes of hexane, then with hexane—2% EtOAc to yield the desired product as a white solid.

Step B: Magnesium 3-benzyloxyphenylsulfinate Bromide

To a stirred suspension of Rieke Mg (0.5 g, 21 mmol) in refluxing dry THF (45 mL), under argon, was added benzyl 3-bromophenyl ether, as described above in Step A, (5.0 g, 19 mmol) in dry THF (50 mL) dropwise, at a rate that maintained reflux with the heat source removed. The resulting mixture was heated to reflux for 30 min, then cooled to −78° C. and SO₂ was bubbled into the solution slowly for 1 hour. The reaction mixture was allowed to warm slowly to ambient temperature and stirred for 18 hours. Argon was bubbled into the mixture for 1 hour, then the solution was concentrated in vacuo to give the desired product as a solid.

Step C: 3-Benzyloxyphenylsulfonyl Chloride

Magnesium 3-benzyloxyphenylsulfinate bromide, as described above in Step B, (4.5 g, 14 mmol) was dissolved in dry CH₂Cl₂ (175 mL) and cooled to 0° C. under argon. Sulfuryl chloride (19 mL of a 1.0 M solution in CH₂Cl₂, 19 mmol) was added dropwise, and the mixture was stirred for 18 hours at ambient temperature, during which time a precipitate formed. The precipitate was removed by filtration and the filtrate was concentrated under reduced pressure to give the product as a yellow oil.

Step D: (R)-1-(3-Benzyloxyphenylsulfonyl)-3-(tert-butoxycarbonylamino) pyrrolidine To a stirred solution of 3-benzyloxyphenylsulfonyl chloride, as described above in Step C, (1.8 g, 7.2 mmol) in CH₂Cl₂ (50 mL) was added N,N-diisopropylethylamine (1.8 mL, 10.3 mmol) followed by (R)-3-(tert-butoxycarbonylamino)pyrrolidine (1.77 g, 9.5 mmol) and the reaction mixture was stirred at ambient temperature for 4 hours. The mixture was washed with 10% aqueous citric acid (75 mL), then water (50 mL), then saturated aqueous NaHCO₃ (50 mL). The organic layer was dried over MgSO₄, filtered, and concentrated in vacuo. The crude product was purified by flash column chromatography on silica, eluting with hexane—20% EtOAc to yield the desired product as a white solid.

Step E: (R)-3-(tert-Butoxycarbonylamino)-1-(3-hydroxyphenylsulfonyl)pyrrolidne

To a solution of (R)-1-(3-benzyloxyphenylsulfonyl)-3-(tert-butoxycarbonylamino)pyrrolidine, as described above in Step D, (3.1 g, 7.17 mmol) in EtOH (150 mL) was added 20% Pd(OH)$_2$ on carbon (900 mg) and the reaction mixture was stirred under an atmosphere of hydrogen (ca. 1 atm) at ambient temperature for 18 hours. The mixture was filtered through a pad of celite, washing with EtOH, and the filtrate was concentrated in vacuo to give the titled product as a white solid.

Step F: (R)-3-Amino-1-(3-hydroxyphenylsulfonylpyrolidine Hydrochloride

A solution of (R)-3-(tert-butoxycarbonylamino) 1 -(3-hydroxyphenylsulfonyl)pyrrolidine, as described above in Step E, (2.4 g, 7.0 mmol) in EtOAc (100 mL) at 0° C. was saturated with HCl (g). After 15 min. the mixture was concentrated in vacuo to yield the amine hydrochloride as a white solid.

Step G: (R)-2-Fluoro-4(5-{[1-(3-hydroxyphenylsulfonyl) pyrrolidin-3-ylamino]methyl}imidazol-1-ylmethy) benzonitrile (R)-3-Amino-1-(3-hydroxyphenylsulfonyl)pyrrolidine hydrochloride, as described above in Step F. (360 mg, 1.29 nimol) and 1-(4-cyano-3-fluorobenzyl)-5-imidazolecarboxaldehyde, as described in Example 1, Step G. (326 mg, 1.42 mmol) were stirred in MeOH (8 mL) and N,N-diisopropylethylamine was added dropwise adjust the mixture to ca. pH 5, as judged by wetted pH paper. The mixture was stirred for 1 hour at ambient temperature then NaCNBH$_3$ (97 mg, 1.54 mmol) was added and stirring was continued for 18 hours. The reaction was quenched with saturated aqueous NaHCO$_3$ (2 mL) and most of the MeOH was removed under reduced pressure. The residual solution was partitioned between saturated aqueous NaHCO$_3$ (10 mL) and CHCl$_3$ (20 mL). The aqueous layer was extracted further with CHCl$_3$ (3×15 mL). The combined organic extracts were dried over MgSO$_4$, filtered, and concentrated in vacuo. The crude product was purified by flash column chromatography on silica, eluting with a gradient of EtOAc—5% MeOH—0.5% NH$_4$OH to EtOAc—10% MeOH—1% NH$_4$OH to yield the titled product as a white foam.

Step H: (21R)-20,21,22,23-Tetrahydro-5H,19H-18,21-methano-6,10:12,16-dimetheno-16H-imidazo[4,3-n][1,8,12,15,7]oxatriazathiacycloheneicosine-9-carbonitrile 17,17-dioxide Hydrochloride A mixture of (R)-2-fluoro-4-(5-{[1-(3-hydroxyphenylsulfonyl) pyrrolidin-3-ylamino] methyl}imidazol-1-ylmethyl)benzonitrile, as described above in Step G, (420 mg, 0.92 mmol) and Cs$_2$CO$_3$ (451 mg, 1.38 mmol) in dry, degassed DMF (10 mL) was stirred at 50° C. under argon for 18 hours. The solvent was removed under reduced pressure, and the residue was purified by flash column chromatography on silica, eluting with CHCl$_3$—5% MeOH—0.5% NH$_4$OH to yield the desired product which was converted to the hydrochloride salt by treatment with HCl in EtOAc.

Elemental analysis calculated for C$_{22}$H$_{21}$N$_5$O$_3$S.2 HCl.0.6 H$_2$O.0.25 EtOAc: C: 51.03; H: 4.88; N: 12.94; Found: C: 51.04; H: 4.51; N: 12.94; FAB MS: 436 (MH$^+$).

Example 8

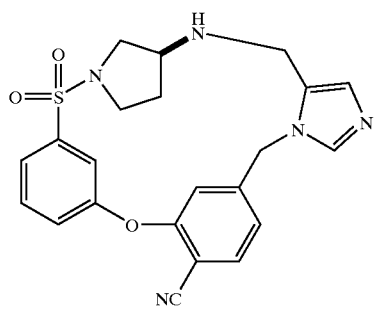

Preparation of (21S)-20,21,22,23-Tetrahydro-5H, 19H-18,21-methano-6,10:12,16-dimetheno-16H-imidazo[4,3-n][1,8,12,15,7]oxatriazathia-cycloheneicosine-9-carbonitrile 17,17-dioxide Hydrochloride Following the procedure described in Example 7, but using (S)-3-(tert-butoxycarbonylamino)pyrrolidine in place of (R)-3-(tert-butoxycarbonylamino) pyrrolidine in Step D, the above-titled compound was prepared.

Elemental analysis calculated for C$_{22}$H$_{21}$N$_5$O$_3$S.2 HCl.0.45 H$_2$O.0.15 EtOAc: C: 51.24; H: 4.78; N: 13.22; Found: C: 51.22; H: 4.41; N: 12.99; FAB MS: 436 (MH$^+$).

Example 9

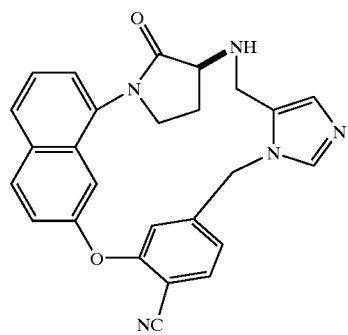

Preparation of (20S)-19,20,21,22-Tetrahydro-19-oxo-5H-18,20-ethano-12,14-etheno-6,10-metheno-18H-benz[d]imidazo[4,3-k][1,6,9,12]oxatriaza-cyclooctadecosine-9-carbonitrile Hydrochloride Step A: 8-(tert-Butoxycarbonylamino)-2-naphthol A mixture of 8-amino-2-naphthol (500 mg, 3.14 mmol) and di-tert-butyl dicarbonate (685 mg, 3.14 mmol) in CH$_2$Cl$_2$ (10 mL) and THF (5 mL) was stirred at 70° C. for 18 hours, then poured into saturated aqueous Na$_2$CO$_3$ (25 mL) and CH$_2$Cl$_2$ (75 mL). The aqueous layer was extracted further with CH$_2$Cl$_2$ (2×50 mL). The combined organic extracts were dried over Na$_2$SO$_4$, filtered, and concentrated in vacuo. The crude product was purified by flash column chromatography on silica, eluting with a gradient of CH$_2$Cl$_2$—0 to 7% EtOAc to yield the desired product as a light brown solid.

Step B: 7-Benzyloxy-1-(tert-butoxycarbonylamino) naphthalene

A mixture of 8-(tert-butoxycarbonylamino)-2-naphthol, as described above in Step A, (93 mg, 0.36 mmol), benzyl bromide (64 mg, 0.37 mmol), and Cs$_2$CO$_3$ (146 mg, 0.45 mmol) in dry DMF (3 mL) was stirred, under argon, at ambient temperature for 18 hours. The reaction mixture was poured into saturated aqueous NaHCO$_3$ (15 mL) and EtOAc (20 mL). The organic layer was dried over Na$_2$SO$_4$, filtered, and concentrated in vacuo. The crude product was purified by flash column chromatography on silica, eluting with a gradient of hexane—5 to 15% diethyl ether to yield the desired product as a pale solid.

Step C: 1-Arino-7-benzyloxynqphthalene

A solution of 7-benzyloxy-1-(tert-butoxycarbonylarnino) naphthalene, as described above in Step B, (100 mg, 0.29 mmol) in EtOAc (10 mL) at 0° C. was saturated with HCl (g). After 15 min, the mixture was concentrated in vacuo. The residue was partitioned between saturated aqueous Na$_2$CO$_3$ (5 mL) and CH$_2$Cl$_2$ (10 mL). The aqueous layer was extracted further with CH$_2$Cl$_2$ (2×10 mL). The combined organic extracts were dried over Na$_2$SO$_4$, filtered, and concentrated in vacuo to yield the desired amine as a pale solid.

Step D: (20S)-19,20,21,22-Tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride Following the procedure described in Example 1, but using 1-amino-7-benzyloxynaphthalene (as described in Example 9, Step C) in place of 3-benzyloxybenzylamine, and (S)-N-(tert-butoxycarbonyl)methionine in place of (R)-N-(tert-butoxycarbonyl)methionine in Step J, the above compound was prepared.

Elemental analysis calculated for C$_{26}$H$_{21}$N$_5$O$_2$.2 HCl.1.45 H$_2$O: C: 58.42; H: 4.88; N: 13.10; Found: C: 58.38; H: 4.62; N: 12.91; FAB MS: 436 (MH$^+$).

Example 9A

Preparation of (S)-3-Amino-1-(7-hydroxynaphthalen-1-yl)-2-oxopyrrolidine Hydrochloride Following the procedures described in Example 1, Steps J–N, but using 1-amino-7-benzyloxynaphthalene in place of 3-benzyloxybenzylamine, and (S)-N-(tert-butoxycarbonyl) methionine in place of (R)-N-(tert-butoxycarbonyl) methionine in Step J, the above-titled compound was obtained.

Example 10

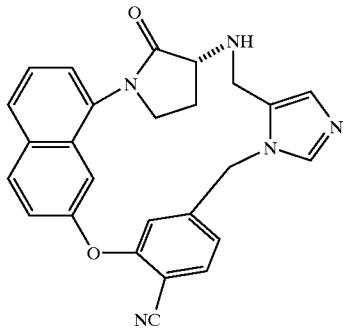

Preparation of (20R)-19,20,21,22-tetrahydro-19-oxo-5H-18,20-ethano-12,14-etheno-6,10-metheno-18H-benz[d]imidazo[4,3-k][1,6,9,12]oxatriaza-cyclooctadecosine-9-carbonitrile Hydrochloride Following the procedure described in Example 1, but using 1-amino-7-benzyloxynaphthalene (as described in Example 9, Step C) in place of 3-benzyloxybenzylamine in Step J, the above-titled compound was prepared.

Elemental analysis calculated for C$_{26}$H$_{21}$N$_5$O$_2$.2 HCl.1.3 H$_2$O: C: 58.71; H: 4.85; N: 13.17; Found: C: 58.69; H: 5.11; N: 12.86; FAB MS: 436 (MH$^+$).

Example 10A

Preparation of (R)-3-Amino-1-(7-hydroxynaphthalen-1-yl)-2-oxopyrrolidine Hydrochloride Following the procedures described in Example 1, Steps J–N, but using 1-amino-7-benzyloxynaphthalene in place of 3-benzyloxybenzylamine in Step J, the above-titled compound was obtained.

Example 11

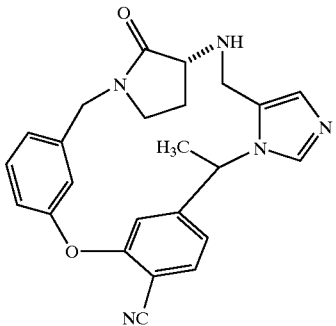

Preparation of (20R)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile Hydrochloride, Diastereomers A & B Step A: α,α-Dibromo-4-cyano-3-fluorotoluene To a solution of 4-cyano-3-fluorotoluene from Example 1, Step C, (4.0 g, 29.6 mmol) in carbon tetrachloride (250 mL) was added N-bromosuccinimide (10.5 g, 59.2 mmol) and 2,2'-azobisisobutyronitrile (490 mg, 3.0 mmol). The reaction mixture was heated to reflux under argon for 24 hours, then cooled to room temperature, filtered, and concentrated under reduced pressure. The residue was purified by silica gel chromatography, eluting with a gradient of hexane—3% to 7% EtOAc, to yield the titled product as a yellow-brown solid.

Step B: 4-Cyano-3-fluorobenzaldehyde

To a solution of α,α-dibromo-4-cyano-3-fluorotoluene, as described above in Step A, (5.60 g, 19.1 mmol) in EtOH (255 mL) and water (45 mL) was added AgNO$_3$. The mixture was heated to reflux for 3 hours, then stood at ambient temperature for 18 hours, then the solid was removed by filtration and the filtrate was concentrated under reduced pressure to a volume of approximately 20 mL. Water (30 mL) was added, and the mixture was concentrated to dryness in vacuo. The residue was partitioned between saturated aqueous NaHCO$_3$ (20 mL) and CH$_2$Cl$_2$ (50 mL). The aqueous layer was extracted further with CH$_2$Cl$_2$ (2×50 mL). The combined organic extracts were dried over Na$_2$SO$_4$, filtered, and concentrated in vacuo. The residue was dried for several days at ca. 0.5 mm Hg to yield the desired aldehyde as a pale solid.

Step C: 1-(4-Cyano-3-fluorophenyl)ethanol

To a solution of 4-cyano-3-fluorobenzaldehyde, as described above in Step B, (250 mg, 1.68 mmol) in THF, under argon, at −78° C. was added MeMgBr dropwise (0.59 mL of a 3.0 M solution in Et$_2$O, 1.77 mmol). The reaction mixture was stirred at −78° C. for 1 hour, then quenched with saturated aqueous NH$_4$Cl, allowed to warm to ambient temperature, and extracted with CH$_2$Cl$_2$ (2×40 mL). The combined organic extracts were dried over Na$_2$SO$_4$, filtered, and concentrated in vacuo. The residue was purified by silica gel chromatography, eluting with a gradient of hexane—20% to 40% EtOAc, to yield the titled product as a white solid.

Step D: 4-(tert-Butyldimethylsilyloxymethyl)-1-(triphenylmethyl)imidazole 4-(Hydroxymethyl)-1-(triphenylmethyl)imidazole, as described in Example 1, Step A, (1.97 g, 5.72 mmol) and 4-(dimethylamino) pyridine (280 mg, 2.29 mmol) were stirred in CH$_2$Cl$_2$ (15 mL) and tert-butyldimethylsilyl chloride (905 mg, 6.01 mmol) was added. After 1 min, triethylamine (0.88 mL, 6.31 mmol) was added dropwise over 3 min. The reaction mixture was stirred for 45 min, then CH$_2$Cl$_2$ (150 mL) was added and the solution was washed with 0.1 N HCl (50 mL). The organic layer was dried (Na$_2$SO$_4$), and concentrated in vacuo. The residue was purified by silica gel chromatography, eluting with hexane—30% EtOAc, to yield the titled product as a white solid.

Step E: 5-(tert-Butyldimethylsilyloxymethyl)-1-[1-(4-cyano-3-fluorophenyl)ethyl]imidazole A mixture of 4-(tert-butyldimethylsilyloxymethyl)-1-(triphenylmethyl)imidazole, as described above in Step D, (485 mg, 1.07 mmol), 1-(4-cyano-3-fluorophenyl)ethanol, as described above in Step C, (160 mg, 0.969 mmol), and N,N-diisopropylethylamine (0.219 mL, 1.26 mmol) in CH$_2$Cl$_2$ (12 mL) was cooled to −78° C., under argon. Trifluoromethanesulfonic anhydride (0.196 mL, 1.17 mmol) was added dropwise, and the mixture was stirred for 18 hours while it slowly warmed to ambient temperature. Methanol (15 mL) was added and the CH$_2$Cl$_2$ was distilled off in vacuo. The resulting methanolic solution was heated to reflux for 3 hours, then concentrated in vacuo to give a residue which was partitioned between saturated aqueous Na$_2$CO$_3$ (10 mL) and CH$_2$Cl$_2$ (20 mL). The aqueous layer was extracted further with CH$_2$Cl$_2$ (20 mL). The combined organic extracts were dried over Na$_2$SO$_4$, filtered, and concentrated in vacuo. The residue was purified by silica gel chromatography, eluting with a gradient of CH$_2$Cl$_2$—0% to 5% MeOH, to yield the titled product as a pale foam.

Step F: 1-[1-(4-Cyano-3-fluorophenyl)ethyl]-5-(hydroxymethyl)imidazole

To a solution of 5-(tert-butyldimethylsilyloxymethyl)-1-[1-(4-cyano-3-fluorophenyl)ethyl]imidazole, as described above in Step E, (101 mg, 0.281 mmol) in THF (2 mL) was added tetrabutylammonium fluoride (0.309 mL of a 1.0 M solution in THF, 0.309 mmol) dropwise. The reaction mixture was stirred for 1 hour, then poured into saturated aqueous NaHCO$_3$ (20 mL) and extracted with CH$_2$Cl$_2$ (3×20 mL). The combined organic extracts were dried over Na$_2$SO$_4$, filtered, and concentrated in vacuo. The residue was purified by silica gel chromatography, eluting with a gradient of CH$_2$Cl$_2$—0% to 10% MeOH, to yield the desired product as a pale solid.

step G: (20R)-19,20,21,22-Tetrahydro-5-methyl-19-oxo-17H-18,20-ethano-6,10:12,16-dimetheno-16H-imidazo[3,4-h][1,8,11,14]oxatriazacycloeicosine-9-carbonitrile Hydrocloride, Diasteromers A & B Following the procedure described in Example 1, but using 1-[1-(4-cyano-3-fluorophenyl)ethyl]-5-(hydroxymethyl)imidazole (as described in Example 11, Step F) in place of 1-(4-cyano-3-flurobenzyl)-5-(hydroxymethyl)imidazol in Step G, the above diastereomers were obtained. The product was obtained as a ca. 1:1 mixture of two diastereomers which were separated by preparative HPLC on a Chiralpak AS column, eluting with hexane—20% EtOH—20% MeOH—0.1% Et$_2$NH to yield the separated products, diastereomer A (which eluted first under the described HPLC conditions) and diastereomer B (which eluted second under the described HPLC conditions).

(20R)-19,20,21,22-Tetrahydro-5-methyl-19-oxo-17H-18,20-ethano-6,10:12,16-dimetheno-16H-imidazo[3,4-h][1,8,11,14]oxatriazacycloeicosine-9-carbonitrile Hydrochloride, Diastereomer A Elemental analysis calculated for C$_{24}$H$_{23}$N$_5$O$_2$.2HCl.0.85H$_2$O.0.30 EtOc: C: 57.30; H: 5.55; N: 13.26; C: 57.28; H; 5.56; N; 13.23; FAB MS: 414 (MH$^+$).

(20R)-19,20,21,22-Tetrahydro-5-methyl-19-oxo-17H-18,20-ethano-6,10:12,16-dimetheno-16H-imidazo[3,4-h][1,8,11,14]oxatriazacycloeicosine-9-carbonitrile hydrochloride, Diastereomer B Elemental analysis calculated for C$_{24}$H$_{23}$N$_5$O$_2$.2HCl.1.05H$_2$O.0.50 EtOAc: C: 56.84; H: 5.71; N: 12.75; Found: C: 56.83; H: 5.63; N: 12.78; FAB MS: 414 (MH$^+$).

Example 12

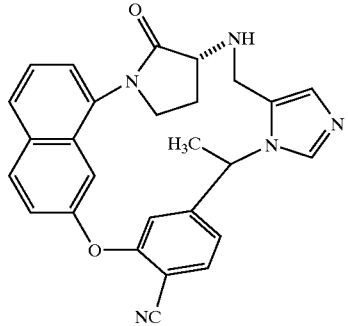

Preparation of (20R)-19,20,21,22-Tetrahydro-5-methyl-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride, Diastereomers A & B Following the procedure described in Example 1, but using 1-[1-(4-cyano-3-fluorophenyl)ethyl]-5-(hydroxymethyl)imidazole (as described in Example 11, Step F) in place of 1-(4-cyano-3-fluorobenzyl)-5-(hydroxymethyl)imidazole in Step G, and (R)-3-amino-1-(7-hydroxynaphth-1-yl)-2-oxopyrrolidine hydrochloride in place of (R)-3-amino-1-(3-hydroxybenzyl)-2-oxopyrrolidine hydrochloride in Step O, the above-titled compound was prepared. The product was obtained as a ca. 1:1 mixture of two diastereomers which were separated by preparative HPLC on a Deltapak C-18 column, eluting with a gradient of 0.1% aqueous NH$_4$HCO$_3$—0% to 60% CH$_3$CN to to yield the separated products, diastereomer A (which eluted first under the described HPLC conditions) and diastereomer B (which eluted second under the described HPLC conditions).

(20R)-19,20,21,22-Tetrahydro-5-methyl-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride, Diastereomer A Elemental analysis calculated for $C_{27}H_{23}N_5O_2 \cdot 2HCl \cdot 2.35H_2O \cdot 0.40$ EtOAc: C: 57.25; H: 5.53; N: 11.67; Found: C: 57.25; H: 5.15; N: 11.31; FAB MS: 450 (MH$^+$).

(20R)-19,20,21,22-Tetrahydro-5-methyl-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride, Diastereomer B Elemental analysis calculated for $C_{27}H_{23}N_5O_2 \cdot 2HCl \cdot H_2O \cdot 1.05$ EtOAc: C: 59.20; H: 5.64; N: 11.07; Found: C: 59.20; H: 5.63; N: 11.01; FAB MS: 450 (MH$^+$).

Example 13

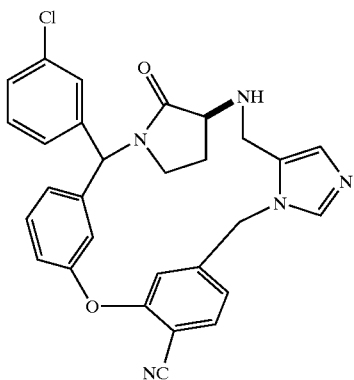

Preparation of (20S)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile Hydrochloride, Diastereomer A Step A: (3-Benzyloxyphenyl)(3-chlorophenyl)methanol To a stirred suspension of Rieke Mg (0.93 g, 38 mmol) in refluxing dry THF (15 mL), under argon, was added benzyl 3-bromophenyl ether as described in Example 7, Step A, (9.0 g, 34 mmol) in dry THF (90 mL) dropwise, at a rate that maintained reflux with the heat source removed. The resulting mixture was heated to reflux for 1 hour, then allowed to cool to ambient temperature. The solution of Grignard reagent was added dropwise to a stirred solution of 3-chlorobenzaldehyde in THF (50 mL) at −78° C. The reaction mixture was stirred at −78° C. for 1 hour, then quenched with saturated aqueous NH$_4$Cl (200 mL), allowed to warm to ambient temperature, and extracted with Et$_2$O (500 mL). The organic layer was dried over MgSO$_4$, filtered, and concentrated in vacuo. The residue was purified by silica gel chromatography, eluting with hexane—7% EtOAc, to yield the titled product as a colorless oil.

Step B: (3-Benzyloxyphenyl)(3-chlorophenyl)methyl Azide

To a stirred solution of (3-benzyloxyphenyl)(3-chlorophenyl)methanol, as described above in Step A, (4.0 g, 12.3 mmol) and diphenylphosphoryl azide (4.1 g, 14.9 mmol) in dry toluene (35 mL) at 0° C., was added 1,8-diazabicyclo[5.4.0]undec-7-ene (2.1 g, 13.8 mmol). The resulting mixture was allowed to warm to ambient temperature, and stirred under argon for 18 hours, then washed with 5% hydrochloric acid (10 mL). The organic layer was dried over Na$_2$SO$_4$, filtered, and concentrated in vacuo. The crude product was purified by flash column chromatography on silica, eluting with hexane—2% EtOAc to yield the product as a colorless oil.

Step C: (3-Benzyloxyphenyl)(3-chlorophenyl)methylamine (3-Benzyloxyphenyl)(3-chlorophenyl)methyl azide, as described above in Step B, (6.2 g, 17.7 mmol) was dissolved in dry THF (150 mL) and the solution was cooled to −70° C. Lithium aluminum hydride (21.2 mL of a 1.0 M solution in THF, 21.2 mmol) was added dropwise, then the reaction mixture was warmed to 0° C. and stirred for 2 hours. The reaction was quenched with EtOAc (0.75 mL), then water (0.75 mL), then 15% NaOH (0.75 mL), and finally water (2.2 mL). The resulting mixture was filtered, concentrated under reduced pressure and purified by flash column chromatography on silica, eluting with hexane—15% EtOAc, to yield the titled product as a colorless oil.

Step D: (3S)-2-(tert-Butoxycarbonylamino)-4-(methylmercapto)-N-[(3-benzyloxyphenyl)(3-chlorophenyl)methyl]butyramide, Diastereomers A & B To (S)-N-(tert-butoxycarbonyl)methionine (1.60 g, 6.7 mmol) in dry CH$_2$Cl$_2$ (5 mL) under argon were added PYBOP (3.50 g, 6.7 mmol), (3-benzyloxyphenyl)(3-chlorophenyl)methylamine, as described above in Step C, (2.0 g, 6.2 mmol), and N,N-diisopropylethylamine (1.2 mL, 6.9 mmol). The reaction mixture was stirred for 2 hours, then extracted with quenched with aqueous NaHCO$_3$ (20 mL), and extracted with CH$_2$Cl$_2$ (2×20 mL). The combined organic extracts were dried over Na$_2$SO$_4$, filtered, and concentrated in vacuo. The crude product was purified by flash column chromatography on silica, eluting with hexane—20% EtOAc to yield a mixture (ca. 1:1) of diastereomeric amides as a white solid.

Step E: (3S)-2-(tert-Butoxycarbonylamino)-4-(dimethylsulfonium)-N-[(3-benzyloxyphenyl)(3-chlorophenyl)methyl]butyramide Iodide, Diastereomers A & B (3S)-2-(tert-Butoxycarbonylamino)-4-(methylmercapto)-N-[(3-benzyloxyphenyl)(3-chlorophenyl)methyl]butyramide, diastereomers A & B, as described above in Step D, (3.30 g, 5.94 mmol) was dissolved in iodomethane (20 mL, 320 mmol) and the solution was stirred under argon for 18 hours. The iodomethane was removed by distillation under reduced pressure to give the sulfonium salt diastereomers (ca. 1:1) as a yellow solid.

Step F: (3S)-{1-[(3-Benzyloxyphenyl)(3-chlorophenyl)methyl]-2-oxopyrrolidin-3-yl}carbamic Acid tert-Butyl Ester, Diastereomers A & B (3S)-2-(tert-Butoxycarbonylamino)-4-(dimethylsulfonium)-N-[(3-benzyloxyphenyl)(3-chlorophenyl)methyl]butyramide iodide, diastereomers A & B, as described above in Step E, (4.10 g, 5.94 mmol) was stirred in dry THF (90 mL), under argon, at 0° C. and lithium bis(trimethylsilyl)amide (1.0 M in THF, 5.6 mL, 5.6 mmol) was added dropwise. The reaction mixture was stirred at 0° C. for 2 hours, then quenched with saturated aqueous NH$_4$Cl (50 mL) and most of the THF was removed under reduced pressure. The residual solution was partitioned between saturated aqueous NaHCO$_3$ (25 mL) and CHCl$_3$ (75 mL). The aqueous layer was extracted further with CHCl$_3$ (2×25 mL). The combined organic extracts were dried over MgSO$_4$, filtered, and concentrated in vacuo. The crude product was purified by flash column chromatography on silica, eluting with a gradient of hexane—20% to 25%

EtOAc to yield the mixture (ca. 1:1) of diastereomeric pyrrolidinones as a white solid.

Step G: (3S)-{1-[(3-Chlorophenyl)(3-hydroxyphenyl) methyl]-2-oxopyrrolidin-3-yl}carbamic Acid tert-Butyl Ester Diastereomers A & B To a solution of (3S)-{1-[(3-benzyloxyphenyl)(3-chlorophenyl) methyl]-2-oxopyrrolidin-3-yl}carbamic acid tert-butyl ester, diastereomers A & B, as described above in Step F, (1.30 g, 2.62 mmol) in EtOH (125 mL) and EtOAc (25 mL) was added 20% Pd(OH)$_2$ on carbon (250 mg) and acetic acid (5 mL) and the reaction mixture was stirred under an atmosphere of hydrogen (ca. 1 atm) at ambient temperature for 18 hours. The mixture was filtered through a pad of celite, washing with EtOH, and the filtrate was concentrated in vacuo to give a crude product. This was purified by flash column chromatography on silica, eluting with a gradient of CHCl$_3$—20% to 30%, to yield the separated products, diastereomer A (higher R$_F$ on silica gel) and diastereomer B (lower R$_F$ on silica gel), as colorless oils.

Step H: (3S)-3-Amino-1-[(3-chlorophenyl)(3-hydroxyphenyl)methyl]-2-oxopyrrolidine Trifluoroacetate Diastereomer A A solution of (3S)-{(1-[(3-chlorophenyl)(3-hydroxyphenyl)methyl]-2-oxopyrrolidin-3-yl}carbamic acid tert-butyl ester, diastereomer A, as described above in Step G, (480 mg, 1.15 mmol) in EtOAc (75 mL) at 0° C. was saturated with HCl (g). After 15 min, the mixture was concentrated in vacuo to yield the amine, which was purifed by preparative HPLC on a Deltapak C-18 column, eluting with a gradient of 0.1% aqueous trifluoroacetic acid—5% to 60% CH$_3$CN to provide the titled product as a white foam.

Step I: (3S)-4-[5-({1-[(3-Chlorophenyl)(3-hydroxyphenyl) methyl]-2-oxopyrrolidin-3-ylamino}methyl)imidazol-1-ylmethyl]-2-fluorobenzonitrile, Diastereomer A (3S)-3-Amino-1-[(3-chlorophenyl)(3-hydroxyphenyl) methyl]-2-oxopyrrolidine trifluoroacetate, diastereomer A, as described above in Step H, (95 mg, 0.221 mmol) and 1-(4-cyano-3-fluorobenzyl)-5-imidazolecarboxaldehyde, as described in Example 1, Step G, (56 mg, 0.244 mmol), were stirred in MeOH (1 mL) and N,N-diisopropylethylamine was added dropwise to adjust the mixture to ca. pH 5, as judged by wetted pH paper. The mixture was stirred for 1 hour at ambient temperature then NaCNBH$_3$ (17 mg, 0.27 mmol) was added and stirring was continued for 18 hours. The MeOH was removed under reduced pressure, and the residue was partitioned between saturated aqueous NaHCO$_3$ (1 mL) and CHCl$_3$ (3 mL). The aqueous layer was extracted further with CHCl$_3$ (2×3 mL). The combined organic extracts were dried over MgSO$_4$, filtered, and concentrated in vacuo. The crude product was purified by flash column chromatography on silica, eluting with CHCl$_3$—4% MeOH—0.4% NH$_4$OH to yield the titled product as a white solid.

Step J: (20S)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile Hydrochloride, Diastereomer A A mixture of (3S)-4-[5-({1-[(3-chlorophenyl)(3-hydroxyphenyl) methyl]-2-oxopyrrolidin-3-ylamino}methyl)imidazol-1-ylmethyl]-2-fluorobenzonitrile, diastereomer A, as described above in Step I, (62 mg, 0.117 mmol) and Cs$_2$CO$_3$ (57 mg, 0.175 mmol) in dry, degassed DMF (6 mL) was stirred at 50° C. under argon for 2 hours. The solvent was removed under reduced pressure. The crude product was purified by flash column chromatography on silica, eluting with CHCl$_3$—3% MeOH—0.3% NH$_4$OH to yield the desired product which was converted to the hydrochloride salt by treatment with HCl in EtOAc.

Elemental analysis calculated for C$_{29}$H$_{24}$ClN$_5$O$_2$·1.9HCl·1.6H$_2$O: C: 57.45; H: 4.83; N: 11.55; Found: C: 57.45; H: 4.82; N: 11.39; FAB MS: 510 (MH$^+$).

Example 14

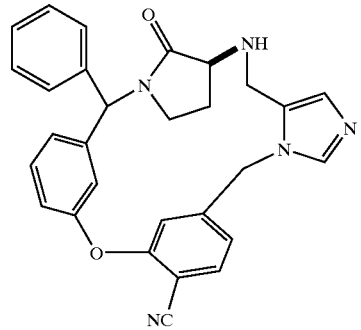

Preparation of (20S)-19,20,21,22-Tetrahydro-19-oxo-17-phenyl-5H,18H-18,20-ethano-6,10:12,16-dimetheno-16H-imidazo[3,4-h][1,8,11,14] oxatriazacycloeicosine-9-carbonitrile Hydrochloride, Diastereomer B Step A: (3S)-{1-[(3-Hydroxyphenyl)(phenyl)methyl]-2-oxopyrrolidin-3-yl}carbamic Acid tert-Butyl Ester Diastereomers A & B To a solution of (3S)-{1-[(3-benzyloxyphenyl)(3-chlorophenyl)methyl]-2-oxopyrrolidin-3-yl}carbamic acid tert-butyl ester, diastereomers A & B, as described in Example 13, Step F, (1.20 g, 2.41 mmol) in EtOH (125 mL) and EtOAc (25 mL) was added 20% Pd(OH)$_2$ on carbon (1.20 g) and the reaction mixture was shaken in a Parr hydrogenation apparatus under an atmosphere of hydrogen (ca. 50 atm) at ambient temperature for 3 days. The mixture was filtered through a pad of celite, washing with EtOH, and the filtrate was concentrated in vacuo to give a crude product. This was purified by flash column chromatography on silica, eluting with a gradient of CHCl$_3$—20% to 30%, to yield the separated products, diastereomer A (higher R$_F$ on silica gel) and diastereomer B (lower R$_F$ on silica gel), as colorless oils.

Step B: (3S)-3-Amino-1-[(3-hydroxyphenyl)(phenyl) methyl]-2-oxopyrrolidine Trifluoroacetate, diastereomer B A solution of (3S)-{1-[(3-hydroxyphenyl)(phenyl) methyl]-2-oxopyrrolidin-3-yl}carbamic acid tert-butyl ester, diastereomer B, as described above in Step A, (88 mg, 1.15 mmol) in EtOAc (15 mL) at 0° C. was saturated with HCl (g). After 15 min, the mixture was concentrated in vacuo to yield the amine, which was purifed by preparative HPLC on a Deltapak C-18 column, eluting with a gradient of 0.1% aqueous trifluoroacetic acid—5% to 60% CH$_3$CN to provide the titled product as a white foam.

Step: (3S)-2-Fluoro-4-[5-({1-[(3-hydroxyphenyl)(phenyl) methyl]-2-oxopyridin-3-ylamino}methyl)imidazol-1-ylmethyl]benzonitrile, Diastereomer B (3S)-3-Amino-1-[(3-hydroxyphenyl)(phenyl)methyl]-2-oxopyrrolidine trifluoroacetate, diastereomer B, as described above in Step B, (26 mg, 0.060 mmol) and 1-(4-cyano-3-fluorobenzyl)-5-imidazolecarboxaldehyde from Example 1, Step G, (20 mg, 0.087 mmol), were stirred in MeOH (1 mL) and N,N-diisopropylethylamine was added dropwise to adjust the mixture to ca. pH 5, as judged by wetted pH paper. The mixture was stirred for 1 hour at ambient temperature then NaCNBH$_3$ (6 mg, 0.095 mmol) was added and stirring was continued for 18 hours. The MeOH was removed under reduced pressure, and the residue was partitioned between saturated aqueous NaHCO₃ (1 mL) and CHCl₃ (3 mL). The aqueous layer was extracted further with CHCl₃ (2×3 mL). The combined organic extracts were dried over MgSO₄, filtered, and concentrated in vacuo. The crude product was purified by flash column chromatography on silica, eluting with a gradient of CHCl₃—2% to 5% MeOH—0.2% to 0.5% NH₄OH to yield the titled product as a glassy solid.

Step D: (2S)-19,20,21,22-Tetrahydro-19-oxo-17-phenyl-5H,18H-18,20- ethano-6,10:12,16-dimetheno-16H-imidazol[3,4-h][1,8,11,14]oxatriazacycloeicosine-9-carbonitrile Hydrochloride, Diastereomer B To a solution of (3S)-2-fluoro-4-[5-({1-[(3-hydroxyphenyl)(phenyl) methyl]-2-oxopyrrolidin-3-ylamino}methyl)imidazol-1-ylmethyl]benzonitrile, diastereomer B, as described above in Step C, (30 mg, 0.060 mmol) in acetonitrile (5 mL) was added KF on alumina (40 wt %) (20 mg) and 18-crown-6 (1.6 mg, 0.006 mmol), and the mixture was heated to reflux for 6 hours. The reaction mixture was cooled, filtered, then the solvent was removed under reduced pressure. The crude product was purified by flash column chromatography on silica, eluting with CHCl₃—2% to 4% MeOH—0.2% to 0.4% NH₄OH to yield the desired product which was converted to the hydrochloride salt by treatment with HCl in EtOAc.

Elemental analysis calculated for C₂₉H₂₅N₅O₂.2HCl.2.3H₂O.0.55 CH₃CN: C: 57.40; H: 5.39; N: 12.34; Found: C: 57.40; H: 5.26; N: 12.32; FAB MS: 476 (MH⁺).

Example 15

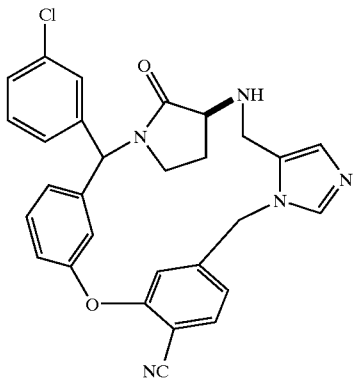

Preparation of (20S)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile Hydrochloride, Diastereomer B Following the procedure described in Example 14, but using (3S)-{1-[(3-chlorophenyl)(3-hydroxyphenyl)methyl]-2-oxopyrrolidin-3-yl}carbamic acid tert-butyl ester, diastereomer B (as described in Example 13, Step G) in place of (3S)-{1-[(3-hydroxyphenyl)(phenyl)methyl]-2-oxopyrrolidin-3-yl}carbamic acid tert-butyl ester, diastereomer B, in Step B.

Elemental analysis calculated for C₂₉H₂₄ClN₅O₂.2HCl.1.7H₂O.0.35 EtOAc: C: 56.66; H: 5.04; N: 10.87; Found: C: 56.61; H: 4.95; N: 10.87; FABMS: 510 (MH⁺).

Example 16

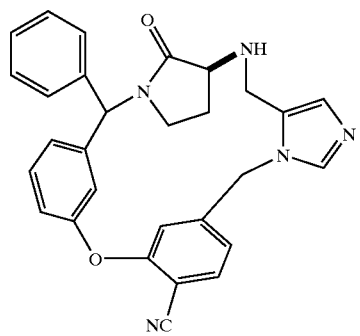

Preparation of (20S)-19,20,21,22-Tetrahydro-19-oxo-17-phenyl-5H,18H-18,20-ethano-6,10:12,16-dimetheno-16H-imidazo[3,4-h][1,8,11,14]oxatriazacycloeicosine-9-carbonitrile Hydrochloride, Diastereomer A Following the procedures described in Example 13, but using (3S)-{1-[(3-hydroxyphenyl)(phenyl)methyl]-2-oxopyrrolidin-3-yl}carbamic acid tert-butyl ester, diastereomer A, (as described in Example 14, Step A) in place of (3S)-{1-[(3-chlorophenyl)(3-hydroxyphenyl)methyl]-2-oxopyrrolidin-3-yl}carbamic acid tert-butyl ester, diastereomer A in Step H, the above-titled compound was prepared.

Elemental analysis calculated for C₂₉H₂₅N₅O₂.2HCl.2.5H₂O.0.1 EtOAc: C: 58.72; H: 5.33; N: 11.65; Found: C: 58.48; H: 5.34; N: 11.64; FAB MS: 476 (MH⁺).

Example 17

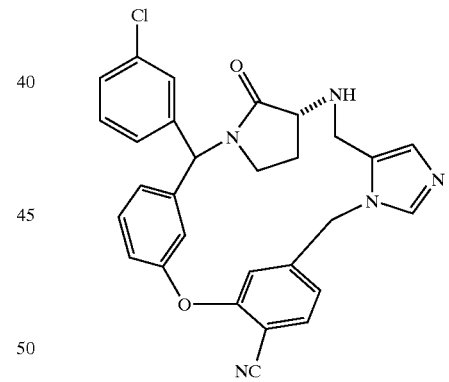

Preparation of (20R)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile Hydrochloride, Diastereomer A Following the procedure described in Example 13, but using (R)-N-(tert-butoxycarbonyl)methionine in place of (S)-N-(tert-butoxycarbonyl)methionine, the above-titled compound was prepared.

Elemental analysis calculated for C₂₉H₂₄ClN₅O₂.1.9HCl.1.6H₂O: C: 57.28; H: 4.95; N: 11.52; Found: C: 57.24; H: 4.98; N: 11.58; FAB MS: 510 (MH⁺).

Example 18

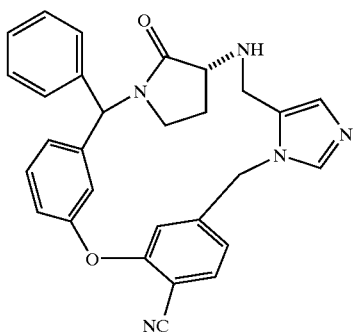

Preparation of (20R)-19,20,21,22-Tetrahydro-19-oxo-17-phenyl-5H,18H-18,20-ethano-6,10:12,16-dimetheno-16H-imidazo[3,4-h][1,8,11,14]oxatriazacycloeicosine-9-carbonitrile Hydrochloride, Diastereomer B Following the procedures described in Example 14, but using (R)-N-(tert-butoxycarbonyl)methionine in place of (S)-N-(tert-butoxycarbonyl)methionine, the above-titled compound was prepared.

Elemental analysis calculated for $C_{29}H_{25}N_5O_2 \cdot 2HCl \cdot 1.9H_2O \cdot 0.2$ EtOAc: C: 59.71; H: 5.43; N: 11.68; Found: C: 59.70; H: 5.43; N: 11.65; FAB MS: 476 (MH$^+$).

Example 19

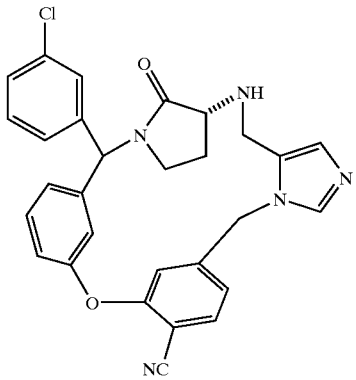

Preparation of (20R)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile Hydrochloride, Diastereomer B Following the procedures described in Example 15, but using (R)-N-(tert-butoxycarbonyl)methionine in place of (S)-N-(tert-butoxycarbonyl)methionine, the above-titled compound was prepared.

Elemental analysis calculated for $C_{29}H_{24}ClN_5O_2 \cdot 2HCl \cdot 2.1H_2O \cdot 0.2$ EtOAc: C: 56.06; H: 5.02; N: 10.97; Found: C: 56.07; H: 4.99; N: 10.96; FAB MS: 510 (MH$^+$).

Example 20

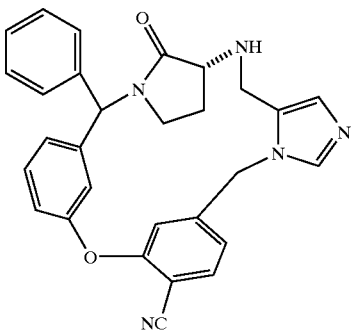

Preparation of (20R)-19,20,21,22-Tetrahydro-19-oxo-17-phenyl-5H,18H-18,20-ethano-6,10:12,16-dimetheno-16H-imidazo[3,4-h][1,8,11,14]oxatriazacycloeicosine-9-carbonitrile Hydrochloride, Diastereomer A Following the procedure described in Example 16, but using (R)-N-(tert-butoxycarbonyl)methionine in place of (S)-N-(tert-butoxycarbonyl)methionine, the above-titled compound was prepared.

Elemental analysis calculated for $C_{29}H_{25}N_5O_2 \cdot 1.8HCl \cdot 1.2H_2O$: C: 62.09; H: 5.24; N: 12.49; Found: C: 62.06; H: 5.24; N: 12.43; FAB MS: 476 (MH$^+$).

Example 21

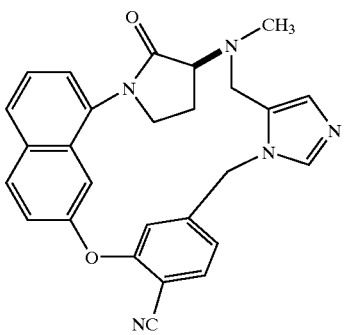

Preparation of (20S)-19,20,21,22-Tetrahydro-21-methyl-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride Step A: (20S)-19,20,21,22-Tetrahydro-21-methyl-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride A mixture of (20S)-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile hydrochloride as described in Example 9, (110 mg, 0.22 mmol), formaldehyde (0.055 mL of a 37 wt % solution in water, 0.68 mmol), and N,N-diisopropylethylamine (0.085 mL, 0.49 mmol) was stirred in MeOH (2 mL) for 20 min at ambient temperature. NaCNBH$_3$ (28 mg, 0.44 mmol) was added and the mixture was adjusted to pH=5.0–5.5 by addition of acetic acid. After 30 min, the reaction mixture was concentrated in vacuo. The residue was partitioned between saturated aqueous NaHCO$_3$ (20 mL) and CH$_2$Cl$_2$ (50 mL). The aqueous layer was extracted further with CH$_2$Cl$_2$ (50 mL). The combined organic extracts were dried over Na$_2$SO$_4$, filtered, and concentrated in vacuo. The crude product was purified by flash column chromatography on silica, eluting with a gradient of CH$_2$Cl$_2$—1% MeOH—0.1% NH$_4$OH to CH$_2$Cl$_2$—5% MeOH—0.5% NH$_4$OH to yield the titled product which was converted to the hydrochloride salt by treatment with HCl in EtOAc.

Elemental analysis calculated for C$_{27}$H$_{23}$N$_5$O$_2$.2HCl.0.65 EtOAc: C: 61.32; H: 5.25; N: 12.08; Found: C: 61.42; H: 5.30; N: 12.08; FAB MS: 450 (MH$^+$).

Example 22

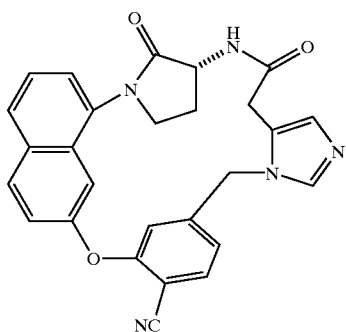

Preparation of (20R)-19,20,22,23-Tetrahydro-19,22-dioxo-5H,21H-18,20-ethano-12,14-etheno-6,10-methenobenz[d]imidazo[4,3-l][1,6,9,13]oxatriazacyclononadecosine-9-carbonitrile Hydrochloride Step A: Methyl (Imidazol-4-yl)acetate Hydrochloride A solution of 4-imidazoleacetic acid hydrochloride (4.00 g, 24.6 mmol) in MeOH (100 mL) was saturated with HCl (g). Trimethyl orthoformate (10 mL, 91 mmol) was added and the mixture was stood at ambient temperature for 18 hours, then concentrated to dryness in vacuo to afford the titled ester as a white solid.

Step B: Methyl [1-(Triphenylmethyl)-1H-imidazol-4-yl]acetate

To a solution of methyl 4-imidazoleacetate hydrochloride, as described above in Step A, (4.30 g, 24.3 mmol) in dry DMF (50 mL) were added triethylamine (7.45 mL, 53.5 mmol), then triphenylmethyl bromide (8.64 g, 26.7 mmol). The mixture was stirred at ambient temperature for 18 hours, then partitioned between H$_2$O (250 mL) and EtOAc (250 mL). The organic layer was dried over Na$_2$SO$_4$, filtered and concentrated under reduced pressure. The residue was purified by flash column chromatography on silica, eluting with EtOAc, to yield the product as a pale solid.

Step C: Methyl [1-(4-Cyano-3-fluorobenzyl)-1H-imidazol-5-yl]acetate

A mixture of methyl [1-(triphenylmethyl)-1H-imidazol-4-yl]acetate, as described above in Step B, (536 mg, 1.40 mmol) and 4-cyano-3-fluorobenzyl bromide, as described in Example 1, Step D, (300 mg, 1.40 mmol) in acetonitrile (3 mL) was heated to 50° C. for 2 hours. The mixture was allowed to cool, and the solid collected by filtration. The acetonitrile filtrate was concentrated in vacuo to a volume of approximately 1 mL and then reheated to 50° C. for 2 hours, cooled, and the solid removed by filtration. The two crops of precipitated imidazolium salts were combined in MeOH (30 mL) and the solution was heated to reflux for 2 hours, then concentrated in vacuo. The residue was partitioned between saturated aqueous NaHCO$_3$ (20 mL) and CHCl$_3$ (30 mL). The aqueous layer was extracted further with CHCl$_3$ (2×15 mL). The combined organic extracts were dried over Na$_2$SO$_4$, filtered, and concentrated in vacuo. The crude product was purified by flash column chromatography on silica, eluting with CHCl$_3$—3% MeOH—0.3% NH$_4$OH to CHCl$_3$—5% MeOH—0.5% NH$_4$OH to yield the titled product as a white solid.

Step D: Lithium [1-(4-Cyano-3-fluorobenzyl)-1H-imidazol-5-yl]acetate

Methyl [1-(4-cyanobenzyl)-1H-imidazol-5-yl]acetate, as described above in Step C, (free base) (260 mg, 0.95 mmol) was dissolved in THF (5 mL) and H$_2$O (1 mL). Lithium hydroxide (40 mg, 0.95 mmol) was added and the resulting mixture was stirred at ambient temperature for 1 hour, then adjusted to pH 7 with 1.0 N aqueous HCl and concentrated to dryness in vacuo to give the titled lithium salt.

Step E: (R)-2-[1-(4-Cyano-3-fluorobenzyl)-1H-imidazol-5-yl]-N-(1-(7-hydroxynaphthalen-1-yl)-2-oxopyrrolidin-3-yl)acetamide A mixture of lithium [1-(4-cyano-3-fluorobenzyl)-1H-imidazol-5-yl]acetate, as described above in Step D, (46 mg, 0.18 mmol), (R)-3-amino-1-(7-hydroxynaphthalen-1-yl)-2-oxopyrrolidine hydrochloride, as described in Example 10A (45 mg, 0.16 mmol), HOBT (24 mg, 0.18 mmol), EDC (35 mg, 0.18 mmol), and N,N-diisopropylethylamine (0.084 mL, 0.48 mmol) was stirred in DMF (1 mL) at ambient temperature for 18 hours. The solvent was removed under reduced pressure and the residue was partitioned between saturated aqueous NaHCO$_3$ (1 mL) and CHCl$_3$ (2 mL). The aqueous layer was extracted further with CHCl$_3$ (2×2 mL). The combined organic extracts were dried over MgSO$_4$, filtered, and concentrated in vacuo. The crude product was purified by flash column chromatography on silica, eluting with a gradient of EtOAc—10% MeOH—1% NH$_4$OH to EtOAc—15% MeOH—1.5% NH$_4$OH to yield the titled product as a white solid.

Step F: (20R)-19,20,22,23-Tetrahydro-19,22-dioxo-5H,21H-18,20-ethano-12,14-etheno-6,10-methenobenz[d]imidazo[4,3-l][1,6,9,13]oxatriazacyclononadecosine-9-carbonitrile Hydrochloride A mixture of (R)-2-[1-(4-cyano-3-fluorobenzyl)-1H-imidazol-5-yl]-N-(1-(7-hydroxynaphthalen-1-yl)-2-oxopyrrolidin-3-yl)acetamide, as described above in Step E, (30 mg, 0.062 mmol) and Cs$_2$CO$_3$ (26 mg, 0.079 mmol) in dry DMSO (6 mL) was stirred at ambient temperature under argon for 18 hours. Acetic acid (60 mL, 1.0 mmol) was added and the solvent was removed under reduced pressure. The residue was partitioned between saturated aqueous NaHCO$_3$ (1 mL) and CHCl$_3$ (3 mL). The aqueous layer was extracted further with CHCl$_3$ (2×2 mL). The combined organic extracts were dried over MgSO$_4$, filtered, and concentrated in vacuo. The crude product was purified by flash column chromatography on silica, eluting with CHCl$_3$—7% MeOH—0.7% NH$_4$OH to yield the desired product which was converted to the hydrochloride salt by treatment with HCl in EtOAc.

Elemental analysis calculated for C$_{27}$H$_{21}$N$_5$O$_3$.HCl.1.5H$_2$O.0.15 EtOAc: C: 61.36; H: 4.89; N: 12.97; Found: C: 61.33; H: 4.72; N: 12.96; FAB MS: 465 (MH$^+$).

Example 23

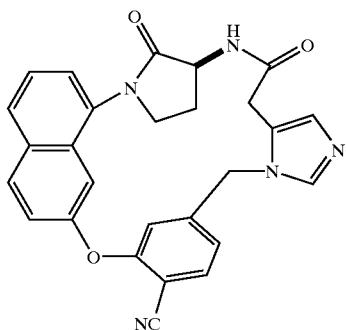

Preparation of (20S)-19,20,22,23-Tetrahydro-19,22-dioxo-5H,21H-18,20-ethano-12,14-etheno-6,10-methenobenz[d]imidazo[4,3-l][1,6,9,13]oxatriazacyclononadecosine-9-carbonitrile Hydrochloride Following the procedures described in Example 22, but using (S)-3-amino-1-(7-hydroxynaphthalen-1-yl)-2-oxopyrrolidine hydrochloride (as described in Example 9A) in place of (R)-3-amino-1-(7-hydroxy-naphthalen-1-yl)-2-oxopyrrolidine hydrochloride in Step E, the above-titled compound was prepared.

Elemental analysis calculated for $C_{27}H_{21}N_5O_3 \cdot HCl \cdot 2.5H_2O$: C: 59.50; H: 4.99; N: 12.85; Found: C: 59.41; H: 4.65; N: 12.88; FAB MS: 465 (MH$^+$).

Example 24

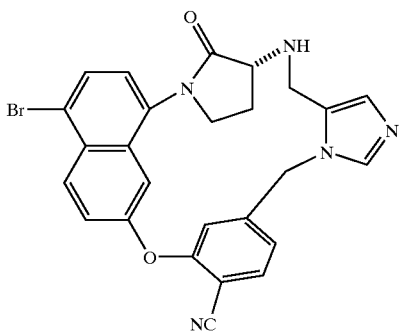

Preparation of (20R)-15-Bromo-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride

Step A: 1-(tert-Butoxycarbonylamino)naphth-7-ylmethanesulfonate

A mixture of 8-(tert-butoxycarbonylamino)-2-naphthol, as described in Example 9, Step A, (4.05 g, 15.6 mmol) and triethylamine (3.30 mL, 23.7 mmol) was stirred in dry CH$_2$Cl$_2$ (150 mL), under argon, at 0° C. and methanesulfonic anhydride (2.99 g, 17.2 mmol) was added in one portion. The resulting mixture was stirred at 0° C. for 20 min, then poured into saturated aqueous NaHCO$_3$ (100 mL) and the CH$_2$Cl$_2$ layer was extracted. The aqueous layer was extracted further with CH$_2$Cl$_2$ (100 mL). The combined organic extracts were dried over Na$_2$SO$_4$, filtered, and concentrated in vacuo to provide the titled compound as a pale solid.

Step B: 4-Bromo-1-(tert-butoxycarbonylamino)naphth-7-ylmethanesulfonate

To a stirred solution of 1-tert-butoxycarbonylaminonaphth-7-yl methanesulfonate, as described above in Step A, (2.05 g, 6.08 mmol) in acetic acid (50 mL) was added N-bromosuccinimide (1.14 g, 6.38 mmol) in one portion. The reaction mixture was stirred at ambient temperature for 2 hours, then H$_2$O (100 mL) and CH$_2$Cl$_2$ (100 mL) were added and the resulting mixture was cooled to 0° C. The aqueous layer was adjusted to pH of about 7 by addition of 10 N aqueous NaOH and the organic layer was extracted. The aqueous phase was extracted with a further portion of CH$_2$Cl$_2$ (100 mL), and the combined organic extracts were dried over Na$_2$SO$_4$, filtered, and concentrated in vacuo. The residue was triturated with 1:1 hexane-EtOAc to provide the titled product as a grey solid.

Step C: 4-Bromo-1-(tert-butoxycarbonylamino)naphth-7-ol

A solution of 4-bromo-1-tert-butoxycarbonylaminonaphth-7-yl methanesulfonate, as described above in Step B, (2.00 g, 4.80 mmol) in THF (50 mL) and 10% aqueous NaOH (85 mL) was heated to 65° C. for 60 hours. The cooled mixture was adjusted to pH of about 7 by addition of conc. aqueous HCl and concentrated to dryness under reduced pressure to provide the desired phenol.

Step D: 4-Bromo-1-(tert-butoxycarbonylamino)-7-(tert-butyldimethylsilyloxy) naphthalene

A mixture of 4-bromo-1-tert-butoxycarbonylaminonaphth-7-ol, as described above in Step C, (1.62 g, 4.80 mmol), tert-butyldimethylsilyl chloride (1.09 g, 7.20 mmol), and imidazole (0.82 g, 12 mmol), was stirred in dry DMF (40 mL) at ambient temperature for 18 hours. The solvent was removed under reduced pressure, and the residue was partitioned between H$_2$O (100 mL) and Et$_2$O (200 mL). The organic extract was dried over Na$_2$SO$_4$, filtered, and concentrated in vacuo. The crude product was purified by flash column chromatography on silica, eluting with CH$_2$Cl$_2$—50% hexane to yield the desired product as a pale solid.

Step E: 1-Amino-4-bromo-7-(tert-butyldimethylsilyloxy) naphthalene Hydrochloride

A solution of 4-bromo-1-tert-butoxycarbonylamino-7-tert-butyldimethylsilyloxynaphthalene, as described above in Step D, (1.9 g, 4.2 mmol) in EtOAc (50 mL) at ambient temperature was saturated with HCl (g). After 45 min, the mixture was concentrated in vacuo to yield the amine hydrochloride as a pale solid.

Step F: (R)-2-(tert-Butoxycarbonylamino)-4-(methylmercapto)-N-[4-bromo-7-(tert-butyldimethylsilyloxy)naphthalen-1-yl]butyramide

To (R)-N-(tert-Butoxycarbonyl)methionine (1.33 g, 5.48 mmol) in dry H$_2$Cl$_2$ (5 mL) under argon were added PYBOP (2.85 g, 5.48 mmol), 1-amino-4-bromo-7-(tert-butyldimethylsilyloxy)naphthalene hydrochloride, as described above Step E, (800 mg, 2.19 mmol), and N,N-diisopropylethylamine (1.7 mL, 9.9 mmol). The reaction mixture was stirred for 3 hours, then partitioned between 10% aqueous citric acid (100 mL) and CH$_2$Cl$_2$ (100 mL). The organic extract was dried over Na$_2$SO$_4$, filtered, and concentrated in vacuo. The crude product was purified by flash column chromatography on silica, eluting with a gradient of hexane—5% EtOAc to hexane—20% EtOAc to yield the product as a pale foam.

Step G: (R)-2-(tert-Butoxycarbonylamino)-4-(dimethylsulfonium)-N-[4-bromo-7-(tert-butyldimethylsilyloxy)naphthalen-1-yl]butyramide Iodide

(R)-2-(tert-Butoxycarbonylamino)-4-(methylmercapto)-N-[4-bromo-7-(tert-butyldimethylsilyloxy)naphthalen-1-yl]

butyramide, as described above in Step F, (865 mg, 1.48 mmol) was dissolved in iodomethane (20 mL, 321 mmol) and the solution was stirred under argon for 18 hours. The iodomethane was removed by distillation under reduced pressure to give the sulfonium salt.

Step H: (R)-1-[4-Bromo-7-(tert-butyldimethylsilyloxy) naphthalen-1-yl]-3-(tert-butoxycarbonylamino)-2-oxopyrrolidine (R)-2-(tert-Butoxycarbonylamino)-4-(dimethylsulfonium)-N-[4-bromo-7-(tert-butyldimethylsilyloxy)naphthalen-1-yl]butyramide iodide, as described above in Step G, (1.07 g, 1.48 mmol) was stirred in dry THF, under argon, at 0° C. and lithium bis(trimethylsilyl)amide (1.0 M in THF, 1.4 mL, 1.4 mmol) was added dropwise. The reaction mixture was stirred at 0° C. for 3 hours, then quenched with saturated aqueous NH$_4$Cl (25 mL) and most of the THF was removed under reduced pressure. The residual solution was partitioned between saturated aqueous NaHCO$_3$ (25 mL) and CH$_2$Cl$_2$ (75 mL). The aqueous layer was extracted further with CH$_2$Cl$_2$ (2×25 mL). The combined organic extracts were dried over Na$_2$SO$_4$, filtered, and concentrated in vacuo. The crude product was purified by flash column chromatography on silica, eluting with a gradient of hexane—10% EtOAc to hexane—50% EtOAc to yield the pyrrolidinone as a white solid.

Step I: (R)-1-[4-Bromo-7-hydroxynaphthalen-1-yl]-3-(tert-butoxycarbonylamino)-2-oxopyrrolidine To a stirred solution of (R)-1-[4-bromo-7-(tert-butyldimethylsilyloxy) naphthalen-1-yl]-3-(tert-butoxycarbonylamino)-2-oxopyrrolidine, as described above in Step H, (470 mg, 0.88 mmol) in THF (4 mL) was added TBAF (1.0 mL of a 1 M solution in THF, 1 mmol), dropwise. The mixture was stirred at ambient temperature for 30 min, then poured into saturated aqueous NaHCO$_3$ (10 mL) and CH$_2$Cl$_2$ (25 mL). The aqueous layer was extracted further with CH$_2$Cl$_2$ (2×25 mL). The combined organic extracts were dried over Na$_2$SO$_4$, filtered, and concentrated in vacuo. The crude product was purified by flash column chromatography on silica, eluting with CH$_2$Cl$_2$—20% EtOAc to yield the desired phenol.

(20R)-15-Bromo-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride Following the procedure described in Example 1, but using (R)-1-[4-bromo-7-hydroxynaphthalen-1-yl]-3-(tert-butoxycarbonylamino)-2-oxopyrrolidine (as described in Example 24, Step I) in place of (R)-3-(tert-butoxycarbonylamino)-1-(3-hydroxybenzyl)-2-oxopyrrolidine in Step N, the above compound was prepared.

Elemental analysis calculated for C$_{26}$H$_{20}$BrN$_5$O$_2$.2HCl.1.1H$_2$O.025 EtOAc: C: 51.54; H: 4.20; N: 11.13; Found: C: 51.51; H: 3.96; N: 11.10; FAB MS: 514 (MH$^+$).

Example 25

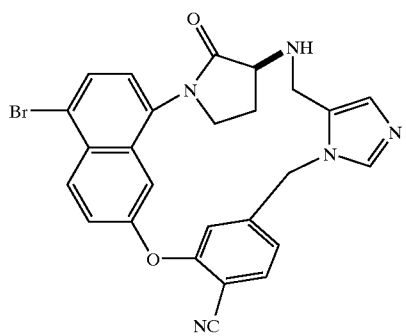

Preparation of (20S)-15-Bromo-19,20,21,22-tetrahydro-19-oxo-5H-18,20-ethano-12,14-etheno-6,10-metheno-18H-benz[d]imidazo[4,3-k][1,6,9,12]oxatriaza-cyclooctadecosine-9-carbonitrile Hydrochloride Following the procedure described in Example 24, but using (S)-N-(tert-butoxycarbonyl)methionine in place of (R)-N-(tert-butoxycarbonyl)methionine in Step F, the above-titled compound was prepared.

Elemental analysis calculated for C$_{26}$H$_{20}$BrN$_5$O$_2$.2HCl.1.05H$_2$O.0.45 EtOAc: C: 51.69; H: 4.32; N: 10.84; Found: C: 51.71; H: 3.94; N: 10.72; FAB MS: 514 (MH$^+$).

Example 26

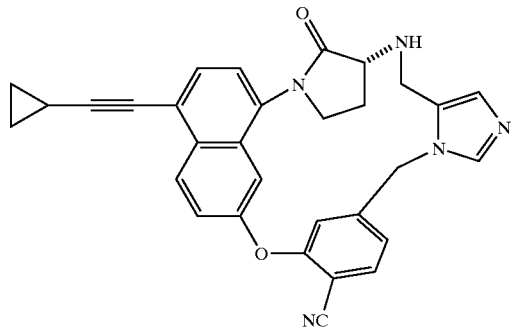

Preparation of (20R)-15-Cyclopropylethynyl-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile Trifluoroacetate Step A: [2-(Tri-n-butylstannyl)-1-ethynyl]cyclopropane To n-butyllithium (7.28 mL of a 2.5 M solution in hexane, 18.2 mmol) at −5° C. was added dry THF (80 mL) dropwise, maintaining the temperature below 5° C. 5-Chloro-1-pentyne (7.75 mL , 73.1 mmol) was added at 5° C., and the solution was stirred for 3 hours. The reaction was quenched by the addition of tri-n-butyltin chloride (21.0 mL, 77.4 mmol), and was allowed to stir for an additional 10 min. The solution was poured into saturated aqueous NaHCO$_3$ (500 mL) and hexane (500 mL). The hexane layer was washed with H$_2$O (200 mL), then brine (200 mL), then dried over Na$_2$SO$_4$, filtered, and concentrated in vacuo to provide the titled product as a yellow oil.

Step B: (20R)-15-Cyclopropylethynyl-19,20,21,22-tetrahydro-19-oxo-5H-18,20-ethano-12,14-etheno-6,10- metheno-18H-benz[d]imidazol[4,3-k][1,6,9,12] oxatriazacyclooctadecosine-9-carbonitrile Trifluoroacetate To a stirred solution of (20R)-15-bromo-19,20,21,22-tetrahydro-19-oxo-5H-18,20-ethano-12,14-etheno-6,10-metheno-18H-benz[d]imidazo[4,3-k][1,6,9,12] oxatriazacyclooctadecosine-9-carbonitrile, as described in Example 24, (70 mg, 0.136 mmol) in dry DMF (1 mL) were added [2-(tri-n-butylstannyl)-1-ethynyl]cyclopropane, as described above in Step A, (193 mg, 0.543 mmol) and tetrakis(triphenylphosphine)palladium (30 mg, 0.026 mmol). The resulting mixture was purged with argon for 5 min, then heated to 110° C. for 3 hours. The reaction mixture was allowed to cool, then was partitioned between saturated aqueous $NaHCO_3$ (5 mL) and EtOAc (15 mL). The aqueous layer was extracted further with EtOAc (2×15 mL). The combined organic extracts were dried over $Na_2SO_4$, filtered, and concentrated in vacuo. The crude mixture was purified by HPLC on a reversed phase C18 column, eluting with a gradient of 0.1% aqueous TFA—5% to 95% 0.1% TFA/$CH_3CN$, to give the titled product.

Elemental analysis calculated for $C_{31}H_{25}N_5O_2 \cdot 2CF_3CO_2H \cdot 0.85\ H_2O$: C: 56.58; H: 3.89; N: 9.43; Found: C: 56.59; H: 3.98; N: 9.32; FAB MS: 500 (MH$^+$).

Example 27

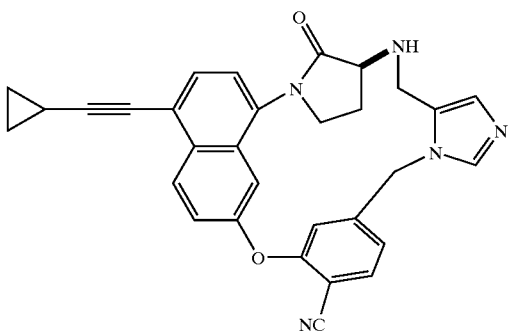

Preparation of (20S)-15-Cyclopropylethynyl-19,20, 21,22-tetrahydro-19-oxo-5H-18,20-ethano-12,14-etheno-6,10-metheno-18H-benz[d]imidazo[4,3-k][1, 6,9,12]oxatriazacyclooctadecosine-9-carbonitrile Trifluoroacetate Following the procedure described in Example 26, but using (20S)-15-bromo-19,20,21,22-tetrahydro-19-oxo-5H-18,20-ethano-12,14-etheno-6,10-metheno-18H-benz[d] imidazo[4,3-k][1,6,9,12]oxatriazacyclooctadecosine-9-carbonitrile, as described in Example 25, in place of (20R)-15-bromo-19,20,21,22-tetrahydro-19-oxo-5H-18,20-ethano-12,14-etheno-6,10-metheno-18H-benz[d]imidazo[4, 3-k][1,6,9,12]oxatriazacyclooctadecosine-9-carbonitrile in Step B, the above-titled compound was prepared.

Elemental analysis calculated for $C_{31}H_{25}N_5O_2 \cdot 2CF_3CO_2H \cdot 0.85H_2O$: C: 56.24; H: 3.94; N: 9.37; Found: C: 56.26; H: 3.87; N: 9.22; FAB MS: 500 (MH$^+$).

Example 28

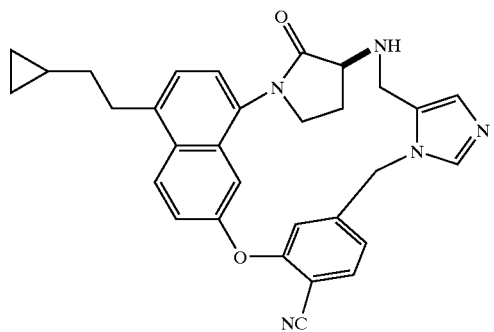

Preparation of (20S)-15-(2-Cyclopropylethyl)-19,20, 21,22-tetrahydro-19-oxo-5H-18,20-ethano-12,14-etheno-6,10-metheno-18H-benz[d]imidazo[4,3-k][1, 6,9,12]oxatriazacyclooctadecosine-9-carbonitrile Trifluoroacetate Step A: (20S)-15-(2-Cyclopropylethyl)-19,20,21,22-tetrahydro-19-oxo-5H-18,20-ethano-12,14-etheno-6,10-metheno-18H-benz[d]imidazo[4,3-k][1,6,9,12] oxatriazacyclooctadecosine-9-carbonitrile Trifluoroacetate A mixture of (20S)-15-cyclopropylethynyl-19,20,21,22-tetrahydro-19-oxo-5H-18,20-ethano-12,14-etheno-6,10-metheno-18H-benz[d]imidazo[4,3-k][1,6,9,12] oxatriazacyclooctadecosine-9-carbonitrile trifluoroacetate, as described in Example 27, (30 mg, 0.041 mmol) and 10% Pt-C (3 mg) in EtOH (2 mL) was stirred under an atmosphere of hydrogen (ca. 1 atm) at ambient temperature for 36 hours. The mixture was filtered through a pad of celite, washing with EtOH, and the filtrate was concentrated in vacuo to give a crude product. The crude mixture was purified by HPLC on a reversed phase C18 column, eluting with a gradient of 0.1% aqueous TFA −5% to 95% 0.1% TFA/$CH_3CN$, to give the titled product.

Elemental analysis calculated for $C_{31}H_{29}N_5O_2 \cdot 1.35CF_3CO_2H \cdot 2.25H_2O$: C: 57.98; H: 5.03; N: 10.03; Found: C: 58.01; H: 5.04; N: 9.75; FAB MS: 504 (MH$^+$).

Example 29

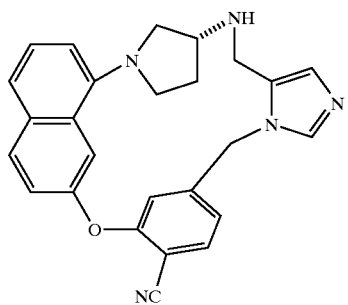

Preparation of (20R)-19,20,21,22-Tetrahydro-5H-18,20-ethano-12,14-etheno-6,10-metheno-18H-benz [d]imidazo[4,3-k][1,6,9,12] oxatriazacyclooctadecosine-9-carbonitrile Hydrochloride Step A: 8-(tert-Butoxycarbonylamino)-2-naphthol A mixture of 8-amino-2-naphthol (50.6 g, 0.318 mol) and di-tert-butyl dicarbonate (72.8 g, 0.334 mol) in $CH_2Cl_2$ (1.4

L) and THF (1 L) was heated to reflux for 36 hours. The mixture was allowed to cool to ambient temperature, then filtered and concentrated in vacuo. The residue was purified by flash column chromatography on silica, eluting with a gradient of $CH_2Cl_2$—0 to 10% EtOAc to yield the desired product as a light brown solid.

Step B: 1-(tert-Butoxycarbonylamino)-7-(tert-butyldimethylsilyloxy)naphthalene

A mixture of 8-(tert-butoxycarbonylamino)-2-naphthol, as described above in Step A, (43.2 g, 0.167 mol), tert-butyldimethylsilyl chloride (32.7 g, 0.217 mol), and imidazole (25.0 g, 0.367 mol) in dry, degassed DMF (400 mL) was stirred, under argon, at ambient temperature for 30 min. The solvent was removed under reduced pressure and the residue was partitioned between $H_2O$ (1 L) and $Et_2O$ (2 L). The aqueous layer was extracted further with $Et_2O$ (1 L) and the combined organic extracts were dried over $Na_2SO_4$, filtered, and concentrated in vacuo. The crude product was purified by flash column chromatography on silica, eluting with hexane—50% $CH_2Cl_2$ to yield the desired product as a pale solid.

Step C: 1-Amino-7-(tert-butyldimethylsilyloxy)naphthalene Hydrochloride

A solution of 1-(tert-butoxycarbonylamino)-7-(tert-butyldimethylsilyloxy)naphthalene, as described above in Step B, (5.00 g, 13.4 mmol) in EtOAc (240 mL) and $Et_2O$ (60 mL) at ambient temperature was saturated with HCl (g). After 1 hour, the mixture was concentrated in vacuo to yield the desired product as a pale solid.

Step D: (R)-2-(tert-Butoxycarbonylamino)-4-(methylmercapto)-N-[7-(tert-butyldimethylsilyloxy) naphthalen-1-yl]butyramide To (R)-N-(tert-butoxycarbonyl)methionine (27.3 g, 109 mmol) in dry $CH_2Cl_2$ (45 mL) at 0° C., under argon, were added PYBOP (57 g, 109 mmol), 1-amino-7-(tert-butyldimethylsilyloxy)naphthalene hydrochloride, as described above in Step C above (13.6 g, 44 mmol), and N,N-diisopropylethylamine (26.7 mL, 153 mmol). The reaction mixture was allowed to warm to ambient temperature and was stirred for 4 hours, then partitioned between 10% aqueous citric acid (400 mL) and $CH_2Cl_2$ (1 L). The organic layer was dried over $MgSO_4$, filtered, and concentrated in vacuo. The crude product was purified by flash column chromatography on silica, eluting with a gradient of hexane—10% to 25% EtOAc to yield the titled product.

Step E: (R)-2-(tert-Butoxycarbonylamino)-4-(dimethylsulfonium)-N-[7-(tert-butyldimethylsilyloxy) naphthalen-1-yl]butyramide Iodide (R)-2-(tert-Butoxycarbonylamino)-4-(methylmercapto)-N-[7-(tert-butyldimethylsilyloxy)naphthalen-1-yl] butyramide, as described above in Step D, (18.1 g, 35.8 mmol) was dissolved in iodomethane (110 mL, 1.77 mol) and the solution was stirred under argon for 18 hours. The iodomethane was removed by distillation under reduced pressure to give the desired sulfonium salt.

Step F: (R)-3-(tert-Butoxycarbonylamino)-1-[7-(tert-butyldimethylsilyloxy) naphthalen-1-yl]-2-oxopyrrolidine (R)-2-(tert-Butoxycarbonylamino)-4-(dimethylsulfonium)-N-[7-(tert-butyldimethylsilyloxy) naphthalen-1-yl]butyramide iodide, as described in Step E, (23.1 g, 35.7 mmol) was stirred in dry THF (400 mL), under argon, at 0° C. and lithium bis(trimethylsilyl)amide (1.0 M in THF, 35.4 mL, 35.4 mmol) was added dropwise. The reaction mixture was stirred at 0° C. for 4 hours, then quenched with saturated aqueous $NH_4Cl$ (150 mL). The resulting mixture was partitioned between dilute aqueous $NaHCO_3$ (2 L) and $CH_2Cl_2$ (2 L). The aqueous layer was extracted further with $CH_2Cl_2$ (2 L). The combined organic extracts were dried over $Na_2SO_4$, filtered, and concentrated in vacuo. The crude product was purified by flash column chromatography on silica, eluting with a gradient of hexane—5% to 50% EtOAc to yield the titled product as a white solid.

Step G: (R)-3-(tert-Butoxycarbonylamino)-1-[7-(tert-butyldimethylsilyloxy) naphthalen-1-yl]-2-thioxopyrrolidine A mixture of (R)-3-(tert-butoxycarbonylamino)-1-[7-(tert-butyl-dimethylsilyloxy)naphthalen-1-yl]-2-oxopyrrolidine, as described above in Step F, (113 mg, 0.247 mmol) and Lawesson's Reagent (50 mg, 0.124 mmol) in dry toluene (0.5 mL), under argon, was heated to 80° C. for 1 hour. The reaction mixture was allowed to cool, then poured directly onto a silica gel column and chromatographed, eluting with a gradient of hexane—5% to 25% EtOAc to yield the titled product as a clear oil.

Step H: (R)-3-(tert-Butoxycarbonylamino)-1-[7-(tert-butyldimethylsilyloxy) naphthalen-1-yl]pyrrolidine (R)-3-(tert-Butoxycarbonylamino)-1-[7-(tert-butyldimethylsilyloxy) naphthalen-1-yl]-2-thioxopyrrolidine, as described above in Step G, (1.04 g, 2.19 mmol) was dissolved in EtOH (100 mL) and Raney Ni (5 g of a slurry in EtOH) was added. The mixture was stirred at ambient temperature for 18 hours, then an additional portion of Raney Ni (3 g of a slurry in EtOH) was added. After a further 4 hours stirring, the reaction mixture was filtered through a pad of celite, washing with EtOH. The filtrate was concentrated in vacuo to provide the desired product.

Step I: (R)-3-(tert-Butoxycarbonylamino)-1-[7-hydroxynaphthalen-1-yl]pyrrolidine To a stirred solution of (R)-3-(tert-butoxycarbonylamino)-1-[7-(tert-butyldimethylsilyloxy) naphthalen-1-yl]pyrrolidine, as described above in Step H, (970 mg, 2.19 mmol) in THF (15 mL) was added TBAF (2.40 mL of a 1 M solution in THF, 2.40 mmol), dropwise. The mixture was stirred at ambient temperature for 30 min, then poured into saturated aqueous $NaHCO_3$ (50 mL) and $CH_2Cl_2$ (100 mL). The aqueous layer was extracted further with $CH_2Cl_2$ (2×50 mL). The combined organic extracts were dried over $Na_2SO_4$, filtered, and concentrated in vacuo. The crude product was purified by flash column chromatography on silica, eluting with a gradient of $CH_2C_2$—0% to 20% EtOAc to yield the desired phenol.

Step J: (R)-3-Amino-1-[7-hydroxynaphthalen-1-yl]pyrrolidine Hydrochloride

A solution of (R)-3-(tert-butoxycarbonylamino)-1-[7-hydroxynaphthalen-1-yl]pyrrolidine, as described above in Step I, (625 mg, 1.90 mmol) in EtOAc (80 mL) at 0° C. was saturated with HCl (g). After 30 min, the mixture was concentrated in vacuo to yield the amine hydrochloride as a pale solid.

Step K: (R)-2-Fluoro-4-(5-{[1-(7-hydroxynaphthalen-1-yl) pyrrolidin-3-ylamino]methyl}imidazol-1-ylmethyl) benzonitrile (R)-3-Amino-1-[7-hydroxynaphthalen-1-yl]pyrrolidine hydrochloride, as described in Step J, (85 mg, 0.32 mmol) and 1-(4-cyano-3-fluorobenzyl)-5-imidazolecarboxaldehyde, as described in Example 1, Step G, (75 mg, 0.33 mmol), were stirred in MeOH (1 mL) and N,N-diisopropylethylamine was added dropwise to adjust the mixture to ca. pH 5, as judged by wetted pH paper. The mixture was stirred for 1 hour at ambient temperature then $NaCNBH_3$ (26 mg, 0.42 mmol) was added and stirring was continued for 18 hours. The reaction was quenched with saturated aqueous NaHCO₃ (1 mL) and most of the MeOH was removed under reduced pressure. The residual solution was partitioned between saturated aqueous NaHCO₃ (3 mL) and CH₂Cl₂ (10 mL). The aqueous layer was extracted further with CH₂Cl₂ (2×10 mL). The combined organic extracts were dried over Na₂SO₄, filtered, and concentrated in vacuo. The crude product was purified by flash column chromatography on silica, eluting with a gradient of CH₂Cl₂—1% to 6% MeOH—0.1% to 0.6% NH₄OH to yield the titled product as a colorless oil.

Step L: (20R)-19,20,21,22-Tetrahydro-5H-18,20-ethano-12, 14-etheno-6,10-metheno-18H-benz[d]imidazo[4,3-k][1,6,9, 12]oxatriazacyclooctadecosine-9-carbonitrile Hydrochloride A mixture of (R)-2-fluoro-4-(5-{[1-(7-hydroxynaphthalen-1yl)pyrrolidin-3-ylamino] methyl}imidazol-1-ylmethyl)benzonitrile, as described above in Step K, (138 mg, 0.31 mmol) a nd Cs₂CO₃ (255 mg, 0.78 mmol) in dry, degassed DMF (31 mL) was stirred at 65° C. under argon for 5 hours. Acetic acid (60 mL, 1.0 mmol) was added and the solvent was removed under reduced pressure. The residue was partitioned between saturated aqueous NaHCO₃ (10 mL) and CH₂Cl₂ (20 mL). The aqueous layer was extracted further with CH₂Cl₂ (3×20 mL). The combined organic extracts were dried over Na₂SO₄, filtered, and concentrated in vacuo. The crude product was purified by flash column chromatography on silica, eluting with a gradient of CH₂Cl₂—1% to 10% MeOH—0.1to 1% NH₄OH to yield the titled product which was converted to the hydrochloride salt by treatment with HCl in EtOAc.

Elemental analysis calculated for C₂₆H₂₃N₅O.3HCl.1.25H₂O.0.95 DMF: C: 58.06; H: 5.38; N: 12.65; Found: C: 58. 10; H: 5.59; N: 12.65; FAB MS: 422 (MH⁺).

Example 29A

Preparation of (S)-3-(tert-Butoxycarbonyiamino)-1-[7-(tert-butyldimethyisilyloxy)naphthalen-1-yl]-2-oxopyrolidine Following the procedures described in Example 29, Steps A–H, but using (S)-N-(tert-butoxycarbonyl)methionine in place of (R)-N-(tert-butoxycarbonyl)methionine in Step D, the above-titled compound was obtained.

Example 30

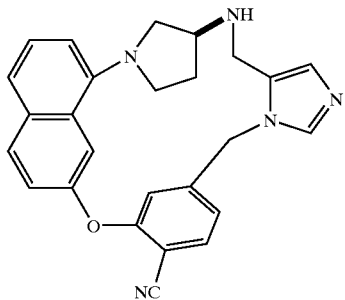

Preparation of (20S)-19,20,21,22-Tetrahydro-5H-18, 20-ethano-12,14-etheno-6,10-metheno-18H-benz[d] imidazo[4,3-k][1,6,9,12]oxatriazacyclooctadecosine- 9-carbonitrile Hydrochloride The above-titled compound was prepared following the procedure described in Example 29, but using (S)-N-(tert-butoxycarbonyl)methionine in place of (R)-N-(tert-butoxycarbonyl)methionine in Step D.

Elemental analysis calculated for C₂₆H₂₃N₅O.3HCl.2.5H₂O.0.55CH₃CN: C: 56.97; H: 5.19; N: 12.25; Found: C: 56.80; H: 5.34; N: 12.24; FAB MS: 422 (MH⁺).

Example 31

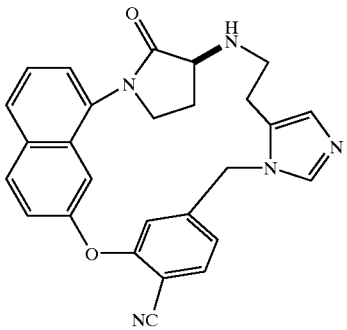

Preparation of (20S)-19,20,22,23-Tetrahydro-19-oxo-5H,21H-18,20-ethano-12,14-etheno-6,10-methenobenz[d]imidazo[4,3-l][1,6,9,13] oxatriazacyclononadecosine- 9-carbonitrile Hydrochloride Step A: (S)-3-Amino-1-[7-(tert-butyldimethylsilyloxy) naphthalen-1-yl]-2-oxopyrrolidine Hydrochloride A solution of (S)-3-(tert-butoxycarbonylamino)-1-[7-(tert-butyldimethylsilyloxy)naphthalen-1-yl]-2-oxopyrrolidine, as described in Example 29A, (4.00 g, 8.76 mmol) in EtOAc (250 mL) was cooled to 0° C. and HCl (g) was bubbled in slowly for 5 min. The reaction mixture was stood at 0° C. for 30 min, then HCl (g) was bubbled in slowly for 5 min again. After standing for a further 30 min at 0° C., the mixture was concentrated in vacuo to provide the titled product.

Step B: Lithium [1-(Triphenylmethyl)-1H-imidazol-4-yl] acetate

Methyl [1-(triphenylmethyl)-1H-imidazol-4-yl]acetate, as described in Example 22, Step B, (free base) (12.5 g, 32.7 mmol) was dissolved in THF (175 mL) and H₂O (35 mL). Lithium hydroxide monohydrate (1.44 g, 34.3 mmol) was added and the resulting mixture was stirred at ambient temperature for 1 hour, then adjusted to pH 7 with 1.0 N aqueous HCl and concentrated to dryness in vacuo to give the titled lithium salt.

Step C: (S)-N-[1-(7-Hydroxynaphthalen-1-yl)-2-oxopyrrolidin-3-yl]-2-[1-(triphenylmethyl)-1H-imidazol-4-yl]acetamide A mixture of lithium [1-(triphenylmethyl)-1H-imidazol-4-yl]acetate, as described above in Step B, (4.40 g, 11.6 mmol), (S)-3-amino-1-[7-(tert-butyldimethylsilyloxy) naphthalen-1-yl]-2-oxopyrrolidine hydrochloride, as described above in Step A (3.86 g, 9.84 mmol), HOBT (1.60 g, 11.8 mmol), EDC (2.30 g, 12.0 mmol), and N,N-diisopropylethylamine (6.00 mL, 34.4 mmol) was stirred in DMF (80 mL) at ambient temperature for 18 hours. The solvent was removed under reduced pressure and the residue was partitioned between saturated aqueous NaHCO₃ (50 mL) and CHCl₃ (75 mL). The aqueous layer was extracted further with CHCl₃ (2×50 mL). The combined organic extracts were dried over MgSO₄, filtered, and concentrated in vacuo. The crude product was dissolved in dry THF (75 mL) and TBAF (5 mL of a 1.0 M solution in TBF, 5 mmol)

was added. The resulting mixture was stirred at ambient temperature for 30 min, then quenched with saturated aqueous NH$_4$Cl (30 mL) and most of the TBF was removed under reduced pressure. The residual mixture was poured into saturated aqueous NaHCO$_3$ (50 mL) and CH$_2$Cl$_2$ (100 mL). The aqueous layer was extracted further with CH$_2$Cl$_2$ (2×50 mL). The combined organic extracts were dried over MgSO$_4$, filtered, and concentrated in vacuo. The residue was purified by flash column chromatography on silica, eluting with a gradient of CH$_2$Cl$_2$—2% to 4% MeOH to yield the titled product.

Step D: (S)-N-{1-[7-(tert-Butyldiphenylsilyloxy)naphthalen-1-yl]-2-oxopyrrolidin-3-yl}-2-[1-(triphenylmethyl)-1H-imidazol-4-yl]acetamide A mixture of (S)-N-[1-(7-hydroxynaphthalen-1-yl)-2-oxopyrrolidin-3-yl]-2-[1-(triphenylmethyl)-1H-imidazol-4-yl]acetamide, as described above in Step C, (6.50 g, 11.0 mmol), tert-butyldiphenylsilyl chloride (4.55 g, 16.6 mol), and imidazole (1.87 g, 27.5 mol) in dry, degassed DMF (100 mL) was stirred, under argon, at 50° C. for 18 hours. The solvent was removed under reduced pressure and the residue was partitioned between saturated aqueous NaHCO$_3$ (75 mL) and CH$_2$Cl$_2$ (125 mL). The aqueous layer was extracted further with CH$_2$Cl$_2$ (125 mL) and the combined organic extracts were dried over MgSO$_4$, filtered, and concentrated in vacuo. The crude product was purified by flash column chromatography on silica, eluting with CH$_2$Cl$_2$—1% MeOH—0.1% NH$_4$OH to yield the desired product as a pale solid.

Step E: (S)-N-{1-[7-(tert-Butyldiphenylsilyloxy)naphthalen-1-yl]-2-oxopyrrolidin-3-yl}-2-[1-(triphenylmethyl)-1H-imidazol-4-yl]thioacetamide A mixture of (S)-N-{1-[7-(tert-butyldiphenylsilyloxy)naphthalen-1-yl]-2-oxopyrrolidin-3-yl}-2-[1-(triphenylmethyl)-1H-imidazol-4-yl]acetamide, as described above in Step D, (3.00 g, 3.61 mmol) and Lawesson's Reagent (728 mg, 1.80 mmol) in dry THF (45 mL), under argon, was heated to 45° C. for 90 min. The solvent was removed under reduced pressure and the residue was partitioned between saturated aqueous Na$_2$CO$_3$ (125 mL) and CH$_2$Cl$_2$ (300 mL). The aqueous layer was extracted further with CH$_2$Cl$_2$ (150 mL) and the combined organic extracts were dried over MgSO$_4$, filtered, and concentrated in vacuo. The crude product was purified by flash column chromatography on silica, eluting with hexane—40% EtOAc—1% MeOH—0.1% NH$_4$OH to yield the desired product.

Step F: (S)-1-[7-(tert-Butyldiphenylsilyloxy)naphthalen-1-yl]-2-oxo-3-({2-[1-(triphenylmethyl)- 1H-imidazol-4-yl]ethyl}amino)pyrrolidine A mixture of (S)-N-{1-[7-(tert-butyldiphenylsilyloxy)naphthalen-1-yl]-2-oxopyrrolidin-3-yl}-2-[1-(triphenylmethyl)-1H-imidazol-4-yl]thioacetamide, as described above in Step E, (1.85 g, 2.18 mmol) and Raney Ni (3.7 g of a slurry in EtOH) was stirred in MeOH (80 mL) at 35° C. for 5 hours. The mixture was filtered through a pad of celite, washing with MeOH, and the filtrate was concentrated to provide the titled product as a foam.

Step G: (S)-{1-[7-(tert-Butyldiphenylsilyloxy)naphthalen-1-yl]-2-oxo-pyrrolidin-3-yl}-{2-[1-(triphenylmethyl)-1H-imidazol-4-yl]ethyl}carbamic Acid tert-Butyl Ester To a stirred solution of (S)-1-[7-(tert-butyldiphenylsilyloxy)naphthalen-1-yl]-2-oxo-3-({2-[1-(triphenylmethyl)-1H-imidazol-4-yl]ethyl}amino)pyrrolidine, as described above in Step F, (1.20 g, 1.47 mmol) in degassed DMF (15 mL) was added di-tert-butyl dicarbonate (352 mg, 1.61 mmol) and the resulting mixture was stirred at ambient temperature for 18 hours. The solvent was removed under reduced pressure and the residue was purified by flash column chromatography on silica, eluting with EtOAc—1% MeOH—0.1% NH$_4$OH to yield the desired product.

Step H: 4-Cyano-3-fluorobenzyl Alcohol

To a stirred solution of 4-cyano-3-fluorobenzaldehyde, as described in Example 11, Step B, (620 mg, 4.16 mmol) in EtOH (30 mL) at 0° C. was added NaBH$_4$ (157 mg, 4.16 mmol) in one portion. The reaction mixture was stirred at 0° C. for 10 min, then 10% aqueous citric acid (10 mL) was added and the solvent was removed under reduced pressure. The residue was partitioned between saturated aqueous NaHCO$_3$ (10 nmL) and CH$_2$Cl$_2$ (30 mL). The aqueous layer was extracted further with CH$_2$Cl$_2$ (30 mL). The combined organic extracts were dried over MgSO$_4$, filtered, and concentrated in vacuo to provide the titled compound as a white solid.

Step I: (S)-{1-[7-(tert-Butyldiphenylsilyloxy)naphthalen-1-yl]-2-oxo-pyrrolidin-3-yl}-{2-[3-(4-cyano-3-fluorobenzyl)-3H-imidazol-4-yl]ethyl}carbamic Acid tert-Butyl Ester To a stirred solution of (S)-{1-[7-(tert-butyldiphenylsilyloxy)naphthalen-1-yl]-2-oxo-pyrrolidin-3-yl}-{2-[1-(triphenylmethyl)-1H-imidazol-4-yl]ethyl}carbamic acid tert-butyl ester, as described above in Step G, (720 mg, 0.785 mmol) and 4-cyano-3-fluorobenzyl alcohol, as described above in Step H, (142 mg, 0.940 mmol) in dry CH$_2$Cl$_2$ (7 mL) were added N,N-diisopropylethylamine (0.342 mL, 1.96 mmol), followed by trifluoromethanesulfonic anhydride (0.158 mL, 0.940 mmol), dropwise. The reaction mixture was allowed to warm slowly to ambient temperature and was stirred for 18 hours, then concentrated in vacuo. The residue was dissolved in MeOH (25 mL) and the resulting solution was stirred at ambient temperature for 18 hours. The solvent was evaporated under reduced pressure, and the residue was partitioned between saturated aqueous NaHCO$_3$ (5 mL) and CHCl$_3$ (20 mL). The aqueous layer was extracted further with CHCl$_3$ (20 mL). The combined organic extracts were dried over MgSO$_4$, filtered, and concentrated in vacuo. The crude product was purified by flash column chromatography on silica, eluting with EtOAc—1% MeOH—0.1% NH$_4$OH to yield the desired product as a pale foam.

Step J: (S)-{2-[3-(4-Cyano-3-fluorobenzyl)-3H-imidazol-4-yl]ethyl}-{1-[7-hydroxynaphthalen-1-yl]-2-oxo-pyrrolidin-3-yl}carbamic Acid tert-Butyl Ester To a stirred solution of (S)-{1-[7-(tert-butyldiphenylsilyloxy)naphthalen-1-yl]-2-oxo-pyrrolidin-3-yl}-{2-[3-(4-cyano-3-fluorobenzyl)-3H-imidazol-4-yl]ethyl}carbamic acid tert-butyl ester, as described above in Step I, (500 mg, 0.619 mmol) in ThF (5 mL) was added TBAF (0.68 mL of a 1 M solution in THF, 0.68 mmol), dropwise. The mixture was stirred at ambient temperature for 30 min, then concentrated in vacuo. The residue was purified by flash column chromatography on silica, eluting with CHCl$_3$—2% MeOH—0.2% NH$_4$OH to yield the desired phenol as a white foam.

Step K: (20S)-19,20,22,23-Tetrahydro-19-oxo-5H,21H-18,20-ethano-12,14-etheno-6,10-methenobenz[d]imidazo[4,3-1][1,6,9,13]oxatriazacyclononadecosine-9-carbonitrile Hydrochloride A mixture of (S)-{2-[3-(4-cyano-3-fluorobenzyl)-3H-imidazol-4-yl]ethyl}-{1-[7-hydroxynaphthalen-1-yl]-2-oxo-pyrrolidin-3-yl}carbamic acid tert-butyl ester, as described above in Step J, (325 mg, 0.57 mmol) and Cs$_2$CO$_3$ (371 mg, 1.14 mmol) in dry, degassed DMF (100 mL) was stirred at 45° C., under argon, for 18 hours. Acetic acid (0.12 mL, 2.1 mmol) was added and the solvent was removed under reduced pressure. The residue was partitioned between saturated aqueous NaHCO$_3$ (10 mL) and CH$_2$Cl$_2$ (20 mL). The aqueous layer was extracted further with CH$_2$Cl$_2$ (3×20 mL). The combined organic extracts were dried over Na$_2$SO$_4$, filtered, and concentrated in vacuo. The crude product was purified by flash column chromatography on silica, eluting with CHCl$_3$—3% MeOH—0.3% NH$_4$OH to yield (20S)-21-tert-butoxycarbonyl-19,20,22,23-tetrahydro-19-oxo-5H,21H-18,20-ethano-12,14-etheno-6,10-methenobenz[d]imidazo[4,3-1][1,6,9,13] oxatriazacyclononadecosine-9-carbonitrile. This was further purified by HPLC on a Chiralpak AD column, eluting with 2-propanol—30% hexane—0.1% Et$_2$NH. The product-containing fractions were combined and concentrated in vacuo, and the residue was partitioned between saturated aqueous NaHCO$_3$ (10 mL) and CH$_2$Cl$_2$ (20 mL). The aqueous layer was extracted further with CH$_2$Cl$_2$ (3×20 mL). The combined organic extracts were dried over Na$_2$SO$_4$, filtered, and concentrated in vacuo. The residue was dissolved in EtOAc (5 mL) and the solution was cooled to 0° C., then saturated with HCl (g). After standing at 0° C. for 15 min, the mixture was concentrated to dryness under reduced pressure to yield the titled product as a white solid.

Elemental analysis calculated for C$_{27}$H$_{23}$N$_5$O$_2$.2HCl.1.35H$_2$O.0.30 EtOAc: C: 59.09; H: 5.29; N: 12.22; Found: C: 59.08; H: 4.98; N: 12.18; FAB MS: 450 (MH$^+$).

Example 32

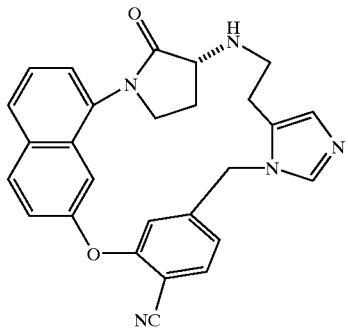

Preparation of (20R)-19,20,22,23-Tetrahydro-19-oxo-5H,21H-18,20-ethano-12,14-etheno-6,10-methenobenz[d]imidazo[4,3-1][1,6,9,13] oxatriazacyclononadecosine-9-carbonitrile Hydrochloride The above-titled compound was prepared following the procedure described in Example 31, but using (R)-3-(tert-butoxycarbonylamino)-1-[7-(tert-butyldimethylsilyloxy) naphthalen-1-yl]-2-oxopyrrolidine, as described in Example 29, Step F, in place of (S)-3-(tert-butoxycarbonylamino)-1-[7-(tert-butyldimethylsilyloxy)naphthalen-1-yl]-2-oxopyrrolidine in Step A.

Elemental analysis calculated for C$_{27}$H$_{23}$N$_5$O$_2$.1.8HCl.2.5H$_2$O.0.4CH$_3$CN: C: 57.90; H: 5.42; N: 13.12; Found: C: 57.88; H: 5.48; N: 13.09; FAB MS: 450 (MH$^+$).

Example 33

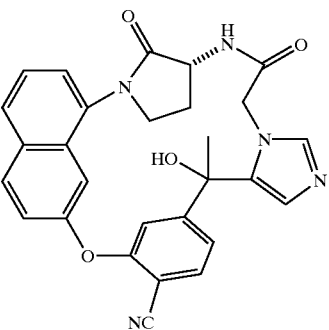

Preparation of (20R)-19,20,22,23-Tetrahydro-5-hydroxy-5-methyl-19,22-dioxo-5H,21H-18,20-ethano-12,14-etheno-6,10-methenobenz[d]imidazo [3,4-1][1,6,9,12]oxatriazacyclononadecosine-9-carbonitrile Hydrochloride, Diastereomers A & B Step A: (4-Cyano-3-fluorophenyl)[1-(triphenylmethyl) imidazol-4-yl]methanol To a solution of 4-iodo-1-(triphenylmethyl)imidazole (2.93 g, 6.71 mmol) in dry CH$_2$Cl$_2$ (30 mL), under argon, was added MeMgBr (2.35 mL of a 3.0M solution in Et$_2$O, 7.05 mmol), dropwise. The resulting solution was stirred at ambient temperature for 1 hour, then transferred dropwise into a stirred solution of 4-cyano-3-fluorobenzaldehyde, as described in Example 11, Step B, (1.00 g, 6.71 mmol) in dry THF (30 mL), under argon, at −78° C. After 30 min, the reaction mixture was quenched with saturated aqueous NH$_4$Cl (50 mL) and extracted with CH$_2$Cl$_2$ (3×50 mL). The combined organic extracts were dried over Na$_2$SO$_4$, filtered, and concentrated in vacuo. The residue was triturated with EtOAc to yield the desired alcohol as a white solid.

Step B: 4-Cyano-3-fluorophenyl 1-(Triphenylmethyl) imidazol-4-yl Ketone

To a solution of (4-cyano-3-fluorophenyl)[1-(triphenylmethyl)imidazol-4-yl]methanol, as described above in Step A, (10.0 g, 21.8 mmol) in CH$_2$Cl$_2$ (300 mL) was added MnO$_2$ (18.9 g, 218 mmol) and the resulting mixture was heated to reflux for 18 hours. The mixture was allowed to cool, then filtered through a pad of celite, washing with CH$_2$Cl$_2$. The filtrate was concentrated under reduced pressure to provide the titled product as a white solid.

Step C: 1-(4-Cyano-3-fluorophenyl)-1-[1-(triphenylmethyl) imidazol-4-yl]ethanol

To a solution of 4-cyano-3-fluorophenyl 1-(triphenylmethyl)imidazol-4-yl ketone, as described above in Step B, (7.0 g, 15.3 mmol) in dry THF (280 mL), under argon, at −78° C., was added MeMgBr (5.3 mL of a 3.0M solution in Et$_2$O, 15.9 mmol), dropwise. After 1 hour, the reaction mixture was quenched with saturated aqueous NH$_4$Cl (100 mL) and extracted with CH$_2$Cl$_2$ (2×150 mL). The combined organic extracts were dried over MgSO$_4$, filtered, and concentrated in vacuo. The residue was purified by silica gel chromatography, eluting with a gradient of hexane—30% to 50% EtOAc, to yield the titled product as pale solid.

Step D: {5-[1-(4-Cyano-3-fluorophenyl)-1-hydroxyethyl] imidazol-1-yl}acetic Acid Methyl Ester To a stirred solution of 1-(4-cyano-3-fluorophenyl)-1-[1-(triphenylmethyl)imidazol-4-yl]ethanol, as described above in Step C, (200 mg, 0.42 mmol), methyl glycolate (35 mg, 0.39 mmol), and N,N-diisopropylethylamine (65 mg, 0.51 mmol) in dry CH$_2$Cl$_2$ (10 mL), under argon, at −78° C., was added trifluoromethanesulfonic anhydride (110 mg, 0.39 mmol) dropwise. The mixture was allowed to warm slowly to ambient temperature, then the solvent was removed in vacuo. The residue was dissolved in MeOH (10 mL) and the solution was heated to reflux for 1 hour, then concentrated to dryness. The residue was purified by silica gel chromatography, eluting with 4% MeOH—0.4% NH$_4$OH in CHCl$_3$, to yield the titled product as a white solid.

Step E: {5-[1-(4-Cyano-3-fluorophenyl)-1-hydroxyethyl] imidazol-1-yl}acetic Acid, Lithium Salt A mixture of {5-[1-(4-cyano-3-fluorophenyl)-1-hydroxyethyl]imidazol-1-yl}acetic acid methyl ester, as described above in Step D, (50 mg, 0.165 mmol) and LiOH (7.3 mg, 0.174 mmol) was stirred in THF (1.7 mL) and H$_2$O (0.3 mL) at ambient temperature for 2 hours. The solution was adjusted to pH≈7 by the addition of 1.0 N aqueous HCl and then concentrated in vacuo to give the desired product.

Step F: (R)-2-{5-[1-(4-Cyano-3-fluorophenyl)-1-hydroxyethyl]imidazol-1-yl}-N-(1-(7-hydroxynaphthalen-1-yl)-2-oxopyrrolidin-3-yl)acetamide A solution of {5-[1-(4-cyano-3-fluorophenyl)-1-hydroxyethyl]imidazol-1-yl}acetic acid, lithium salt, as described above in Step E, (40 mg, 0.136 mmol), (R)-3-amino-1-[7-hydroxynaphthalen-1-yl]pyrrolidine hydrochloride, as described in Example 29, Step J, (42 mg, 0.151 mmol), 1-hydroxybenzotriazole hydrate (23 mg, 0.17 mmol), EDC (33 mg, 0.17 mmol), and N,N-diisopropylethylamine (40 mg, 0.31 mmol) in dry, degassed DMF (1 mL) was stirred at ambient temperature for 18 hours. The solvent was removed under reduced pressure and the residue was partitioned between saturated aqueous NaHCO$_3$ (1 mL) and CHCl$_3$ (3 mL). The aqueous layer was extracted further with CHCl$_3$ (2×2 mL). The combined organic extracts were dried over Na$_2$SO$_4$, filtered, and concentrated under reduced pressure. The crude product was purified by preparative thin layer chromatography, eluting with a gradient of CH$_2$Cl$_2$—6% MeOH—0.6% NH$_4$OH to give the titled product.

Step G: (20R)-19,20,22,23-Tetrahydro-5-hydroxy-5-methyl-19,22-dioxo-5H,21H-18,20-ethano-12,14-etheno-6,10-methenobenz[d]imidazo[3,4-1][1,6,9,12] oxatriazacyclononadecosine-9-carbonitrile Hydrochloride, Diastereomers A & B A stirred mixture of (R)-2-{5-[1-(4-cyano-3-fluorophenyl)-1-hydroxyethyl]imidazol-1-yl}-N-(1-(7-hydroxynaphthalen-1-yl)-2-oxopyrrolidin-3-yl)acetamide, as described above in Step F, (14 mg, 0.027 mmol) and Cs$_2$CO$_3$ (13 mg, 0.040 mmol) in dry, degassed DMF (1 mL) under argon was heated to 50° C. for 48 hours. The solvent was removed under reduced pressure and the residue was partitioned between saturated aqueous NaHCO$_3$ (1 mL) and CHCl$_3$ (2 mL). The aqueous layer was extracted further with CHCl$_3$ (2×2 mL). The combined organic extracts were dried over MgSO$_4$, filtered, and concentrated under reduced pressure. The residue was purified by flash column chromatography, eluting with a gradient of CH$_2$Cl$_2$—1% to 5% MeOH—0.1% to 0.5% NH$_4$OH to give the desired product, which was treated with HCl in acetonitrile—water and lyophilized to give the titled compound.

FAB MS: 494 (MH$^+$).

Example 34

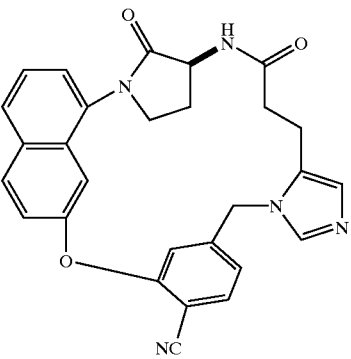

Preparation of (20S)-19,20,21,22,23,24-Hexahydro-19,22-dioxo-5H,18H-18,20-ethano-12,14-etheno-6,10-methenobenz[d]imidazo[4,3-m][1,6,9,14] oxatriazacycloeicosine-9-carbonitrile Hydrochloride Step A: Methyl 3-(Imidazol-4-yl)acrylate Hydrochloride A solution of 4-imidazoleacrylic acid hydrochloride (20.0 g, 145 mmol) in MeOH (300 mL) was saturated with HCl (g). The resulting solution was refluxed for 90 min., then concentrated to dryness in vacuo to afford the titled ester as a white solid.

Step B: Methyl 3-(Imidazol-4-yl)propionate Hydrochloride

To a solution of methyl 3-(imidazol-4-yl)acrylate hydrochloride, as described above in Step A, (500 mg, 2.65 mmol) in EtOH (100 mL) was added 10% Pd on carbon (250 mg) and the reaction mixture was shaken under an atmosphere of hydrogen (45 psi) at ambient temperature for 18 hours on a Parr hydrogenation apparatus. The mixture was filtered through a pad of celite, washing with EtOH, and the filtrate was filtered through a pad of celite, washing with EtOH, and the filtrate was concentrated in vacuo to give the titled product.

Step C: Methyl 3-[1-(Triphenylmethyl)-1H-imidazol-4-yl] propionate

To a solution of methyl 3-(imidazol-4-yl)propionate hydrochloride, as described above in Step B, (20.2 g, 106 mmol) in dry CHCl$_3$ (500 mL) were added triethylamine (44 mL, 318 mmol), then a solution of triphenylmethyl chloride (29.5 g, 106 mmol) in CHCl$_3$ (100 mL). The mixture was stirred at ambient temperature for 18 hours, then washed with H$_2$O (250 mL). The organic layer was dried over Na$_2$SO$_4$, filtered and concentrated under reduced pressure to yield the product as a pale solid.

Step D: Methyl 3-[1-(4-Cyano-3-fluorobenzyl)-1H-imidazol-5-yl]propionate

A mixture of methyl 3-[1-(triphenylmethyl)-1H-imidazol-4-yl]propionate, as described above in Step C, (5.00 g, 12.6 mmol) and 4-cyano-3-fluorobenzyl bromide, as described in Example 1, Step D, (2.70 g, 12.6 mmol) in EtOAc (30 mL) was heated to 50° C. for 5 hours. The mixture was allowed to cool, and the solid collected by filtration. The EtOAc filtrate was concentrated in vacuo to a volume of approximately 15 mL and then reheated to 50° C. for 3 hours, cooled, and the solid removed by filtration. The two crops of precipitated imidazolium salts were combined in MeOH (120 mL) and CHCl$_3$ (200 mL). The aqueous layer was extracted further with CHCl$_3$ (2×100 mL). The combined organic extracts were dried over Na$_2$SO$_4$, filtered, and concentrated in vacuo. The crude product was purified by flash column chromatography on silica, eluting with a gradient of CH$_2$Cl$_2$—1% MeOH—0.1% NH$_4$OH to CH$_2$Cl$_2$—5% MeOH—0.5% NH$_4$OH to yield the titled product.

Step E: Lithium 3-[1-(4-Cyano-3-fluorobenzyl)-1H-imidazol-5-yl]propionate

Methyl 3-[1-(4-cyano-3-fluorobenzyl)-1H-imidazol-5-yl] propionate, as described above in Step D, (870 mg, 3.04 mmol) was dissolved in THF (20 mL) and H₂O (4 mL). Lithium hydroxide (129 mg, 3.07 mmol) was added and the resulting mixture was stirred at ambient temperature for 2 hours, then adjusted to pH 7 with 1.0 N aqueous HCl and concentrated to dryness in vacuo to give the titled lithium salt.

Step F: (S)-3-[1-(4-Cyano-3-fluorobenzyl)-1H-imidazol-5-yl]-N-(1-(7-hydroxynaphthalen-1-yl)-2-oxopyrrolidin-3-yl) propionamide A mixture of lithium 3-[1-(4-cyano-3-fluorobenzyl)-1H-imidazol-5-yl]propionate, as described above in Step E (55 mg, 0.20 mmol), (S)-3-amino-1-(7-hydroxynaphthalen-1-yl)-2-oxopyrrolidine hydrochloride, as described in Example 9A, (56 mg, 0.20 mmol), PYBOP (105 mg, 0.20 mmol), and N,N-diisopropylethylamine (0.075 mL, 0.43 mmol) was stirred in DMF (0.5 mL) at ambient temperature for 4 hours. The reaction mixture was partitioned between saturated aqueous NaHCO₃ (5 mL) and CHCl₃ (10 mL). The aqueous layer was extracted further with CHCl₃ (2×10 mL). The combined organic extracts were dried over Na₂SO₄, filtered, and concentrated in vacuo. The crude product was purified by flash column chromatography on silica, eluting with a gradient of CH₂Cl₂—1% MeOH—0.1% NH₄OH to CH₂Cl₂—8% MeOH—0.8% NH₄OH to yield the titled product.

Step G: (20S)-19,20,21,22,23,24-Hexahydro-19,22-dioxo-5H,18H-18,20-etheno-6,10-methenobenz[d]imidazo[4,3-m][1,6,9,14]oxatriazacycloeicosine-9-carbonitrile Hydrochloride A mixture of (S)-3-[1-(4-cyano-3-fluorobenzyl)-1H-imidazol-5-yl]-N-(1-(7-hydroxynaphthalen-1-yl)-2-oxopyrrolidin-3-yl)propionamide, as described above in Step F. (77 mg, 0.15 mmol) and Cs₂CO₃ (126 mg, 0.39 mmol) in dry DMF (50 mL) was stirred at 60° C. under argon for 18 hours. Acetic acid (120 mL, 2.0 mmol) was added and the solvent was removed under reduced pressure. The residue was partitioned between saturated aqueous NaHCO₃ (5 mL) and CHCl₃ (10 mL). The aqueous layer was extracted further with CHCl₃ (2×10 mL). The combined organic extracts were dried over MgSO₄, filtered, and concentrated in vacuo. The crude residue was purified by flash column chromatography on silica, eluting with a gradient of CH₂Cl₂—1% MeOH—0.1% NH₄OH to CH₂Cl₂—7% MeOH—0.7% NH₄OH to yield the desired product which was converted to the hydrochloride salt by treatment with HCl in EtOAc.

Elemental analysis calculated for C₂₈H₂₃N₅O₃·HCl·0.75MeOH·0.4CH₂Cl₂: C: 61.21; H: 4.90; N: 12.24; Found: C: 61.18; H: 4.87; N: 11.91;

Example 35

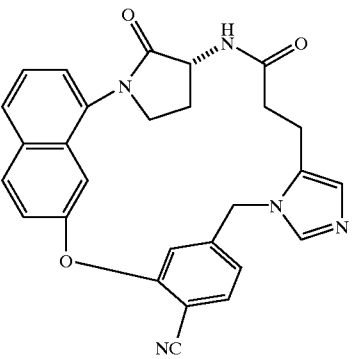

Preparation of (20R)-19,20,21,22,23,24-Hexahydro-19,22-dioxo-5H,18H-18,20-ethano-12,14-etheno-6,10-methenobenz[d]imidazo[4,3-m][1,6,9,14]oxatliazacycloeicosine-9-carbonitrile Hydrochloride Following the procedure described in Example 34, but using (R)-3-amino-1-(7-hydroxynaphthalen-1-yl)-2-oxopyrrolidine hydrochloride (as described in Example 10A) in place of (S)-3-amino-1-(7-hydroxy-naphthalen-1-yl)-2-oxopyrrolidine hydrochloride in Step F, the above-titled compound was prepared.

Elemental analysis calculated for C₂₈H₂₃N₅O₃·HCl·0.8MeOH·0.35CH₂Cl₂: C: 61.49; H: 4.94; N: 12.30; Found C: 61.51; H: 4.88; N: 11.95; FAB MS: 478 (MH⁺).

Example 36

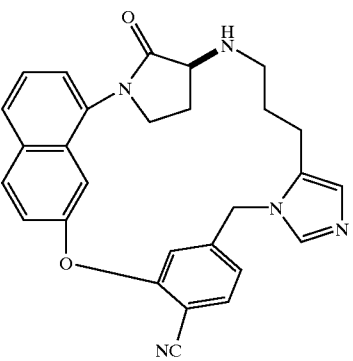

Preparation of (20S)-19,20,21,22,23,24-Hexahydro-19-oxo-5H,18H-18,20-ethano-12,14-etheno-6,10-methenobenz[d]imidazo[4,3-m][1,6,9,14]oxatriazacycloeicosine-9-carbonitrile Hydrochloride Step A: 3-[1-(4-Cyano-3-fluorobenzyl)-1H-imidazol-5-yl]-N-methoxymethylpropionamide A mixture of lithium 3-[1-(4-cyano-3-fluorobenzyl)-1H-imidazol-5-yl]propionate, as described in Example 34, Step E, (500 mg, 1.79 mmol), N,O-dimethylhydroxylamine hydrochloride (874 mg, 8.96 mmol), HOBT (270 mg, 2.00 mmol), EDC (418 mg, 2.18 mmol), and N,N-diisopropylethylamine (1.87 mL, 10.74 mmol) was stirred in DMF (5 mL) at ambient temperature for 18 hours. EtOAc (50 mL) was added, the mixture was filtered, and the filtrate was concentrated in vacuo. The residue was purified by flash column chromatography on silica, eluting with a gradient of CHCL$_3$—1% MeOH—0.1% NH$_4$OH to CHCl$_3$—4% MeOH—0.4% NH$_4$OH to yield the titled product.

Step B: 3-[1-(4-Cyano-3-fluorobenzyl)-1H-imidazol-5-yl]propionaldehyde

To a solution of 3-[1-(4-cyano-3-fluorobenzyl)-1H-imidazol-5-yl]-N-methoxy-N-methylpropionamide, as described above in Step A, (505 mg, 1.60 mmol) in dry THF (30 mL) at −78° C., under argon, was added diisobutylaluminum hydride (3.5 mL of a 1.0 M solution in CH$_2$Cl$_2$, 3.5 mmol), dropwise. The reaction mixture was stirred at −78° C. for 2 hours, then quenched with MeOH (1 mL) followed by saturated aqueous sodium potassium tartrate (20 mL). The mixture was allowed to warm to ambient temperature, then extracted with CH$_2$Cl$_2$ (3×30 mL). The combined organic extracts were dried over Na$_2$SO$_4$, filtered, and concentrated under reduced pressure. The crude product was purified by flash column chromatography, eluting with a gradient of CH$_2$Cl$_2$—1% to 6% MeOH—0.1% to 0.6% NH$_4$OH to give a mixture of the desired aldehyde and its methyl hemiacetal. Treatment of this mixture with dilute HCl in MeOH/H$_2$O followed by concentration from toluene afforded the desired aldehyde.

(20S)-19,20,21,22,23,24-Hexahydro-19-oxo-5H-18,20-ethano-12,14-etheno-6,10-methenobenz[d]imidazo[4,3m][1,6,9,14]oxatriazacycloeicosine-9-carbonitrile Trifluoroacetate Following the procedure described in Example 1, Steps O–P, but using (S)-3-amino-1-(7-hydroxynaphthalen-1-yl)-2-oxopyrrolidine hydrochloride (as described in Example 9A) in place of (R)-3-amino-1-(3-hydroxybenzyl)-2-oxopyrrolidine hydrochloride, and 3-[1-(4-cyano-3-fluorobenzyl)-1H-imidazol-5-yl]propionaldehyde, as described above in Step B, in place of 1-(4-cyano-3-fluorobenzyl)-5-imidazolecarboxaldehyde in Step O, the above-titled compound was prepared. Final purification was achieved using reversed-phase HPLC on a C18 column, eluting with a gradient of H$_2$O—5% to 95% CH$_3$CN—0.1% TFA.

Elemental analysis calculated for C$_{28}$H$_{25}$N$_5$O$_2$.2CF$_3$CO$_2$H.1.65H$_2$O.0.75CH$_2$Cl$_2$: C: 50.10; H: 4.08; N: 8.92; Found: C: 50.11; H: 4.08; N: 9.11; FAB MS: 464 (MH+).

Example 37

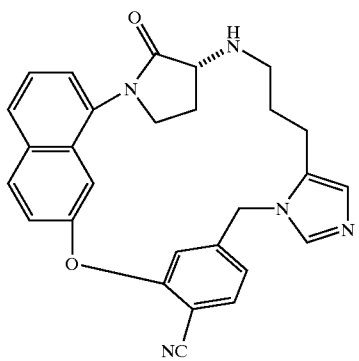

Preparation of (20R)-19,20,21,22,23,24-Hexahydro-19-oxo-5H,18H-18,20-ethano-12,14-etheno-6,10-methenobenz[d]imidazo[4,3-m][1,6,9,14]oxatriazacycloeicosine-9-carbonitrile Trifluoroacetate Following the procedure described in Example 1, Steps O–P, by using (R)-3-amino-1-(7-hydroxynaphthalen-1-yl)-2-oxopyrrolidine hydrochloride (as described in Example 10A) in place of (R)-3-amino-1-(3-hydroxybenzyl)-2-oxopyrrolidine hydrochloride, and 3-[1-(4-cyano-3-fluorobenzyl)-1H-imidazol-5-yl]propionaldehyde, as described in Example 36, Step B, in place of 1-(4-cyano-3-fluorobenzyl)-5-imidazolecarboxaldehyde in Step O, the above-titled compound was prepared. Final purification was achieved using reversed-phase HPLC on a C18 column, eluting with a gradient of H$_2$O—5% to 95% CH$_3$CN—0.1% TFA.

Elemental analysis calculated for C$_{28}$H$_{25}$N$_5$O$_2$.2CF$_3$CO$_2$H.1.2H$_2$O.0.75CH$_2$: C: 50.63; H: 4.01; N: 9.02; Found: C: 50.64; H: 3.98; N: 9.13; FAB MS: 464 (MH+).

Example 38

Preparation of 15-Bromo-19,20,21,22-tetrahydro-19-oxo-17H-18,20-ethano-6,10:12,16-dimetheno-16H-imidazo[3,4-h][1,8,11,14]oxatriazacycloeicosine-9-carbonitrile Hydrochloride

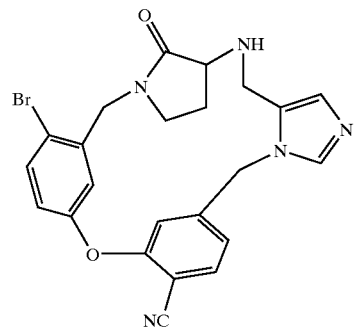

Step A: 3-(tert-Butoxycarbonylamino)-2-oxopyrrolidine

3-Amino-2-oxopyrrolidine was prepared according to the procedure described by R. Pellegata et al., Synthesis, 22, 614–616 (1978). To a solution of 3-amino-2-oxopyrrolidine (6.96 g, 69.5 mmol) in DMF (30 mL) was added triethylamine (7.03 g, 69.5 mmol) and di-tert-butyl dicarboxylate (15.2 g, 69.5 mmol). The reaction mixture was stirred at ambient temperature for 18 hours, then concentrated in vacuo. The residue was partitioned between saturated aqueous NaHCO$_3$ and EtOAc. The layers were separated and the organic extract was washed with H$_2$O, then brine, then dried over Na$_2$SO$_4$, filtered, and concentrated in vacuo to provide the titled product.

Step B: Methanesulfonic Acid 4-Bromo-3-methylphenyl Ester

To a stirred solution of 4-bromo-3-methylphenol (9.87 g, 52.8 mmol) and triethylamine (10.70 g, 106 mmol) in CH$_2$Cl$_2$ (50 mL) at 0° C. was added methanesulfonyl chloride (7.25 g, 63.3 mmol), dropwise. After 30 min at 0° C., the reaction mixture was concentrated in vacuo. The residue was partitioned between saturated aqueous NaHCO$_3$ and EtOAc. The layers were separated and the organic extract was washed with aqueous NaHCO$_3$, then 3 N aqueous HCl, then brine, then dried over Na$_2$SO$_4$, filtered, and concentrated in vacuo to provide the titled product.

Step C: Methanesulfonic Acid 4-Bromo-3-bromomethylphenyl Ester

A mixture of methanesulfonic acid 4-bromo-3-methylphenyl ester, as described above in Step B, (14.3 g, 53.9 mmol), N-bromosuccinimide (14.4 g, 80.9 mmol), and 2,2'-azobisisobutyronitrile (1.34 g, 8.16 mmol) in CCl$_4$ was heated at 80° C. for 18 hours. The solvent was removed

131 under reduced pressure and the residue was purified by silica gel chromatography, eluting with a gradient of hexane—5% to 20% EtOAc, to yield the titled product.

Step D: Methanesulfonic Acid 4-Bromo-3-(3-tert-butoxycarbonylamino-2-oxopyrrolidin-1-ylmethyl)phenyl Ester To a solution of 3-(tert-butoxycarbonylamino)-2-oxopyrrolidine, as described above in Step A, (1.00 g, 4.99 mmol) in THF (10 mL) was added sodium hydride (230 mg of a 60% dispersion in oil, 5.75 mmol) in THF (5 mL), dropwise. The resulting mixture was stirred for 30 min at ambient temperature, then a solution of methanesulfonic acid 4-bromo-3-bromomethylphenyl ester, as described above in Step C, (1.96 g, 5.70 mmol) in THF (6 mL) was added dropwise and stirring was continued for 2 hours. The reaction was quenched with saturated aqueous $NH_4Cl$ (3 mL), then concentrated in vacuo. The residue was partitioned between saturated aqueous $NaHCO_3$ and EtOAc. The layers were separated and the organic extract was washed with $H_2O$, then brine, then dried over $Na_2SO_4$, filtered, and concentrated in vacuo. The residue was purified by silica gel chromatography, eluting with $CH_2Cl_2$—5% MeOH, to yield the titled product.

Step E: 3-Amino-1-(2-bromo-5-methanesulfonyloxybenzyl)-2-oxopyrrolidine Hydrochloride A solution of methanesulfonic acid 4-bromo-3-(3-tert-butoxycarbonyl-amino-2-oxopyrrolidin-1-ylmethyl)phenyl ester, as described above in Step D, (720 mg, 1.55 mmol) in EtOAc (40 mL) at 0° C. was saturated with HCl (g). After 15 min, the mixture was concentrated in vacuo to yield the above-titled amine hydrochloride.

Step F: 4-(5-{[1-(2-Bromo-5-methanesulfonyloxybenzyl)-2-oxopyrrolidin-3-ylamino]methyl}imidazol-1-ylmethyl)-2-fluorobenzonitrile 3-Amino-1-(2-bromo-5-methanesulfonyloxybenzyl)-2-oxopyrrolidine, as described above in Step E, (640 mg, 1.12 mmol), 1-(4-cyano-3-fluorobenzyl)-5-imidazolecarboxaldehyde, as described above in Example 3, Step G, (333 mg, 1.45 mmol) were stirred in MeOH (8 mL) and the solution was acidified to pH≈5 to 6, as judged by wetted pH indicator paper, with acetic acid. Stirring was continued for 30 min, then $NaCNBH_3$ (118 mg, 1.88 mmol) was added. Stirring was continued for 18 hours, then the reaction was quenched with saturated aqueous $NaHCO_3$ (2 mL) and most of the MeOH was removed under reduced pressure. The residual solution was partitioned between saturated aqueous $NaHCO_3$ (10 mL) and EtOAc (20 mL). The aqueous layer was extracted further with EtOAc (2×20 mL). The combined organic extracts were washed with brine, dried over $Na_2SO_4$, filtered, and concentrated in vacuo. The crude product was purified by flash column chromatography on silica, eluting with a gradient of $CH_2Cl_2$—1% to 5% MeOH, to yield the desired product.

Step G: 15-Bromo-19,20,21,22-tetrahydro-19-oxo-17H-18,20-ethano-6,10:12,16-dimetheno-16H-imidazo[3,4-h][1,8,11,14]oxatriazacycloeicosine-9-carbonitrile Hydrochloride A mixture of 4-(5-{[1-(2-bromo-5-methanesulfonyloxybenzyl)-2-oxopyrrolidin-3-ylamino]methyl]imidazol-1-ylmethyl)-2-fluorobenzonitrile, as described above in Step F, (293 mg, 0.51 mmol) and $Cs_2CO_3$ (470 mg, 1.44 mmol) in dry, degassed DMF (100 mL) was stirred at 80° C. under argon for 72 hours. The solvent was removed under reduced pressure and the residue was partitioned between saturated aqueous $NaHCO_3$ (20 mL) and EtOAc (40 mL). The organic extract was washed with brine, then dried over $Na_2SO_4$, filtered, and concentrated in vacuo.

132

The crude product was purified by flash column chromatography on silica, eluting with a gradient of $CH_2Cl_2$—1% to 5% MeOH—0.1% to 0.5% $NH_4OH$ to yield the desired product as a racemic mixture. The enantiomers were separated by preparative HPLC on a Chiralcel OD column, eluting with hexane—50% EtOH—0.1% $Et_2NH$ to yield the separated products, enantiomer A (which eluted first under the described HPLC conditions) and enantiomer B (which eluted second under the described HPLC conditions):

15-Bromo-19,20,21,22-tetrahydro-19-oxo-17H-18,20-ethano-6,10:12,16-dimetheno-16H-imidazo[3,4-h][1,8,11,14]oxatriazacycloeicosine-9-carbonitrile, Enantiomer A Hydrochloride Elemental analysis calculated for $C_{23}H_{20}BrN_5O_2 \cdot 2HCl \cdot 2.5H_2O \cdot 0.95$ MeOH: C: 45.89; H: 4.95; N: 11.17; Found: C: 45.85; H: 4.56; N: 10.82; FAB MS: 478 ($MH^+$).

15-Bromo-19,20,21,22-tetrahydro-19-oxo-17H-18,20-ethano-6,10:12,16-dimetheno-16H-imidazo[3,4-h][1,8,11,14]oxatriazacycloeicosine-9-carbonitrile, Enantiomer B Hydrochloride Elemental analysis calculated for $C_{23}H_{20}BrN_5O_2 \cdot 2HCl \cdot 1.35$ MeOH: C: 49.19; H: 4.65; N: 11.78; Found: C: 49.51; H: 4.75; N: 11.77; FAB MS: 478 ($MH^+$).

Example 39

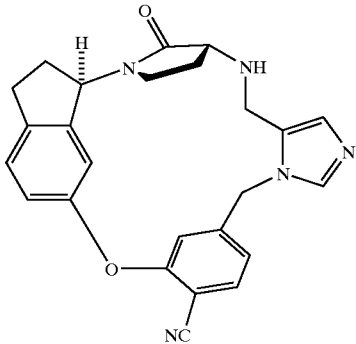

Preparation of (17R,20R)-19,20,21,22-Tetrahydro-19-oxo-17H-15,17:18,20-diethano-6,10:12,16-dimetheno-16H-imidazo[3,4-h][1,8,11,14] oxatriazacycloeicosine-9-carbonitrile Hydrochloride Step A: 6-tert-Butyldiphenylsilyloxy-1-indanone 6-Hydroxy-1-indanone was prepared according to the procedure described by Nayak & Chakraborti, *Tetrahedron Lett.*, 38, 8749–8752 (1997). A mixture of 6-hydroxy-1-indanone (5.00 g, 33.8 mmol), tert-butyldiphenylsilyl chloride (23.1 g, 84.2 mmol), and imidazole (6.90 g, 101.4 mmol) in degassed DMF (100 mL) was heated at 60° C. for 18 hours. The solvent was removed in vacuo and the residue purified by silica gel chromatography, eluting with a gradient of hexane—10% to 15% EtOAc, to yield the titled product.

Step B: 6-tert-Butyldiphenylsilyloxy-1-indanol

To a solution of 6-tert-butyldiphenylsilyloxy-1-indanone, as described above in Step A, (16.5 g, 42.7 mmol) in MeOH (500 mL) was added $NaBH_4$ (3.2 g, 84.6 mmol) portionwise, over 5 min. The resulting mixture was stirred at ambient temperature for 1 hour, then cooled to 0° C. The chilled solution was adjusted to pH 4.5 with dilute aqueous HCl, then most of the MeOH was removed under reduced pressure. The residue was partitioned between saturated aqueous NaHCO$_3$ (75 mL) and CHCl$_3$ (150 mL). The organic layer was removed, and the aqueous phase was extracted further with CHCl$_3$ (2×100 mL). The combined organic extracts were washed with brine, then dried over MgSO$_4$, filtered, and concentrated in vacuo. The residue was purified by silica gel chromatography, eluting with hexane—10% to EtOAc, to yield the titled product.

Step C: 6-tert-Butyldiphenylsilyloxy-1-indanyl Azide

To a solution of 6-tert-butyldiphenylsilyloxy-1-indanol, as described above in Step B, (5.80 g, 14.9 mmol) and diphenylphosphoryl azide (4.98 g, 18.1 mmol) in toluene (30 mL) at 0° C. was added 1,8-diazabicyclo[5.4.0]undec-7-ene (2.50 mL, 16.4 mmol), dropwise. The mixture was allowed to slowly warm to ambient temperature and was stirred for 18 hours, then washed with H2O (10 mL), then dilute HCl (10 mL), then dried over MgSO$_4$, filtered, and concentrated in vacuo. The residue was purified by silica gel chromatography, eluting with hexane—1% EtOAc, to yield the titled product.

Step D: 6-tert-Butyldiphenylsilyloxy-1-indanylamine

To a solution of 6-tert-butyldiphenylsilyloxy-1-indanyl azide, as described above in Step C, (6.10 g, 14.7 mmol) in TBF (150 mL) at 0° C. was added LiAlH$_4$ (1.0 M in THF, 17.7 mL, 17.7 mmol), dropwise. The reaction mixture was stirred at 0° C. for 1 hour then EtOAc (0.7 mL) was added, followed by H$_2$O (0.7 mL), then 15% aqueous NaOH (0.7 mL), then H$_2$O (2.1 mL). The quenched mixture was stirred at ambient temperature for 18 hours, then filtered, and concentrated in vacuo. The residue was purified by silica gel chromatography, eluting with CHCl$_3$—1% MeOH—0.1% NH$_4$OH, to yield the titled product.

Step E: (2R)-2-(tert-Butoxycarbonylamino)-4-(methylmercapto)-N-[6-(tert-butyldiphenylsilyloxy)indan-1-yl]butyramide, Diastereomers A & B To (R)-N-(tert-butoxycarbonyl)methionine (1.20 g, 4.8 mmol) in dry CH$_2$Cl$_2$ (5 mL), at 0° C., under argon were added PYBOP (2.50 g, 4.8 mmol), 6-tert-butyldiphenylsilyloxy-1-indanylamine, as described above in Step D, (1.7 g, 4.4 mmol), and N,N-diisopropylethylamine (0.84 mL, 4.8 mmol). The reaction mixture was stirred for 1 hour, then poured into 10% aqueous citric acid (10 mL), and the organic layer was extracted. The aqueous phase was washed with CH$_2$Cl$_2$ (5 mL), and the combined organic extracts were dried over MgSO$_4$, filtered, and concentrated in vacuo. The crude product was purified by flash column chromatography on silica, eluting with hexane—10% EtOAc to yield the desired product as a mixture of diastereomers.

Step F: (2R)-2-(tert-Butoxycarbonylamino)-4-(dimethylsulfonium)-N-[6-(tert-butyldiphenylsilyloxy)indan-1-yl]butyramide Iodide, Diastereomers A & B (R)-2-(tert-Butoxycarbonylamino)-4-(methylmercapto)-N-[6-(tert-butyldiphenylsilyloxy)indan-1-yl]butyramide, diastereomers A & B, as described above in Step E, (2.30 g, 3.70 mmol) was dissolved in iodomethane (20 mL, 322 mmol) and the solution was stirred under argon for 18 hours. The iodomethane was removed by distillation under reduced pressure to give the sulfonium salt.

Step G: (3R)-3-(tert-Butoxycarbonylamino)-1-[6-(tert-butyldiphenylsilyloxy) indan-1-yl]-2-oxopyrrolidine, Diastereomers A & B (R)-2-(tert-Butoxycarbonylamino)-4-(dimethylsulfonium)-N-[6-(tert-butyldiphenylsilyloxy)indan-1-yl]butyramide iodide, diastereomers A & B, as described above in Step F, (2.80 g, 3.72 mmol) was stirred in dry THF (50 mL), under argon, at 0° C. and lithium bis(trimethylsilyl)amide (1.0 M in THF, 3.5 mL, 3.5 mmol) was added dropwise. The reaction mixture was stirred at 0° C. for 2 hours, then quenched with saturated aqueous NH$_4$Cl (50 mL) and most of the TBF was removed under reduced pressure. The residual solution was partitioned between saturated aqueous NaHCO$_3$ (20 mL) and CHCl$_3$ (50 mL). The aqueous layer was extracted further with CHCl$_3$ (50 mL). The combined organic extracts were dried over MgSO$_4$, filtered, and concentrated in vacuo. The crude product was purified by flash column chromatography on silica, eluting with a gradient of hexane—20% to 35% EtOAc to yield the titled compounds, diastereomer A (the isomer of higher RF) and diastereomer B (the isomer of lower RF).

Step H: (R,R)-3-Amino-1[6-(tert-butyldiphenylsilyloxy)indan-1-yl]-2-oxopyrrolidine, Trifluoroacetate (3R)-3-(tert-Butoxycarbonylamino)-1-[6-(tert-butyldiphenylsilyloxy) indan-1-yl]-2-oxopyrrolidine, diastereomer B, as described above in Step G, (the (R,R)-isomer), (270 mg, 0.47 mmol) was dissolved in CH$_2$Cl$_2$ (5 mL) and TFA (0.72 mL, 9.4 mmol) was added dropwise. The resulting mixture was stirred at ambient temperature for 18 hours, then concentrated under reduced pressure to afford the desire product.

Step I: (R,R)-4-(5-{[1-(6-Hydroxyindan-1-yl)-2-oxopyrrolidin-3-ylamino]methyl}imidazol-1-ylmethyl)-2-fluoro-benzonitrile (RR)-3-Amino-1-[6-(tert-butyldiphenylsilyloxy)indan-1-yl]-2-oxopyrrolidine, trifluoroacetate, as described above in Step H, (170 mg, 0.29 mmol) and 1-(4-cyano-3-fluorobenzyl)-5-imidazolecarboxaldehyde, as described above in Example 1, Step G, (60 mg, 0.26 mmol), were stirred in MeOH (3 mL) for 30 min at ambient temperature, then NaCNBH$_3$ (22 mg, 0.35 mmol) was added and stirring was continued for 18 hours. The solvent was evaporated and the residue dissolved in THF (5 mL). To this solution was added TBAF (1.0 M in THF, 0.34 mL, 0.34 mmol) and stirring was continued for 15 min, then the solvent was evaporated. The residue was partitioned between saturated aqueous NaHCO$_3$ (5 mL) and CHCl$_3$ (10 mL). The aqueous layer was extracted further with CHCl$_3$ (2×5 mL). The combined organic extracts were dried over MgSO$_4$, filtered, and concentrated in vacuo. The crude product was purified by flash column chromatography on silica, eluting with CHCl$_3$—5% MeOH—0.5% NH$_4$OH to yield the titled product.

Step J: (17R,20R)-19,20,21,22-Tetrahydro-19-oxo-17H-15,17:18,20-diethano-6,10:12,16-dimetheno-16H-imidazo[3,4-h][1,8,11,14]oxatriazacycloeicosine-9-carbonitrile Hydrochloride A mixture of (R,R)-4-(5-{[1-(6-hydroxyindan-1-yl)-2-oxopyrrolidin-3-ylamino]methyl}imidazol-1-ylmethyl)-2-fluoro-benzonitrile, as described above in Step I, (137 mg, 0.31 mmol) and Cs$_2$CO$_3$ (201 mg, 0.62 mmol) in dry, degassed DMF (40 mL) was stirred at 50° C. under argon for 1 hour. The solvent was removed under reduced pressure, and the residue was partitioned between saturated aqueous NaHCO$_3$ (1 mL) and CHCl$_3$ (3 mL). The aqueous layer was extracted further with CHCl$_3$ (2×3 mL). The combined organic extracts were dried over MgSO$_4$, filtered, and concentrated in vacuo. The crude product was purified by flash column chromatography on silica, eluting with CHCl$_3$—6% MeOH—0.6% NH$_4$OH to yield the desired product which was converted to the hydrochloride salt by treatment with HCl in EtOAc.

Elemental analysis calculated for $C_{25}H_{23}N_5O_2 \cdot 2HCl \cdot H_2O \cdot 0.2$ EtOAc: C: 58.02; H: 5.40; N: 13.11; Found: C: 58.01;H: 5.48;N: 13.17; ES MS: 426 (MH$^+$).

Example 39A

Preparation of (3S)-3-(tert-Butoxycarbonylamino)-1-[6-(tert-butyldiphenylsilyloxy) indan-1-yl]-2-oxopyrrolidine Diastereomers A & B Following the procedures described in Example 39, Steps A–G, but using (S)-N-(tert-butoxycarbonyl)methionine in place of (R)-N-(tert-butoxycarbonyl) methionine in Step E, the above-titled compounds were obtained.

Example 40

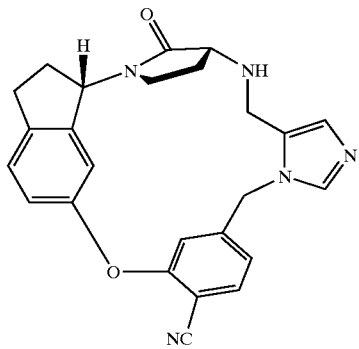

Preparation of (17S,20R)-19,20,21,22-Tetrahydro-19-oxo-17H-15,17:18,20-diethano-6,10:12,16-dimetheno-16H-imidazo[3,4-h][1,8,11,14] oxatriazacycloeicosine-9-carbonitrile Hydrochloride Following the procedures described in Example 39, but using (3R)-3-(tert-butoxycarbonylamino)-1-[6-tert-butyldiphenylsilyloxy)indan-1-yl]-2-oxopyrrolidine, diastereomer A, in place of (3R)-3-(tert-butoxycarbonylamino)-1-[6-(tert-butyldiphenylsilyloxy)indan-1-yl]-2-oxopyrrolidine, diastereomer B, in Step H the above-titled compound was obtained.

Elemental analysis calculated for $C_{25}H_{23}N_5O_2 \cdot 2.2$ HCl $\cdot 2.2$ H$_2$O $\cdot$ 0.15 EtOAc: C: 55.13; H: 5.55; N: 12.56; Found: C: 55.10; H: 5.28; N: 12.55; ES MS: 426 (MH$^+$).

Example 41

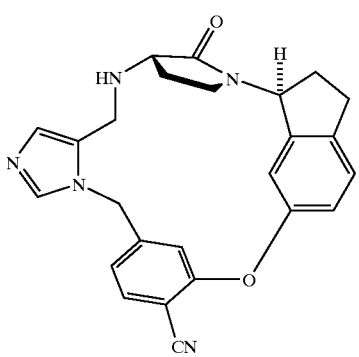

Preparation of (17S,20S)-19,20,21,22-Tetrahydro-19-oxo-17H-15,17:18,20-diethano-6,10:12,16-dimetheno-16H-imidazo[3,4-h][1,8,11,14] oxatriazacycloeicosine-9-carbonitrile Hydrochloride Following the procedures described in Example 39, but using (3S)-3-(tert-butoxycarbonylamino)-1-[6-(tert-butyldiphenylsilyloxy)indan-1-yl]-2-oxopyrrolidine, diastereomer B, as described in Example 39A, in place of (3R)-3-(tert-butoxycarbonylamino)-1-[6-(tert-butyldiphenylsilyloxy)indan-1-yl]-2-oxopyrrolidine, diastereomer B, in Step H, the above-titled compound was obtained.

Elemental analysis calculated for $C_{25}H_{23}N_5O_2 \cdot 2HCl \cdot 0.5H_2O \cdot 0.2CHCl_3$: C: 56.96; H: 4.97; N: 13.18; Found: C: 56.98; H: 4.93; N: 13.46; ES MS: 426 (MH$^+$).

Example 42

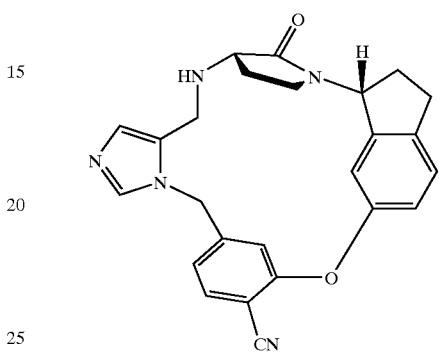

Preparation of (17R,20S)-19,20,21,22-Tetrahydro-19-oxo-17H-15,17:18,20-diethano-6,10:12,16-dimetheno-16H-imidazo[3,4-h][1,8,11,14] oxatriazacycloeicosine-9-carbonitrile Hydrochloride Following the procedures described in Example 39, but using (3S)-3-(tert-butoxycarbonylamino)-1-[6-(tert-butyldiphenylsilyloxy)indan-1-yl]-2-oxopyrrolidine, diastereomer A, as described in Example 39A, in place of (3R)-3-(tert-butoxycarbonylamino)-1-[6-(tert-butyldiphenylsilyloxy)indan-1-yl]-2-oxopyrrolidine, diastereomer B, in Step H, the above-titled compound was obtained.

Elemental analysis calculated for $C_{25}H_{23}N_5O_2 \cdot 2HCl \cdot 0.5H_2O \cdot 0.2CHCl_3$: C: 51.75; H: 4.61; N: 11.74; Found: C: 51.73; H: 4.64; N: 11.91; ES MS: 426 (MH$^+$).

Example 43

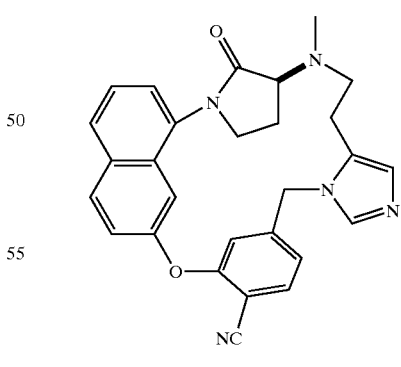

(20S)-19,20,22,23-Tetrahydro-21-methyl-19-oxo-5H,21H-18,20-ethano-12,14-etheno-6,10-methenobenz[d]imidazo[4,3-1][1,6,9,13] oxatriazacyclononadecosine-9-carbonitrile Hydrochloride Step A: (20S)-19,20,22,23-Tetrahydro-21-methyl-19-oxo-5H,21H-18,20-ethano-12,14-etheno-6,10-methenobenz[d]

imidazo[4,3-1][1,6,9,13]oxatriazacyclononadecosine-9-carbonitrile Hydrochloride (20S)-19,20,22,23-Tetrahydro-19-oxo-5H,21H-18,20-ethano-12,14-etheno-6,10-methenobenz[d]imidazo[4,3-1][1,6,9,13]oxatriazacyclononadecosine-9-carbonitrile hydrochloride, as described in Example 31, (83 mg, 0.16 mmol) and N,N-diisopropylethylamine (0.059 mL, 0.34 mmol) were stirred in MeOH (3 mL) and the solution was adjusted to pH≈5.5 with acetic acid. Formaldehyde (37 wt % in H$_2$O, 0.157 mL, 1.93 mmol) was added and the mixture was stirred for 30 min at ambient temperature, then NaCNBH$_3$ (13 mg, 0.35 mmol) was added and stirring was continued for 18 hours. The solvent was evaporated and the residue was partitioned between saturated aqueous NaHCO$_3$ (2 mL) and CHCl$_3$ (5 mL). The aqueous layer was extracted further with CHCl$_3$ (5 mL). The combined organic extracts were dried over MgSO$_4$, filtered, and concentrated in vacuo. The crude product was purified by flash column chromatography on silica, eluting with CHCl$_3$—3% MeOH—0.3% NH$_4$OH to yield the desired product desired product which was converted to the hydrochloride salt by treatment with HCl in CHCl$_3$.

Elemental analysis calculated for C$_{28}$H$_{25}$N$_5$O$_2$.2HCl.1.6H$_2$O.0.65 CHCl$_3$: C: 53.66; H: 4.83; N: 10.91; Found: C: 53.58; H: 4.87; N: 11.13; ES MS: 464 (MH$^+$).

Example 44

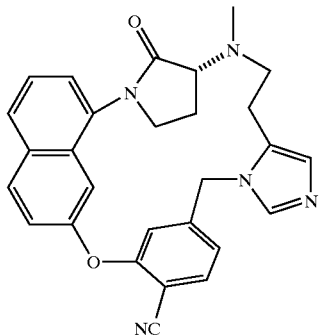

(20R)-19,20,22,23-Tetrahydro-21-methyl-19-oxo-5H,21H-18,20-ethano-12,14-etheno-6,10-methenobenz[d]imidazo[4,3-1][1,6,9,13]oxatriazacyclononadecosine-9-carbonitrile Hydrochloride Step A: (20R)-19,20,22,23-Tetrahydro-21-methyl-19-oxo-5H,21H-18,20-ethano-12,14-etheno-6,10-methenobenz[d]imidazo[4,3-1][1,6,9,13]oxatriazacyclononadecosine-9-carbonitrile Hydrochloride Following the procedures described in Example 43, but using (20R)-19,20,22,23-tetrahydro-19-oxo-5H,21H-18,20-ethano-12,14-etheno-6,10-methenobenz[d]imidazo[4,3-1][1,6,9,13]oxatriazacyclononadecosine-9-carbonitrile hydrochloride, as described in Example 32, in place of (20S)-19,20,22,23-tetrahydro-19-oxo-5H,21H-18,20-ethano-12,14-etheno-6,10-methenobenz[d]imidazo[4,3-1][1,6,9,13]oxatriazacyclononadecosine-9-carbonitrile hydrochloride in Step A, the above-titled compound was obtained.

Elemental analysis calculated for C$_{28}$H$_{25}$N$_5$O$_2$.2HCl.2.5H$_2$O.0.25CHCl$_3$:. C: 55.50; H: 5.32; N: 11.46; Found: C: 55.36; H: 5.40; N: 11.76; ES MS: 464 (MH$^+$).

Example 45

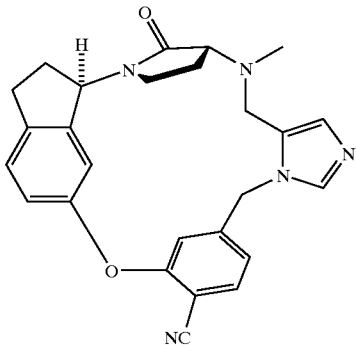

Preparation of (17R,20R)-19,20,21,22-Tetrahydro-21-methyl-19-oxo-17H-15,17:18,20-diethano-6,10:12,16-dimetheno-16H-imidazo[3,4-h][1,8,11,14¹oxatriazacycloeicosine-9-carbonitrile Hydrochloride Step A: (17R,20R)-19,20,21,22-Tetrahydro-21-methyl-19-oxo-17H-15,17:18,20-diethano-6,10:12,16-dimetheno-16H-imidazo[3,4-h][1,8,11,14oxatriazacycloeicosine-9-carbonitrile Hydrochloride Following the procedures described in Example 43, but using (17R,20R)-19,20,21,22-tetrahydro-19-oxo-17H-15,17:18,20-diethano-6,10:12,16-dimetheno-16H-imidazo[3,4-h][1,8,11,1⁴]oxatriazacycloeicosine-9-carbonitrile hydrochloride, as described in Example 39, in place of (20S)-19,20,22,23-tetrahydro-19-oxo-5H,21H-18,20-ethano-12,14-etheno-6,10-methenobenz[d]imidazo[4,3-1][1,6,9,13]oxatriazacyclononadecosine-9-carbonitrile hydrochloride in Step A, the above-titled compound was obtained.

Elemental analysis calculated for C$_{26}$H$_{25}$N$_5$O$_2$.2HCl.1.7H$_2$O.CHCl$_3$: C: 49.02; H: 4.77; N: 10.59; Found: C: 48.99; H: 4.75; N: 10.80; ES MS: 440 (MH$^+$).

Example 46

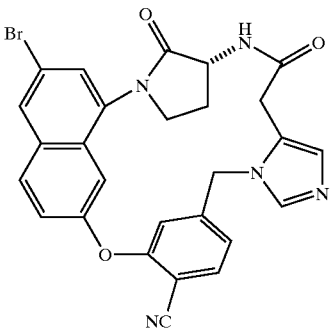

Preparation of (20R)-16-Bromo-19,20,22,23-tetrahydro-19,22-dioxo-5H,21H-18,20-ethano-12,14-etheno-6,10-methenobenz[d]imidazo[4,3-1][1,6,9,13]oxatriazacyclononadecosine-9-carbonitrile Hydrochloride Step A: 1-Aminonaphth-7-yl methanesulfonate A solution of 8-(tert-butoxycarbonylamino)-naphth-7-yl Methanesulfonate, as described in Example 24, Step A, (27.3 g, 80.8 mmol) in EtOAc (400 mL) at 0° C. was saturated with HCl (g). The resulting mixture was stood at 0° C. for 15 min, then concentrated in vacuo. The residue was partitioned between saturated aqueous $Na_2CO_3$ (100 mL) and $CH_2Cl_3$ (500 mL) and the organic layer was dried over $Na_2SO_4$, filtered, and concentrated in vacuo to afford the titled product.

Step B: 1-Nitronaphth-7-yl Methanesulfonate

To a stirred solution of 1-aminonaphthy-7-yl Methanesulfonate, as described above in Step B, (17.6 g, 74.3 mmol) in EtOH (60 mL) and $HBF_4$ (48 wt % in $H_2O$, 120 mL), at 0° C., was added a solution of $NaNO_2$ (5.64 g, 81.7 mmol) in $H_2O$ (12 mL), dropwise. The reaction mixture was stirred for 20 min, then the solid was isolated by filtration, washed with cold $HBF_4$ (48 wt % in $H_2O$, 20 mL), then cold EtOH (2×40 mL), then cold $Et_2O$ (3×40 mL), then air dried. The diazonium salt was suspended in cold $H_2O$ (160 mL) and added slowly to vigorously stirred mixture of copper powder (14.2 g, 223 mmol) and $NaNO_2$ (103 g, 1.49 mol) in $H_2O$ (200 mL) in a 2 L Erlenmeyer flask. The mixture was stirred for 2 hours then partitioned between $H_2O$ (100 mL) and $CH_2Cl_2$ (500 mL). The aqueous layer was extracted further with $CH_2Cl_2$ (2×500 mL). The combined organic extracts were dried over $Na_2SO_4$, filtered, and concentrated in vacuo. The crude product was purified by flash column chromatography on silica, eluting with a gradient of hexane—20% to 40% EtOAc to yield the titled compound.

Step C: 8-Nitro-2-naphthol

A stirred solution of 1-nitronaphthy-7-yl methanesulfonate, as described above in Step B, (6.14 g, 23.0 mmol) and 1.0 N aqueous NaOH (115 mL) in THF (230 mL) and EtOH (230 mL) was heated at 40° C. for 3 hours, then cooled to ambient temperature and adjusted to pH≈5 with aqueous HCl. Most of the organic solvents were removed under reduced pressure, then the residue was partitioned between $H_2O$ (200 mL) and $CH_2Cl_2$ (500 mL). The aqueous layer was extracted further with $CH_2Cl_2$ (500 mL). The combined organic extracts were dried over $Na_2SO_4$, filtered, and concentrated in vacuo to provide the titled compound.

Step D: 7-tert-Butoxy-1-nitronaphthalene

Isobutylene (150 mL) was condensed into a stirred mixture of 8-nitro-2-naphthol, as described above in Step C, (4.35 g, 23.0 mmol) in $CH_2Cl_2$ (200 mL) at −78° C. Trifluoromethanesulfonic acid (0.203 mL, 2.30 mmol) was added and the mixture was allowed to slowly warm to −20° C. over about 4 hours. Triethylamine (2.56 mL, 18.4 mmol) was added and the mixture was allowed to warm to ambient temperature, then concentrated under reduced pressure. The crude product was purified by flash column chromatography on silica, eluting with hexane—5% EtOAc to yield the titled product.

Step E: 1-Amino-6-tert-butoxy4-nitronaphthalene

To a stirred solution of 7-tert-butoxy-1-nitronaphthalene, as described above in Step D, (3.35 g, 13.7 mmol) and hydroxylamine hydrochloride (5.94 g, 85.5 mmol) in 95% EtOH (140 mL) at 60° C. was added KOH (11.9 g, 212 mmol) in MeOH (75 mL), dropwise over 30 min. The reaction mixture was stirred at 60° C. for 6 hours, then poured into $H_2O$ (200 mL) and extracted with $CH_2Cl_2$ (3×300 mL). The combined organic extracts were dried over $Na_2SO_4$, filtered, and concentrated in vacuo. The crude product was purified by flash column chromatography on silica, eluting with a gradient of hexane—20% to 40% EtOAc to yield the titled product.

Step F: 1-Amino-2-bromo-6-tert-butoxy-4-nitronaphthalene

To a stirred solution of 1-amino-6-tert-butoxy-4-nitronaphthalene, as described above in Step E, (2.02 g, 7.76 mmol) in acetic acid (55 mL) was added N-bromosuccinimide (1.45 g, 8.15 mmol), portionwise. The reaction mixture was stirred at ambient temperature for 1 hour, then $H_2O$ (150 mL) and $CH_2Cl_2$ (300 mL) were added and the organic layer was extracted. The organic extract was washed with saturated aqueous $Na_2CO_3$ (2×100 mL), then brine (100 mL), then dried over $Na_2SO_4$, filtered, and concentrated in vacuo. The residue was triturated with hexane-$Et_2O$ to provide the titled product.

Step G: 3-Bromo-7-tert-butoxy-1-nitronaphthalene

To a stirred solution of 1-amino-2-bromo-6-tert-butoxy-4-nitronaphthalene, as described above in Step F, (2.40 g, 7.08 mmol) in $CH_2Cl_2$ (150 mL), at −15° C., was added $BF_3 \cdot OEt_2$ (1.35 mL, 10.6 mmol). To this mixture was added a solution of 90% tert-butyl nitrite (1.12 mL, 8.49 mmol) in $CH_2Cl_2$ (9 mL), dropwise. The reaction mixture was stirred at −15° C. for 1 hour, then 50 wt % $H_3PO_2$ (9.34 mL, 70.8 mmol) and $CuO_2$ (50 mg, 0.349 mmol) were added and the resulting mixture was stirred vigorously at 0° C. for 40 min. The mixture was partitioned between saturated aqueous $Na_2CO_3$ (75 mL) and $CH_2Cl_2$ (150 mL). The aqueous layer was extracted further with $CH_2Cl_2$ (150 mL). The combined organic extracts were dried over $Na_2SO_4$, filtered, and concentrated in vacuo. The crude product was purified by flash column chromatography on silica, eluting with a gradient of hexane—0% to 8% diethyl ether to yield the titled compound.

Step H: 1-Amino-3-bromo-7-tert-butoxynaphthalene

A mixture of 3-bromo-7-tert-butoxy-1-nitronaphthalene, as described above in Step G, (1.08 g, 3.33 mmol), $NH_4Cl$ (89 mg, 1.67 mmol), and iron powder (930 mg, 16.7 mmol) in EtOH (70 mL) and $H_2O$ (30 mL) was heated to reflux for 7 hours, then cooled and filtered through a pad of celite, washing with EtOH. The filtrate was concentrated under reduced pressure and the residue was partitioned between dilute aqueous $NaHCO_3$ (50 mL) and $CH_2Cl_2$ (150 mL). The aqueous layer was extracted further with $CH_2Cl_2$ (50 mL). The combined organic extracts were dried over $Na_2SO_4$, filtered, and concentrated in vacuo. The crude product was purified by flash column chromatography on silica, eluting with a gradient of hexane—5% to 20% EtOAc to afford the titled compound.

Step I: (R)-1-(3-Bromo-7-tert-butoxynaphthalen-1-yl)-3-(tert-butoxycarbonylamino)-2-oxopyrrolidine Following the procedures described in Example 1, Steps J–L, but using 1-amino-3-bromo-7-tert-butoxynaphthalene, as described above in Step H, in place of 3-benzyloxybenzylamine in Step J, the above-titled compound was obtained.

Step J: (R)-3-Amino-1-(3-bromo-7-hydroxynaphthalen-1-yl)-2-oxopyrrolidine Hydrochloride A solution of (R)-1-(3-bromo-7-tert-butoxynaphthalen-1-yl)-3-(tert-butoxycarbonylamino)-2-oxopyrrolidine, as described above in Step I, (50 mg, 0.105 mmol) in EtOAc (5 mL) at 0° C. was saturated with HCl (g). After 15 min, the mixture was concentrated in vacuo to yield the amine hydrochloride salt.

Step K: (20R)-16-bromo-19,20,22,23-tetrahydro-19,22-dioxo-5H,21H-18,20-ethano-12,14-etheno-6,10-methenobenz[d]imidazo[4,3-1]1,6,9,13]oxatriazacyclononadecosine-9-carbonitrile Hydrochloride Following the procedures described in Example 22, but using (R)-3-amino-1-(3-bromo-7-hydroxynaphthalen-1-yl)-2-oxopyrrolidine hydrochloride, as described above in Step J, in place of (R)-3-amino-1-(7-hydroxynaphthalen-1-yl)-2-oxopyrrolidine hydrochloride in Step E, the above-titled compound was obtained.

Elemental analysis calculated for $C_{27}H_{20}BrN_5O_3 \cdot 1.9HCl \cdot 0.2$ EtOAc: C: 53.21; H: 3.77; N: 11.16; Found: C: 53.26; H: 3.72; N: 11.16; ES MS: 542 (MH$^+$).

Example 46A

Preparation of (S)-1-(3-Bromo-7-tert-butoxynaphthalen-1-yl)-3-(tert-butoxycarbonylamino)-2-oxopyrrolidine Following the procedures described in Example 1, Steps J–L, but using 1-amino-3-bromo-7-tert-butoxynaphthalene, as described in Example 46, Step H, in place of 3-benzyloxybenzylamine, and (S)-N-(tert-butoxycarbonyl) methionine in place of (R)-N-(tert-butoxycarbonyl) methionine in Step J, the above-titled compound was obtained.

Example 47

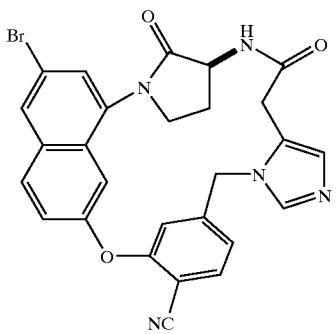

Preparation of (20S)-16-Bromo-19,20,22,23-tetrahydro-19,22-dioxo-5H,21H-18,20-ethano-12,14-etheno-6,10-methenobenz[d]imidazo[4,3-l][1,6,9,13] oxatriazacyclononadecosine-9-carbonitrile Hydrochloride Following the procedures described in Example 46, but using (S)-1-(3-bromo-7-tert-butoxynaphthalen-1-yl)-3-(tert-butoxycarbonylamino)-2-oxopyrrolidine, as described above in Example 46A, in place of (R)-1-(3-bromo-7-tert-butoxynaphthalen-1-yl)-3-(tert-butoxycarbonylamino)-2-oxopyrrolidine in Step J, the above-titled compound was obtained.

Elemental analysis calculated for $C_{27}H_{20}BrN_5O_3 \cdot 2HCl \cdot 0.25$ EtOAc$\cdot 0.2CHCl_3$: C: 50.75; H: 3.55; N: 10.88; Found: C: 50.76; H: 3.55; N: 10.59; ES MS: 542 (MH$^+$).

Example 48

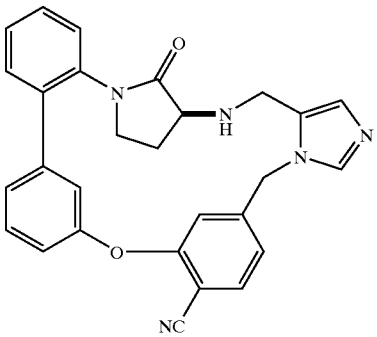

Preparation of (23S)-22,23,24,25-Tetrahydro-22-oxo-16H,21H-21,23-ethano-6,10:12,16-dimethenobenz[g]imidazo[4,3-n][1,9,12,15] oxatriazacycloheneicosine-9-carbonitrile Hydrochloride Step A: 2-(3-Methoxyphenyl)nitrobenzene 3-Methoxyphenyl boronic acid (7.4 g, 48.71 mmol), 1-bromonitrobenzene (10.25 g, 40.59 mmol) and $K_2CO_3$ (28.05 g, 202.9 mmol) were dissolved in $H_2O$ (85 mL) and ethylene glycol dimethyl ether (170 mL). The solution was degassed, Pd(PPh$_3$)$_4$ (1.7 g, 1.50 mmol) was added and the vessel was heated to 110° C. under argon for 5 hours. The reaction was cooled, diluted with water and extracted with EtOAc (3×). The combined organic extracts were dried over $Na_2SO_4$, filtered and concentrated in vacuo. The residue was crystallized from EtOAc/Hex. The mother liquor was concentrated in vacuo and chromatographed on silica gel, eluting with a gradient of 1 to 10% EtOAc in hexanes, to yield the above-titled compound.

Step B: 2-(3-Hydroxyphenyl)nitrobenzene 2-(3-Methoxyphenyl)nitrobenzene, as described above in Step A, (8.6 g, 37.52 mmol) was dissolved in $CH_2Cl_2$ (500 mL) and cooled to −78° C. BBr$_3$ (1.0 M sol. in $CH_2Cl_2$, 43 mL, 43 mmol) was slowly added and the reaction was warmed to ambient temperature and stirred for 18 hours. The reaction was partitioned between saturated aqueous $NaHCO_3$ and $CH_2Cl_2$ and extracted with $CH_2Cl_2$ (3×). The combined organic extracts were dried over $Na_2SO_4$, filtered and concentrated in vacuo, to yield the above-titled compound.

Step C: 2-(3-tert-Butyldimethylsilyloxyphenyl) nitrobenzene 2-(3-Hydroxyphenyl)nitrobenzene, as described above in Step B, (8.07 g, 37.52 mmol), imidazole (7.66 g, 112.56 mmol) and tert-butyldimethylsilyl chloride (6.22 g, 41.27 mmol) were dissolved in DMF (30 mL) and stirred for 0.75 hour. The DMF was removed in vacuo and the resulting residue was taken up in water and dimethyl ether and extracted with dimethyl ether (3×). The combined organic extracts were dried over $Na_2SO_4$, filtered and concentrated in vacuo. The residue was chromatographed on silica gel, eluting with a gradient of 0% to 4% EtOAc in hexanes, to yield the above-titled compound.

Step D: 2-(3-tert-Butyldimethylsilyloxyphenyl)aniline 2-(3-tert-Butyldimethylsilyloxyphenyl)nitrobenzene, as described above in Step C, (11.94 g, 36.24 mmol) was dissolved in EtOH (250 mL) and EtOAc (250 mL), degassed with argon and Pd/C (1.19 g, 10 wt %) was added. The vessel Was subjected to $H_2$ (1 atm) while vigorously stirring for 2.5 hour. The reaction was filtered through a celite pad and concentrated in vacuo, to yield the above-titled compound.

143

Step E: (S)-3-(tert-Butoxycarbonylamino)-1-[3'-(tert-butyldimethylsilyloxy)biphen-2-yl]-2-oxopyrrolidine Following the procedures described in Example 24, Steps F–H, but using 2-(3-tert-butyldimethylsilyloxyphenyl) aniline rather than 1-amino-4-bromo-7-(tert-butyldimethylsilyloxy)naphthalene hydrochloride, and (S)-N-(tert-butoxycarbonyl) methionine rather than (R)-N-(tert-butoxycarbonyl)methionine, the above-titled compound was obtained.

Step F: (S)-3-Amino-1-[3'-(tert-butyldimethylsilyloxy)biphen-2-yl)-2-oxopyrrolidine (S)-3-(tert-Butoxycarbonylamino)-1-[3'-(tert-butyldimethylsilyloxy) biphen-2-yl]-2-oxopyrrolidine, as described above in Step E, (888 mg, 1.84 mmol) was dissolved in $CH_2Cl_2$ (20 mL), cooled to 0° C., and trifluoroacetic acid (4 mL) was added. After 3 hours, the reaction mixture was poured into saturated aqueous $NaHCO_3$ and extracted with $CH_2Cl_2$ (3×). The combined organic extracts were dried over $Na_2SO_4$, filtered and concentrated in vacuo, to yield the above-titled compound.

Step G: (S)-4-[5-({1-[3'-(tert-Butyldimethylsilyloxy)biphen-2-yl)-2-oxopyrrolidin-3-ylamino}methyl)imidazol-1-ylmethyl]-2-fluorobenzonitrile Following the procedure described in Example 1, Step O, but using (S)-3-amino-1-[3'-(tert-butyldimethylsilyloxy)biphen-2-yl)-2-oxopyrrolidine, as described above in Step F, in place of (R)-3-amino-1-(3-hydroxybenzyl)-2-oxopyrrolidine hydrochloride, the above-titled compound was obtained.

Step H: (S)-2-Fluoro-4-(5-{[1-(3'-hydroxybiphen-2-yl)-2-oxopyrrolidin-3-ylaminolmethyl}imidazol-1-ylmethyl)benzonitrile Following the procedure described in Example 24, Step I, but using (S)-4-[5-({1-[3'-(tert-butyldimethylsilyloxy)biphen-2-yl)-2-oxopyrrolidin-3-ylamino}methyl) imidazol-1-ylmethyl]-2-fluorobenzonitrile, as described above in Step G, in place of (R)-1-[4-bromo-7-(tert-butyldimethylsilyloxy)naphthalen-1-yl]-3-(tert-butoxycarbonylamino)-2-oxopyrrolidine, the above-titled compound was obtained.

Step I: (23S)-22,23,24,25-Tetrahydro-22-oxo-16H,21H-21,23-ethano-6,10:12,16-dimethenobenz[g]imidazo[4,3-n][1,9,12,15]oxatriazacycloheneicosine-9-carbonitrile Hydrochloride Following the procedures described in Example 1, Step P, but using (S)-2-fluoro4-(5-{[1-(3'-hydroxybiphen-2-yl)-2-oxopyrrolidin-3-ylamino]methyl]imidazol-1-ylmethyl)benzonitrile, as described above in Step H, in place of (R)-2-fluoro-4-(5-{[1-(3-hydroxybenzyl)-2-oxopyrrolidin-3-ylamino]methyl}imidazol-1-ylmethyl)benzonitrile, the above-titled compound was obtained.

Elemental analysis calculated for $C_{28}H_{23}N_5O_2 \cdot 2HCl \cdot 2.00H_2O \cdot 0.30$ EtOAc: C: 58.75; H: 5.30; N: 11.73; Found: C: 58.74; H: 5.41; N: 11.71; FAB MS: 462 (MH$^+$).

144

Example 49

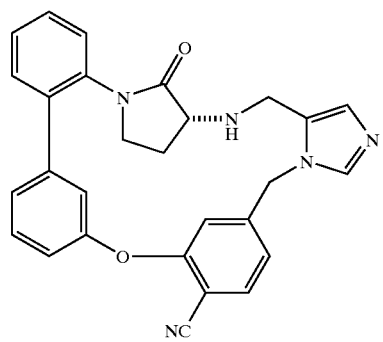

Preparation of (23R)-22,23,24,25-Tetrahydro-22-oxo-16H,21H-21,23-ethano-6,10:12,16-dimethenobenz[g]imidazo[4,3-n][1,9,12,15] oxatriazacycloheneicosine-9-carbonitrile Hydrochloride Following the procedures described in Example 48, but using (R)-N-(tert-butoxycarbonyl)methionine in place of (S)-N-(tert-butoxycarbonyl)methionine in Step E, the above-titled compound was obtained.

Elemental analysis calculated for $C_{28}H_{23}N_5O_2 \cdot 2HCl \cdot 2.20H_2O \cdot 0.15$ EtOAc: C: 58.49; H: 5.25; N: 11.93; Found: C: 58.49; H: 5.37; N: 11.90; FAB MS: 462 (MH$^+$).

Example 50

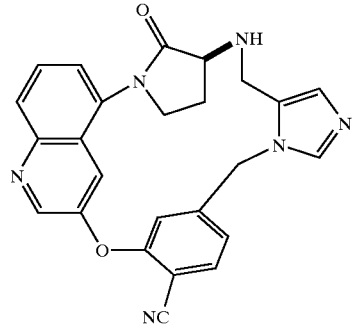

Preparation of (20S)-25-aza-19,20,21,22-Tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride Step A: N-Acetyl-3-aminoquinoline 3-Aminoquinoline (6.04 g, 41.89 mmol) and $Et_3N$ (5.85 mL, 41.89 mmol) were dissolved in $CH_2Cl_2$ (75 mL). Acetic anhydride (3.95 mL, 41.89 mmol) was added and reaction stirred at ambient temperature for 18 hours. The reaction mixture was poured into $H_2O$ and filtered. The filtered solid was dried in vacuo to yield the above-titled compound.

Step B: N-Acetyl-3-amino-5-nitroquinoline

N-Acetyl-3-aminoquinoline, as described above in Step A, (9.76 g, 52.41 mmol) was dissolved in neat $H_2SO_4$ (100 mL) and cooled to 0° C. $HNO_3$ (6.6 mL, 104.8 mmol) was slowly added over 20 minutes and the reaction was stirred at 0° C. for 45 min, then at ambient temperature 45 min. The reaction mixture was poured onto ice, solid KOH was added to neutralize the acid, and the mixture was stirred for 18 hours. The mixture was extracted with EtOAc (2×). The combined organic extracts were dried over $Na_2SO_4$, filtered and concentrated in vacuo. The residue was treated with hot EtOAc and filtered. The filtrate was concentrated and crystallized from EtOAc/Hex (3×). The recovered solids were combined and dried in vacuo to yield the above-titled compound.

Step C: 3-Amino-5-nitroquinoline

N-Acetyl-3-amino-5-nitroquinoline, as described above in Step B, (5.89 g, 25.5 mmol) was dissolved in EtOH (200 mL) and KOH (2 N aqueous solution, 19.2 mL, 38.4 mmol) was added. The reaction mixture was heated to reflux for 48 hours, cooled, poured into water, and concentrated to in vacuo to remove the EtOH. The resulting solid was collected by filtration and dried to afford the desired product.

Step D: 3-Hydroxy-5-nitroquinoline

3-Amino-5-nitroquinoline, as described above in Step C, (4.48 g, 23.68 mmol) was dissolved in $H_2SO_4$ (6N aqueous solution, 50 mL, 300 mmol) and cooled to approximately 5° C. A 0° C. solution of $NaNO_2$ (1.63g, 23.68 mmol) in water (5 mL) was added dropwise to the amine solution. After 45 min at 5 to 10° C., the reaction was poured into refluxing 5% aqueous $H_2SO_4$ (300 mL). The resulting mixture was heated for 5 min, then cooled and extracted once with $CH_2Cl_2$. The aqueous layer was basified with solid $NaHCO_3$ and extracted once with $CH_2Cl_2$. The aqueous layer was then neutralized with aqueous HCl and filtered. The filtered solid was dried in vacuo to yield the above-titled compound.

Step E: 3-(tert-Butyldimethylsilyloxy)-5-nitroquinoline

3-Hydroxy-5-nitroquinoline, as described above in Step D, (2.86 g, 15.04 mmol), tert-butyldimethylsilyl chloride (2.95 g, 19.55 mmol) and imidazole (3.07 g, 45.12 mmol) were dissolved in DMF (20 mL) and stirred for 2 hours. The reaction mixture was poured into $H_2O$ and extracted with $Et_2O$ (2×). The combined organic extracts were dried over $Na_2SO_4$, filtered and concentrated in vacuo, to yield the above-titled compound.

Step F: 5-Amino-3-(tert-butyldimethylsilyloxy)quinoline 3-(tert-Butyldimethylsilyloxy)-5-nitroquinoline, as described above in Step E, (4.58 g, 15.04 mmol) was dissolved in EtOH (150 mL) and EtOAc (150 mL), the vessel was degassed, Pd/C (0.458 g, 10 wt %) was added and the mixture was subjected to $H_2$ (1 atm) with vigorous stirring for 1 hour. The mixture was filtered through a celite pad and concentrated in vacuo. The residue was chromatographed on silica gel, eluting with a gradient of 0% to 10% EtOAc in $CH_2Cl_2$, to yield the above-titled compound.

Step G: (S)-2-(tert-Butoxycarbonylamino)-N-[3-(tert-butyldimethylsilyloxy) quinolin-5-yl]-4-hydroxybutyramide 5-Amino-3-(tert-butyldimethylsilyloxy)quinoline, as described above in Step F, (409 mg, 1.49 mmol) was dissolved in $CH_2Cl_2$ (8 mL) and $AlMe_3$ (2 M in $CH_2Cl_2$, 0.745 mL, 1.49 mmol) was added dropwise. After 15 min, (S)-N-(tert-butoxycarbonyl)homoserine lactone (250 mg, 1.242 mmol) in $CH_2Cl_2$ (1.5 mL) was added dropwise and the reaction mixture was stirred for 18 hours at ambient temperature. The reaction was quenched with 10% aqueous citric acid (1 mL) and stirred for 20 min. The mixture was poured into saturated aqueous potassium sodium tartrate and extracted with $CH_2Cl_2$ (3×). The combined organic extracts were dried over $Na_2SO_4$, filtered, and concentrated in vacuo. The residue was chromatographed on silica gel, eluting with a gradient of $CH_2Cl_2$—1 to 6% MeOH—0.1 to 0.6% $NH_4OH$, to yield the above-titled compound.

Step H: (S)-3-tert-Butoxycarbonylamino)-1-[3-(tert-butyldimethylsilyloxy) quinolin-5-yl]-2-oxopyrrolidine Tri-n-butylphosphine (0.238 mL, 0.954 mmol) was added to solution of di-tert-butyl azodicarboxylate (220 mg, 0.954 mmol) in $CH_2Cl_2$ (1.5 mL) at 0° C. The resulting solution was stirred for 15 min, then added dropwise to a solution of (S)-2-(tert-butoxycarbonylamino)-N-[3-(tert-butyldimethylsilyloxy)quinolin-5-yl]-4-hydroxybutyramide, as described above in Step G, (349 mg, 0.734 mmol) in THF (7 mL) at 0° C. The reaction mixture was allowed to slowly warm to ambient temperature and was stirred for 18 hours. The solution was poured into saturated aqueous $NaHCO_3$ and extracted with $CH_2Cl_2$ (3×). The combined organic extracts were dried over $Na_2SO_4$, filtered, and concentrated in vacuo. The residue was chromatographed on silica gel, eluting with a gradient of $CH_2Cl_2$—2% to 20% EtOAc, to yield the above-titled compound.

Step I: (S)-3-(tert-Butoxycarbonylamino)-1-(3-hydroxyquinolin-5-yl)-2-oxopyrrolidine (S)-3-tert-Butoxycarbonylamino)-1-[3-(tert-butyldimethylsilyloxy) quinolin-5-yl]-2-oxopyrrolidine, as described in Step H, (175 mg, 0.382 mmol) was dissolved in THF (5 mL) and TBAF (1.0 M in THF, 0.44 mL, 0.44 mmol) was added. After 1 hour, the reaction mixture was poured into saturated aqueous $NaHCO_3$ and extracted with $CH_2Cl_2$ (3×). The combined organic extracts were dried over $Na_2SO_4$, filtered and concentrated in vacuo. The crude product was purified by flash column chromatography on silica, eluting with a gradient of $CH_2Cl_2$—1% to 10% MeOH—0.1% to 1% $NH_4OH$ to yield the desired product.

Step J: (S)-3-Amino-1-(3-hydroxyquinolin-5-yl)-2-oxopyrrolidine Hydrochloride (S)-3-(tert-Butoxycarbonylamino)-1-(3-hydroxyquinolin-5-yl)-2-oxopyrrolidine, as described above in Step I, (161 mg, 0.382 mmol) was dissolved in EtOAc (5 mL) and MeOH (5 mL), and HCl (g) was bubbled in until the mixture was saturated. The solvents were removed in vacuo to yield the above-titled compound.

Step K: (20S)-25-aza-19,20,21,22-Tetrahydro-19-oxo-5H-18,20-ethano-12,14-etheno-6,10-metheno-18H-benz[d] imidazo[4,3-k][1,6,9,12]oxatriazacyclooctadecosine-9-carbonitrile Hydrochloride Following the procedures described in Example 1, but using (S)-3-amino-1-(3-hydroxyquinolin-5-yl)-2-oxopyrrolidine hydrochloride, as described above in Step J, in place of (R)-3-amino-1-(3-hydroxybenzyl)-2-oxopyrrolidine hydrochloride in Step O, the above-titled compound was obtained.

Elemental analysis calculated for $C_{25}H_{20}N_6O_2·3HCl·0.35$ $EtOAc·1.75H_2O$: C: 52.13; H: 4.86; N: 13.82; Found: C: 52.10; H: 4.58; N: 13.79; FAB MS: 437 ($MH^+$).

Example 51

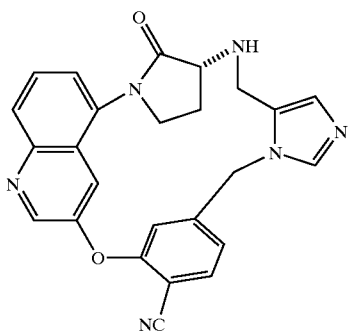

Preparation of (20R)-25-aza-19,20,21,22-Tetrahydro-19-oxo-5H-18,20-ethano-12,14-etheno-6,10-metheno-18H-benz[d]imidazo[4,3-k][1,6,9, 12] oxatriaza-cyclooctadecosine-9-carbonitrile Hydrochloride Following the procedures described in Example 50, but using (R)-N-(tert-butoxycarbonyl)homoserine lactone in place of (S)-N-(tert-butoxycarbonyl) homoserine lactone in Step G, the above-titled compound was obtained.

Elemental analysis calculated for $C_{25}H_{20}N_6O_2 \cdot 3HCl \cdot 0.5$ EtOAc $\cdot 1.95H_2O$: C: 51.88; H: 4.98; N: 13.45; Found: C: 51.87; H: 5.04; N: 13.49; FAB MS: 437 (MH$^+$).

Example 52

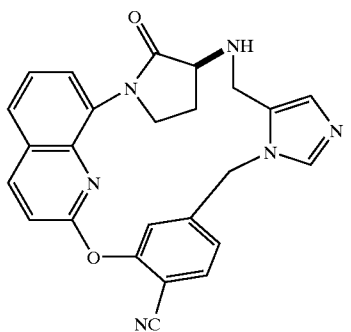

Preparation of (20S)-19,20,21,22-Tetrahydro-19-oxo-5H-18,20-ethano-12,14-etheno-6,10-metheno-18H-benz[d]imidazo[4,3-k][1,3,6,9,1 2]oxatetraaza-cyclooctadecosine-9-carbonitrile Hydrochloride Step A: N-Acetyl-2-bromo-6-nitroaniline 2-Bromoaniline (15 g, 87.2 mmol) was dissolved in acetic anhydride (76 mL, 0.610 mol) and cooled to 6° C. HNO$_3$ (11 mL, 0.174 mol) was added dropwise and reaction mixture was stirred for 18 hours at 6° C. The reaction mixture was poured into H$_2$O and extracted with CH$_2$Cl$_2$ (3x). The combined organic extracts were dried over Na$_2$SO$_4$, filtered and concentrated in vacuo. The residue was crystallized from EtOAc—hexane, to yield the above-titled compound.

Step B: Methyl 2-Acetamido-3-nitrocinnamate

N-Acetyl-2-bromo-6-nitroaniline, as described above in Step A, (6.3 g, 24.3 mmol), acrylic acid methyl ester (4.4 mL, 48.64 mmol), triethylamine (4.2 mL, 30.4 mmol) and palladium (11) acetate (275 mg, 1.22 mmol) were dissolved in acetonitrile (75 mL) and heated to 75° C. for 18 hours. The cooled reaction mixture was poured into saturated aqueous Na$_2$CO$_3$ and extracted with CH$_2$Cl$_2$ (3x). The combined organic extracts were dried over Na$_2$SO$_4$, filtered and concentrated in vacuo. The residue was crystallized from MeOH—H$_2$O to yield the above-titled compound.

Step C: 1,2-Dihydro-8-nitroquinolin-2-one

Methyl 2-acetamido-3-nitrocinnamate, as described above in Step B, (5.76 g, 21.8 mmol) was dissolved in 3 N aqueous HCl (220 mL) and the solution was heated at reflux for 72 hours, cooled, neutralized with NaHCO$_3$ and extracted with CH$_2$Cl$_2$ (3x). The combined organic extracts were dried over Na$_2$SO$_4$, filtered and concentrated in vacuo, to yield the above-titled compound.

Step D: 2-Methoxy-8-nitroquinoline

To a stirred solution of 1,2-dihydro-8-nitroquinolin-2-one, as described above in Step C, (2.55 g, 13.41 mmol) in DMF (80 mL) were added Cs$_2$CO$_3$ (13.11 g, 40.23 mmol) and iodomethane (1.37 mL, 14.75 mmol) and the mixture was stirred vigorously for 2.5 hours. The reaction mixture was poured into water at 0° C. and the solid was isolated by filtration. The resulting solid was dried in vacuo, to yield the above-titled compound.

Step E: 8-Amino-2-methoxyquinoline

2-Methoxy-8-nitroquinoline, as described above in Step D, (2.07 g, 10.14 mmol) was dissolved in EtOH (150 mL) and EtOAc (150 mL), the vessel was degassed, Pd/C (200 mg, 10 wt %) was added and the vessel was filled with H$_2$ (1 atm). After 1 hour, the reaction was filtered through a pad of celite and concentrated in vacuo. The residue was chromatographed on silica gel, eluting with CH$_2$Cl$_2$, to yield the above-titled compound.

Step F: (S)-3-(tert-Butoxycarbonylamino)-1-(2-methoxyquinolin-8-yl)-2-oxopyrrolidine Following the procedures described in Example 50, Steps G–H, but using 8-amino-2-methoxyquinoline, as described above in Step E, in place of 5-amino-3-(tert-butyldimethylsilyloxy)quinoline in Step G, the above-titled compound was obtained.

Step G: (S)-3-(tert-Butoxycarbonylamino)-1-(2-hydroxyquinolin-8-yl)-2-oxopyrrolidine (S)-3-(tert-Butoxycarbonylamino)-1-(2-methoxyquinolin-8-yl)-2-oxopyrrolidine, as described above in Step F, (287 mg, 0.803 mmol) and KI (240 mg, 1.44 mmol) were dissolved in AcOH (10 mL) and heated to 120° C. for 1 hour. The reaction mixture was concentrated in vacuo, to yield the above-titled compound.

Step H: (S)-3-Amino-1-(2-hydroxyguinolin-8-yl)-2-oxopyrrolidine (S)-3-(tert-Butoxycarbonylamino)-1-(2-hydroxyquinolin-8-yl)-2-oxopyrrolidine, as described above in Step G, (275 mg, 0.803 mmol) was dissolved in MeOH (15 mL) and EtOAc (15 mL) and the solution was saturated with HCl (g). The mixture was stood for 5 min, then concentrated in vacuo. The residue was suspended in CH$_2$Cl$_2$ and was chromatographed on silica gel, eluting with a gradient of CH$_2$Cl$_2$—2 to 15% MeOH—0.2 to 2% NH$_4$OH, to yield the above-titled compound.

Step I: (20S)-19,20,21,22-Tetrahydro-19-oxo-5H-18,20-ethano-12,14-etheno-6,10-metheno-18H-benz[d]imidazo[4,3-k][1,3,6,9,12]oxatetraaza-cyclooctadecosine-9-carbonitrile Hydrochloride Following the procedures described in Example 1, but using (S)-3-amino-1-(2-hydroxyquinolin-8-yl)-2-oxopyrrolidine, as described in Step H, rather than (R)-3-amino-1-(3-hydroxybenzyl)-2-oxopyrrolidine hydrochloride in Step O, the above-titled compound was obtained.

Elemental analysis calculated for $C_{25}H_{20}N_6O_2 \cdot 2.2HCl \cdot 0.35$ EtOAc: C: 57.91; H: 4.60; N: 15.35; Found: C: 57.86; H: 4.85; N: 15.42; FAB MS: 437 (MH$^+$).

Example 53

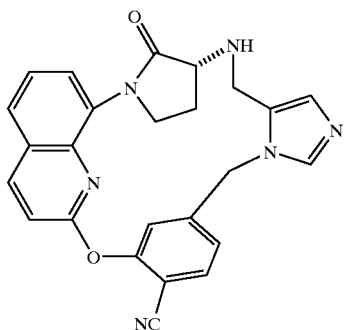

Preparation of (20R)-19,20,21,22-Tetrahydro-19-oxo-5H-18,20-ethano-12,14-etheno-6,10-metheno-18H-benz[d]imidazo[4,3-k][1,3,6,9,12]oxatetraazacyclooctadecosine-9-carbonitrile Hydrochloride Following the procedures described in Example 52, but using (R)-N-(tert-butoxycarbonyl)homoserine lactone rather than (S)-N-(tert-butoxycarbonyl) homoserine lactone in Step F, the above-titled compound was obtained.

Elemental analysis calculated for $C_{25}H_{20}N_6O_2 \cdot 2.3HCl \cdot 0.8$ EtOAc: C: 57.32; H: 4.90; N: 14.23; Found: C: 57.26; H: 5.01; N: 14.20; FAB MS: 437 (MH$^+$).

Example 54

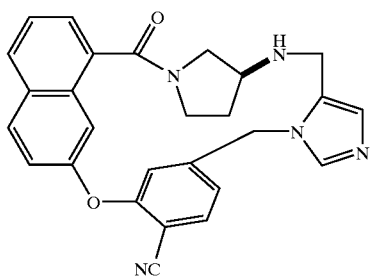

Preparation of (21S)-19,20,22,23-Tetrahydro-18-oxo-5H,21H-19,21-ethano-12,14-etheno-6,10-methenobenz[d]imidazo[4,3-l][1,7,10,13]oxatriazacyclononadecosine-9-carbonitrile Hydrochloride Step A: 7-Hydroxy-1-iodonaphthalene To a solution of 8-amino-2-naphthol (10.0 g, 62.80 mmol) in THF (50 mL) and 3 N aqueous HCl (100 mL) at 0° C. was added a solution of NaNO$_2$ (4.76 g, 69.08 mmol) in H$_2$O (20 mL). The resulting mixture was stirred for 15 min, then a solution of potassium iodide (41.8 g, 251.8 mmol) in H$_2$O (30 mL) was added. After 40 min, the reaction was diluted with EtOAc and filtered. The filtrate was extracted with EtOAc (2×), the combined organic extracts were dried over Na$_2$SO$_4$, filtered and concentrated in vacuo in the presence of silica gel. The powder was chromatographed on silica gel, eluting with hexane—10% EtOAc, to yield the above-titled compound.

Step B: 1-Iodo-7-(triisopropylsilyloxy)naphthalene

1-Iodo-7-hydroxynaphthalene, as described in Step A, (15.84 g, 58.65 mmol), imidazole (5.59 g, 82.11 mmol) and triisopropylsilyl chloride (17.6 mL, 82.11 mmol) were dissolved in DMF (40 mL) and heated to 40° C. for 18 hours. The reaction was poured into H$_2$O and extracted with hexanes (3×). The combined organic extracts were dried over Na$_2$SO$_4$, filtered and concentrated in vacuo, to yield the above-titled compound.

Step C: 7-(Triisopropylsilyloxy)-1-naphthlenecarboxylic Acid

To a solution of 1-iodo-7-(triisopropylsilyloxy) naphthiene, as described above in Step B, (26.16 g, 61.35 mmol) in THF (450 mL), at −78° C., was added tert-butyllithium (1.7 M in pentane, 72 mL, 122.4 mmol) dropwise. The reaction mixture was stirred for 45 min, then CO$_2$ (g) was bubbled into the solution for 1 hour. The reaction mixture was warmed to ambient temperature and stirred for 18 hours, then was poured into H$_2$O, the aqueous solution was acidified with TFA and extracted with EtOAc (2×). The combined organic extracts were dried over Na$_2$SO$_4$, filtered and concentrated in vacuo. The residue was chromatographed on silica gel, eluting with CH$_2$Cl$_2$—10% EtOAc, to yield the above-titled compound.

Step D: (S)-3-(tert-Butoxycarbonyl)-1-[7-(triisopropylsilyloxy)naphthlene-1-carbonylpyrrolidine 7-(Triisopropylsilyloxy)-1-naphthlenecarboxylic acid, as described above in Step C (300 mg, 0.871 mmol), PYBOP (476 mg, 0.914 mmol), N,N-diiso-propylethylamine (0.152 mL, 0.742 mmol) and (S)-3-(tert-butoxycarbonylamino) pyrrolidine (211 mg, 1.13 mmol) were combined in CH$_2$Cl$_2$. After 6 hours, the reaction mixture was poured into 10% aqueous citric acid and extracted with CH$_2$Cl$_2$ (3×). The combined organic extracts were dried over Na$_2$SO$_4$, filtered and concentrated in vacuo, to yield the above-titled compound.

Step E: (21S)-19,20,22,23-Tetrahydro-1 8-oxo-5H,21H-19,21-ethano-12,14-etheno-6,10-methenobenz[d]imidazo[4,3-l][1,7,10,13]oxatriazacyclononadecosine-9-carbonitrile Hydrochloride Following the procedures described in Example 50, but using (S)-3-(tert-butoxycarbonyl)-1-[2-(triisopropylsilyloxy)-8-yl-carbonyl-naphthlene] pyrrolidine, as described above in Step D, in place of (S)-3-tert-butoxycarbonyl-amino)-1-[3-(tert-butyldimethylsilyloxy)quinolin-5-yl]-2-oxopyrrolidine in Step I, the above-titled compound was obtained.

Elemental analysis calculated for $C_{27}H_{23}N_5O_2 \cdot 2HCl \cdot 0.3$ EtOAc$\cdot 1.25H_2O$: C: 59.27; H: 5.27; N: 12.26; Found: C: 59.26; H: 5.13; N: 12.29; FAB MS: 450 (MH$^+$).

Example 55

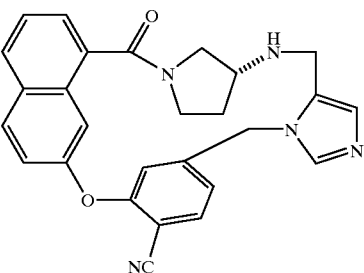

Preparation of (21R)-19,20,22,23-Tetrahydro-18-oxo-5H,21H-19,21-ethano-12,14-etheno-6,10-methenobenz[d]imidazo[4,3-l][1,7,10,13]oxatriazacyclononadecosine-9-carbonitrile Hydrochloride Following the procedures described in Example 54, but using (R)-3-(tert-butoxycarbonylamino)pyrrolidine rather than (S)-3-(tert-butoxycarbonylamino) pyrrolidine in Step D, the above-titled compound was obtained.

Elemental analysis calculated for $C_{27}H_{23}N_5O_2 \cdot 2HCl \cdot 0.15$ EtOAc$\cdot 1.75H_2O$: C: 58.44; H: 5.28; N: 12.35; Found: C: 58.43; H: 4.95; N: 12.31; FAB MS: 450 (MH$^+$).

Example 56

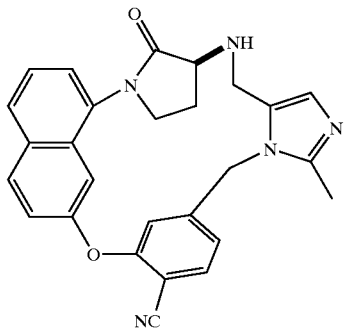

Preparation of (20S)-19,20,21,22-Tetrahydro-3-methyl-19-oxo-5H-18,20-ethano-12,14-etheno-6,10-metheno-18H-benz[d]imidazo[4,3-k][1,6,9,12] oxatriazacyclooctadecosine-9-carbonitrile Hydrochloride Step A: 1-(4-Cyano-3-fluorobenzyl)-2-methyl-5-imidazolecarboxaldehyde To a solution of 4-cyano-3-fluorobenzyl bromide, as described in Example 1, Step D, (1.26 g, 5.9 mmol) in DMF (10 mL), at 0° C., was added 4-formyl-2-methylimidazole (0.650 g, 5.9 mmol) and cesium carbonate (2.9 g, 8.9 mmol). After 2 hours, the reaction mixture was poured into EtOAc—30% hexane, washed with $H_2O$, then brine, dried over Na2SO4, filtered, and concentrated in vacuo to provide the crude product. The crude material was purified by silica gel chromatography, eluting with a gradient of $CHCl_3$—2% to 5% MeOH, to obtain the above-titled product.

Step B: (20S)-19,20,21,22-Tetrahydro-3-methyl-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride Following the procedures described in Example 1, but using (S)-3-amino-1-(7-hydroxynaphthalen-1-yl)-2-oxopyrrolidine hydrochloride, as described in Example 9A, in place of (R)-3-amino-1-(3-hydroxybenzyl)-2-oxopyrrolidine hydrochloride and using 1-(4-cyano-3-fluorobenzyl)-2-methyl-5-imidazolecarboxaldehyde, as described above in Step A, in place of 1-(4-cyano-3-fluorobenzyl)-5-imidazole-carboxaldehyde in Step O, the above-titled compound was obtained.

Elemental analysis calculated for $C_{27}H_{23}N_5O_2 \cdot 2HCl \cdot 0.7H_2O$: C: 60.61; H: 4.97; N: 13.09; Found: C: 60.27; H: 4.58; N: 12.88; FAB MS: 450 (MH$^+$).

Example 57

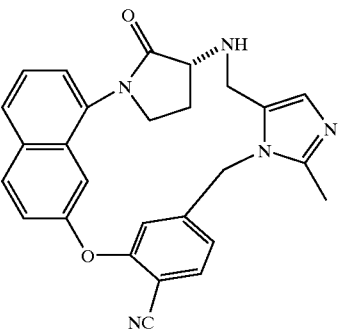

Preparation of (20R)-19,20,21,22-Tetrahydro-3-methyl-19-oxo-5H-18,20-ethano-12,14-etheno-6,10-metheno-18H-benz[d]imidazo[4,3-k][1,6,9,12] oxatriazacyclooctadecosine-9-carbonitrile Hydrochloride Following the procedures described in Example 1, but using (R)-3-amino-1-(7-hydroxynaphthalen-1-yl)-2-oxopyrrolidine hydrochloride, as described in Example 10A, in place of (R)-3-amino-1-(3-hydroxybenzyl)-2-oxopyrrolidine hydrochloride and using 1-(4-cyano-3-fluorobenzyl)-2-methyl-5-imidazolecarboxaldehyde, as described in Example 56, Step A, in place of 1-(4-cyano-3-fluorobenzyl)-5-imidazolecarboxaldehyde in Step O, the above-titled compound was obtained.

Elemental analysis calculated for $C_{27}H_{23}N_5O_2 \cdot 2HCl \cdot 0.55H_2O$: C: 60.91; H: 4.94; N: 13.16; Found: C: 60.92; H: 4.84; N: 13.11; FAB MS: 450 (MH$^+$).

Example 58

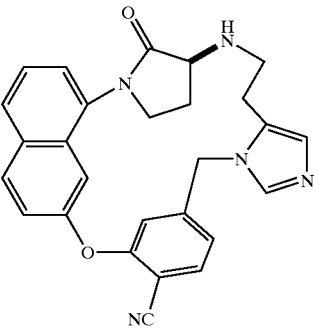

Preparation of (20S)-19,20,22,23-Tetrahydro-5H, 21H-18,20-ethano-12,14-etheno-6,10-methenobenz [d]imidazo[4,3-l][1,6,9,13] oxatriazacyclononadecosine-9-carbonitrile Hydrochloride Step A: (S)-N-{1-[7-(tert-Butyldiphenylsilyloxy) naphthalen-1-yl]-2-thioxopyrrolidin-3-yl}-2-[1-(triphenylmethyl)-1H-imidazol-4-yl]thioacetamide A mixture of (S)-N-{1-[7-(tert-butyldiphenylsilyloxy) naphthalen-1-yl]-2-oxopyrrolidin-3-yl}-2-[1-(triphenylmethyl)-1H-imidazol-4-yl]acetamide, as described in Example 31, Step D, (3.00 g, 3.61 mmol) and Lawesson's Reagent (728 mg, 1.80 mmol) in dry THF (45 mL), under argon, was heated to 45° C. for 90 min. The solvent was removed under reduced pressure and the residue was partitioned between saturated aqueous Na₂CO₃ (125 mL) and CH₂Cl₂ (300 mL). The aqueous layer was extracted further with CH₂Cl₂ (150 mL) and the combined organic extracts were dried over MgSO₄, filtered, and concentrated in vacuo. The crude product was purified by flash column chromatography on silica, eluting with hexane—40% EtOAc—1% MeOH—0.1% NHOH to yield the desired product.

Step B: (20S)-19,20,22,23-Tetrahydro-5H,21H-18,20-ethano-12,14-etheno-6,10-methenobenz[d]imidazo[4,3-l][1,6,9,13]oxatriazacyclononadecosine-9-carbonitrile Hydrochloride Following the procedures described in Example 31, but using (S)-N-{1-[7-(tert-butyldiphenylsilyloxy)naphthalen-1-yl]-2-thioxopyrrolidin-3-yl}-2-[1-(triphenylmethyl)-1H-imidazol-4-yl]thioacetamide in place of (S)-N-{1-[7-(tert-butyldiphenylsilyloxy)naphthalen-1-yl]-2-oxopyrrolidin-3-yl}-2-[1-(triphenylmethyl)-1H-imidazol-4-yl]thioacetamide in Step F, the above-titled compound was obtained.

Elemental analysis calculated for C₂₇H₂₅N₅O.3HCl.0.4CH₂Cl₂.0.25 EtOAc: C: 56.76; H: 5.17; N: 11.65; Found: C: 56.88; H: 5.43; N: 11.76; FAB MS: 436 (MH⁺).

Example 59

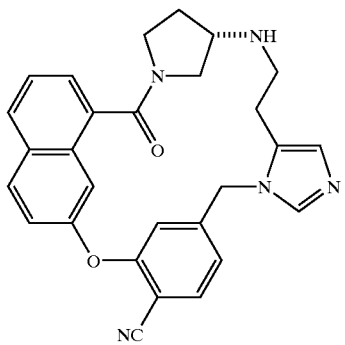

Preparation of (21S)-19,20,22,23,24-Pentahydro-18-oxo-5H,21H-19,21-ethano-12,14-etheno-6,10-methenobenz[d]imidazo[4,3-m][1,7,10,14]oxatriazacycloeicosine-9-carbonitrile Trifluoroacetate Step A: (S)-1-(tert-Butoxycarbonyl)-3-(trifluoroacetamido)pyrrolidine To a stirred solution of (S)-3-(trifluoroacetamido)pyrrolidine hydrochloride (2.08 g, 9.5 mmol) and N,N-diisopropylethylamine (1.82 mL, 10.5 mmol) in CH₂Cl₂ (25 mL) was added di-tert-butyl dicarbonate (2.08 g, 9.5 mmol) in CH₂Cl₂ (25 mL). The reaction mixture was stirred at ambient temperature for 2 hours, then partitioned between saturated aqueous Na₂CO₃ (30 mL) and CH₂Cl₂ (50 mL). The aqueous layer was extracted further with CH₂Cl₂ (50 mL). The combined organic extracts were dried over Na₂SO₄, filtered, and concentrated in vacuo to give the titled product.

Step B: (S)-3-Amino-1-(tert-butoxycarbonyl)pyrrolidine

To a stirred solution of (S)-1-(tert-butoxycarbonyl)-3-(trifluoro-acetamido)pyrrolidine, as described above in Step A, (2.80 g, 9.5 mmol) in THF (80 mL) and H₂O (10 mL) was added 1.0 N aqueous lithium hydroxide (10.5 mL, 10.5 mmol) and the resulting mixture was stirred at ambient temperature for 18 hours, then adjusted to pH 7 with 1.0 N aqueous HCl and concentrated to dryness in vacuo to give the titled compound.

Step C: (S)-N-[1-(tert-Butoxycarbonyl)pyrrolidin-3-yl]-2-[1-(triphenylmethyl)-1H-imidazol-4-yl]acetamide A mixture of (S)-3-amino-1-(tert-butoxycarbonyl) pyrrolidine, as described above in Step B, (842 mg, 4.52 mmol), lithium [1-(triphenylmethyl)-1H-imidazol-4-yl] acetate, as described in Example 31, Step B, (1.69 g, 4.52 mmol), EDC (953 mg, 4.97 mmol), HOBT (672 mg, 4.97 mmol) and N,N-diisopropylethylamine (1.2 mL, 6.78 mmol) in DMF (10 mL) was stirred for 18 hours. The mixture was poured into saturated aqueous NaHCO₃ and extracted with CH₂Cl₂ (3×). The combined organic extracts were dried over Na₂SO₄, filtered and concentrated in vacuo. The residue was chromatographed on silica gel, eluting with a gradient of CH₂Cl₂—1% to 5% MeOH—0.1% to 0.5% NH₄OH, to yield the above-titled compound.

Step D: (S)-N-[1-(tert-Butoxycarbonyl)pyrrolidin-3-yl]-2-[1-(triphenylmethyl)-1H-imidazol-4-yl]thioacetamide (S)-N-[1-(tert-Butoxycarbonyl)pyrrolidin-3-yl]-2-[1-(triphenylmethyl)-1H-imidazol-4-yl]acetamide, as described above in Step C, (1.27 g, 2.37 mmol) was dissolved in toluene (20 mL), Lawesson's Reagent (478 mg, 1.18 mmol) was added and the reaction mixture was heated to 50° C. for 5 hours. The mixture was concentrated in vacuo and the residue was chromatographed on silica gel, eluting with a gradient of CH₂Cl₂—1% to 5% MeOH—0.1% to 0.5% NH₄OH, to yield the above-titled compound.

Step E: (S)-1-(tert-Butoxycarbonyl)-3-({2-[1-(triphenylmethyl)-1H-imidazol-4-yl]ethyl}amino)pyrrolidine To a solution of (S)-N-[1-(tert-butoxycarbonyl)pyrrolidin-3-yl]-2-[1-(triphenylmethyl)-1H-imidazol-4-yl]thioacetamide, as described above in Step D, 1.29 g, 2.33 mmol) in TBF (65 mL) and MeOH (65 mL), was added NiCl₂.6H₂O (2.22 g, 9.33 mmol). The mixture was cooled to 0° C. and NaBH₄ (2 M in THF, 4.7 mL, 9.33 mmol) was slowly added. After 30 min, the solvent was partially removed in vacuo, and the residual mixture was partitioned between saturated aqueous Na₂CO₃ containing NH₄OH and Et₂O. The organic layer was removed and the aqueous layer was further extracted with EtOAc (2×). The combined organic extracts were combined, dried over Na₂SO₄, filtered and concentrated in vacuo. The residue was chromatographed on silica gel, eluting with a gradient of CH₂Cl₂—1% to 10% MeOH—0.1% to 1% NH₄OH, to yield the above-titled compound.

Step F: (S)-N-[1-(tert-Butoxycarbonyl)pyrrolidin-3-yl]-N-{2-[1-(triphenylmethyl)-1H-imidazol-4-yl]ethyl}carbamic Acid Triisopropylsilyl Ester To a stirred solution of (S)-1-(tert-butoxycarbonyl)-3-({2-[1-(triphenylmethyl)-1H-imidazol-4-yl]ethyl}amino) pyrrolidine, as described above in Step E, (411 mg, 0.786 mmol) in CH₂Cl₂ (10 mL), was added triethylamine (0.110 mL, 0.786 mmol) and the mixture was cooled to −78° C. Solid CO₂ (1.73 g, 39.3 mmol) was added and after 30 min, triisopropylsilyl chloride (0.172 mL, 0.802 mmol) was added and the reaction mixture was warmed to ambient temperature. After 1 hour, the reaction was diluted with water and extracted with CH₂Cl₂ (3×). The combined organic extracts were dried over Na₂SO₄, filtered and concentrated in vacuo. The residue was chromatographed on silica gel, eluting with a gradient of CH₂Cl₂—1% to 3% MeOH—0.1% to 0.3% NH₄OH, to yield the above-titled compound.

Step G: (S)-N-[1-(tert-Butoxycarbonyl)pyrrolidin-3-yl]-N-{2-[1-(4-cyano-3-fluorobenzyl)-1H-imidazol-5-yl]ethyl}carbamic Acid Triisopropylsilyl Ester To a stirred solution of (S)-N-[1-(tert-butoxycarbonyl)pyrrolidin-3-yl]-N-{2-[1-(triphenylmethyl)-1H-imidazol-4- yl]ethyl}carbamic acid triisopropylsilyl ester, as described above in Step F, (519 mg, 0.715 mmol) and 4-cyano-3-fluoro-benzyl alcohol, as described in Example 31, Step H, (108 mg, 0.715 mmol) in $CH_2Cl_2$ (7 mL) was added N,N-diisopropylethylamine (0.311 mL, 1.78 mmol), followed by dropwise addition of trifluoromethanesulfonic anhydride (0.120 mL, 0.715 mmol). The reaction mixture was allowed to warm slowly to ambient temperature and was stirred for 18 hours, then concentrated in vacuo. The residue was dissolved in MeOH (10 mL) and the resulting solution was heated to 40° C. for 2 hours. The solvent was removed in vacuo and the residue was chromatographed on silica gel, eluting with a gradient of $CH_2Cl_2$—1% to 4% MeOH—0.1% to 0.4% $NH_4OH$, to yield the above-titled compound.

Step H: (S)-N-{2-[1-(4-Cyano-3-fluorobenzyl)-1H-imidazol-5-yl]ethyl}-N-(pyrrolidin-3-yl)carbamic Acid Triisopropylsilyl Ester (S)-N-[1-(tert-Butoxycarbonyl)pyrrolidin-3-yl]-N-{2-[1-(4-cyano-3-fluorobenzyl)-1H-imidazol-5-yl]ethyl}carbamic acid triisopropylsilyl ester, as described above in Step G, (395 mg, 0.643 mmol) was dissolved in $CH_2Cl_2$ (10 mL) and TFA (2 mL, 2.56 mmol) was added. After 2 hours, the reaction was neutralized with triethylamine, diluted with water and extracted with $CH_2Cl_2$ (3×). The combined organic extracts were washed with brine, dried over $Na_2SO_4$, filtered and concentrated in vacuo, to yield the above-titled compound.

Step I: (S)-N-{2-[1-(4-Cyano-3-fluorobenzyl)-1H-imidazol-5-yl]ethyl}-N-{1-[7-(triisopropylsilyloxy)naphthalene-1-carbonyl]pyrrolidin-3-yl}carbamic Acid Triisopropylsilyl Ester (S)-N-{2-[1-(4-Cyano-3-fluorobenzyl)-1H-imidazol-5-yl]ethyl}-N-(pyrrolidin-3-yl)carbamic acid triisopropylsilyl ester, as described above in Step H, (242 mg, 0.471 mmol), 7-(triisopropylsilyloxy)-1-naphthlenecarboxylic acid, as described in Example 54, Step C, (162 mg, 0.471 mmol), PYBOP (245 mg, 0.471 mmol), and triethylamine (0.085 mL, 0.612 mmol) were combined in $CH_2Cl_2$ (4 mL). The reaction mixture was stirred at ambient temperature for 4 hours, then poured into 10% aqueous citric acid and extracted with $CH_2Cl_2$ (3×). The combined organic extracts were dried over $Na_2SO_4$, filtered and concentrated in vacuo, to yield the above-titled compound.

Step J: (S)-2-Fluoro-4-(5-{2-[1-(7-hydroxynaphthlene-1-carbonyl)pyrrolidin-3-ylamino}ethyl]imidazol-1-ylmethyl)benzonitrile To a solution of (S)-N-{2-[1-(4-cyano-3-fluorobenzyl)-1H-midazol-5-yl]ethyl}-N-{1-[7-(triisopropylsilyloxy)naphthalene-1-carbonyl]pyrrolidin-3-yl}carbamic acid triisopropylsilyl ester, as described above in Step I, (382 mg, 0.471 mmol) in THF (10 mL) was added TBAF (1 M in THF, 1.41 mL, 1.41 mmol). The mixture was poured into saturated aqueous $NaHCO_3$ and extracted with $CH_2Cl_2$ (3×). The combined organic extracts were dried over $Na_2SO_4$, filtered and concentrated in vacuo. The residue was chromatographed on silica gel, eluting with a gradient of $CH_2Cl_2$—1% to 9% MeOH—0.1% to 0.9% $NH_4OH$, to yield the above-titled compound.

Step K: (21S)-19,20,22,23,24-Pentahydro-18-oxo-5H,21H-19,21-ethano-12,14-etheno-6,10-methenobenz[d]imidazo[4,3-m][7,10,14]oxatriazacycloeicosine-9-carbonitrile Trifluoroacetate A stirred mixture of (S)-2-fluoro-4-(5-{2-[1-(7-hydroxynaphthlene-1-carbonyl)pyrrolidin-3-ylamino]ethyl}imidazol-1-ylmethyl)benzonitrile, as described above in Step J, (165 mg, 0.341 mmol) and $Cs_2CO_3$ (280 mg, 0.853 mmol) in DMF (35 mL) was heated to 40° C. for 3 hours. The reaction was quenched with AcOH and the solvent was removed in vacuo. The residue was partitioned between $CH_2Cl_2$ and saturated aqueous $NaHCO_3$ and extracted with $CH_2Cl_2$ (3×). The combined organic extracts were dried over $Na_2SO_4$, filtered and concentrated in vacuo. The residue was chromatographed on silica gel, eluting with a gradient of $CH_2Cl_2$—1% to 6% MeOH—0.1% to 0.6% $NH_4OH$, to yield a product which was further purified via preparative HPLC on a C-18 column, eluting with a gradient of 0.1% aqueous TFA—5% to 100% $CH_3CN$, to yield the above-titled compound.

Elemental analysis calculated for $C_{28}H_{25}N_5O_2 \cdot 2.5CF_3CO_2H \cdot 0.75H_2O$: C: 52.00; H: 3.84; N: 9.19; Found: C: 51.99; H: 3.65; N: 9.33; FAB MS: 464 $(MH^+)$.

Example 60

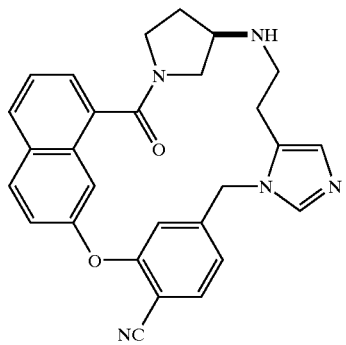

Preparation of (21R)-19, 20, 2,2,23,24-Pentahydro-18-oxo-5H,21H-19,21-ethano-12,14-etheno-6,10-methenobenz[d]imidazo[4,3-m][1,7,10,14]oxatriazacycloeicosine-9-carbonitrile Trifluoroacetate Following the procedures described in Example 59, but using (R)-3-(trifluoroacetarnido)pyrrolidine hydrochloride in place of (S)-3-(trifluoroacetamido) pyrrolidine hydrochloride in Step A, the above-titled compound was obtained.

Elemental analysis calculated for $C_{28}H_{25}N_5O_2 \cdot 2.5CF_3CO_2H \cdot 1.4H_2O$: C: 51.22; H: 3.95; N: 9.05; Found: C: 51.21; H: 3.68; N: 9.32; FAB MS: 464 $(MH^+)$.

Example 61

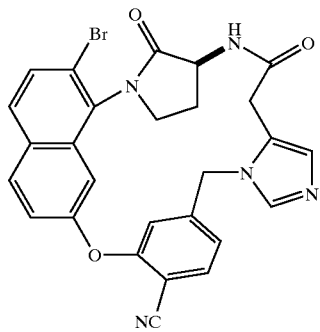

Preparation of (20S)-17-Bromo-19,20,22,23-tetrahydro-19,22-dioxo-5H,21H-18,20-ethano-12,14-etheno-6,10-methenobenz[d]imidazo[4,3-l][1,6,9,13]oxatriazacyclononadecosine- 9-carbonitrile Hydrochloride Step A: 1-(tert-Butoxycarbonylamino)-7-(triisopropylsilyloxy)naphthalene A solution of 8-(tert-butoxycarbonylamino)-2-naphthol, as described in Example 9, Step A, (8.00 g, 30.9 mmol), triisopropylsilyl chloride (7.92 mL, 37.0 mmol), and imidazole (4.20 g, 61.7 mmol) in DMF (75 mL) was stirred at ambient temperature for 18 hours, then poured into 10% aqueous citric acid (100 mL) and extracted with EtOAc (2×100 mL). The combined organic extracts were washed with $H_2O$, then brine, then dried over $Na_2SO_4$, filtered, and concentrated in vacuo. The crude product was purified by flash column chromatography on silica, eluting with $CH_2Cl_2$—50% hexane to yield the desired product.

Step B: 1-(tert-Butoxycarbonylamino)-7-(triisopropylsilyloxy)-2-(trimethylsilyl)naphthalene To a solution of 1-(tert-butoxycarbonylamino)-7-(triisopropylsilyloxy) naphthalene, as described above in Step A, (12.47 g, 30.0 mmol) and N,N,N',N'-tetramethylethylenediamine (10.0 mL, 66.0 mmol) in THF (300 mL) at −78° C. was added sec-butyllithium (1.3 M in cyclohexane, 24.2 mL, 31.5 mmol) dropwise. The reaction mixture was stirred at −78° C. for 5 min, then trimethylsilyl chloride (4.2 mL, 33.0 mmol) was added dropwise and stirring was continued for 30 min. sec-Butyllithium (1.3 M in cyclohexane, 24.2 mL, 31.5 mmol) was added and the mixture was stirred dropwise was stirred at −78° C. for 5 hours, then quenched with saturated aqueous $NH_4Cl$ (400 mL) and extracted with $CH_2Cl_2$ (2×500 mL). The combined organic extracts were dried over $Na_2SO_4$, filtered, and concentrated in vacuo. The crude product was purified by flash column chromatography on silica, eluting with a gradient of hexane—30% to 50% $CH_2Cl_2$ to yield the above-titled product.

Step C: 1-(tert-Butoxycarbonylamino)-7-(hydroxy)-2-(trimethylsilyl)naphthalene

To a stirred solution of 1-(tert-butoxycarbonylamino)-7-(triisopropylsilyloxy)-2-(trimethylsilyl)naphthalene, as described above in Step B, (9.72 g, 19.9 mmol) in THF (200 mL) at 0° C. was added TBAF (1.0 M in THF, 20.9 mL, 20.9 mmol). The resulting mixture was stirred at 0° C. for 15 min then poured into dilute aqueous $NH_4Cl$ (250 mL) and extracted with $CH_2Cl_2$ (500 mL). The organic extract was dried over $Na_2SO_4$, filtered, and concentrated in vacuo. The crude product was purified by flash column chromatography on silica, eluting with $CH_2Cl_2$—10% EtOAc to yield the desired product.

Step D: 1-(tert-Butoxycarbonylamino)-2-(trimethylsilyl)naphth-7-ylmethanesulfonate A mixture of 1-(tert-butoxycarbonylamino)-7-(hydroxy)-2-(trimethylsilyl)naphthalene, as described above in Step C, (6.48 g, 19.5 mmol) and triethylamine (4.10 mL, 29.3 mmol) was stirred in dry $CH_2Cl_2$ (200 mL) at 0° C. and methanesulfonic anhydride (3.75 g, 21.5 mmol) was added in one portion. The resulting mixture was stirred at 0° C. for 15 min, then poured into saturated aqueous $NaHCO_3$ (300 mL) and the $CH_2Cl_2$ layer was extracted. The aqueous layer was extracted further with $CH_2Cl_2$ (200 mL). The combined organic extracts were dried over $Na_2SO_4$, filtered, and concentrated in vacuo to provide the titled compound.

Step E: 2-Bromo-1-(tert-butoxycarbonylamino)naphth-7-yl Methanesulfonate

To a stirred solution of 1-(tert-butoxycarbonylamino)-2-(trimethylsilyl) naphth-7-yl methanesulfonate, as described above in Step D, (5.85 g, 14.3 mmol) in $CH_2Cl_2$ (170 mL) at −78° C. was added N-bromosuccinimide (1.14 g, 6.38 mmol) in one portion. The reaction mixture was allowed to warm and was stirred at ambient temperature for 6 days, then poured into saturated aqueous $NaHCO_3$ and extracted with $CH_2Cl_2$ (2×). The combined organic extracts were dried over $Na_2SO_4$, filtered, and concentrated in vacuo. The residue was triturated with hexane—$Et_2O$ to provide the titled product.

Step F: 2-Bromo-1-(tert-butoxycarbonylamino)-7-hydroxynaphthalene

To a stirred solution of 2-bromo-1-(tert-butoxycarbonylamino)naphth-7-yl methanesulfonate, as described above in Step E, (5.87 g, 14.09 mmol) in DMSO (70 mL) was added potassium tert-butoxide (5.17 g, 42.27 mmol) in one portion. The reaction mixture was stirred at ambient temperature for 1 hour, then neutralized with aqueous HCl, diluted with water and extracted with $Et_2O$ (2×). The combined organic extracts were washed with water (3×), dried over $Na_2SO_4$, filtered and concentrated in vacuo, to yield the above-titled compound.

Step G: 2-Bromo-1-(tert-butoxycarbonylamino)-7-(tert-butyldimethylsilyloxy)naphthalene 2-Bromo-1-(tert-butoxycarbonylamino)-7-hydroxynaphthalene, as described above in Step F, (4.80 g, 14.19 mmol), tert-butyldimethylsilyl chloride (2.8 g, 18.45 mmol) and imidazole (2.2 g, 32.64 mmol) were dissolved in DMF (25 mL) and stirred for 18 hours. The mixture was poured into $H_2O$ and extracted with $Et_2O$ (2×). The combined organic extracts were dried over $Na_2SO_4$, filtered and concentrated in vacuo. The residue was chromatographed on silica gel, eluting with $CH_2Cl_2$—50% hexanes, to yield the above-titled compound.

Step H: 1-Amino-2-bromo-7-(tert-butyldimethylsilyloxy) naphthalene

To a solution of 2-bromo-1-(tert-butoxycarbonylamino)-7-(tert-butyldimethylsilyloxy)naphthalene, as described above in Step G, (6.0 g, 13.26 mmol) in $CH_2Cl_2$ (100 mL) at 0° C. was added TFA (10 mL). After 45 min, the mixture was poured into saturated aqueous $NaHCO_3$ and extracted with $CH_2Cl_2$ (3×). The combined organic extracts were dried over $Na_2SO_4$, filtered and concentrated in vacuo. The residue was chromatographed on silica gel, eluting with a gradient of hexane—5% to 20% $CH_2Cl_2$, to yield the above-titled product.

Step I: (S)-1-[2-Bromo-7-(tert-butyldimethylsilyloxy)naphthalen-1-yl]-3-(tert-butoxycarbonylamino)-2-oxopyrrolidine Following the procedures described in Example 50, Steps G–H, but using 1-amino-2-bromo-7-(tert-butyldimethylsilyloxy)naphthalene, as described above in Step H, rather than 5-amino-3-(tert-butyldimethylsilyloxy) quinoline in Step G, the above-titled compound was obtained.

Step J: (S)-3-Amino-1-[2-bromo-7-(tert-butyldimethylsilyloxy)naphthalen-1-yl]-2-oxopyrrolidine (S)-1-[2-Bromo-7-(tert-butyldimethylsilyloxy)naphthalen-1-yl]-3-(tert-butoxycarbonylamino)-2-oxopyrrolidine, as described above in Step I, (245 mg, 0.458 mmol) was dissolved in a 10% TFA solution in $CH_2Cl_2$ (5 mL). After 30 min, the mixture was poured into saturated aqueous $Na_2CO_3$ and extracted with $CH_2Cl_2$ (3×). The combined organic extracts were dried over $Na_2SO_4$, filtered and concentrated in vacuo. The residue was chromatographed on silica gel, eluting with a gradient of $CH_2Cl_2$—1% to 4% MeOH—0.1% to 0.4% $NH_4OH$, to yield the above-titled compound.

Step K: (S)-N-{1-[2-Bromo-7-(tert-butyldimethylsilyloxy)naphthalen-1-yl]-2-oxopyrrolidin-3-yl}-2-[1-(4-cyano-3-fluorobenzyl)-1H-imidazol-5-yl]acetamide Following the procedures described in Example 22, but using (S)-3-amino-1-[2-bromo-7-(tert-butyldimethylsilyloxy)naphthalen-1-yl]-2-oxopyrrolidine, as described above in Step J, in place of (R)-3-amino-1-(7-hydroxynaphthalen-1-yl)-2-oxopyrrolidine hydrochloride in Step E, the above-titled compound was obtained.

Step L: (S)-N-{1-(2-Bromo-7-hydroxynaphthalen-1-yl)-2-oxopyrrolidin-3-yl}-2-[1-(4-cyano-3-fluorobenzyl)-1H-imidazol-5-yl]acetamide (S)-N-{1-[2-Bromo-7-(tert-butyldimethylsilyloxy)naphthalen-1-yl]-2-oxopyrrolidin-3-yl}-2-[1-(4-cyano-3-fluorobenzyl)-1H-imidazol-5-yl]acetamide, as described above in Step K, (171 mg, 0.264 mmol) was dissolved in THF (5 mL) and TBAF (1.0 M in THF, 0.26 mL, 0.26 mmol) was added. After 45 min, the mixture was poured into saturated aqueous $NaHCO_3$ and extracted with $CH_2Cl_2$ (3×). The combined organic extracts were dried over $Na_2SO_4$, filtered and concentrated in vacuo. The residue was chromatographed on silica gel, eluting with a gradient of $CH_2Cl_2$—1% to 10% MeOH—0.1% to 1% $NH_4OH$, to yield the above-titled compound.

Step M: (20S)-17-Bromo-19,20,22,23-tetrahydro-19,22-dioxo-5H,21H-18,20-ethano-12,14-etheno-6,10-methenobenz[d]imidazo[4,3-1]1,6,9,13]oxatriazacyclononadecosine-9-carbonitrile Hydrochloride Following the procedure described in Example 1, Step P, but using (S)-N-{1-(2-bromo-7-hydroxynaphthalen-1-yl)-2-oxopyrrolidin-3-yl}-2-[1-(4-cyano-3-fluorobenzyl)-1H-imidazol-5-yl]acetamide, as described above in Step L, rather than (R)-2-fluoro-4-(5-{[1-(3-hydroxybenzyl)-2-oxopyrrolidin-3-ylamino]methyl}imidazol-1-ylmethyl)benzonitrile in Step P, the above-titled compound was obtained.

Elemental analysis calculated for $C_{27}H_{20}BrN_5O_3 \cdot HCl \cdot 0.4$ Toluene$\cdot 0.55CH_2Cl_2$: C: 55.03; H: 3.85; N: 10.57; Found: C: 54.99; H: 4.01; N: 10.56; ES MS: 542 ($MH^+$).

Example 62

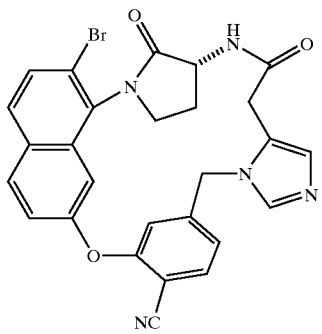

Preparation of (20R)-17-Bromo-19,20,22,23-tetrahydro-19,22-dioxo-5H,21H-18,20-ethano-12,14-etheno-6,10-methenobenz[d]imidazo[4,3-1][1,6,9,13]oxatriazacyclononadecosine-9-carbonitrile Hydrochloride Step A: (R)-1-[2-Bromo-7-(tert-butyldimethylsilyloxy)naphthalen-1-yl]-3-(tert-butoxycarbonylamino)-2-oxopyrrolidine Following the procedures described in Example 50, Steps G–H, but using 1-amino-2-bromo-7-(tert-butyldimethylsilyloxy)naphthalene, as described in Example 61, Step H, in place of 5-amino-3-(tert-butyldimethylsilyloxy)quinoline, and (R)-N-(tert-butoxycarbonyl)homoserine lactone in place of (S)-N-(tert-butoxycarbonyl)homoserine lactone in Step G, the above-titled compound was obtained.

Step B: (20R)-17-Bromo-19,20,22,23-tetrahydro-19,22-dioxo-5H,21H-18,20-ethano-12,14-etheno-6,10-methenobenz[d]imidazo[4,3-1][1,6.9,13 loxatriazacyclononadecosine-9-carbonitrile Hydrochloride Following the procedures described in Example 61, but using (R)-1-[2-bromo-7-(tert-butyldimethylsilyloxy)naphthalen-1-yl]-3-(tert-butoxycarbonylamino)-2-oxopyrrolidine, as described above in Step A, in place of (S)-1-[2-Bromo-7-(tert-butyldimethylsilyloxy)naphthalen-1-yl]-3-(tert-butoxycarbonylamino)-2-oxopyrrolidine in Step J, the above-titled compound was obtained.

Elemental analysis calculated for $C_{27}H_{20}BrN_5O_3 \cdot HCl \cdot 0.35$ Toluene$\cdot 0.5CH_2Cl_2$: C: 55.04; H: 3.82; N: 10.72; Found: C: 54.99; H: 4.04; N: 10.72; ES MS: 542 ($MH^+$).

Example 63

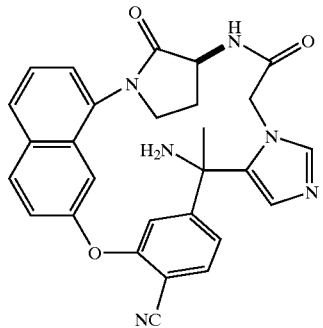

Preparation of (20S)-5-amino-19,20,22,23-tetrahydro-5-methyl-19,22-dioxo-5H,21H-18,20-ethano-12,14-etheno-6,10-methenobenz[d]imidazo[3,4-1][1,6,9,12]oxatriazacyclononadecosine-9-carbonitrile Hydrochloride, Diastereomers A & B Step A: 1-(4-Cyano-3-fluorophenyl)-1-[1-(triphenylmethyl)imidazol-4-yl]ethylamine To $SOCl_2$ (50 mL) at 0° C. was added 1-(4-cyano-3-fluorophenyl)-1-[1-(triphenylmethyl)imidazol-4-yl]ethanol, as described in Example 33, Step C, (5.0 g, 10.6 mmol). The reaction mixture was removed from the ice-water bath and allowed to warm to ambient temperature. After 1 hour of stirring, the solution was concentrated in an ice water bath under reduced pressure. The resulting chloride was dissolved in dry $CH_2Cl_2$ (15 mL) and added to a solution of $NH_3$ in $CH_2Cl_2$ (100 mL) at −78° C. The reaction mixture was stirred overnight at ambient temperature, then partitioned between saturated aqueous $NaHCO_3$ (75 mL) and $CH_2Cl_2$ (150 mL). The aqueous layer was extracted further with $CH_2Cl_2$ (2×75 mL). The combined organic extracts were dried over $MgSO_4$, filtered, and concentrated in vacuo. The residue was purified by silica gel chromatography, eluting with a gradient of $CH_2Cl_2$—0% to 2% MeOH—0% to 0.2% $NH_4OH$ to give the titled product.

Step B: N-(tert-Butoxycarbonyl)-1-(4-cyano-3-fluorophenyl)-1-[1-(triphenylmethyl)imidazol-4-yl-1ethylamine To a solution of 1-(4-cyano-3-fluorophenyl)-1-[1-(triphenylmethyl)imidazol-4-yl]ethylamine, as described above in Step A, (2.2 g, 4.7 mmol) in dry $CH_2Cl_2$ (20 mL), under argon, was added di-tert-butyl dicarbonate (1.2 g, 5.6 mmol) and N,N-diisopropylethylamine (1.2 mL, 7.1 mmol). The reaction mixture was heated to reflux overnight. The reaction mixture was concentrated in vacuo and the residue was purified by silica gel chromatography, eluting with a gradient of hexane—20% to 30% EtOAc, to yield the titled product.

Step C: Methyl {5-[1-(tert-butoxycarbonylamino)-1-(4-cyano-3-fluorophenyl)ethyl]imidazol-1-yl}acetate To a stirred solution of N-(tert-butoxycarbonyl)-1-(4-cyano-3-fluoro-phenyl)-1-[1-(triphenylmethyl)imidazol-4-yl]ethylamine, as described above in Step B, (2.6 g, 4.5 mmol), methyl glycolate (532 mg, 5.9 mmol), and N,N-diisopropylethyl-amine (1.6 g, 11.7 mmol) in dry $CH_2Cl_2$ (100 mL), under argon, at −78° C., was added trifluoromethanesulfonic anhydride (1.7 g, 5.9 mmol) dropwise. The mixture was allowed to warm slowly to ambient temperature, then the solvent was removed in vacuo. The residue was dissolved in MeOH (50 mL) and the solution was heated to reflux for 1 hour, then concentrated to dryness. The residue was purified by silica gel chromatography, eluting with EtOAc—2% MeOH—0.2% $NH_4OH$. The product was further purified by preparative HPLC using a C-18 column and eluting with a gradient of $H_2O$—0.2% triethylamine—0.1% AcOH—0% to 60% $CH_3CN$ to yield the titled product.

Step D: Lithium {5-[1-(tert-Butoxycarbonylamino)-1-(4-cyano-3-fluorophenyl)ethyl]imidazol-1-yl}acetate A mixture of methyl {5-[1-(tert-butoxycarbonylamino)-1-(4-cyano-3-fluorophenyl)ethyl]imidazol-1-yl}acetate, as described above in Step C, (321 mg, 0.798 mmol) and LiOH (21.0 mg, 0.877 mmol) was stirred in THF (5 mL) and $H_2O$ (1.8 mL) at ambient temperature for 1 hour. The solution was adjusted to pH≈7 by the addition of 1.0 N aqueous HCl and then concentrated in vacuo to give the desired product.

Step E: (S)-2-{5-[1-(tert-Butoxycarbonylamino)-1-(4-cyano-3-fluorophenyl)ethyl]imidazol-1-yl}-N-(1-(7-hydroxynaphthalen-1-yl)-2-oxopyrrolidin-3-yl)acetamide, Diastereomers A & B A solution of lithium {5-[1-(tert-butoxycarbonylamino)-1-(4-cyano-3-fluorophenyl)ethyl]imidazol-1-yl}acetate, as described above in Step D, (115 mg, 0.291 mmol), (S)-3-amino-1-(7-hydroxynaphthalen-1-yl)-2-oxopyrrolidine hydrochloride, as described in Example 9A, (120 mg, 0.323 mmol), 1-hydroxybenzotriazole hydrate (48 mg, 0.355 mmol), EDC (74 mg, 0.388 mmol), and N,N-diisopropylethylamine (0.113 mL, 0.646 mmol) in dry, degassed DMF (2 mL) was stirred at ambient temperature for 18 hours. The solvent was removed under reduced pressure and the residue was partitioned between saturated aqueous $NaHCO_3$ (20 mL) and $CH_2Cl_2$ (20 mL). The aqueous layer was extracted further with $CH_2Cl_2$ (2×20 mL). The combined organic extracts were dried over $Na_2SO_4$, filtered, and concentrated under reduced pressure. The crude product was purified by silica gel chromatography, eluting with a gradient of $CH_2Cl_2$—0% to 10% MeOH to give the titled product.

Step F: (S)-2-{5-[1-Amino-1-(4-cyano-3-fluorophenyl)ethyl]imidazol-1-yl}-N-(1-(7-hydroxynaphthalen-1-yl)-2-oxopyrrolidin-3-yl)acetamide Hydrochloride, Diastereomers A & B A solution of (S)-2-{5-[1-(tert-butoxycarbonylamino)-1-(4-cyano-3-fluorophenyl)ethyl]imidazol-1-yl}-N-(1-(7-hydroxynaphthalen-1-yl)-2-oxopyrrolidin-3-yl)acetamide, diastereomers A & B, as described above in Step E, (160 mg, 0.261 mmol) in EtOAc (15 mL) at 0° C. was saturated with HCl (g). After 15 min, the mixture was concentrated in vacuo to yield the desired product.

Step G: (20S)-5-Amino-19,20,22,23-tetrahydro-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile Hydrochloride, Diastereomers A & B A stirred mixture of (S)-2-{5-[1-amino-1-(4-cyano-3-fluorophenyl)ethyl]imidazol-1-yl}-N-(1-(7-hydroxynaphthalen-1-yl)-2-oxopyrrolidin-3-yl)acetamide hydrochloride, diastereomers A & B, as described above in Step F, (130 mg, 0.254 mmol) and $Cs_2CO_3$ (165 mg, 0.507 mmol) in dry, degassed DMF (60 mL) under argon was heated to 65° C. for 6 hours. The solvent was removed under reduced pressure and the residue was partitioned between saturated aqueous $NaHCO_3$ (10 mL) and $CHCl_3$ (20 mL). The aqueous layer was extracted further with $CHCl_3$ (2×20 mL). The combined organic extracts were dried over $MgSO_4$, filtered, and concentrated under reduced pressure. The residue was purified by preparative HPLC on a Chiralpak AD column and eluting a gradient of hexane—0.1% diethylamine—60% to 100% 2-propanol to give diastereomer A (which eluted first) and diastereomer B (which eluted second). These compounds were further purified by flash column chromatography, eluting with a gradient of $CH_2Cl_2$—1% to 12% MeOH—0.1% to 0.5% $NH_4OH$ to give the desired products, which were treated with HCl in EtOAc to give the titled compounds as salts.

(20S)-5-Amino-19,20,22,23-tetrahydro-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile, Diastereomer A, Hydrochloride Elemental analysis calculated for $C_{28}H_{24}N_6O_3 \cdot HCl \cdot 1.4 H_2O \cdot 0.3CH_2Cl_2$: C: 55.16; H: 4.81; N: 13.64; Found: C: 55.16; H: 4.80; N: 13.50; ES MS: 493 ($MH^+$).

(20S)-5-Amino-19,20,22,23-tetrahydro-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile, Diastereomer B, Hydrochloride Elemental analysis calculated for $C_{28}H_{24}N_6O_3 \cdot HCl \cdot 2.5H_2O$: C: 55.08; H: 5.12; N: 13.77; Found: C: 54.94; H: 5.20; N: 13.87; ES MS: 493 ($MH^+$).

Example 64

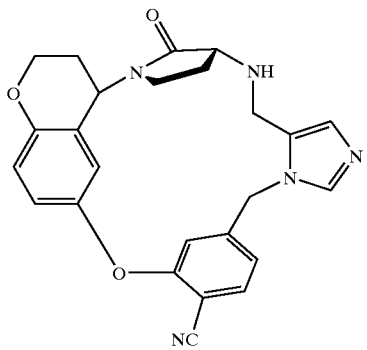

Preparation of (20R)-15,16,17,17a,19,20,21,22-octahydro-15-oxa-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride, Diastereomer B Step A: 6-Hydroxy-2,3-dihydro-4H-chromen-4-one A solution of 6-methoxy-2,3-dihydro-4H-chromen-4-one in 48% aqueous HBr (250 mL) and HOAc (250 mL) was heated to 75° C. for 6 hours. The reaction mixture was cooled, adjusted to pH≈5 by the addition of saturated aqueous $Na_2CO^3$ and extracted with $CHCl_3$ (2×75 mL). The combined organic extracts were dried over $MgSO_4$, filtered, and concentrated in vacuo to give the desired compound.

Step B: 6-tert-Butyldiphenylsilyloxy-2,3-dihydro-4H-chromen-4-one

A mixture of 6-hydroxy-2,3-dihydro-4H-chromen-4-one (1.65 g, 10.1 mmol), tert-butyldiphenylsilylchloride (6.87 g, 25.2 mmol), and imidazole (2.1 g, 30.3 mmol) in degassed DMF (30 mL) was heated at 60° C. for 18 hours. The solvent was removed in vacuo and the residue purified by silica gel chromatography, eluting with hexane—20% EtOAc, to yield the titled product.

Step C: (20R)-15,16,17,17a, 19,20,21,22-Octahydro-15-oxa-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride Diastereomer B Following the procedures described in Example 39, but using 6-tert-butyldiphenylsilyloxy-2,3-dihydro-4H-chromen-4-one, as described above in Step B, in place of 6-tert-butyldiphenylsilyloxy-1-indanone in Step B, the above-titled compound was obtained.

Elemental analysis calculated for $C_{25}H_{23}N_5O_3$.2 HCl.1.5 $H_2O$.0.25$CHCl_3$: C: 53.17; H: 4.97; N: 12.28; Found: C: 53.19; H: 4.97; N: 12.03; ES MS: 442 (MH$^+$).

Example 64A

Preparation of (3R)-3-(tert-Butoxycarbonylamino)-1-[6-(tert-butyldiphenylsilyloxy)-3,4-dihydro-2H-chromen-4-yl]-2-oxopyrrolidine, Diastereomer A Following the procedures described in Example 39, Steps B–G, but using 6-tert-butyldiphenylsilyloxy-2,3-dihydro-4H-chromen-4-one, as described in Example 64, Step B, in place of of 6-tert-butyldiphenylsilyloxy-1-indanone in Step B, the above-titled compound was obtained.

Example 64B

Preparation of (3S)-3-(tert-Butoxycarbonylamino)-1-[6-(tert-butyldiphenylsilyloxy)-3,4-dihydro-2H-chromen-4-yl]-2-oxopyrrolidine Diastereomers A & B Following the procedures described in Example 39, Steps B–G, but using 6-tert-butyldiphenylsilyloxy-2,3-dihydro-4H-chromen-4-one, as described in Example 64, Step B, in place of of 6-tert-butyldiphenylsilyloxy-1-indanone in Step B, and (S)-N-(tert-butoxycarbonyl)methionine in place of (R)-N-(tert-butoxycarbonyl) methionine in Step E, the above-titled compounds were obtained.

Example 65

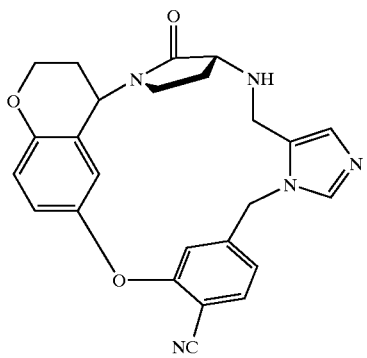

Preparation of (20R)-15,16,17,17a,19,20,21,22-Octahydro-15-oxa-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride, Diastereomer B Following the procedures described in Example 39, but using (3R)-3-(tert-butoxycarbonylamino)-1-[6-(tert-butyldiphenylsilyloxy)-3,4-dihydro-2H-chromen-4-yl]-2-oxopyrrolidine, diastereomer A, as described in Example 64A, in place of (3R)-3-(tert-butoxycarbonylamino)-1-[6-(tert-butyldiphenylsilyloxy)indan-1-yl]-2-oxopyrrolidine, diastereomer B, in Step H, the above-titled compound was obtained.

ES MS: 442 (MH$^+$).

Example 66

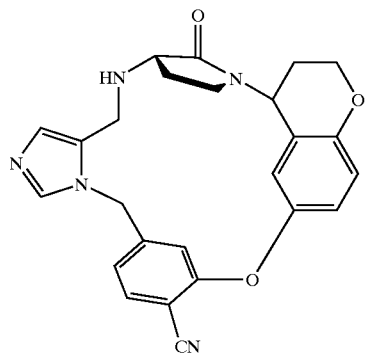

Preparation of (20S)-15,16,17,17a,19,20,21,22-Octahydro-15-oxa-19-oxo-5H-18,20-ethano-12,14-etheno-6,10-metheno-18H-benz[d]imidazo[4,3-k][1,6,9,12]oxatriazacyclooctadecosine-9-carbonitrile Hydrochloride, Diastereomer B Following the procedures described in Example 39, but using (3S)-3-(tert-butoxycarbonylamino)-1-[6-(tert-butyldiphenylsilyloxy)-3,4-dihydro-2H-chromen-4-yl]-2-oxopyrrolidine, diastereomer B, as described in Example 64B, in place of (3R)-3-(tert-butoxycarbonylamino)-1-[6-(tert-butyldiphenylsilyloxy)indan-1-yl]-2-oxopyrrolidine, diastereomer B, in Step H, the above-titled compound was obtained.

Elemental analysis calculated for $C_{25}H_{23}N_5O_3$.2 HCl.0.15 EtOAc.0.65$CHCl_3$: C: 52.09; H: 4.47; N: 11.57; Found: C: 52.23; H: 4.80; N: 11.58; ES MS: 442 (MH$^+$).

Example 66

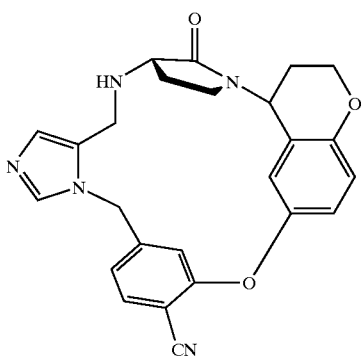

Preparation of (20S)-15,16,17,17a, 19,20,21,22-Octahydro-15-oxa-19-oxo-5H-18,20-ethno12,14-etheno-6,10-metheno-18H-benz[d]imidazo[4,3-k][1,6,9,12]oxatriazacyclooctadecosine-9-carbonitrile Hydrochloride, Diastereomer A Following the procedures described in Example 39, but using (3S)-3-(tert-butoxycarbonylamino)-1-[6-(tert-butyldiphenylsilyloxy)-3,4-dihydro-2H-chromen-4-yl]-2-oxopyrrolidine, diastereomer A, as described in Example 64B, in place of (3R)-3-(tert-butoxycarbonylamino)-1-[6-(tert-butyldiphenylsilyloxy)indan-1-yl]-2-oxopyrrolidine, diastereomer B, in Step H, the above-titled compound was obtained.

Elemental analysis calculated for $C_{25}H_{23}N_5O_3 \cdot 2$ HCl $\cdot 2$ $H_2O \cdot 0.2$ $CHCl_3$: C: 52.61; H: 5.13; N: 12.18; Found: C: 52.62; H: 5.18; N: 11.99; ES MS: 442 (MH$^+$).

Example 67

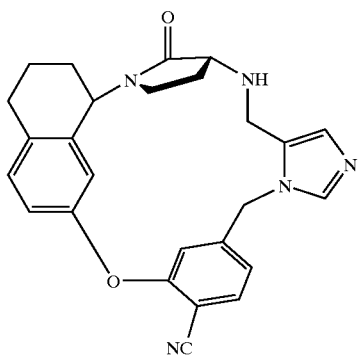

Preparation of (20R)-15,16,17,17a, 19,20,21,22-Octahydro-19-oxo-5H-18,20-ethano-12,14-etheno-6,10-metheno-18H-benz[d]imidazo[4,3-k][1,6,9,12]oxatriaza-cyclooctadecosine-9-carbonitrile Hydrochloride, Diastereomer B Following the procedures described in Example 39, but using 7-hydroxy-3,4-dihydronaphthalen-1(2H)-one, in place of 6-hydroxy-1-indanone in Step A, the above-titled compound was obtained.

ES MS: 440 (MH$^+$).

Example 67A

Preparation of (3R)-3-(tert-Butoxycarbonylamino)-1-(7-(tert-butyldiphenylsilyloxy)-1,2,3,4-tetrahydronaphthalen-1-yl)-2-oxopyrrohidine, Diastereomer A Following the procedures described in Example 39, Steps A–G, but using 7-hydroxy-3,4-dihydronaphthalen-1(2H)-one, in place of of 6-hydroxy-1-indanone in Step A, the above-titled compound was obtained.

Example 67B

Preparation of (3S)-3-(tert-Butoxycarbonylamino)-1-(7-(tert-butyldiphenylsilyloxy)-1,2,3,4-tetrahydronaphthalen-1-yl)-2-oxopyrrolidine, Diastereomers A & B Following the procedures described in Example 39, Steps A–G, but using 7-hydroxy-3,4-dihydronaphthalen-1(2H)-one in place of 6-hydroxy-1-indanone in Step A, and (S)-N-(tert-butoxycarbonyl)methionine in place of (R)-N-(tert-butoxycarbonyl)methionine in Step E, the above-titled compounds were obtained.

Example 68

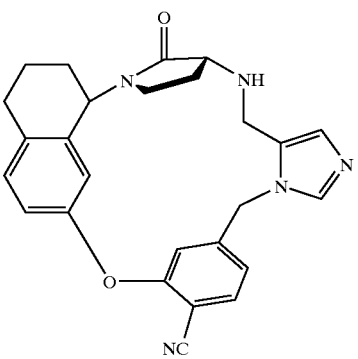

Preparation of (20R)-15,16,17,17a,19,20,21,22-Octahydro-19-oxo-5H-18,20-ethano-12,14-etheno-6,10-metheno-18H-benz[d]imidazo[4,3-k][1,6,9,12]oxatriaza-cyclooctadecosine-9-carbonitrile Hydrochloride, Diastereomer A Following the procedures described in Example 39, but using (3R)-3-(tert-butoxycarbonylamino)-1-(7-(tert-butyldiphenylsyloxy)-1,2,3,4-tetrahydronaphthalen-1-yl)-2-oxopyrrolidine, diastereomer A, as described in Example 67A, in place of (3R)-3-(tert-butoxycarbonylamino)-1-[6-(tert-butyldiphenylsilyloxy)indan-1-yl]-2-oxopyrrolidine, diastereomer B, in Step H, the above-titled compound was obtained.

ES MS: 440 (MH$^+$).

Example 69

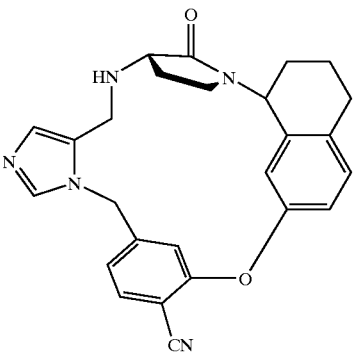

Preparation of (20S)-15,16,17,17a,19,20,21,22-Octahydro-19-oxo-5H-18,20-ethano-12,14-etheno-6,10-metheno-18H-benz[d]imidazo[4,3-k][1,6,9,12]oxatriaza-cyclooctadecosine-9-carbonitrile Hydrochloride, Diastereomer B Following the procedures described in Example 39, but using (3S)-3-(tert-butoxycarbonylamino)-1-(7-(tert-butyldiphenylsilyloxy)-1,2,3,4-tetrahydronaphthalen-1-yl)-2-oxopyrrolidine, diastereomer B, as described in Example 67B, in place of (3R)-3-(tert-butoxycarbonylamino)-1-[6-(tert-butyldiphenyisilyloxy)indan-1-yl]-2-oxopyrrolidine, diastereomer B, in Step H, the above-titled compound was obtained.

ES MS: 440 (MH$^+$).

Example 70

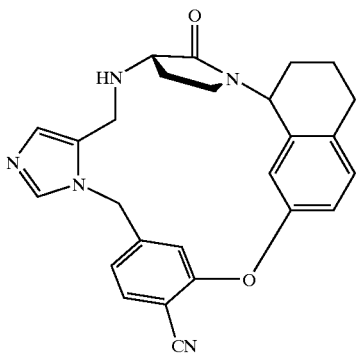

Preparation of (20S)-15,16,17,17a,19,20,21,22-Octahydro-19-oxo-5H-18,20-ethano-12,14-etheno-6,10-metheno-18H-benz[d]imidazo[4,3-k][1,6,9,12]oxatriaza-cyclooctadecosine-9-carbonitrile Hydrochloride, Diastereomer A Following the procedures described in Example 39, but using (3S)-3-(tert-butoxycarbonylamino)-1-(7-(tert-butyldiphenylsilyloxy)-1,2,3,4-tetrahydronaphthalen-1-yl)-2-oxopyrrolidine, diastereomer A, as described in Example 67B, in place of (3R)-3-(tert-butoxycarbonylamino)-1-[6-(tert-butyldiphenylsilyloxy)indan-1-yl]-2-oxopyrrolidine, diastereomer B, in Step H, the above-titled compound was obtained.

ES MS: 440 (MH$^+$).

Example 71

In vitro Inhibition of Ras Farnesyl Transferase

Transferase Assays. Isoprenyl-protein transferase activity assays are carried out at 30° C. unless noted otherwise. A typical reaction contains (in a final volume of 50 μL): [$^3$M]farnesyl diphosphate, Ras protein, 50 mM HEPES, pH 7.5, mM MgCl$_2$, 5 mM dithiothreitol, 10 μM ZnCl$_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. After thermally pre-equilibrating the assay mixture in the absence of enzyme, reactions are initiated by the addition of isoprenyl-protein transferase and stopped at timed intervals (typically 15 min) by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethylsulfoxide and then diluted 20-fold into the enzyme assay mixture. Substrate concentrations for inhibitor IC$_{50}$ determinations are as follows: FTase, 650 nM Ras-CVLS (SEQ. ID. NO.: 25), 100 nM farnesyldiphosphate.

The compounds of the instant invention are tested for inhibitory activity against human FPTase by the assay described above.

The compounds of the instant invention described in the above Examples 1–70 were tested for inhibitory activity against human FPTase by the assay described above and were found to have an IC$_{50}$ of ≦10 μM.

Example 72

Modified In vitro GGTase Inhibition Assay

The modified geranylgeranyl-protein transferase inhibition assay is carried out at room temperature. A typical reaction contains (in a final volume of 50 μL): [$^3$H] geranylgeranyldiphosphate, biotinylated Ras peptide, 50 mM HEPES, pH 7.5, a modulating anion (for example 10 mM glycerophosphate or 5 mM ATP), 5 mM MgCl$_2$, 10 μM ZnCl$_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 2). Reactions are initiated by the addition of GGTase and stopped at timed intervals (typically 15 min) by the addition of 200 μL of a 3 mg/ml suspension of strepta-vidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethylsulfoxide and then diluted 25-fold into the enzyme assay mixture. IC$_{50}$ values are determined with Ras peptide near K$_M$ concentrations. Enzyme and substrate concentrations for inhibitor IC$_{50}$ determinations are as follows: 75 pM GGTase-I, 1.6 mM Ras peptide, 100 nM geranylgera-nyldiphosphate.

The compounds of the instant invention, including those compounds described in the above Examples 1–70, are tested for inhibitory activity against human GGTase-type I by the assay described above.

Example 73

Cell-based In Vitro Ras Farnesylation Assay

The cell line used in this assay is a v-ras line derived from either Rat1 or NIH3T3 cells, which expressed viral Ha-ras p21. The assay is performed essentially as described in DeClue, J. E. et al., Cancer Research 51:712–717, (1991). Cells in 10 cm dishes at 50–75% confluency are treated with the test compound (final concentration of solvent, methanol or dimethylsulfoxide, is 0.1%). After 4 hours at 37° C., the cells are labeled in 3 ml methionine-free DMEM supplemented with 10% regular DMEM, 2% fetal bovine serum and 400 $\mu$Ci[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 ml of a 25% suspension of protein A-Sepharose coated with rabbit anti rat IgG is added for 45 min. The immuno-precipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyltransfer to protein.

Example 74

Cell-based In Vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 75

Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the "dyad symmetry response element" cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoRI and HpaI. The ends of the linear DNA fragments were filled in with the Kienow fragment of E. coli DNA Polymerase I. The "blunt ended" DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha E. coli cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid, pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Kienow fragment of E. coli DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with E. coli Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) 1. Virol., 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(−)/SEAP was constructed as follows. The SEAP gene was PCRed, in two segments from a human placenta cDNA library (Clontech) using the following oligos.

Sense strand N-terminal SEAP: 5' GAGAGGGAAT-TCGGGCCCTTCCTGCATGCTGCTGCT-GCTGCTGCTGCTGGGC 3' (SEQ.ID.NO.: 3)

Antisense strand N-terminal SEAP: 5' GAGAGAGCTC-GAGGTTAACCCGGGTGCGCGGCGTCGGTGGT 3' (SEQ.ID.NO.: 4)

Sense strand C-terminal SEAP: 5' GAGAGAGTCTA-GAGTTAACCCGTGGTCCCCGCGTTGCTTCCT 3' (SEQ.ID.NO.: 5)

Antisense strand C-terminal SEAP: 5' GAAGAG-GAAGCTTGGTACCGCCACTGGGCTGTAG-GTGGTGGCT 3' (SEQ.ID.NO.: 6)

The N-terminal oligos (SEQ.ID.NO.: 3 and SEQ.ID.NO.: 4) were used to generate a 1560 bp N-terminal PCR product that contained EcoRI and HpaI restriction sites at the ends. The Antisense N-terminal oligo (SEQ.ID.NO.: 4) introduces an internal translation STOP codon within the SEAP gene along with the HpaI site. The C-terminal oligos (SEQ.ID.NO.: 5 and SEQ.ID.NO.: 6) were used to amplify a 412 bp C-terminal PCR product containing HpaI and HindIII restriction sites. The sense strand C-terminal oligo (SEQ.ID.NO.: 5) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electrophoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid pCMV-SEAP-A

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter was cut with EcoRI generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.

Sense strand: 5' GGCAGAGCTCGTTTAGTGAACCGT-CAG 3' (SEQ.ID.NO.: 7)

Antisense strand: 5' GAGAGATCTCAAGGACGGT-GACTGCAG 3' (SEQ.ID.NO.: 8)

These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf(−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP-A (deposited in the ATCC under Budapest Treaty on August 27, 1998, and designated ATCC), contains modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Alternative Construction of a Constitutively Expressing SEAP Plasmid pCMV-SEAP-B An expression plasmid constitutively expressing the SEAP protein can be created by placing the sequence encoding a truncated SEAP gene downstream of the cytomegalovirus (CMV) IE-1 promoter and upstream of the 3' unstranslated region of the bovine growth hormone gene.

The plasmid pCMVIE-AKI-DHR (Whang, Y., Silberklang, M., Morgan, A., Munshi, S., Lenny, A. B., Ellis, R. W., and Kieff, E. (1987) J. Virol., 61:1796–1807) containing the CMV immediate early promoter and bovine growth hormone poly-A sequence can be cut with EcoRI generating two fragments. The vector fragment can be isolated by agarose electrophoresis and religated. The resulting plasmid is named pCMV-AKI. The DNA sequence encoding the truncated SEAP gene can be inserted into the pCMV-AKI plasmid at a unique Bgl-II in the vector. The SEAP gene is cut out of plasmid pGEMzf(−)/SEAP (described above) using EcoRI and HindIII. The fragments are filled in with Klenow DNA polymerase and the 1970 base pair fragment is isolated from the vector fragment by agarose gel electrophoresis. The pCMV-AKI vector is prepared by digesting with Bgl-II and filling in the ends with Klenow DNA polymerase. The final construct is generated by blunt end ligating the SEAP fragment into the vector and transforming the ligation reaction into E. coli DH5a cells. Transformants can then be screened for the proper insert and mapped for restriction fragment orientation. Properly oriented recombinant constructs would be sequenced across the cloning junctions to verify the correct sequence. The resulting plasmid, named pCMV-SEAP-B contains a modified SEAP sequence downstream of the cytomegalovirus immediate early promoter, IE1, and upstream of a bovine growth hormone poly-A sequence. The plasmid would express SEAP in a constitutive nammer when transfected into mammalian cells.

Cloning of a Myristylated Viral-H-ras Expression Plasmid p2SMS600

A DNA fragment containing viral-H-ras can be PCRed from plasmid "HB-11 (deposited in the ATCC under Budapest Treaty on Aug. 27, 1997, and designated ATCC 209,218) using the following oligos.

Sense strand:
 5' TCTCCTCGAGGCCACCATGGGGAGTAG-CAAGAGCAAGCCTAAGGACCCCAGC-CAGCGCCGGATGACAGAATACAAGCT-TGTGGTGG 3'. (SEQ.ID.NO.: 9)

Antisense:
 5' CACATCTAGATCAGGACAGCACAGACT-TGCAGC 3'. (SEQ.ID.NO.: 10)

A sequence encoding the first 15 aminoacids of the v-src gene, containing a myristylation site, is incorporated into the sense strand oligo. The sense strand oligo also optimizes the "Kozak" translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid, pSMS600, in which the recombinant myr-viral-H-ras gene is constitutively transcribed from the CMV promoter of the pCI vector.

Cloning of a Viral-H-ras-CVLL Expression Plasmid pSMS601

A viral-H-ras clone with a C-terminal sequence encoding the amino acids CVLL can be cloned from the plasmid "HB-11" by PCR using the following oligos.

Sense Strand:

5' TCTCCTCGAGGCCACCATGACAGAATACAAG-CTTGTGGTGG-3' (SEQ.ID.NO.: 11)

Antisense strand:

5' CACTCTAGACTGGTGTCAGAGCAGCACACAC-TTGCAGC-3' (SEQ.ID.NO.: 12)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid, pSMS601, in which the mutated viral-H-ras-CVLL gene is constitutively transcribed from the CMV promoter of the pCI vector.

Cloning of Cellular-H-ras-Leu61 Expression Plasmid pSMS620

The human cellular-H-ras gene can be PCRed from a human cerebral cortex cDNA library (Clontech) using the following oligonucleotide primers.

Sense strand:

5'-GAGAGAATTCGCCACCATGACGGAATATAAGC-TGGTGG-3' (SEQ.ID.NO.: 13)

Antisense Strand:

5'-GAGAGTCGACGCGTCAGGAGAGCACACACTT-GC-3' (SEQ.ID.NO.: 14)

The primers will amplify a c-H-Ras encoding DNA fragment with the primers contributing an optimized 'Kozak' translation start sequence, an EcorI site at the N-terminus and a Sal I site at the C-terminal end. After trimming the ends of the PCR product with EcoRI and Sal I, the c-H-ras fragment can be ligated ligated into an EcorI -Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3' (SEQ. [D.NO.: 15)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcorI and Sal I. The new recombinant plasmid, pSMS620, will constitutively transcribe c-H-ras-Leu61 from the CMV promoter of the pCI vector.

Cloning of a c-N-ras-Val-12 Expression Plasmid pSMS630

The human c-N-ras gene can be PCRed from a human cerebral cortex cDNA library (Clontech) using the following oligonucleotide primers.

Sense Strand:

5'-GAGAGAATTCGCCACCATGACTGAGTACAAA-CTGGTGG-3' (SEQ.ID.NO.: 16)

Antisense Strand:

5'-GAGAGTCGACTTGTTACATCACCACACATGGC-3' (SEQ.ID.NO.: 17)

The primers will amplify a c-N-Ras encoding DNA fragment with the primers contributing an optimized "Kozak" translation start sequence, an EcorI site at the N-terminus and a Sal I site at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3' (SEQ.ID.NO.: 18)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcorI and Sal I. The new recombinant plasmid, pSMS630, will constitutively transcribe c-N-ras-Val-12 from the CMV promoter of the pCI vector.

Cloning of a c-K4B-ras-Val-12 Expression Plasmid pSMS640

The human c-K4B-ras gene can be PCRed from a human cerebral cortex cDNA library (Clontech) using the following oligonucleotide primers.

Sense Strand:

5'-GAGAGGTACCGCCACCATGACTGAATATAAAC-TTGTGG-3' (SEQ.ID.NO.: 19)

Antisense Strand:

5'-CTCTGTCGACGTATTTACATAATTACACACTTT-GTC-3' (SEQ.ID.NO.: 20)

The primers will amplify a c-K4B-Ras encoding DNA fragment with the primers contributing an optimized "Kozak" translation start sequence, a KpnI site at the N-terminus and a Sal I site at the C-terminal end. After trimming the ends of the PCR product with Kpn I and Sal I, the c-K4B-ras fragment can be ligated into a KpnI-Sal I cut mutagenesis vector pAlter-1 (Promega). Mutation of cysteine-12 to a valine can be accomplished using the manufacturer's protocols and the following ligonucleotide:

5'-GTAGTTGGAGCTGTTGGCGTAGGC-3' (SEQ.ID.NO.: 21)

After selection and sequencing for the correct nucleotide substitution, the mutated c-K4B-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K4B-ras-Val-12 from the CMV promoter of the pCI vector.

Cloning of c-K-ras4A-Val-12 Expression Plasmid pSMS650

The human c-K4A-ras gene can be PCRed from a human cerebral cortex cDNA library (Clontech) using the following oligonucleotide primers.

Sense Strand:

5'-GAGAGGTACCGCCACCATGACTGAATATAAAC-TTGTGG-3' (SEQ.ID.NO.: 22)

Antisense strand:

5'-CTCTGTCGACAGATTACATTATAATGCATTTTTA-ATTTTCACAC-3' (SEQ.ID.NO.: 23)

The primers will amplify a c-K4A-Ras encoding DNA fragment with the primers contributing an optimized "Kozak" translation start sequence, a KpnI site at the N-terminus and a Sal I stite at the C-terminal end. After trimming the ends of the PCR product with Kpn I and Sal I, the c-K-ras4A fragment can be ligated into a KpnI-Sal I cut mutagenesis vector pAlter-1 (Promega). Mutation of cysteine-12 to a valine can be accomplished using the manufacturer's protocols and the following oligonucleotide:

5'-GTAGTTGGAGCTG1TTGGCGTAGGC-3' (SEQ.ID.NO.: 24)

After selection and sequencing for the correct nucleotide substitution, the mutated c-K4A-ras-Val-12 can be excised from the pAlter-1 vector, using KpnI and Sal I, and be directly ligated into the vector pCI (Promega) which has been digested with KpnI and Sal I. The new recombinant plasmid, pSMS650, will constitutively transcribe c-K4A-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1×Pen/Strep+1×glutamine+1×NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. (A ras expression plasmid is not included when the cell is transfected with the pCMV-SEAP plasmid.) For 10 cm plates 600 µl of $CaCl_2$-DNA solution is added dropwise while vortexing to 600 µl of 2×HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. No. 31053-028)+0.5% charcoal stripped calf serum+1×(Pen/Strep, Glutamine and nonessential aminoacids). The $CaPO_4$-DNA precipitate is added dropwise to the cells and the plate rocked gently to distribute. DNA uptake is allowed to proceed for 5–6 hours at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1×(Pen/Strep, Glutamine and NEAA). Transfected cells are plated in a 96 well micro-titer plate (100 ml/well) to which drug, diluted in media, has already been added in a volume of 100 µl. The final volume per well is 200 µl with each drug concentration repeated in triplicate over a range of half-log steps.

Incubation of cells and drugs is for 36 hours at 37° C. under $CO_2$. At the end of the incubation period, cells are examined microscopically for evidence of cell distress. Next, 100 µl of media containing the secreted alkaline phosphatase is removed from each well and transferred to a microtube array for heat treatment at 65° C. for 1 hour to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combined with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-CaPO$_4$ precipitate for 10 cm. plate of cells | |
|---|---|
| Ras expression plasmid (1 µg/µl) | 10 µl |
| DSE-SEAP Plasmid (1 µg/µl) | 2 µl |
| Sheared Calf Thymus DNA (1 µg/µl) | 8 µl |
| 2M CaCl$_2$ | 74 µl |
| dH$_2$O | 506 µl |

2×HBS Buffer 280 mM NaCl 10 mM KCl 1.5 mM $Na_2HPO_4 2H_2O$ 12 mM dextrose 50 mM HEPES Final pH=7.05

| Luminesence Buffer (26 ml) | |
|---|---|
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer

Add 0.05M $Na_2CO_3$ to 0.05M $NaHCO_3$ to obtain pH 9.5. Make 1 mM in $MgCl_2$

Example 76

The processing assays employed are modifications of that described by DeClue et al [Cancer Research 51, 712–717, 19911].

K4B-Ras Processing Inhibition Assay

PSN-1 (human pancreatic carcinoma) or viral-K4B-ras-transformed Rat1 cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 µM), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%. Following incubation at 37° C. for two hours 204 µCi/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 µg/ml AEBSF, 10 µg/ml aprotinin, 2 µg/ml leupeptin and 2 µg/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 µg of the pan Ras monoclonal antibody, Y13–259, added. The protein/antibody mixture is incubated on ice at 4° C. for 24 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 µl elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 fig Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C. 15% $CO^2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to hDJ-2 (Neomarkers Cat. #MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of hDJ (the slower-migrating species) is calculated by densitometry. Dose-response curves and $EC_{50}$ values are generated using 4-parameter curve fits in SigmaPlot software.

Example 77

Rap1 Processing Inhibition Assay

Protocol A:

Cells are labeled, incubated and lysed as described in Example 76.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 µg of the Rap1 antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 ml elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 mg Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B:

PSN-1 cells are passaged every 3–4 days in 10 cm plates, splitting near-confluent plates 1:20 and 1:40. The day before the assay is set up, 5×106 cells are plated on 15 cm plates to ensure the same stage of confluency in each assay. The media for these cells is RPM1 1640 (Gibco), with 15% fetal bovine serum and 1×Pen/Strep antibiotic mix.

The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37° C. overnight.

The compounds to be assayed are diluted in DMSO in 1/2-log dilutions. The range of final concentrations to be assayed is generally 0.1–100 µM. Four concentrations per compound is typical. The compounds are diluted so that each concentration is 1000× of the final concentration (i.e., for a 10 µM data point, a 10 mM stock of the compound is needed).

2 µL of each 1000× compound stock is diluted into 1 ml media to produce a 2×stock of compound. A vehicle control solution (2 µL DMSO to 1 ml media), is utilized. 0.5 ml of the 2×stocks of compound are added to the cells.

After 24 hours, the media is aspirated from the assay plates. Each well is rinsed with 1 ml PBS, and the PBS is aspirated. 180 µL SDS-PAGE sample buffer (Novex) containing 5% 2-mercaptoethanol is added to each well. The plates are heated to 100° C. for 5 minutes using a heat block containing an adapter for assay plates. The plates are placed on ice. After 10 minutes, 20 μL of an RNAse/DNase mix is added per well. This mix is 1 mg/ml DNaseI (Worthington Enzymes), 0.25 mg/ml Rnase A (Worthington Enzymes), 0.5M Tris-HCl pH8.0 and 50 mM $MgCl_2$. The plate is left on ice for 10 minutes. Samples are then either loaded on the gel, or stored at −70° C. until use.

Each assay plate (usually 3 compounds, each in 4-point titrations, plus controls) requires one 15-well 14% Novex gel. 25 μl of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking.

The blocking solution is discarded and 20 ml fresh blocking solution containing the anti Rap1a antibody (Santa Cruz Biochemical SC1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C:

This protocol allows the determination of an $EC_{50}$ for inhibition of processing of Rap1a. The assay is run as described in Protocol B with the following modifications. 20 μl of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121; Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant"software (Molecular Dynamics). Unprenylated Rap1a is distinguished from prenylated protein by virtue of the greater apparent molecular weight of the prenylated protein. Dose-response curves and $EC_{50}$ values are generated using 4-parameter curve fits in SigmaPlot software.

Example 78

In Vivo Tumor Growth Inhibition Aassay (Nude Mouse)

In vivo efficacy as an inhibitor of the growth of cancer cells may be confirmed by several protocols well known in the art. Examples of such in vivo efficacy studies are described by N. E. Kohl et al. (Nature Medicine, 1:792–797 (1995)) and N. E. Kohl et al. (Proc. Nat. Acad. Sci. U.S.A., 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound of the formula A:

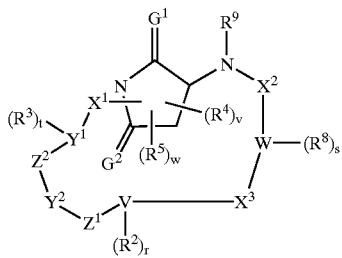

wherein $X^1$ is $(C(R^{1a})_2)_n A^1 (C(R^{1a})_2)_n A^2$;

$X^2$ is $(C(R^{1b})_2)_p A^3 (C(R^{1b})_2)_p$;

$X^3$ is $(C(R^{1c})_2)_q A^4 (C(R^{1c})_2)_q$;

$R^{1a}$, $R^{1b}$ and $R^{1c}$ are independentlys elected from:
  a) hydrogen;
  b) unsubstituted or substituted aryl, unsubstituted or substituted heterocycle, unsubstituted or substituted $C_3$–$C_{10}$ cycloalkyl, $R^{10}O$—, $R^{6a}S(O)_m$, unsubstituted or substituted $C_2$–$C_6$ alkenyl, unsubstituted or substituted $C_2$–$C_6$ alkynyl, —C(O)NR$^6$R$^7$, R$^{10}$C(O) NR$^{10}$—, $(R^{10})_2$NC(O) NR$^{10}$—, R$^{10}$C(O)—, —N(R$^{10}$)$_2$, R$^{10}$OC(O)—, or R$^{10}$OC(O)NR$^{10}$—; and c) unsubstituted or substituted $C_1$–$C_6$ alkyl, wherein one or more of the substituents on the substituted $C_1$–$C_6$ alkyl is selected from unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, unsubstituted or substituted $C_2$–$C_6$ alkynyl, $R^{10}O$—, $R^{6a}S(O)_m$, R$^{10}$C(O)NR$^{10}$—, $(R^{10})_2$NC(O)NR$^{10}$—, R$^{10}$C(O)—, —C(O)NR$^6$R$^7$, R$^{10}$OC(O)—, —N(R$^{10}$)$_2$, R$^{10}$OC(O)NR$^{10}$—, and halo;

$A^1$, $A^3$ and $A^4$ are independently selected from
  a) a bond,
  b) —C(=O)—,
  c) —HC=CH—,
  d) —C≡C—,
  e) O,
  f) NR$^{10}$,
  g) NR$^{10}$C(O),
  h) C(O)NR$^{10}$,
  i) OC(O)NR$^{10}$, j) NR$^{10}$C(O)O,
k) S(=O)$_m$,
l) C(O)O, and
m) OC(O);

A$^2$ is selected from
a) a bond,
b) —C(=O)—,
c) NR$^{10}$C(O),
d) S(=O)$_m$, and
e) OC(O);

R$^2$ is independently selected from:
a) hydrogen,
b) CN,
c) NO$_2$,
d) halogen,
e) aryl, unsubstituted or substituted,
f) heterocycle, unsubstituted or substituted:
g) C$_1$–C$_6$ alkyl, unsubstituted or substituted,
h) OR$^{10}$,
i) N$_3$,
j) R$^{6a}$S(O)$_m$,
k) C$_3$–C$_{10}$ cycloalkyl, umsubstituted or substituted,
l) C$_2$–C$_6$ alkenyl, unsubstituted or substituted,
m) C$_2$–C$_6$ alkynyl, unsubstituted or substituted,
n) (R$^{10}$)$_2$NC(O)NR$^{10}$—,
o) R$^{10}$C(O)—,
p) R$^{10}$C(O)NR$^{10}$—,
q) R$^{10}$OC(O)—,
r) —N(R$^{10}$)$_2$,
s) R$^{10}$OC(O)NR$^{10}$—, and
t) —(C$_1$–C$_6$ alkyl)NR$^{10}$C(O)R$^{13}$;

R$^3$ is independently seleted from:
H, CN, NO$_2$, halo, unsubstituted or substituted C$_1$–C$_6$ alkyl, N$_3$, oxido, unsubstituted or substituted aryl, unsubstituted or substituted heterocycle, unsubstituted or substituted C$_2$–C$_6$ alkenyl, unsubstituted or substituted C$_2$–C$_6$ alkynyl, unsubstituted or substituted aralkyl, unsubstituted or substituted beterocyclylalkyl, C$_1$–C$_6$ perfluoroalkyl, CF$_3$O—, CF$_3$CH$_2$—, unsubstituted or substituted C$_3$–C$_{10}$ cycioalkyl, OR$^{10}$, NR$^6$R$^7$, OR$^6$, —C(O)R$^{10}$, —O(C$_1$–C$_6$ alkyl)OR$^{10}$, —S(O)$_m$R$^{6a}$, —C(O)NR$^6$R$^7$, —NHC(O)R$^{10}$, —(C$_1$–C$_6$ alkyl)OR$^{10}$, and —(C$_1$–C$_6$ alkyl)C(O)R$^{10}$;

R$^4$ and R$^5$ are independently selected from:
H, OR$^{10}$, unsubstituted or substituted C$_1$–C$_6$ alkyl, unsubstituted or substituted C$_2$–C$_8$ alkenyl, unsubstitiuted or substituted C$_2$–C$_8$ alkynyl or substituted aryl, unsubstituted or substituted heterocycle,

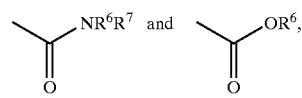

wherein the substituted group is substituted with one or more of:
1) aryl or heterocycle, unsubstituted or substituted with:
   a) C$_1$–C$_6$ alkyl,
   b) (CH$_2$)$_n$OR$^6$,
   c) (CH$_2$)$_n$NR$^6$R$^7$,
   d) halogen,
   e) CN,
   f) aryl or heteroaryl,
   g) perfludro-C$_1$–C$_4$ alkyl,
   h) S(O)$_m$R$^{6a}$,
2) C$_3$–C$_6$ cycloalkyl,
3) OR$^6$,
4) S(O)$_m$R$^{6a}$,

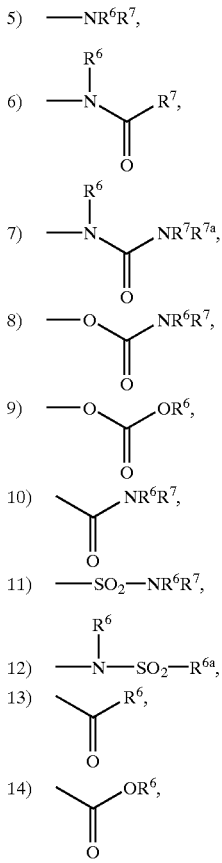

15) N$_3$,
16) halo, and
17) perfluoro, C$_{1-4}$-alkyl; or

R$^4$ and R$^5$ are attached to the same C atom and are combined to form —(CH$_2$)$_u$— wherein one of the carbon atoms is optionally replaced by a m selected from: O, S(O)$_m$, —NC(O)—, and —N(COR$^{10}$)—;
and any of R$^4$ and R$^5$ are optionally attached to the same carbon atom;

R$^6$, R$^7$ and R$^{7a}$ are independently selected from:
H, C$_1$–C$_6$ alkyl, C$_3$–C$_6$ cycloalkyl, heterocycle, aryl, aralkyl, aroyl, heteraroyl, arylsulfonyl, heteroarylsulfony, C$_1$–C$_4$ perfluoroalkyl, unsubstituted or substituted with one or two substituents selected from:
a) C$_1$–C$_6$ alkoxy,
b) substituted or unsubstituted aryl or substituted or unsubstituted heterocycle,
c) halogen,
d) HO, e) 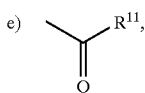

-continued f) 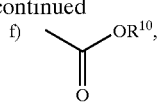

g) —S(O)$_m$R$^{6a}$, or h) N(R$^{10}$)$_2$; or

R$^6$ and R$^7$ may be joined in a ring;

R$^7$ and R$^{7a}$ may be joined in a ring;

R$^{6a}$ is selected from
    a) C$_{3-6}$ cycloakyl, heterocycle, aryl, unsubstituted or substituted with one or more of the following:
        1) C$_{1-4}$ alkoxy,
        2) aryl or heterocycle,
        3) halogen,
        4) HO, 5) 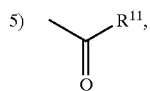

6) SO$_2$R$^{6a}$,
        7) N(R$^{10}$)$_2$; and
    b) C$_1$–C$_6$ alkyl, unsubstituted or substituted with one or more of the following:
        1) —C(R$^{10}$)$_2$C$_{1-4}$ alkoxy,
        2) aryl or heterocyle,
        3) —C(R$^{10}$)$_2$ halogen,
        4) —C(R$^{10}$)$_2$OH, 5) 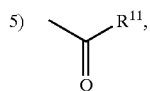

6) —C(R$^{10}$)$_2$SO$_2$R$^{6a}$, and
        7) —C(R$^{10}$)$_2$N(R$^{10}$)$_2$;

R$^8$ is independently selected from
    a) hydrogen,
    b) unsubstituted or substituted C$_2$–C$_6$ alkenyl, unsubstituted or substituted C$_2$–C$_6$ alkynyl, unsubstituted or substituted C$_3$–C$_6$ cycloalkyl, unsubstituted or substituted C$_1$–C$_4$ perfluoroalkyl, F, Cl, Br, R$^{10}$O—, CN, R$^{6a}$S(O)$_m$—, C(O)NR$^6$R$^7$, R$^{10}$(C(O)NR$^{10}$—, NO$_2$, (R$^{10}$)$_2$NC(O)NR$^{10}$—, R$^{10}$C(O)—, R$^{10}$OC(O)—, R$^{10}$OC(O)NR$^{10}$—, N$_3$, or —N(R$^{10}$)$_2$, and
    c) C$_1$–C$_6$ alkyl, unsubstituted or substituted by C$_1$–C$_4$ perfluoroalkyl, F, Cl, Br, R$^{10}$O—, R$^{6a}$S(O)$_m$—, R$^{10}$C(O)NR$^{10}$—, CN, —C(O)NR$^6$R$^7$, (R$^{10}$)$_2$NC(O)NR$^{10}$—, R$^{10}$C(O)—, R$^{10}$C(O)—, N$_3$, —N(R$^{10}$)$_2$, and R$^{10}$OC(O)NR$^{10}$—;

R$^9$ is independently selected from
    1) H, unsubstituted or substituted C$_1$–C$_6$ alkyl, unsubstituted or substituted C$_2$–C$_8$ alkenyl, unsubstituted or substituted C$_2$–C$_8$ alkynyl, unsubstituted or substituted aryl, and unsubstituted or substituted heterocyele, wherein the substituted group is substituted with one or more of:
        a) C$_1$–C$_6$ alkyl, unsubstituted or substituted,
        b) (CH$_2$)$_n$OR$^6$,
        c) (CH$_2$)$_n$NR$^6$R$^7$,
        d) halogen,
        e) CN,
        f) aryl, unsubstituted or substituted,
        g) heterocycle, unsubstituted or substituted,
        h) perfluoro-C$_1$–C$_4$ alkyl,
        i) S(O)$_m$R$^{6a}$,
        j) N(R$^{10}$)$_2$,
        k) NR$^{10}$C(O)R$^{11}$,
        l) NR$^{10}$OC(O)R$^{11}$N(R$^{10}$)$_2$,
    2) C$_3$–C$_6$ cycloalkyl,
    3) S(O)$_{1-2}$R$^{6a}$, 4) 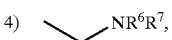

5) —SO$_2$—NR$^6$R$^7$,

6) 

7) 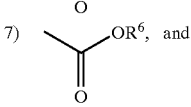 and

8) —(C$_1$–C$_6$ alkyl)NR$^{10}$C(O)R$^{13}$;

R$^{10}$ is independently selected from
    a) hydrogen,
    b) unsubstituted or substituted C$_1$–C$_6$ alkyl,
    c) unsubstituted or substituted C$_3$–C$_6$ cycloalkyl,
    d) 2,2,2-trifluoroethyl,
    e) unsubstituted or substituted heteroaryl,
    f) unsubstituted or substituted aralkyl,
    g) unsubstituted or substituted aryl, and
    h) unsubstituted or substituted heterocyclylalkyl;

R$^{11}$ is independently selected from
    a) unsubstituted or substituted C$_1$–C$_6$ alkyl,
    b) unsubstituted or substituted aralkyl,
    c) unsubstituted or substituted heterocycle,
    d) unsubstituted or substituted aryl, and
    e) unsubstituted or substituted heterocyclylaekyl;

R$^{13}$ is independently selected from
    a) H,
    b) unsubstituted or substituted C$_1$–C$_6$ alkyl,
    c) unsubstituted or substituted C$_2$–C$_6$ alkenyl,
    d) unsubstituted or substituted C$_2$–C$_6$ alkynyl,
    e) unsubstituted or substituted aryl,
    f) unsubstituted or substituted heterocycle,
    g) aralkyl, unsubstituted or substituted,
    h) heterocyclylalkyl, unsubstituted or substituted,
    i) CF$_3$,
    j) CF$_3$O—,
    k) CF$_3$CH$_2$—,
    l) C$_3$–C$_{10}$ cycloalkyl, unsubstituted or substituted,
    m) OR$^{10}$,
    n) —C(O)R$^{10}$,
    o) —O(C$_1$–C$_6$ alkyl)OR$^{10}$,
    p) —C(O)NR$^6$R$^7$,
    q) —(C$_1$–C$_6$ alkyl)OR$^{10}$, and
    r) —(C$_1$–C$_6$ alkyl)C(O)R$^{10}$;

G$^1$ and G$_2$ are independently selected from oxygen or H$_2$;

V is aryl;

W is a 5-membered heterocycle;

Y$^1$ and Y$^2$ are independently selected from
    a) a bond,
    b) C$_1$–C$_8$ alkyl,
    c) C$_2$–C$_8$ alkenyl,
    d) C$_2$–C$_8$ alkynyl,
    e) C$_3$–C$_{20}$ cycloalkyl, f) aryl, and
g) heterocycle;

$Z^1$ and $Z^2$ are independently selected from
a) a bond,
b) O,
c) C(O),
d) $S(O)_m$,
e) $C(O)NR^{10}$,
f) $(C(R^{1a})_2)_n$,
g) $(C(R^{1a})_2)_nO$,
h) $O(C(R^{1a})_2)_n$, and
i) $NR^{10}$;

m is 0, 1 or 2;
n is 0, 1, 2, 3, 4, 5 or 6;
p is 0, 1, 2, 3, 4, 5 or 6;
q is 0, 1, 2, 3, 4, 5 or 6;
r is 0 to 5, provided that r is 0 when V is a bond;
s is 0, 1, 2, 3 or 4; provided that s is 0 when W is a bond;
t is 0, 1, 2, 3 or 4; provided that t is 0 when $Y^1$ is a bond;
u is 4 or 5;
v is 0, 1, 2, 3 or 4; and
w is 0, 1, 2, 3 or 4;
or a pharmaceutically acceptable salt, an optical isomer or stereoisomer thereof.

2. The compound according to claim 1, as illustrated by formula

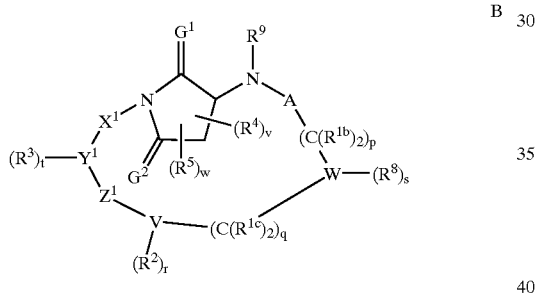

B wherein
$X^1$ is $(C(R^{1a})_2)_nA^1(C(R^{1a})_2)_nA^2$;
$R^{1a}$ is selected from:
a) hydrogen;
b) unsubstituted or substituted aryl, unsubstituted or substituted heterocycle, unsubstituted or substituted $C_3$–$C_{10}$ cycloalkyl, $R^{10}O$—, $R^{6a}S(O)_m$, unsubstituted or substituted $C_2$–$C_6$ alkenyl, unsubstituted or substituted $C_2$–$C_6$ alkynyl, —$C(O)NR^6R^7$, $R^{10}C(O)NR^{10}$—, $(R^{10})_2NC(O)NR^{10}$—, $R^{10}C(O)$—, —$N(R^{10})_2$, $R^{10}OC(O)$—, and $R^{10}OC(O)NR^{10}$—, and
c) unsubstituted or substituted $C_1$–$C_6$ alkyl, wherein the substituent on the substituted $C_1$–$C_6$ alkyl is selected from unsubstitiuted or substituted aryl, unsubstituted or substituted heterocycle, unsubstituted or substituted $C_3$–$C_{10}$cycloalkyl, unsubstituted or substituted $C_2$–$C_6$ alkenyl, unsubstituted or substituted $C_2$–$C_6$ alkynyl, $R^{10}O$—, $R^{6a}S(O)_m$, $R^{10}C(O)NR^{10}$—, —$C(O)NR^6R^7$, $(R^{10})_2NC(O)NR^{10}$—, $R^{10}C(O)$—, $R^{10}OC(O)$—, halo, —$N(R^{10})_2$, and $R^{10}OC(O)NR^{10}$—;

$R^{1b}$ and $R^{1c}$ are independently selected from
a) hydrogen and
b) unsubstituted or substituted $C_1$–$C_6$ alkyl, wherein the substituent on the substituted $C_1$–$C_6$ alkyl is selected from unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, unsubstituted or substituted $C_2$–$C_6$ alkynyl, $R^{10}O$—, $R^{6a}S(O)_m$, —$C(O)NR^6R^7$, $R^{10}C(O)NR^{10}$—, $(R^{10})_2NC(O)NR^{10}$—, $R^{10}C(O)$—, $R^{10}OC(O)$—, halo, —$N(R^{10})_2$, and $R^{10}C(O)NR^{10}$—;

A is selected from
a) a bond,
b) —C(=O)—,
c) O,
d) $NR^{10}$,
e) $NR^{10}OC(O)$,
f) $C(O)NR^{10}$,
g) $OC(O)NR^{10}$,
h) $NR^{10}C(O)O$,
i) $S(=O)_m$,
j) C(O)O, and
k) OC(O);

$A^2$ is selected from
a) a bond,
b) —C(=O)—,
c) $NR^{10}C(O)$, and
d) $S(=O)_m$;

$A^3$ is selected from a bond or C(=O);

$R^2$ is independently selected from:
a) hydrogen,
b) CN,
c) $NO_2$,
d) halogen,
e) aryl, unsubstituted or substituted,
f) heterocycle, unsubstituted or substituted,
g) $C_1$–$C_6$ alkyl, unsubstituted or substituted,
h) $OR^{10}$,
i) $N_3$,
j) $R^{6a}S(O)_m$,
k) $C_3$–$C_{10}$ cycloalkyl, unsubstituted or substituted,
l) $C_2$–$C_6$ alkenyl, unsubstituted or substituted,
m) $C_2$–$C_6$ alkynyl, unsubstituted or substituted,
n) $(R^{10})_2NC(O)NR^{10}$—,
o) $R^{10}C(O)$—,
p) $R^{10}C(O)NR^{10}$—,
q) $R^{10}OC(O)$—,
r) —$N(R^{10})_2$,
s) $R^{10}OC(O)NR^{10}$—, and
t) —$(C_1$–$C_6$ alkyl)$NR^{10}C(O)R^{13}$;

$R^3$ is independently selected from:
H, CN, $NO_2$, halo, unsubstituted or substituted $C_1$–$C_6$ alkyl, $N_3$, oxido, unsubstituted or substituted aryl, unsubstituted or substituted heterocycle, unsubstituted or substituted $C_2$–$C_6$ alkenyl, unsubstituted or substituted $C_2$–$C_6$ alkynyl, unsubstituted or substituted aralkyl, unsubstituted or substituted heterocyclylalkyl, $C_1$–$C_6$ perfluoroalkyl, $CF_3O$—, $CF_3CH_2$—, unsubstituted or substituted $C_3$–$C_{10}$ cycloalkyl, $OR^{10}$, $NR^6R^7$, $OR^6$, —$C(O)R^{10}$, —$O(C_1$–$C_6$ alkyl)$OR^{10}$, —$S(O)_mR^{6a}$, —$C(O)NR^6R^7$, —$NHC(O)R^{10}$, —$(C_1$–$C_6$ alkyl)$OR^{10}$, and —$(C_1$–$C_6$ alkyl)$C(O)R^{10}$;

$R^4$ and $R^5$ are, independently selected from:
H, $OR^{10}$, unsubstituted or substituted $C_1$–$C_6$ alkyl, unsubstituted or substituted aryl, unsubstituted or substituted heterocycle, wherein the substituted group is substituted with one or two of:
1) aryl or heterocycle, unsubstituted or substituted with:

a) $C_1$–$C_6$ alkyl,
b) $(CH_2)_nOR^6$,
c) $(CH_2)_nNR^6R^7$,
d) halogen,
e) CN,
f) aryl or heteroaryl,
g) perfluoro-$C_1$–$C_4$ alkyl,
h) $S(O)_mR^{6a}$,
2) $C_3$–$C_6$ cycloalkyl,
3) $OR^6$,
4) $S(O)_mR^{6a}$, 5) —$NR_6R_7$, 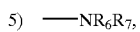

6) 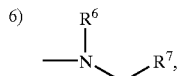

7) 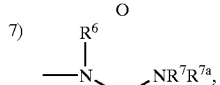

8) 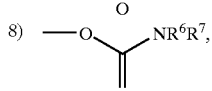

9) 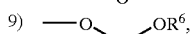

10) 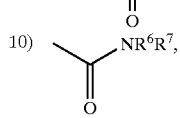

11) —$SO_2$—$NR^6R^7$

12) 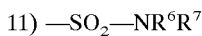

13) 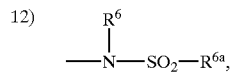

14) 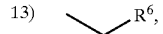

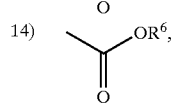

15) $N_3$,
16) halo, and
17) perfluoro-$C_{1-4}$-alkyl; or $R^4$ and $R^5$ are attached to the same C atom and are combined to form —$(CH_2)_u$— wherein one of the carbon atoms is optionally replaced by a moiety selected from: O, $S(O)_m$, $NR^{10}$, —NC(O)—, and —N(COR$^{10}$)—;

and any of $R^4$ and $R^5$ are optionally attached to the same carbon atom;

$R^6$, $R^7$ and $R^{7a}$ are independently selected from:
H, $C_1$–$C_6$ alkyl, $C_3$–$C_6$ cycloalkyl, heterocycle, aryl, aralkyl, aroyl, heteraroyl, arylsulfonyl, heteroarylsulfony, $C_1$–$C_4$ perfluoroalkyl, unsubstituted or substituted with one or two substituents selected from:
a) $C_1$–$C_6$ alkoxy,
b) substituted or unsubstituted aryl or substituted or unsubstituted heterocycle,
c) halogen,
d) HO, e) 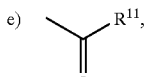

f) 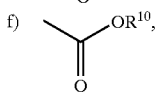

g) —$S(O)_mR^{6a}$, or
h) $N(R^{10})_2$; or $R^6$ and $R^7$ may be joined in a ring;
$R^7$ and $R^{7a}$ may be joined in a ring;
$R^{6a}$ is selected from
a) $C_{3-6}$ cycloalkyl, heterocycle, aryl, unsubstituted or substituted with one or more of the following:
1) $C_{1-4}$ alkoxy,
2) aryl or heterocycle,
3) halogen,
4) HO, 5) 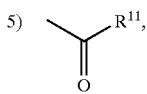

6) $S(O)_2R^{6a}$,
7) $N(R^{10})_2$; and
b) $C_1$–$C_6$ alkyl, unsubstituted or substituted with one or more of the following:
1) —$C(R^{10})_2C_{1-4}$ alkoxy,
2) aryl or heterocycle,
3) —$C(R^{10})_2$halogen,
4) —$C(R^{10})_2$OH, 5) 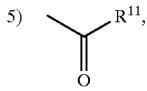

6) —$C(R^{10})_2SO_2R^{6a}$, and
7) —$C(R^{10})_2N(R^{10})_2$ $R^8$ is independently selected from
a) hydrogen,
b) unsubstituted or substituted $C_2$–$C_6$ alkenyl, unsubstituted or substituted $C_2$–$C_6$ alkynyl, unsubstituted or substituted $C_3$–$C_6$ cycloalkyl, unsubstituted or substituted $C_1$–$C_4$ perfluoroalkyl, F, Cl, Br, $R^{10}O$—, CN, $R^{6a}S(O)_m$—, —$C(O)NR^6R^7$, $R^{10}C(O)NR^{10}$—, $NO_2$, $(R^{10})_2NC(O)NR^{10}$—, $R^{10}C(O)$—, $R^{10}OC(O)$—, $R^{10}OC(O)NR^{10}$—, $N_3$, or —$N(R^{10})_2$, and
c) $C_1$–$C_6$ alkyl, unsubstituted or substituted by $C_1$–$C_4$ perfluoroalkyl, F, Cl, Br, $R^{10}O$—, $R^{6a}S(O)_m$—, $R^{10}C(O)NR^{10}$—, —$C(O)NR^6R_7$, CN, $(R^{10})_2NC(O)NR^{10}$—, $R^{10}C(O)$—, $R^{10}OC(O)$—, $N_3$, —$N(R^{10})_2$, and $R^{10}OC(O)NR^{10}$—;

$R^9$ is independently selected from
1) H, unsubstituted or substituted $C_1$–$C_6$ alkyl, unsubstituted or substituted $C_2$–$C_8$ alkenyl, unsubstituted or substituted $C_2$–$C_8$ alkynyl, unsubstituted or substituted aryl, and unsubstituted or substituted heterocycle, wherein the substituted group is substituted with one or more of:
a) $C_1$–$C_6$ alkyl, unsubstituted or substituted,
b) $(CH_2)_nOR^6$, c) $(CH_2)_nNR^6R^7$,
d) halogen,
e) CN,
f) aryl, unsubstituted or substituted,
g) heterocycle, unsubstituted or substituted,
h) perfluoro-$C_1$-$C_4$ alkyl,
i) $S(O)_mR^{6a}$,
j) $N(R^{10})_2$,
k) $NR^{10}C(O)R^{11}$,
l) $NR^{10}C(O)R^{11}N(R^{10})_2$,
2) $C_3$-$C_6$ cycloalkyl,
3) $S(O)_{1-2}R^{6a}$, 4) 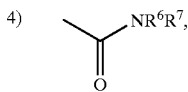

5) —$SO_2$—$NR^6R^7$

6) 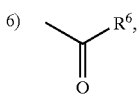

7) 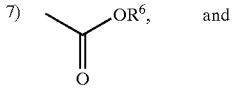 and

8) —$(C_1$-$C_6$ alkyl$)NR^{10}C(O)R^{13}$;

$R^{10}$ is independently selected from
 a) hydrogen,
 b) unsubstituted or substituted $C_1$-$C_6$ alkyl,
 c) $C_3$-$C_6$ cycloalkyl,
 d) 2,2,2-trifluoroethyl,
 e) unsubstituted or substituted heteroaryl,
 f) unsubstituted or substituted aryl,
 g) unsubstituted or substituted aralkyl, and
 h) unsubstituted or substituted heterocyclylalkyl;

$R^{11}$ is independently selected from
 a) unsubstituted or substituted $C_1$-$C_6$ alkyl,
 b) unsubstituted or substituted aralkyl,
 c) unsubstituted or substituted heterocycle,
 d) unsubstituted or substituted aryl, and
 e) unsubstituted or substituted heterocyclylalkyl;

$R^{13}$ is independently selected from
 a) H,
 b) unsubstituted or substituted $C_1$-$C_6$ alkyl,
 c) unsubstituted or substituted $C_2$-$C_6$ alkenyl,
 d) unsubstituted or substituted $C_2$-$C_6$ alkynyl,
 e) unsubstituted or substituted aryl,
 f) unsubstituted or substituted heterocycle,
 g) aralkyl, unsubstituted or substituted,
 h) heterocyclylalkyl, unsubstituted or substituted,
 i) $CF_3$,
 j) $CF_3O$—,
 k) $CF_3CH_2$—,
 l) $C_3$-$C_{10}$ cycloalkyl, unsubstituted or substituted,
 m) $OR^{10}$,
 n) —$C(O)R^{10}$,
 o) —$O(C_1$-$C_6$ alkyl$)OR^{10}$,
 p) —$C(O)NR^6R^7$,
 q) —$(C_1$-$C_6$ alkyl$)OR^{10}$, and
 r) —$(C_1$-$C_6$ alkyl$)C(O)R^{10}$;

$G^1$ and $G^2$ are independently selected from oxygen or $H_2$;
V is aryl;
W is a 5-membered heterocycle;

$Y^1$ is selected from
 a) a bond,
 b) $C_1$-$C_8$ alkyl,
 c) $C_3$-$C_{20}$ cycloalkyl,
 d) aryl or
 e) heterocycle, $Z^1$ is selected from
 a) a bond,
 b) O,
 c) C(O),
 d) $S(O)_m$,
 e) $(C(R^{1a})_2)n$, and
 f) $NR^{10}$;

m is 0, 1 or 2;
n is 0, 1, 2, 3, 4, 5 or 6;
p is 0, 1, 2, 3, or 4;
q is 0, 1, 2, or 3;
r is 0 to 5;
s is 0, 1, 2, 3 or 4;
t is 0, 1, 2, 3 or 4, provided t is 0 when $Y^1$ is a bond;
u is 4 or 5;
v is 0, 1, 2, 3 or 4; and
w is 0, 1, 2, 3 or 4;
or a pharmaceutically acceptable salt, an optical isomer or stereoisomer thereof.

3. A compound which is selected from the group consisting of:

(20R)-19,20,21,22-Tetrahydro-19-oxo-17H-18,20-ethano-6,10:12,16-dimetheno-16H-imidazo[3,4-h][1,8,11,14]oxatriazacycloeicosine-9-carbonitrile;

(20S)-19,20,21,22-Tetrahydro-19-oxo-17H-18,20-ethano-6,10:12,16-dimetheno-16H-imidazo[3,4-h][1,8,11,14]oxatriazacycloeicosine-9-carbonitrile;

(20R)-14-Chloro-19,20,21,22-tetrahydro-19-oxo-17H-18,20-ethano-6,10:12,16-dimetheno-16H-imidazo[3,4-h][1,8,11,14]oxatri-azacycloeicosine-9-carbonitrile;

(20S)-14-Chloro-19,20,21,22-tetrahydro-19-oxo-17H-18,20-ethano-6,10:12,16-dimetheno-16H-imidazo[3,4-h][1,8,11,14]oxatri-azacycloeicosine-9-carbonitrile;

(21R)-20,21,22,23-Tetrahydro-17-oxo-5H,17H,19H-18,21-methano-6,10:12,16-dimethenoimidazo[3,4-h][1,8,11,15]oxatriazacycloheneicosine-9-carbonitrile;

(21S)-20,21,22,23-Tetrahydro-17-oxo-5H,17H,19H-18,21-methano-6,10:12,16-dimethenoimidazo[3,4-h][1,8,11,15]oxatriazacycloheneicosine-9-carbonitrile;

(21R)-20,21,22,23-Tetrahydro-5H,19H-18,21-methano-6,10:12,16-dimetheno-16H-imidazo[4,3-n][1,8,12,15,7]oxatriazathia-cycloheneicosine-9-carbonitrile 17,17-dioxide;

(21S)-20,21,22,23-Tetrahydro-5H,19H-18,21-methano-6,10:12,16-dimetheno-16H-imidazo[4,3-n][1,8,12,15,7]oxatriazathia-cycloheneicosine-9-carbonitrile 17,17-dioxide;

(20S)-19,20,21,22-Tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;

(20R)-19,20,21,22-Tetrahydro-19-oxo-5H-18,20-ethano-12,14-etheno- 6,10-metheno-18H-benz[d]imidazo[4,3-k][1,6,9,12]oxatriazacyclooctadecosine-9-carbonitrile;

(5R,20R)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;

(5S,20R)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;

(5R,20S)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;

(5S,20S)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile;

(5R,20R)-19,20,21,22-Tetrahydro-5-methyl-19-oxo-5H-18,20-ethano-12,14-etheno-6,10-metheno-18H-benz[d]imidazo[4,3-k][1,6,9,12]oxatriaza-cyclooctadecosine-9-carbonitrile;

(5S,20R)-19,20,21,22-Tetrahydro-5-methyl-19-oxo-5H-18,20-ethano-12,14-etheno-6,10-metheno-18H-benz[d]imidazo[4,3-k][1,6,9,12]oxatriaza-cyclooctadecosine-9-carbonitrile;

(5R,20S)-19,20,21,22-Tetrahydro-5-methyl-19-oxo-5H-18,20-ethano-12,14-etheno-6,10-metheno-18H-benz[d]imidazo[4,3-k][1,6,9,12]oxatriaza-cyclooctadecosine-9-carbonitrile;

(5S,20S)-19,20,21,22-Tetrahydro-5-methyl-19-oxo-5H-18,20-ethano-12,14-etheno-6,10-metheno-18H-benz[d]imidazo[4,3-k][1,6,9,12]oxatriaza-cyclooctadecosine-9-carbonitrile;

(17R,20S)-17-(3-Chlorophenyl)-19,20,21,22-tetrahydro-19-oxo-5H,18H- 18,20-ethano-6,10:12,16-dimetheno-16H-imidazo[3,4-h][1,8,11,14]oxatriazacycloeicosine-9-carbonitrile;

(17S,20S)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile;

(17R,20R)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile;

(17S,20R)-17-(3-Chlorophenyl)-19,20,21,22-tetrahydro-19-oxo-5H,18H-18,20-ethano-6,10:12,16-dimetheno-16H-imidazo[3,4-h][1,8,11,14]oxatriazacycloeicosine-9-carbonitrile;

(17R,20S)-19,20,21,22-Tetrahydro-19-oxo-17-phenyl-5H,18H-18,20-ethano-6,10:12,16-dimetheno-16H-imidazo[3,4-h][1,8,11,14]oxatriaza-cycloeicosine-9-carbonitrile;

(17S,20S)-19,20,21,22-Tetrahydro-19-oxo-17-phenyl-5H,18H-18,20-ethano-6,10:12,16-dimetheno-16H-imidazo[3,4-h][1,8,11,14]oxatriaza-cycloeicosine-9-carbonitrile;

(17R,20R)-19,20,21,22-Tetrahydro-19-oxo-17-phenyl-5H,18H-18,20-ethano-6,10:12,16-dimetheno-16H-imidazo[3,4-h][1,8,11,14]oxatriaza-cycloeicosine-9-carbonitrile;

(17S,20R)-19,20,21,22-Tetrahydro-19-oxo-17-phenyl-5H,18H-18,20-ethano-6,10:12,16-dimetheno-16H-imidazo[3,4-h][1,8,11,14]oxatriaza-cycloeicosine-9-carbonitrile;

(20S)-19,20,21,22-Tetrahydro-21-methyl-19-oxo-5H,18,20-ethano-12,14-etheno-6,10-metheno-18H-benz[d]imidazo[4,3-k][1,6,9,12]oxatriaza-cyclooctadecosine-9-carbonitrile;

(20R)-19,20,21,22-Tetrahydro-21-methyl-19-oxo-5H,18,20-ethano-12,14-etheno-6,10-metheno-18H-benz[d]imidazo[4,3-k][1,6,9,12]oxatriaza-cyclooctadecosine-9-carbonitrile;

(20R)-19,20,22,23-Tetrahydro-19,22-dioxo-5H,21H-18,20-ethano-12,14-etheno-6,10-methenobenz[d]imidazo[4,3-l][1,6,9,13]oxatriaza-cyclononadecosine-9-carbonitrile;

(20S)-19,20,22,23-Tetrahydro-19,22-dioxo-5H,21H-18,20-ethano-12,14-etheno-6,10-methenobenz[d]imidazo[4,3-l][1,6,9,13]oxatriaza-cyclononadecosine-9-carbonitrile;

(20R)-15-Bromo-19,20,21,22-tetrahydro-19-oxo-5H-18,20-ethano-12,14-etheno-6,10-metheno-18H-benz[d]imidazo[4,3-k][1,6,9,12]oxatriaza-cyclooctadecosine-9-carbonitrile;

(20S)-15-Bromo-19,20,21,22-tetrahydro-19-oxo-5H-18,20-ethano-12,14-etheno-6,10-metheno-18H-benz[d]imidazo[4,3-k][1,6,9,12]oxatriaza-cyclooctadecosine-9-carbonitrile;

(20R)-15-Cylopropylethynyl-19,20,21,22tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;

(20S)-15-Cyclopropylethynyl-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;

(20S)-15-(2-Cyclopropylethyl)-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile; (20R)-15-(2-Cyclopropylethyl)-19,20,21,22-tetrahydro-19-oxo-5H-18,20-ethano-12,14-etheno-6,10-metheno-18H-benz[d]imidazo[4,3-k][1,6,9,12]oxatriazacyclooctadecosine-9-carbonitrile;

(20R)-19,20,21,22-Tetrahydro-5H-18,20-ethano-12,14-etheno-6,10-metheno-18H-benz[d]imidazo[4,3-k][1,6,9,12]oxatriazacyclooctadecosine-9-carbonitrile;

(20S)-19,20,21,22-Tetrahydro-5H-18,20-ethano-12,14-etheno-6,10-metheno-18H-benz[d]imidazo[4,3-k][1,6,9,12]oxatriazacyclooctadecosine-9-carbonitrile;

(20S)-19,20,22,23-Tetrahydro-19-oxo-5H,21H-18,20-ethano-12,14-etheno-6,10-methenobenz[d]imidazo[4,3-l][1,6,9,13]oxatriazacyclononadecosine-9-carbonitrile;

(20R)-19,20,22,23-Tetrahydro-19-oxo-5H,21H-18,20-ethano-12,14-etheno-6,10-methenobenz[d]imidazo[4,3-l][1,6,9,13]oxatrizacyclononadecosine-9-carbonitrile;

(5R,20R)-19,20,22,23-Tetrahydro-5-hydroxy-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile;

(5S,20R)-19,20,22,23-Tetrahydro-5-hydroxy-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile;

(5S,20S)-19,20,22,23-Tetrahydro-5-hydroxy-5-methyl-19,22-dioxo-5H,21H- 18,20-ethano-12,14-etheno-6,10-methenobenz[d]imidazo[3,4-l][1,6,9,12]oxatriazacyclononadecosine-9-carbonitrile;

(5R,20S)-19,20,22,23-Tetrahydro-5-hydroxy-5-methyl-19,22-dioxo-5H,21H-18,20-ethano-12,14-etheno-6,10-methenobenz[d]imidazo[3,4-l][1,6,9,12]oxatriazacyclononadecosine-9-carbonitrile;

(20S)-19,20,21,22,23,24-hexahydro-19,22-dioxo-5H,18H-18,20-ethano-12,14-etheno-6,10-methenobenz[d]imidazo[4,3-m][1,6,9,14]oxatriazacycloeiscosine-9-carbonitrile;

(20R)-19,20,21,22,23,24-hexahydro-19,22-dioxo-5H,
18H-18,20-ethano-12,14-etheno-6,10-methenobenz[d]
imidazo[4,3-m][1,6,9,14]oxatriazacycloeiscosine-9-
carbonitrile;

(20S)-19,20,21,22,23,24-hexahydro-19-oxo-5H,18H-18,
20-ethano-12,14-etheno-6,10-methenobenz[d]imidazo
[4,3-m][1,6,9,14]oxatriazacycloeiscosine-9-
carbonitrile;

(20R)-19,20,21,22,23,24-hexahydro-19-oxo-5H,18H-18,
20-ethano-12,14-etheno-6,10-methenobenz[d]imidazo
[4,3-m][1,6,9,14]oxatriazacycloeiscosine-9-
carbonitrile;

15-Bromo-19,20,21,22-tetrahydro-19-oxo-17H-18,20-
ethano-6,10:12,16-dimetheno-16H-imidazo[3,4-h][1,
8,11,14]oxatriazacycloeicosine-9-carbonitrile;

(17R,20R)-19,20,21,22-tetrahydro-19-oxo-17H-15,
17:18,20-diethano-6,10:12,16-dimetheno-16H-
imidazo[3,4-h][1,8,11,14]oxatraacycloeicosine-9-
carbonitrile;

(17S,20R)-19,20,21,22-tetrahydro-19-oxo-17H-15,17:18,
20-diethano-6,10:12,16-dimetheno-16H-imidazo[3,4-
h][1,8,11,14]oxatriazacycloeicosine-9-carbonitrile;

17S,20S)-19,20,21,22-tetrahydro-19-oxo-17H-15,17:18,
20-diethano-6,10:12,16-dimetheno-16H-imidazo[3,4-
h][1,8,11,14]oxatriazacycloeicosine-9-carbonitrile;

(17R,20S)-19,20,21,22-tetrahydro-19-oxo-17H-15,17:18,
20-diethano- 6,10:12,16-dimetheno-16H-imidazo[3,4-
h][1,8,11,14]oxatriazacycloeicosine-9-carbonitrile;

(20S)-19,20,22,23-Tetrahydro-21-methyl-9-oxo-5H,21H-
18,20-ethano-12,14-etheno-6,10-methenobenz[d]
imidazo[4,3-l][1,6,9,13]oxatriazacyclononadecosine-
9-carbonitrile;

(20R)-19,20,22,23-Tetrahydro-21-methyl-19-oxo-5H,
21H-18,20-ethano-12,14-etheno-6,10-methenobenz[d]
imidazo[4,3-l][1,6,9,13]oxatriazacyclononadecosine-
9-carbonitrile;

(17R,20R)-19,20,21,22-tetrahydro-21-methyl-19-oxo-
17H-15,17:18,20-diethano-6,10:12,16-dimetheno-
16H-imidazo[3,4-h][1,8,11,14]oxatriazacycloeicosine-
9-carbonitrile;

(17S,20R)-19,20,21,22-tetrahydro-21-methyl-19-oxo-
17H-15,17:18,20-diethano-6,10:12,16-dimetheno-
16H-imidazo[3,4-h][1,8,11,14]oxatriazacycloeicosine-
9-carbonitrile;

(17S,20S)-19,20,21,22-tetrahydro-21-methyl-19-oxo-
17H-15,17:18,20-diethano-6,10:12,16-dimetheno-
16H-imidazo[3,4-h][1,8,11,14]oxatriazacycloeicosine-
9-carbonitrile;

(17R,20S)-19,20,21,22-tetrahydro-21-methyl-19-oxo-
17H-15,17:18,20-diethano-6,10:12,16-dimetheno-
16H-imidazo[3,4-h][1,8,11,14]oxatriazacycloeicosine-
9-carbonitrile;

(20R)-16-bromo-19,20,22,23-tetrahydro-19,22-dioxo-
5H,21H-18,20-ethano-12,14-etheno-6,10-
methenobenz[d]imidazo[4,3-l][1,6,9,13]
oxatriazacyclononadecosine-9-carbonitrile;

(20S)-16-bromo-19,20,22,23-tetrahydro-19,22-dioxo-
5H,21H-18,20-ethano-12,14-etheno-6,10-
methenobenz[d]imidazo[4,3-l][1,6,9,13]
oxatriazacyclononadecosine-9-carbonitrile;

(23S)-22,23,24,25-tetrahydro-22-oxo-16H,21H-21,23-
ethano-6,10:12,16-dimethenobenz[g]imidazo[4,3-n][1,
9,12,15]oxatriazacycloheneicosine-9-carbonitrile;

(23R)-22,23,24,25-tetrahydro-22-oxo-16H,21H-21,23-
ethano-6,10:12,16-dimethenobenz[g]imidazo[4,3-n][1,
9,12,15]oxatriazacycloheneicosine-9-carbonitrile;

(20S)-25-aza-19,20,21,22-tetrahydro-19-oxo-5H-18,20-
ethano-12,14-etheno-6,10-metheno-18H-benz[d]
imidazo[4,3-k][1,6,9,12]oxatriaza-cyclooctadecosine-
9-carbonitrile;

(20R)-25-aza-19,20,21,22-tetrahydro-19-oxo-5H-18,20-
ethano-12,14-etheno-6,10-metheno-18H-benz[d]
imidazo[4,3-k][1,6,9,12]oxatriaza-cyclooctadecosine-
9-carbonitrile;

(20S)-19,20,21,22-tetrahydro-19-oxo-5H-18,20-ethano-
12,14-etheno-6,10-metheno-18H-benz[d]imidazo[4,3-
k][1,3,6,9,12]oxatetraaza-cyclooctadecosine-9-
carbonitrile;

(20R)-19,20,21,22-tetrahydro-19-oxo-5H-18,20-ethano-
12,14-etheno-6,10-metheno-18H-benz[d]imidazo[4,3-
k][1,3,6,9,12]oxatetraaza-cyclooctadecosine-9-
carbonitrile;

(21S)-19,20,22,23-tetrahydro-18-oxo-5H,21H-19,21-
ethano-12,14-etheno-6,10-methenobenz[d]imidazo[4,
3-l][1,7,10,13]oxatriazacyclononadecosine-9-
carbonitrile;

(21R)-19,20,22,23-tetrahydro-18-oxo-5H,21H-19,21-
ethano-12,14-etheno-6,10-methenobenz[d]imidazo[4,
3-l][1,7,10,13]oxatriazacyclononadecosine-9-
carbonitrile;

(20S)-19,20,21,22-tetrahydro-3-methyl-19-oxo-5H,18,
20-ethano-12,14-etheno- 6,10-metheno-18H-benz[d]
imidazo[4,3-k][1,6,9,12]oxatriazacyclooctadecosine-
9-carbonitrile;

(20R)-19,20,21,22-tetrahydro-3-methyl-19-oxo-5H,18,
20-ethano-12,14-etheno-6,10-metheno-18H-benz[d]
imidazo[4,3-k][1,6,9,12]oxatriazacyclooctadecosine-
9-carbonitrile; (20S)-19,20,22,23-tetrahydro-5H,21H-
18,20-ethano-12,14-etheno-6,10-methenobenz[d]
imidazo[4,3-l][1,6,9,13]oxatriazacyclononadecosine-
9-carbonitrile;

(20R)-19,20,22,23-tetrahydro-5H,21H-18,20-ethano-12,
14-etheno-6,10-methenobenz[d]imidazo[4,3-l][1,6,9,
13]oxatriazacyclononadecosine-9-carbonitrile;

(21S)-19,20,22,23,24-pentahydro-18-oxo-5H,21H-19,21-
ethano-12,14-etheno-6,10-methenobenz[d]imidazo[4,
3-m][1,7,10,14]oxatriazacycloeicosine-9-carbonitrile;

(21R)-19,20,22,23,24-pentahydro-18-oxo-5H,21H-19,
21-ethano-12,14-etheno-6,10-methenobenz[d]imidazo
[4,3-m][1,7,10,14]oxatriazacycloeicosine-9-
carbonitrile;

(20S)-17-bromo-19,20,22,23-tetrahydro-19,22-dioxo-
5H,21H-18,20-ethano-12,14-etheno-6,10-
methenobenz[d]imidazo[4,3-l][1,6,9,13]
oxatriazacyclononadecosine-9-carbonitrile;

(20R)-17-bromo-19,20,22,23-tetrahydro-19,22-dioxo-
5H,21H-18,20-ethano-12,14-etheno-6,10-
methenobenz[d]imidazo[4,3-l][1,6,9,13]
oxatriazacyclononadecosine-9-carbonitrile;

(5S,20S)-5-amino-19,20,22,23-tetrahydro-5-methyl-19,
22-dioxo-5H,21H-18,20-ethano-12,14-etheno-6,10-
methenobenz[d]imidazo[3,4-l][1,6,9,12]
oxatriazacyclononadecosine-9-carbonitrile;

(5R,20S)-5-amino-19,20,22,23-tetrahydro-5-methyl-19,
22-dioxo-5H,21H-18,20-ethano-12,14-etheno-6,10-
methenobenz[d]imidazo[3,4-l][1,6,9,12]
oxatriazacyclononadecosine-9-carbonitrile;

(5S,20R)-5-amino-19,20,22,23-tetrahydro-5-methyl-19,
22-dioxo-5H,21H-18,20-ethano-12,14-etheno-6,10-
methenobenz[d]imidazo[3,4-l][1,6,9,12]
oxatrizacyclononadecosine-9-carbonitrile;

(5R,20R)-5-amino-19,20,22,23-tetrahydro-5-methyl-19,
22-dioxo-5H,21H-18,20-ethano-12,14-etheno-6,10-
methenobenz[d]imidazo[3,4-1][1,6,9,12]
oxatrizacyclononadecosine-9-carbonitrile:

(20S)-15,16,17,17a,19,20,21,22-octahydro-15-oxa-19-
oxo-5H-18,20-ethano-12,14-etheno-6,10-metheno-
18H-benz[d]imidazo[4,3-k][1,6,9,12]
oxatriazacyclooctadecosine-9-carbonitrile;

(20R)-15,16,17,17a,19,20,21,22-octahydro-15-oxa-19-
oxo-5H-18,20-ethano-12,14-etheno-6,10-metheno-
18H-benz[d]imidazo[4,3-k][1,6,9,12]
oxatriazacyclooctadecosine-9-carbonitrile;

(20S)-15,16,17,17a,19,20,21,22-octahydro-19-oxo-5H-
18,20-ethano-12,14-etheno-6,10-metheno-18H-benz
[d]imidazo[4,3-k][1,6,9,12]oxatriaza-
cyclooctadecosine-9-carbonitrile;

(20R)-15,16,17,17a,19,20,21,22-octahydro-19-oxo-5H-
18,20-ethano-12,14-etheno-6,10-metheno-18H-benz
[d]imidazo[4,3-k][1,6,9,12]oxatriaza-
cyclooctadecosine-9-carbonitrile;

or a pharmaceutically acceptable salt, an optical isomer or
stereoisomer thereof.

4. The compound according to claim 3 which is:

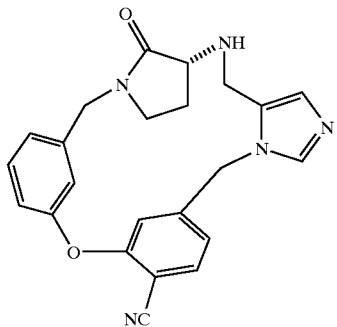

(20R)-19,20,21,22-Tetrahydro-19-oxo-17H-18,20-
ethano-6,10:12,16-dimetheno-16H-imidazo[3,4-h][1,
8,11,14]oxatriazacycloeicosine-9-carbonitrile or a pharmaceutically acceptable salt, an optical isomer or
stereoisomer thereof.

5. The compound according to claim 3 which is:

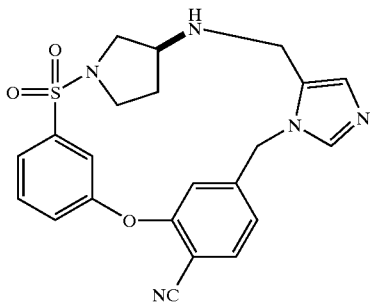

(21S)-20,21,22,23-Tetrahydro-5H,19H-18,21-methano-6,
10:12,16-dimetheno-16H-imidazo[4,3-n][1,8,12,15,7]
oxatriazathia-cycloheneicosine-9-carbonitrile 17,17-
dioxide or a pharmaceutically acceptable salt, an optical isomer or
stereoisomer thereof.

6. The compound according to claim 3 which is:

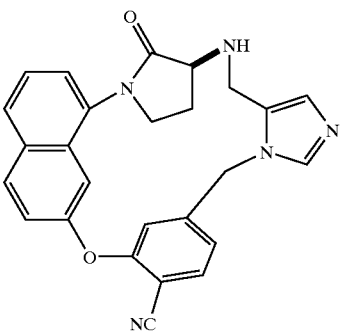

(20S)-19,20,21,22-Tetrahydro-19-oxo-5H-18,20-ethano-
12,14-etheno-6,10-metheno-18H-benz[d]imidazo[4,3-
k][1,6,9,12]oxatriazacyclooctadecosine-9-carbonitrile or a pharmaceutically acceptable salt, an optical isomer or
stereoisomer thereof.

7. The compound according to claim 3 which is:

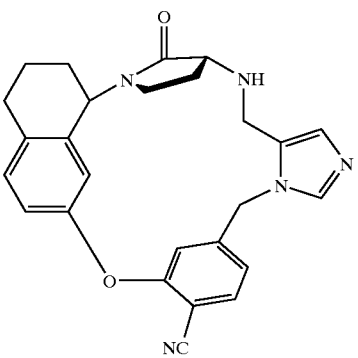

(20R)-15,16,17,17a,19,20,21,22-octahydro-19-oxo-5H-
18,20-ethano-12,14-etheno-6,10-metheno-18H-benz
[d]imidazo[4,3-k][1,6,9,12]oxatriaza-
cyclooctadecosine-9-carbonitrile or a pharmaceutically acceptable salt, an optical isomer or
stereoisomer thereof.

8. The compound according to claim 3 which is:

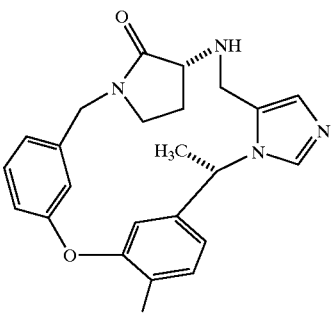

(5S,20R)-19,20,21,22-Tetrahydro-5-methyl-19-oxo-17H-
18,20-ethano-6,10:12,16-dimetheno-16H-imidazo[3,4-
h][1,8,11,14]oxatriaza-cycloeicosine-9-carbonitrile or a pharmaceutically acceptable salt, an optical isomer or
stereoisomer thereof.

9. The compound according to claim 3 which is:

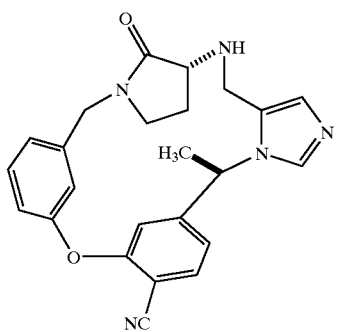

(5R,20R)-19,20,21,22-Tetrahydro-5-methyl-19-oxo-17H-18,20-ethano-6,10:12,16-dimetheno-16H-imidazo[3,4-h][1,8,11,14]oxatriaza-cycloeicosine-9-carbonitrile or a pharmaceutically acceptable salt, an optical isomer or stereoisomer thereof.

10. The compound according to claim 3 which is:

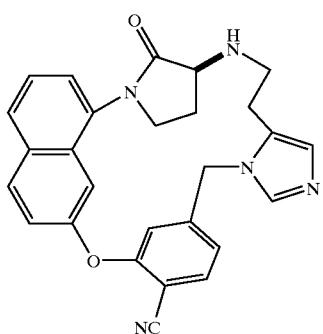

(20S)-19,20,22,23-Tetrahydro-19-oxo-5H,21H-18,20-ethano-12,14-etheno-6,10-methenobenz[d]imidazo[4,3-1][1,6,9,13]oxatriazacyclononadecosine-9-carbonitrile or a pharmaceutically acceptable salt, an optical isomer or stereoisomer thereof.

11. The compound according to claim 3 which is:

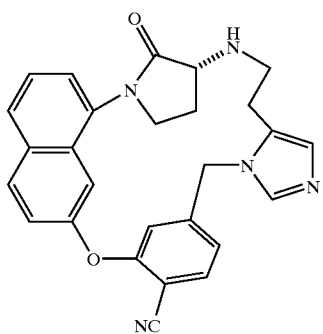

(20R)-19,20,22,23-Tetrahydro-19-oxo-5H,21H-18,20-ethano-12,14-etheno-6,10-methenobenz[d]imidazo[4,3-1][1,6,9,13]oxatriazacyclononadecosine-9-carbonitrile or a pharmaceutically acceptable salt, an optical isomer or stereoisomer thereof.

12. The compound according to claim 3 which is:

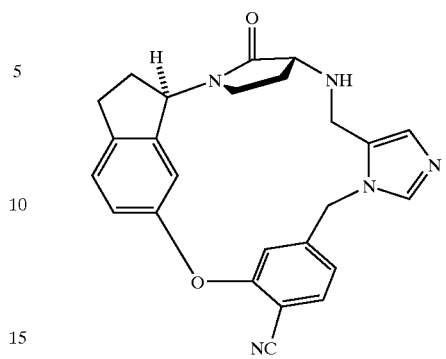

(17R,20R)-19,20,21,22-tetrahydro-19-oxo-17H-15,17:18,20-diethano-6,10:12,16-dimetheno-16H-imidazo[3,4-h][1,8,11,14]oxatriazacycloeicosine-9-carbonitrile or a pharmaceutically acceptable salt, an optical isomer or stereoisomer thereof.

13. The compound according to claim 3 which is:

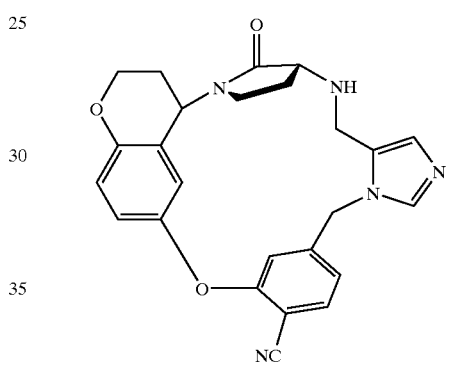

(20R)-15,16,17,17a,19,20,21,22-octahydro-15-oxa-19-oxo-5H-18,20-ethano-12,14-etheno-6,10-metheno-18H-benz[d]imidazo[4,3-k][1,6,9,12]oxatriazacyclooctadecosine-9-carbonitrile or a pharmaceutically acceptable salt, an optical isomer or stereoisomer thereof.

14. A pharmaceutical composition made by combining the compound of claim 1 and a pharmaceutically acceptable carrier.

15. A pharmaceutical composition comprising a pharmaceutical carrier, and dispersed therein, a therapeutically effective amount of a compound of claim 3.

16. A pharmaceutical composition comprising a pharmaceutical carrier, and dispersed therein, a therapeutically effective amount of a compound of claim 3.

17. A process for making a pharmaceutical composition comprising combining a compound of claim 1 and a pharmaceutically acceptable carrier.

18. A method for inhibiting farnesyl-protein transferase which comprises administering to a mammal in need thereof a therapeutically effective amount of a compound of claim 1.

19. A method for inhibiting farnesyl-protein transferase which comprises administering to a mammal in need thereof a therapeutically effective amount of a compound of claim 2.

20. A method for inhibiting farnesyl-protein transferase which comprises administering to a mammal in need thereof a therapeutically effective amount of a compound of claim 3.

21. A method for treating ras mediated cancer which comprises administering to a mammal in need thereof a therapeutically effective amount of a compound of claim 1.

22. A method for treating neurofibromen benign proliferative disorder which comprises administering to a mammal in need thereof a therapeutically effective amount of a compound of claim 1.

23. A method for treating blindness related to retinal vascularization which comprises administering to a mammal in need thereof a therapeutically effective amount of a compound of claim 1.

24. A method for treating infections from hepatitis delta and related viruses which comprises administering to a mammal in need thereof a therapeutically effective amount of a compound of claim 1.

25. A method for preventing restenosis which comprises administering to a mammal in need thereof a therapeutically effective amount of a compound of claim 1.

26. A method for treating polycystic kidney disease which comprises administering to a mammal in need thereof a therapeutically effective amount of a compound of claim 1.

* * * * *

SEQUENCE LISTING

<160> NUMBER OF SEQ ID NOS: 25

<210> SEQ ID NO 1
<211> LENGTH: 4
<212> TYPE: PRT
<213> ORGANISM: Homosapien

<400> SEQUENCE: 1

Cys Val Leu Leu
1

<210> SEQ ID NO 2
<211> LENGTH: 15
<212> TYPE: PRT

```
<213> ORGANISM: Artificial Sequence
<220> FEATURE:
<223> OTHER INFORMATION: completely synthesized

<400> SEQUENCE: 2

Gly Lys Lys Lys Lys Lys Ser Lys Thr Lys Cys Val Ile Met
 1               5                  10                  15

<210> SEQ ID NO 3
<211> LENGTH: 52
<212> TYPE: DNA
<213> ORGANISM: Artificial Sequence
<220> FEATURE:
<223> OTHER INFORMATION: completely synthesized

<400> SEQUENCE: 3
gagagggaat tcgggccctt cctgcatgct gctgctgctg ctgctgctgg gc        52

<210> SEQ ID NO 4
<211> LENGTH: 41
<212> TYPE: DNA
<213> ORGANISM: Artificial Sequence
<220> FEATURE:
<223> OTHER INFORMATION: completely synthesized

<400> SEQUENCE: 4
gagagagctc gaggttaacc cgggtgcgcg gcgtcggtgg t                    41

<210> SEQ ID NO 5
<211> LENGTH: 42
<212> TYPE: DNA
<213> ORGANISM: Artificial Sequence
<220> FEATURE:
<223> OTHER INFORMATION: completely synthesized

<400> SEQUENCE: 5
gagagagtct agagttaacc cgtggtcccc gcgttgcttc ct                   42

<210> SEQ ID NO 6
<211> LENGTH: 43
<212> TYPE: DNA
<213> ORGANISM: Artificial Sequence
<220> FEATURE:
<223> OTHER INFORMATION: completely synthesized

<400> SEQUENCE: 6
gaagaggaag cttggtaccg ccactgggct gtaggtggtg gct                  43

<210> SEQ ID NO 7
<211> LENGTH: 27
<212> TYPE: DNA
<213> ORGANISM: Artificial Sequence
<220> FEATURE:
<223> OTHER INFORMATION: completely synthesized

<400> SEQUENCE: 7
ggcagagctc gtttagtgaa ccgtcag                                    27

<210> SEQ ID NO 8
<211> LENGTH: 27
<212> TYPE: DNA
<213> ORGANISM: Artificial Sequence
<220> FEATURE:
<223> OTHER INFORMATION: completely synthesized

<400> SEQUENCE: 8
```

```
gagagatctc aaggacggtg actgcag                                              27

<210> SEQ ID NO 9
<211> LENGTH: 86
<212> TYPE: DNA
<213> ORGANISM: Artificial Sequence
<220> FEATURE:
<223> OTHER INFORMATION: completely synthesized

<400> SEQUENCE: 9
tctcctcgag gccaccatgg ggagtagcaa gagcaagcct aaggacccca gccagcgccg         60
gatgacagaa tacaagcttg tggtgg                                              86

<210> SEQ ID NO 10
<211> LENGTH: 33
<212> TYPE: DNA
<213> ORGANISM: Artificial Sequence
<220> FEATURE:
<223> OTHER INFORMATION: completely synthesized

<400> SEQUENCE: 10
cacatctaga tcaggacagc acagacttgc agc                                      33

<210> SEQ ID NO 11
<211> LENGTH: 41
<212> TYPE: DNA
<213> ORGANISM: Artificial Sequence
<220> FEATURE:
<223> OTHER INFORMATION: completely synthesized

<400> SEQUENCE: 11
tctcctcgag gccaccatga cagaatacaa gcttgtggtg g                             41

<210> SEQ ID NO 12
<211> LENGTH: 38
<212> TYPE: DNA
<213> ORGANISM: Artificial Sequence
<220> FEATURE:
<223> OTHER INFORMATION: completely synthesized

<400> SEQUENCE: 12
cactctagac tggtgtcaga gcagcacaca cttgcagc                                 38

<210> SEQ ID NO 13
<211> LENGTH: 38
<212> TYPE: DNA
<213> ORGANISM: Artificial Sequence
<220> FEATURE:
<223> OTHER INFORMATION: completely synthesized

<400> SEQUENCE: 13
gagagaattc gccaccatga cggaatataa gctggtgg                                 38

<210> SEQ ID NO 14
<211> LENGTH: 33
<212> TYPE: DNA
<213> ORGANISM: Artificial Sequence
<220> FEATURE:
<223> OTHER INFORMATION: completely synthesized

<400> SEQUENCE: 14
gagagtcgac gcgtcaggag agcacacact tgc                                      33

<210> SEQ ID NO 15
<211> LENGTH: 22
```

-continued

```
<212> TYPE: DNA
<213> ORGANISM: Artificial Sequence
<220> FEATURE:
<223> OTHER INFORMATION: completely synthesized

<400> SEQUENCE: 15
ccgccggcct ggaggagtac ag                                                 22

<210> SEQ ID NO 16
<211> LENGTH: 38
<212> TYPE: DNA
<213> ORGANISM: Artificial Sequence
<220> FEATURE:
<223> OTHER INFORMATION: completely synthesized

<400> SEQUENCE: 16
gagagaattc gccaccatga ctgagtacaa actggtgg                                38

<210> SEQ ID NO 17
<211> LENGTH: 32
<212> TYPE: DNA
<213> ORGANISM: Artificial Sequence
<220> FEATURE:
<223> OTHER INFORMATION: completely synthesized

<400> SEQUENCE: 17
gagagtcgac ttgttacatc accacacatg gc                                      32

<210> SEQ ID NO 18
<211> LENGTH: 21
<212> TYPE: DNA
<213> ORGANISM: Artificial Sequence
<220> FEATURE:
<223> OTHER INFORMATION: completely synthesized

<400> SEQUENCE: 18
gttggagcag ttggtgttgg g                                                  21

<210> SEQ ID NO 19
<211> LENGTH: 38
<212> TYPE: DNA
<213> ORGANISM: Artificial Sequence
<220> FEATURE:
<223> OTHER INFORMATION: completely synthesized

<400> SEQUENCE: 19
gagaggtacc gccaccatga ctgaatataa acttgtgg                                38

<210> SEQ ID NO 20
<211> LENGTH: 36
<212> TYPE: DNA
<213> ORGANISM: Artificial Sequence
<220> FEATURE:
<223> OTHER INFORMATION: completely synthesized

<400> SEQUENCE: 20
ctctgtcgac gtatttacat aattacacac tttgtc                                  36

<210> SEQ ID NO 21
<211> LENGTH: 24
<212> TYPE: DNA
<213> ORGANISM: Artificial Sequence
<220> FEATURE:
<223> OTHER INFORMATION: completely synthesized

<400> SEQUENCE: 21
```

```
gtagttggag ctgttggcgt aggc                                      24

<210> SEQ ID NO 22
<211> LENGTH: 38
<212> TYPE: DNA
<213> ORGANISM: Artificial Sequence
<220> FEATURE:
<223> OTHER INFORMATION: completely synthesized

<400> SEQUENCE: 22
gagaggtacc gccaccatga ctgaatataa acttgtgg                       38

<210> SEQ ID NO 23
<211> LENGTH: 45
<212> TYPE: DNA
<213> ORGANISM: Artificial Sequence
<220> FEATURE:
<223> OTHER INFORMATION: completely synthesized

<400> SEQUENCE: 23
ctctgtcgac agattacatt ataatgcatt ttttaatttt cacac               45

<210> SEQ ID NO 24
<211> LENGTH: 24
<212> TYPE: DNA
<213> ORGANISM: Artificial Sequence
<220> FEATURE:
<223> OTHER INFORMATION: completely synthesized

<400> SEQUENCE: 24
gtagttggag ctgttggcgt aggc                                      24

<210> SEQ ID NO 25
<211> LENGTH: 4
<212> TYPE: PRT
<213> ORGANISM: Homosapien

<400> SEQUENCE: 25

Cys Val Leu Ser
  1
```